(12) United States Patent
Jonckers et al.

(10) Patent No.: US 10,597,390 B2
(45) Date of Patent: Mar. 24, 2020

(54) INDOLES FOR USE IN INFLUENZA VIRUS INFECTION

(71) Applicant: Janssen Sciences Ireland UC, Little Island, Co Cork (IE)

(72) Inventors: Tim Hugo Maria Jonckers, Heist op den Berg (BE); Pierre Jean-Marie Bernard Raboisson, Rosieres (BE); Jérôme Émile Georges Guillemont, Ande (FR); David Craig McGowan, Brussels (BE); Werner Constant Johan Embrechts, Beerse (BE); Ludwig Paul Cooymans, Beerse (BE); Antoine Benjamin Michaut, Val de Reuil (FR)

(73) Assignee: Janssen Sciences Ireland UC, East Gate, Little Island, Co Country (IE)

( * ) Notice: Subject to any disclaimer, the term of this patent is extended or adjusted under 35 U.S.C. 154(b) by 303 days.

(21) Appl. No.: 15/501,730

(22) PCT Filed: Aug. 7, 2015

(86) PCT No.: PCT/EP2015/068257
§ 371 (c)(1),
(2) Date: May 4, 2017

(87) PCT Pub. No.: WO2016/020526
PCT Pub. Date: Feb. 11, 2016

(65) Prior Publication Data
US 2017/0226102 A1    Aug. 10, 2017

(30) Foreign Application Priority Data
Aug. 8, 2014 (EP) .................... 14180331

(51) Int. Cl.
| C07D 401/14 | (2006.01) |
| C07D 417/14 | (2006.01) |
| C07D 403/14 | (2006.01) |
| A61K 31/4439 | (2006.01) |
| A61K 31/506 | (2006.01) |
| A61K 45/06 | (2006.01) |
| C07D 401/04 | (2006.01) |
| C07D 403/04 | (2006.01) |
| C07D 405/14 | (2006.01) |
| C07D 413/14 | (2006.01) |

(52) U.S. Cl.
CPC ........ *C07D 417/14* (2013.01); *A61K 31/4439* (2013.01); *A61K 31/506* (2013.01); *A61K 45/06* (2013.01); *C07D 401/04* (2013.01); *C07D 401/14* (2013.01); *C07D 403/04* (2013.01); *C07D 403/14* (2013.01); *C07D 405/14* (2013.01); *C07D 413/14* (2013.01)

(58) Field of Classification Search
CPC ........................... C07D 471/14; C07D 401/14
USPC ....................................... 544/328
See application file for complete search history.

(56) References Cited

U.S. PATENT DOCUMENTS

| 9,936,699 B2 | 4/2018 | Maue |
| 2017/0217899 A1 | 8/2017 | Maue |

FOREIGN PATENT DOCUMENTS

| CN | 104592038 A | 6/2015 |
| WO | 2005095400 A1 | 10/2005 |
| WO | 2007084557 A2 | 7/2007 |
| WO | 2010/148197 A1 | 12/2010 |
| WO | WO2012/032065 | 3/2012 |
| WO | 2012083117 A1 | 6/2012 |
| WO | WO2012/083122 | 6/2012 |
| WO | WO2013/019828 | 2/2013 |
| WO | 2013030138 A1 | 3/2013 |
| WO | 2013184985 A1 | 12/2013 |
| WO | 2015073476 A1 | 5/2015 |
| WO | 2016020526 A1 | 2/2017 |

OTHER PUBLICATIONS

Michael P. Clark et al: "Discovery of a Novel, First-in-Class, Orally Bioavailable Azaindole Inhibitor (VX-787) of Influenza PB2", Journal of Medicinal Chemistry, vol. 57, No. 15, (Jul. 14, 2014), pp. 6668-6678.

Birney, et al., "Structural Investigations into retro-Diels-Alder Reaction. Experimental and Theoretical Studies", J. Am. Chem. Soc., vol. 124 (18): pp. 5091-5099 (2002).

Shao, et al., Synthesis, Characterization and Antitumor Activity of Tetraplatinum (IV) Analogue Complexes, Chinese Journal of Applied Chemistry, 1992, pp. 57-60, vol. 9(6).

*Primary Examiner* — Kahsay Habte

(57) ABSTRACT

The invention relates to compounds having the structure of formula (I) which can be used for the treatment of or against influenza infections.

7 Claims, No Drawings

INDOLES FOR USE IN INFLUENZA VIRUS INFECTION

This application is a 35 U.S.C. § 371 nationalization of PCT application PCT/EP2015/068257 filed Aug. 7, 2015, which claims priority to European patent application EP 14180331.2 filed Aug. 8, 2014, all of which are incorporated herein by reference.

Influenza is a serious public health problem with a high incidence in the human population resulting in regular large-scale morbidity and mortality. It is a highly contagious airborne disease that causes an acute febrile illness. Systemic symptoms vary in severity from mild fatigue to respiratory failure and death. According to the WHO the average global burden of annual epidemics may be on the order of 1 billion cases, 3-5 million cases of severe illness and 300,000-500,000 deaths annually. Every year, influenza viruses circulate in humans, typically affecting 5-20% of the population in all age groups, with this figure rising up to 30% during major epidemics. Rates of serious illness and death are highest among persons aged >65 years, children aged <2 years, and persons of any age who have medical conditions that place them at increased risk for complications from influenza, such as chronic heart, lung, kidney, liver blood or metabolic diseases, or weakened immune systems. Although deaths are infrequent among children, rates of hospitalization range from approximately 100 to 500 per 100,000 for children<5 years-old depending on the presence or absence of co-morbid conditions. Hospitalization rates among children aged <24 months are comparable to rates reported among persons aged >65 years.

In the US, annual influenza epidemics lead to approximately 30 million outpatient visits, resulting in medical costs of $10 billion annually. Lost earnings due to illness and loss of life represent a cost of over $15 billion annually and the total US economic burden of annual influenza epidemics amounts to over $85 billion.

Pathogens that cause influenza are negative sense, single-stranded RNA viruses, which belong to the family of Orthomyxoviridae. There are three types of influenza viruses: A, B and C. Influenza A viruses are the most common form, which can spread in mammals and birds. The subtypes of influenza A are named by the types of surface proteins hemagglutinin (H) and neuraminidase (N). There are 18 different hemagglutinin and 11 known neuraminidases. Current seasonal influenza viruses found in human are mainly H1N1 and H3N2 subtypes. Influenza B viruses are usually found only in humans. They are not divided into subtypes, but can be further broken down into different strains. Circulating influenza viruses are highly variable each year, and both influenza A and B cause seasonal epidemics all over the world. Influenza C viruses give much milder symptoms, which do not cause epidemics.

All three types of viruses have similar genome structures. The genome comprises 8 segments, encoding 9-11 proteins, depending on the type. Influenza A encodes 11 proteins, which includes the surface proteins (hemagglutinin (HA) and Neuraminidase (NA), the polymerase complex (PA, PB1 and PB2), nucleoprotein (NP), membrane proteins (M1 and M2), and other proteins (NS1, NS2, NEP). Among the three influenza virus types, influenza A has the highest rate of mutation. Influenza B evolves slower than A but faster than C. The segmented genome allows gene exchanging between different viral strains, which generate new variants of influenza viruses.

Influenza virus can be transmitted among humans by direct contact with infected individuals or virus-contaminated material. One can also be infected by inhalation of suspended virus droplets in the air. Those droplets are generated by coughing, sneezing or talking of infected individuals. Seasonal influenza is characterized by a sudden onset of high fever, cough (usually dry), headache, muscle and joint pain, severe malaise (feeling unwell), sore throat and runny nose. Cough can be severe and can last two or more weeks. Most people recover from fever and other symptoms within a week without requiring medical attention. But influenza can cause severe illness or death especially in people at high risk as mentioned above. The time from infection to illness, known as the incubation period, is about two days.

The most effective way to prevent the disease and/or severe outcomes from the illness is vaccination. Safe and effective vaccines are available and have been used for more than 60 years. Among healthy adults, influenza vaccines can provide reasonable protection. However, vaccination comes with several limitations. First, influenza vaccine may be less effective in preventing illness among the elderly, and may only reduce severity of disease and incidence of complications and deaths. In addition, influenza vaccination is most effective when circulating viruses are well-matched with vaccine viruses, and the success of vaccination is largely dependent on the good prediction of the most prevalent virus type of the season. Rapid and continual evolution of influenza viral strains through antigenic drift, coupled with the short-lived nature of vaccine-induced immune responses to current influenza vaccines, means that vaccination with seasonally appropriate strains is required every year for prevention.

The current treatment of influenza uses either direct antiviral drugs, or medicines that release the influenza-induced symptoms. There are two classes of influenza antiviral drugs available on the market: neuraminidase inhibitors and M2 channel inhibitors. Neuraminidase inhibitors oseltamivir or zanamivir are the primary antiviral agents recommended for the prevention and treatment of influenza. These are effective against both influenza type A and B viruses. Development of resistance to these antiviral drugs has been identified during treatment of seasonal influenza and in sporadic oseltamivir-resistant 2009 H1N1 virus, but the public health impact has been limited to date. M2 channel inhibitors, such as amantadine and rimantadine (amantadanes), are active against influenza A strains, but not influenza B strains. Adamantane resistance among circulating influenza A viruses increased rapidly worldwide beginning during 2003-2004. Therefore, amantadine and rimantadine are not recommended for antiviral treatment or chemoprophylaxis of currently circulating influenza A virus strains.

In 2009, the novel swine H1N1 strain caused an unexpected influenza pandemic as a result of reassortment of genes from human, pig, and bird's H1N1 viruses. This past pandemic, together with the ongoing circulation of highly pathogenic avian H5N1 strains and the recent emergence of the H7N9 virus, a new reassortant of avian origin isolated in China, and associated with severe respiratory disease with 40% of mortality, which could potentially adapt for humanto-human transmission, highlighted the vulnerability of the world population to novel influenza strains. Although vaccination remains the main prophylactic strategy for controlling influenza infection, to bridge the period before a new vaccine becomes available and to treat the severe influenza cases, as well as to counter the problem of viral resistance, a wider choice of anti-influenza drugs is required. Development of new influenza antivirals has therefore again become a high priority and an unmet medical need.

The current invention relates to a compound of formula (I) which can be used for the treatment of, or against viral influenza infections:

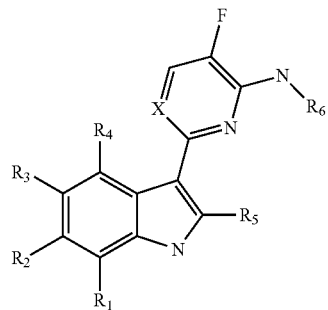

a stereo-isomeric form, a pharmaceutically acceptable salt, solvate or polymorph thereof, wherein X is N or C optionally substituted by —CN, —CF$_3$, —C$_{1-3}$ alkyl-NH—C(O)—C$_{1-3}$ alkyl, —C(O)—NH$_2$, —C(O)—NH—C$_{1-3}$ alkyl, —C(O)—N-(dialkyl) or —CH$_2$—NH—C(O)—CH$_3$;

R$_1$ is F or Cl;

R$_2$ and R$_4$ are each selected from H, halogen, CN, CF$_3$, —O-alkyl or NH$_2$;

R$_3$ is F, Cl, CN, CF$_3$, —C$_{1-3}$ alkyl, —O-alkyl, carboxylic ester or carboxylic amide R$_5$ is Br, CN, CH$_3$, CH$_2$OH, C(O)NH$_2$, NH$_2$ or H;

R$_6$ is C$_{1-8}$ alkyl substituted by carboxylic acid;
    or is C$_{3-8}$ cycloalkyl substituted by carboxylic acid, —N—C$_{1-3}$alkylsulfone, or —N—C(O)—C$_{3-6}$heterocycle optionally substituted by C$_{1-6}$ alkyl;
    or is C$_{3-6}$ heterocycle substituted by —N—C(O)—C$_{3-6}$ heterocycle;
    or is C$_{3-6}$ heterocycle substituted by COOH.

Preferably the compound according to the invention is the compound according to formula (I) wherein R$_1$ and R$_3$ are both F.

Preferred compounds according to the current invention have the structural formula:

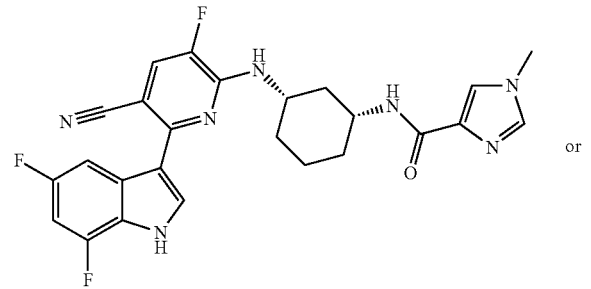

or

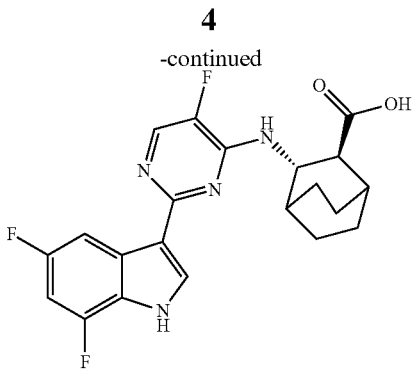

Part of the invention is also a pharmaceutical composition comprising a compound of formula (I) or a stereo-isomeric form, a pharmaceutically acceptable salt, solvate or polymorph thereof together with one or more pharmaceutically acceptable excipients, diluents or carriers.

The pharmaceutical composition may also include additional therapeutic agents like another antiviral agent or an influenza vaccine, or both.

To the invention also belongs a compound of formula (I) or a stereo-isomeric form, a pharmaceutically acceptable salt, solvate or polymorph thereof or a pharmaceutical composition for use as a medicament.

Additionally the invention relates to a compound of formula (i) or a stereo-isomeric form, a pharmaceutically acceptable salt, solvate or polymorph thereof or a pharmaceutical composition for use in the treatment of influenza.

So part of the invention is the use of a compound represented by the following structural formula (I)

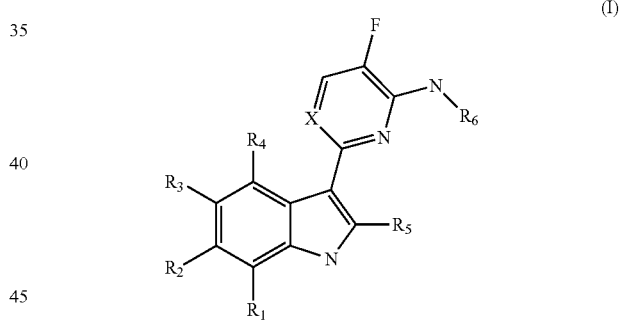

a stereo-isomeric form, a pharmaceutically acceptable salt, solvate or polymorph thereof, wherein X is N or C optionally substituted by —CN, —CF$_3$, —C$_{1-3}$ alkyl-NH—C(O)—C$_{1-3}$ alkyl, —C(O)—NH$_2$, —C(O)—NH—C$_{1-3}$ alkyl, —C(O)—N-(dialkyl) or —CH$_2$—NH—C(O)—CH$_3$;

R$_1$ is F or Cl;

R$_2$ and R$_4$ are each selected from H, halogen, CN, CF$_3$, —O-alkyl or NH$_2$;

R$_3$ is F, Cl, CN, CF$_3$, —C$_{1-3}$ alkyl, —O-alkyl, carboxylic ester or carboxylic amide R$_5$ is Br, CN, CH$_3$, CH$_2$OH, C(O)NH$_2$, NH$_2$ or H;

R$_6$ is C$_{1-8}$ alkyl substituted by carboxylic acid;
    or is C$_{3-8}$ cycloalkyl substituted by carboxylic acid, —N—C$_{1-3}$alkylsulfone, or —N—C(O)—C$_{3-6}$heterocycle optionally substituted by C$_{1-6}$ alkyl;
    or is C$_{3-6}$ heterocycle substituted by —N—C(O)—C$_{3-6}$ heterocycle;
    or is C$_{3-6}$ heterocycle substituted by COOH for inhibiting the replication of influenza virus(es) in a biological sample or patient.

Said use may also comprise the co-administration of an additional therapeutic agent, wherein said additional therapeutic agent is selected from an antiviral agent or influenza vaccine, or both.

The term "alkyl" refers to a straight-chain or branched-chain saturated aliphatic hydrocarbon containing the specified number of carbon atoms.

The term "halogen" refers to F, Cl, Br or I.

The term "cycloalkyl" refers to a carbo-cyclic ring containing the specified number of carbon atoms. For clarity, this may include a C1 or C2 bridge as in, for example, compound 5.

The term "heterocycle" refers to molecules that are saturated or partially saturated comprising one or more heteroatoms selected from N, O or S, in particular from N and O. Said heterocycle may have 4, 5, 6 or 7 ring atoms. In particular, said heterocycle may have 5 or 6 ring atoms.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

EXAMPLES

Scheme 1.

Preparation of Compound 1

Scheme 1. Reagents and conditions (Ts = tosyl). i) TsCl, TBAHS, NaOH, toluene, 3 h, rt ii) NBS, DCM, 18 h, rt iii) bis pinacolatodiboron, Pd(dppf)Cl₂, KOAc, dioxane, 18 h, 75° C. iv) [1,1'-Bis(di-tert-butylphosphino)ferrocene]dichloropalladium(II), K₃PO₄, dioxane/water, D, 10 min, microwave 100° C. v) NaOCH₃/methanol, rt.

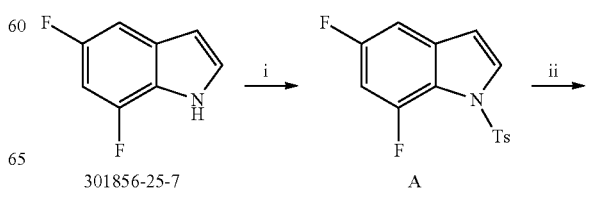

DMSO-d$_6$) δ ppm 2.36 (s, 3H), 6.92 (m, 1H), 7.19 (m, 1H), 7.35 (m, 1H), 7.44 (m, 2H), 7.80 (m, 2H), 7.99 (m, 1H)

Preparation of Intermediate B

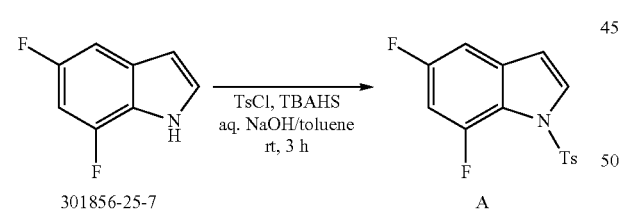

N-bromosuccinimide (9.64 g, 54.18 mmol) was added portion wise to a solution of 5,7-difluoro-1-tosyl-indole (16.65 g, 54.18 mmol) in CH$_2$Cl$_2$ (300 mL) at room temperature. The reaction mixture was stirred at room temperature for 18 h. The mixture was treated with a saturated aq. NaHCO$_3$ solution and the mixture was stirred for 5 min. The organic layer was dried (MgSO$_4$), the solids were removed by filtration and the solvent was removed under reduced pressure. The crude was purified by silica flash column chromatography (gradient:heptane to heptane/DCM 1/1). The desired fractions were collected and evaporated to dryness to afford 3-bromo-5,7-difluoro-1-tosyl-indole as a brown solid. LC-MS ES$^+$ m/z=385.9, Rt: 1.37 min, method A.

Preparation of Intermediate C

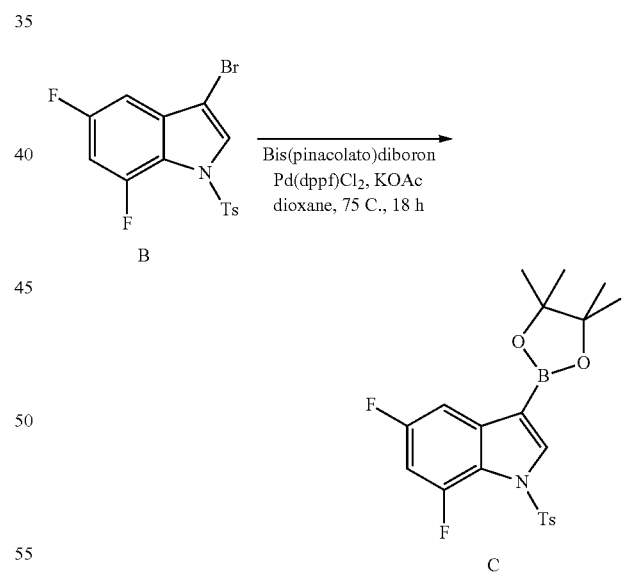

A mixture of 3-bromo-5,7-difluoro-1-tosyl-indole (2 g, 5.18 mmol), bis-pinacolato-diboron [201733-56-4] (1973 mg, 7.77 mmol), Pd(dppf)Cl$_2$ (379 mg, 0.52 mmol) and KOAc (1525 mg, 15.54 mmol) in dioxane (50 mL) was heated to 75° C. for 18 h under nitrogen. The reaction was cooled to room temperature, the solids removed by filtration, and the filtrate was concentrated. The crude C, 5,7-difluoro-3-(4,4,5,5-tetramethyl-1,3,2-dioxaborolan-2-yl)-1-tosyl-1H-indole, was used in the next step without further purification.

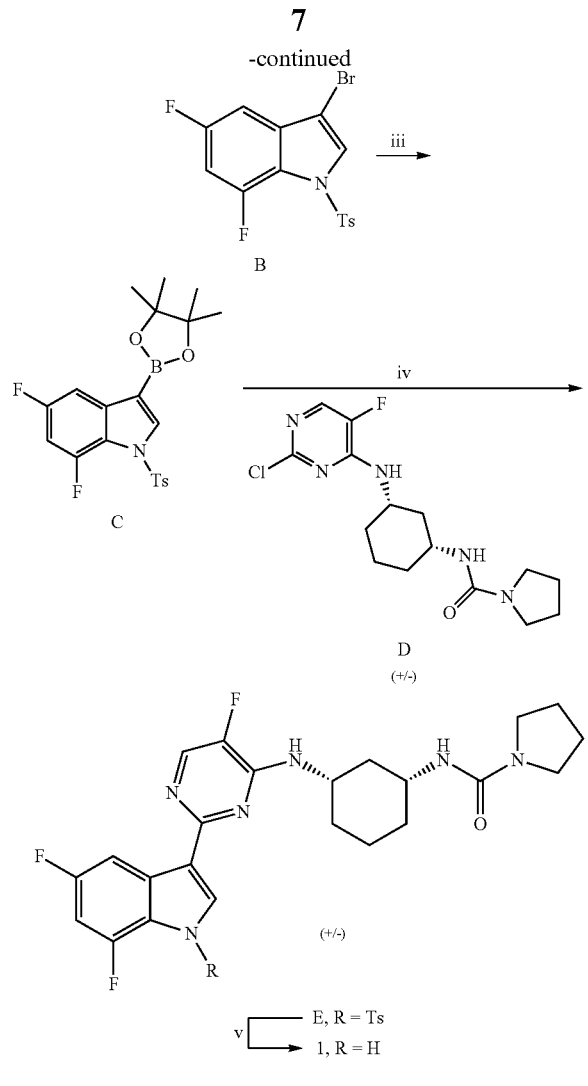

Preparation of Intermediate A 5,7-difluoroindole [301856-25-7] (500 mg, 3.27 mmol) was added to toluene (8 mL) with stirring under nitrogen. Tetrabutylammonium hydrogen sulfate (83 mg, 0.25 mmol) was added followed by NaOH (50% in H$_2$O, 5 mL) and the mixture was stirred vigorously. A solution of p-toluenesulfonyl chloride (654 mg, 3.43 mmol) in toluene (8 mL) was added and the entire mixture was stirred for 3 h. An extra amount of p-toluenesulfonyl chloride (300 mg) was dissolved in toluene (5 mL). The solution was added dropwise and the entire mixture was stirred for 3 h. The reaction was complete and the organic layer was separated and washed with water, dried over MgSO$_4$ and concentrated under reduced pressure to afford a white solid, A. LC-MS ES$^-$ m/z=306.0, Rt: 1.22 min, method A. $^1$H NMR (400 MHz,

Preparation of Intermediate D

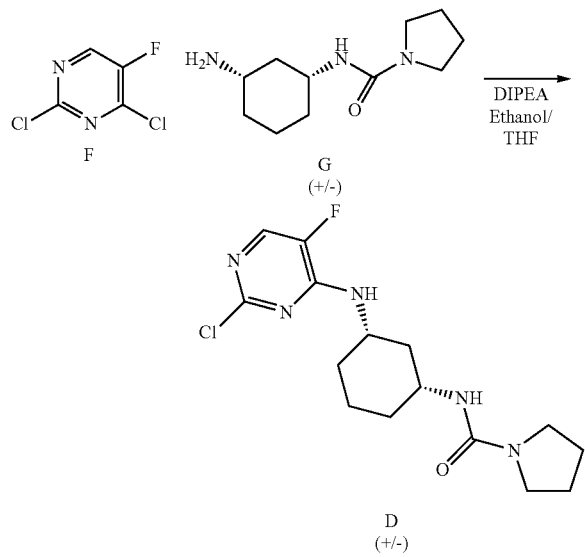

A solution of 2,4-dichloro-5-fluoro-pyrimidine (2.76 g, 16.55 mmol) was stirred at room temperature in ethanol (70 mL) and THF (70 mL). (+/−)-cis-N-(3-aminocyclohexyl)pyrrolidine-1-carboxamide (4.1 g, 16.548 mmol) and N,N-diisopropylethylamine (8.56 mL, 0.75 g/mL, 49.64 mmol) was added dropwise to the reaction mixture and stirred for one hour at 70° C. and then overnight at ambient temperature. The reaction mixture was evaporated, the residue was taken up in water, extracted twice with DCM. The combined organic layers were once washed with water, dried over MgSO$_4$, filtered and evaporated. The residue was purified by silica flash column chromatography (gradient:CH$_2$Cl$_2$ to CH$_2$Cl$_2$/methanol: 90/10). The desired fractions were pooled and evaporated to dryness to afford D as a white solid. LC-MS ES$^+$ m/z=342.3; Rt: 0.75 min, method A.

Preparation of 1

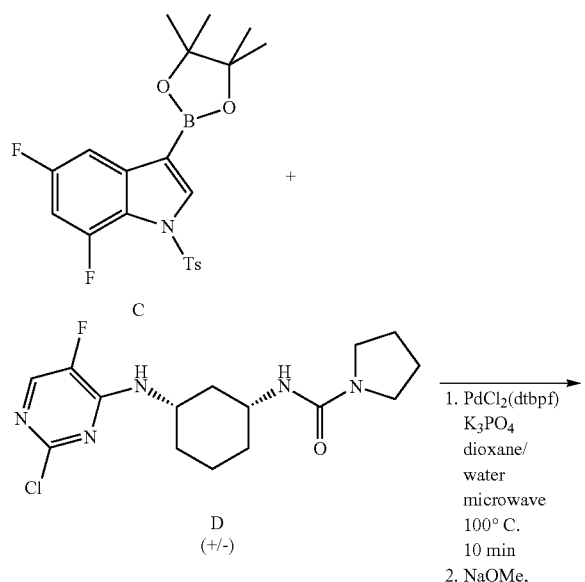

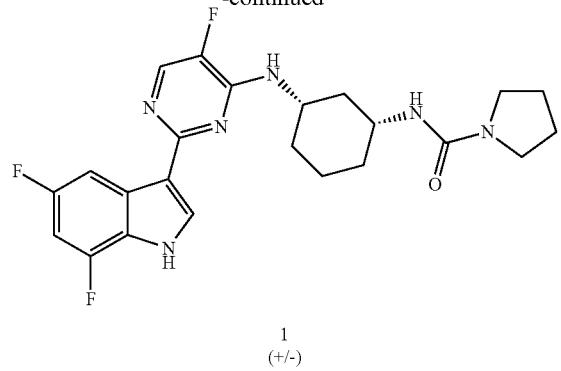

A mixture of C (100 mg, 0.23 mmol), (+/−)-N-((cis)-3-((2-chloro-5-fluoropyrimidin-4-yl)amino)cyclohexyl)pyrrolidine-1-carboxamide (79 mg, 0.23 mmol), [1,1'-bis(di-tert-butylphosphino)ferrocene]dichloropalladium [95408-45-0] (15 mg, 0.023 mmol) and K$_3$PO$_4$ (147 mg, 0.69 mmol) in 1,4-dioxane (3 mL) and water (0.6 mL) was heated 10 to 100° C. for 10 minutes in the microwave oven. The reaction mixture was filtered over packed celite and the filtrate was concentrated under reduced pressure. To the crude was added methanol (2 mL), and sodium methoxide (30% in methanol, 3 mL) at ambient temperature for 2 h. The reaction was complete and the mixture was neutralized with conc. HCl. The crude was purified via Prep HPLC (stationary phase: RP Uptisphere Prep C18 ODB-10 μm, 30×150 mm, mobile phase: 0.25% NH$_4$HCO$_3$ solution in water, methanol). The fractions were collected, and the solvents were removed under reduced pressure to afford 1.

Preparation of Intermediate G

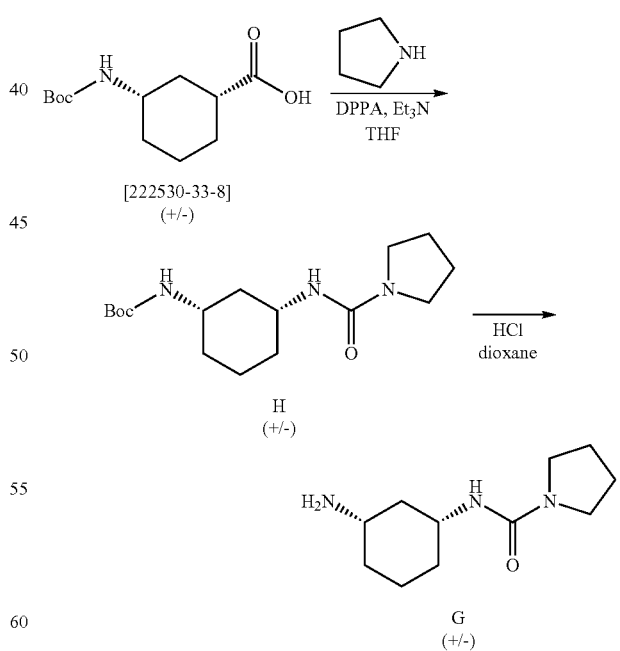

A mixture of (+/−)-cis-3-(boc-amino)cyclohexanecarboxylic acid [222530-33-8](9.51 g, 39.09 mmol), diphenyl phosphoryl azide (12.61 mL, 58.63 mmol) and Et$_3$N (7.61 mL, 54.72 mmol) in THF (250 mL) was refluxed for 2 hours. The solution was allowed to reach room temperature, then pyrrolidine (9.81 mL, 117.26 mmol) was added and the solution was refluxed for 1 hour. The mixture was cooled to 0° C., the precipitate was isolated by filtration and washed with THF, dried in vacuo to afford H, t-butyl (+/−)-(cis-3-(pyrrolidine-1-carboxamido)cyclohexyl)carbamate, as a white powder.

A solution of (+/−)-t-butyl (cis-3-(pyrrolidine-1-carboxamido)cyclohexyl)carbamate (23.77 g, 76.33 mmol) in HCl in 1,4-dioxane (4M, 344 mL) was stirred at room temperature for 4 hours. The solution was concentrated under reduced pressure and then dried in vacuo to afford G, (+/−)-N-((cis)-3-aminocyclohexyl)pyrrolidine-1-carboxamide as a white solid.

Preparation of 2

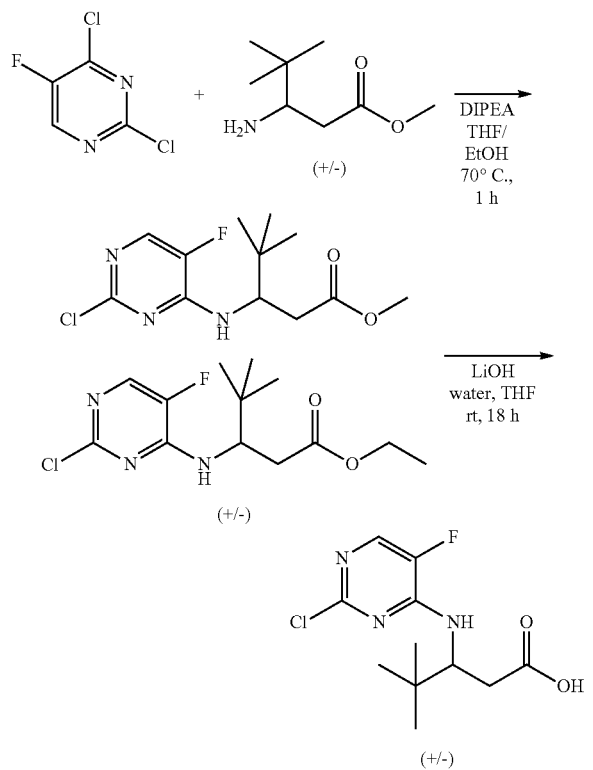

A solution of 2,4-dichloro-5-fluoro-pyrimidine (3 g, 17.97 mmol) was stirred at room temperature in ethanol (70 mL) and THF (70 mL). (+/−)-Methyl 3-amino-4,4-dimethylpentanoate [1273387-45-3] (3.62 g, 22.75 mmol) and N,N-diisopropylethylamine (9.3 mL, 53.90 mmol) were added dropwise and the reaction mixture stirred for one hour at 70° C. then 18 h at ambient temperature. The solvent was removed under reduced pressure; the residue was dissolved in water, and then partitioned with CH₂Cl₂. The combined organic layers were washed with water, dried over MgSO₄, the solids were removed by filtration, and the solvent of the filtrate was removed under reduced pressure. The crude was purified by flash column chromatography over silica chromatography (gradient:CH₂Cl₂ to CH₂Cl₂/methanol: 90/10). The desired fractions were collected and evaporated to dryness to afford a mixture of ethyl and methyl (+/−)-3-((2-chloro-5-fluoropyrimidin-4-yl)amino)-4,4-dimethylpentanoate. The mixture was used in the next step without further purification. LC-MS ES⁺ m/z=290.1; Rt: 1.00 min, m/z=304.1; Rt: 1.08 min; method A.

A mixture of ethyl and methyl (+/−)-3-((2-chloro-5-fluoropyrimidin-4-yl)amino)-4,4-dimethylpentanoate (1 g, 3.45 mmol) and LiOH (827 mg, 34.51 mmol) in THF (20 mL) and water (5 mL) was stirred at ambient temperature for 18 h. The reaction mixture was neutralized with HCl, and the solvents were reduced in volume under reduced pressure. The precipitate was isolated by filtration, washed with water and dried in vacuo at 50° C. to afford a white solid, (+/−)-3-((2-chloro-5-fluoropyrimidin-4-yl)amino)-4,4-dimethylpentanoic acid. LC-MS ES⁺ m/z=276.1; Rt: 0.57 min, method A.

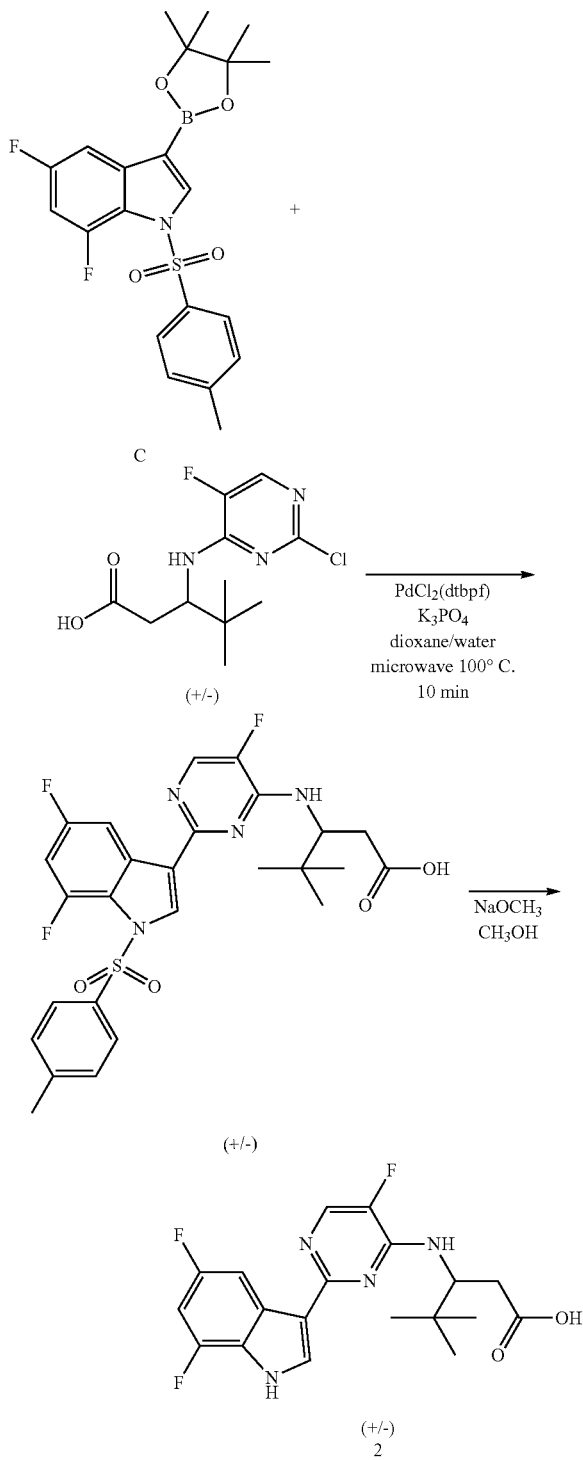

A mixture of C (1 g, 2.31 mmol), (+/−)-3-((2-chloro-5-fluoropyrimidin-4-yl)amino)-4,4-dimethylpentanoic acid (789 mg, 2.86 mmol), [1,1'-bis(di-tert-butylphosphino) ferrocene]dichloropalladium (150 mg, 0.23 mmol), K$_3$PO$_4$ (1470 mg, 6.92 mmol) and water (1.5 mL) in dioxane (15 mL) was heated to 100° C. in the microwave for 10 minutes. The solvent was removed under reduced pressure and the crude (+/−)-3-((2-(5,7-difluoro-1-tosyl-1H-indol-3-yl)-5-fluoropyrimidin-4-yl)amino)-4,4-dimethylpentanoic acid was used as such in the next step.

A mixture of (+/−)-3-((2-(5,7-difluoro-1-tosyl-1H-indol-3-yl)-5-fluoropyrimidin-4-yl)-amino)-4,4-dimethylpentanoic acid (2.5 g, 4.57 mmol) in methanol (30 mL) was treated with sodium methoxide (30% in methanol, 3 mL) at ambient temperature for 2 h. The reaction mixture was neutralized with conc. HCl. The crude was purified via prep. HPLC (stationary phase: RP Uptisphere Prep C18 ODB-10 μm, 30×150 mm, mobile phase: 0.25% NH$_4$HCO$_3$ solution in water, methanol). The best fractions were collected, pooled, and the solvents were removed under reduced pressure to afford 2.

Preparation of 3

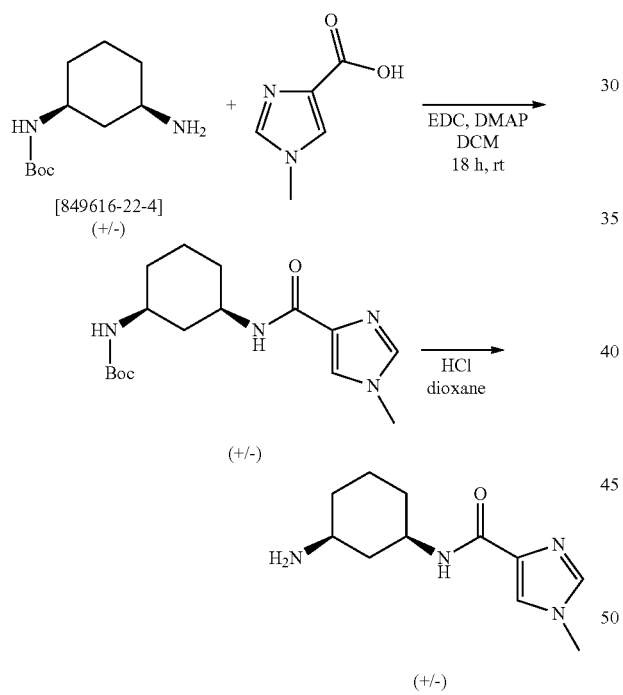

A mixture of (+/−)-tert-butyl ((cis)-3-aminocyclohexyl) carbamate (5 g, 23.3 mmol) and DMAP (7.1 g, 58.3 mmol) in CH$_2$Cl$_2$ (100 mL) was stirred at ambient temperature, then 1-methyl-1 h-imidazole-4-carboxylic acid (2.9 g, 23.3 mmol) was added. After stirring for 10 minutes at room temperature, EDC (6.7 g, 35 mmol) was added. The mixture stirred for 18 h at room temperature. The reaction mixture was washed with citric acid (5% aq.), the organic layer was removed, dried (MgSO$_4$), the solids removed by filtration, and the solvent of the filtrate removed under reduced pressure to give (+/−)-t-butyl ((cis)-3-(1-methyl-1H-imidazole-4-carboxamido)cyclohexyl)carbamate. LC-MS ES$^+$ m/z=323.5; Rt: 0.75 min, method A.

Removal of the boc group proceeded via HCl in dioxane, as in the method to prepare intermediate G, to afford (+/−)-N-((cis)-3-aminocyclohexyl)-1-methyl-1H-imidazole-4-carboxamide.

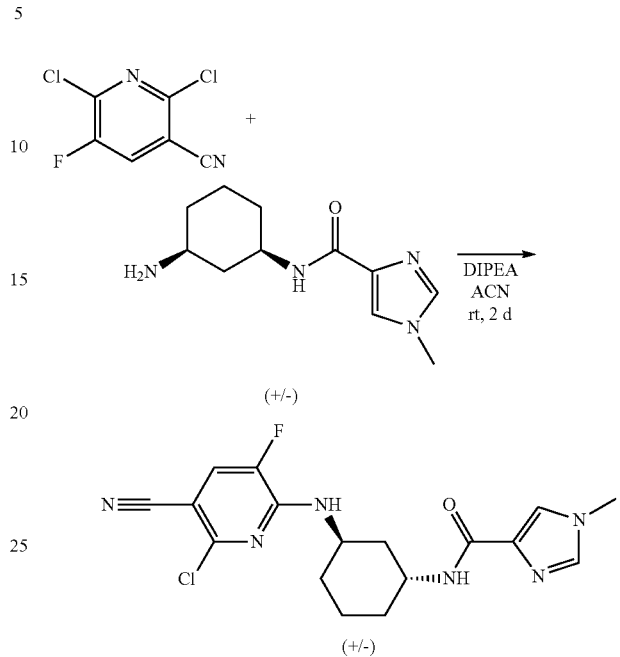

A solution of (+/−)-N-[(cis)-3-aminocyclohexyl]-1-methyl-imidazole-4-carboxamide (4.64 g, 15.7 mmol) and 2,6-dichloro-5-fluoro-3-pyridinecarbonitrile (3 g, 15.7 mmol) was stirred at room temperature in ACN (50 mL). N,N-diisopropylethylamine (10 mL, 54 mmol) was added and the reaction mixture stirred for 2 d at room temperature, then 50° C. for 24 h. The solvents were removed under reduced pressure. CH$_2$Cl$_2$ was added and a white precipitate was isolated via filtration, (+/−)-N-((cis)-3-((6-chloro-5-cyano-3-fluoropyridin-2-yl)amino)cyclohexyl)-1-methyl-1H-imidazole-4-carboxamide, was used in the next step without further purification. LC-MS ES$^+$ m/z=377.1; Rt: 1.58 min, method B.

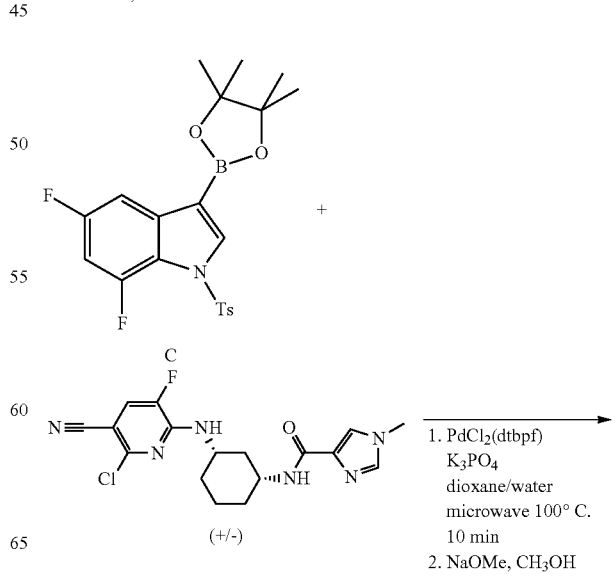

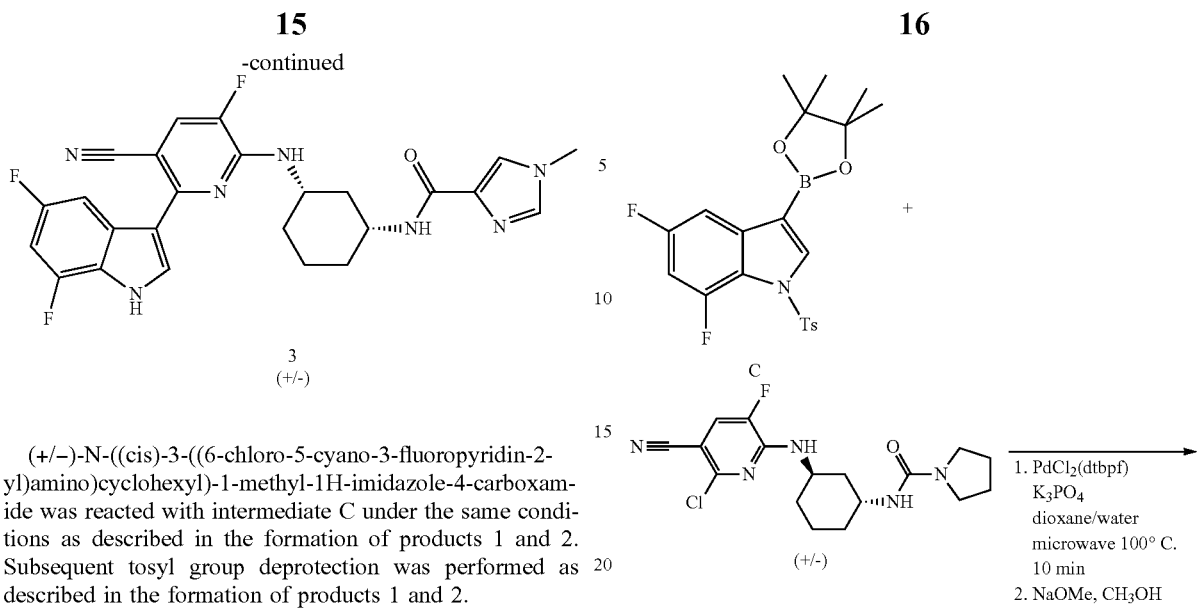

3
(+/−)

(+/−)-N-((cis)-3-((6-chloro-5-cyano-3-fluoropyridin-2-yl)amino)cyclohexyl)-1-methyl-1H-imidazole-4-carboxamide was reacted with intermediate C under the same conditions as described in the formation of products 1 and 2. Subsequent tosyl group deprotection was performed as described in the formation of products 1 and 2.

Preparation of 4

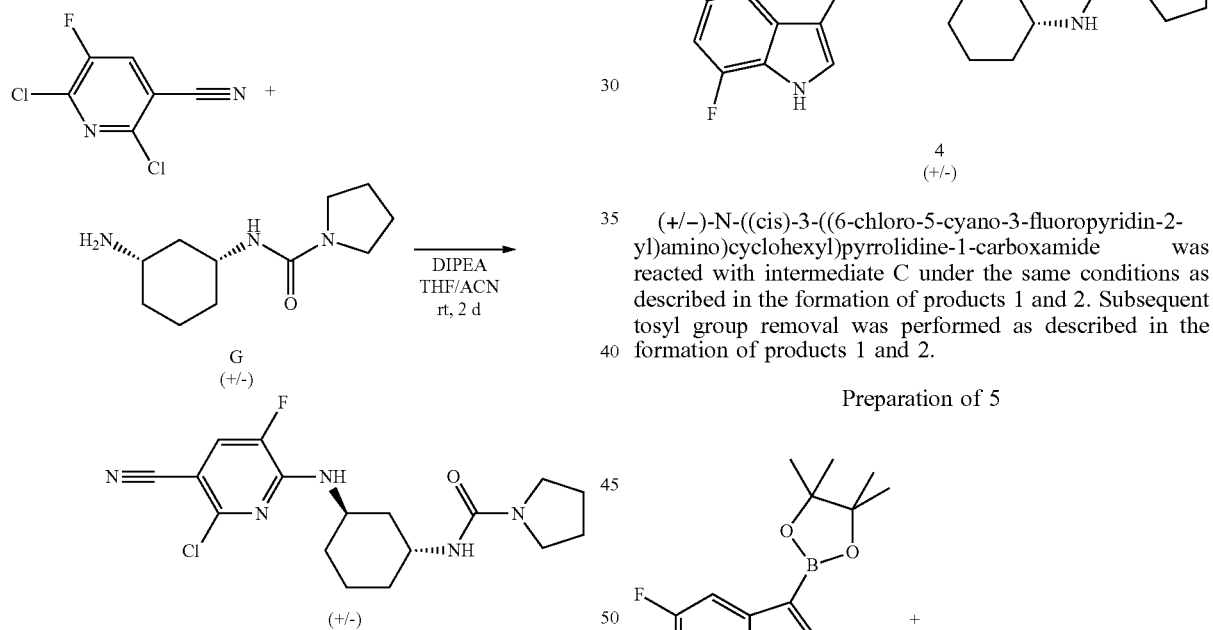

A solution of 2,6-dichloro-5-fluoro-3-pyridinecarbonitrile (4.77 g, 25 mmol) in THF (40 mL) was stirred at room temperature, while a mixture of G (6.19 g, 25 mmol) and N,N-diisopropylethylamine (8.62 mL, 50 mmol) in ACN (20 mL) was added dropwise. The reaction was allowed to stir 2 days at ambient temperature. The solvents were removed under reduced pressure. The crude was dissolved in diisopropylether/ethylacetate:1/1 and washed with water. The organic layer was dried (MgSO₄), the solids were removed by filtration and the solvent of the filtrate was removed under reduced pressure. The residue was triturated in diisopropylether to afford a white solid, (+/−)-N-((cis)-3-((6-chloro-5-cyano-3-fluoropyridin-2-yl)amino)cyclohexyl)pyrrolidine-1-carboxamide dried in vacuo. LCMS ES⁺ m/z=366.1; Rt: 0.88 min, method A.

(+/−)-N-((cis)-3-((6-chloro-5-cyano-3-fluoropyridin-2-yl)amino)cyclohexyl)pyrrolidine-1-carboxamide was reacted with intermediate C under the same conditions as described in the formation of products 1 and 2. Subsequent tosyl group removal was performed as described in the formation of products 1 and 2.

Preparation of 5

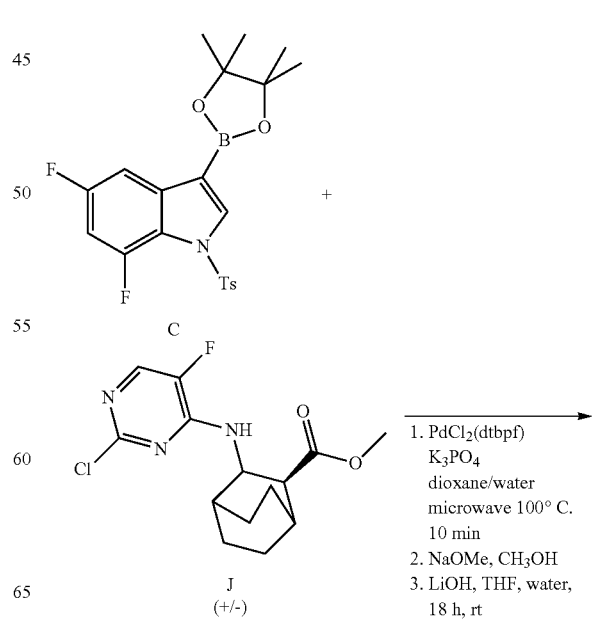

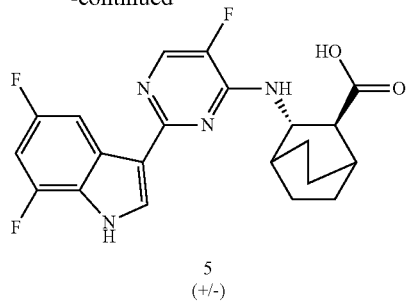

5
(+/-)

J (for preparation see J. Med. Chem. 2014, DOI: 10.1021/jm5007275) was reacted with intermediate C under the same conditions as described in the formation of products 1 and 2. Subsequent tosyl group deprotection was performed as described in the formation of products 1 and 2. A solution of (+/−)-(trans)-methyl 3-((2-(5,7-difluoro-1H-indol-3-yl)-5-fluoropyrimidin-4-yl)amino)bicyclo[2.2.2]octane-2-carboxylate (34 mg, 0.079 mmol) and LiOH (19 mg, 0.79 mmol) in THF (5 mL) and water (1 mL) was stirred at ambient temperature for 18 h. The reaction mixture was neutralized with conc. HCl. The solvent was removed under reduced pressure and the crude was purified via prep. HPLC (stationary phase: RP XBridge Prep C18 OBD-10 μm, 30×150 mm, mobile phase: 0.25% $NH_4HCO_3$ solution in water, $CH_3CN$). The collected fractions were pooled and the solvents were removed under reduced pressure to afford 5.

Preparation of 6

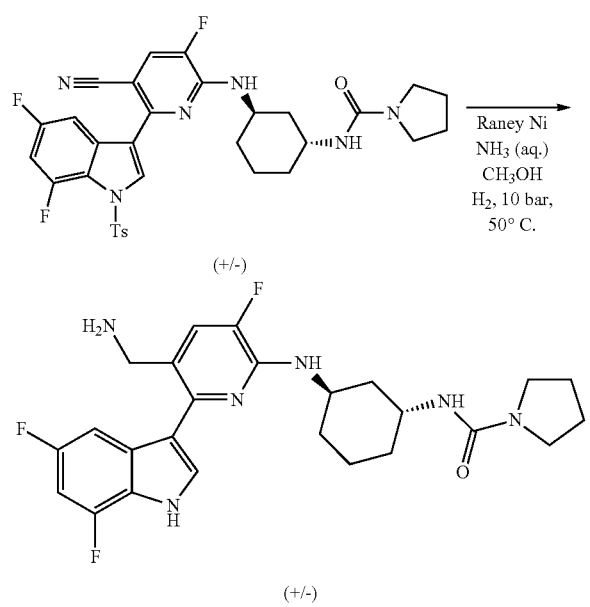

In a pressure reactor was placed (+/−)-N-((cis)-3-((5-cyano-6-(5,7-difluoro-1-tosyl-1H-indol-3-yl)-3-fluoropyridin-2-yl)amino)cyclohexyl)pyrrolidine-1-carboxamide (200 mg, 0.31 mmol), $NH_3$ (aq., 4 mL), methanol (12 mL), and Raney Ni (18 mg). The vessel was sealed, the atmosphere was removed and replaced with hydrogen gas at 5 bar for 20 minutes at ambient temperature, then increased to 10 bar for 9 h at 50° C. The reaction cooled to room temperature and the pressure was released. The reaction mixture was filtered over packed Celite, and the solvent of the filtrate was removed under reduced pressure, to afford (+/−)-N-((cis)-3-((5-(aminomethyl)-6-(5,7-difluoro-1H-indol-3-yl)-3-fluoropyridin-2-yl)amino)cyclohexyl)pyrrolidine-1-carboxamide that was used in the next step without further purification.

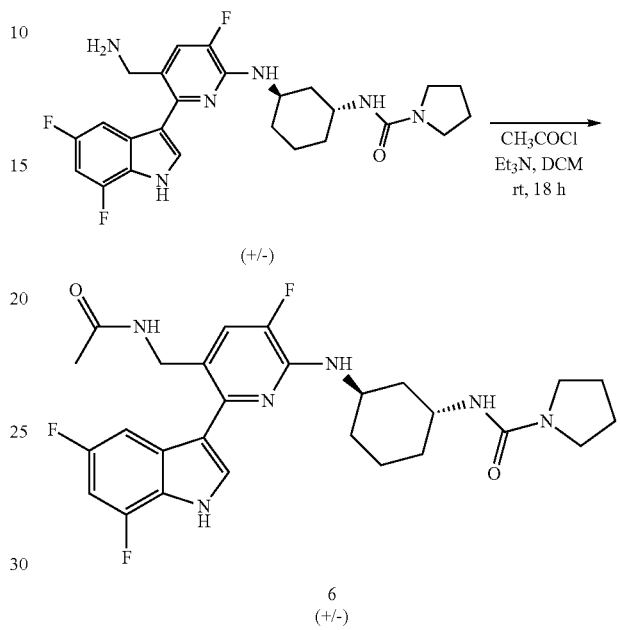

Into a glass tube was placed (+/−)-N-((cis)-3-((5-(aminomethyl)-6-(5,7-difluoro-1H-indol-3-yl)-3-fluoropyridin-2-yl)amino)cyclohexyl)pyrrolidine-1-carboxamide (100 mg, 0.14 mmol), $CH_2Cl_2$ (2 mL), $Et_3N$ (80 μL. 0.58 mmol) and acetyl chloride (31 μL. 0.43 mmol). The reaction mixture stirred at room temperature for 18 h. Water, brine and ethyl acetate were added to the reaction mixture. The aqueous layer was extracted with ethyl acetate. The combined organic layers were dried ($MgSO_4$), the solids were removed by filtration and the solvent of the filtrate was removed under reduced pressure. The crude mixture was purified by preparative LC (silica 15-40 μm, mobile phase gradient: from $CH_2Cl_2/CH_3OH$/aq. $NH_3$ 100/0/0 to 90/10/1). The best fractions were pooled, the solvents were removed under reduced pressure, and dried in vacuo (24 h at 50° C.) to afford 6 as a white solid.

TABLE A

Abbreviations and definitions

| Symbol or Abbreviation | Definition |
|---|---|
| * | Absolute configuration can be determined by appropriate techniques known to a skilled person |
| EtOAc | Ethyl acetate |
| rt | Room temperature |
| Rt | Retention time in minutes |
| OR | Optical Rotation |
| n.d. | Not done |
| SFC | Supercritical Fluid Chromatography |

Preparation of N-((1R*,3S*)-3-((2-(5,7-difluoro-1H-indol-3-yl)-5-fluoropyrimidin-4-yl)-amino)cyclohexyl)pyrrolidine-1-carboxamide (9)

Purification of N-((cis)-3-((2-(5,7-difluoro-1H-indol-3-yl)-5-fluoropyrimidin-4-yl)amino)cyclohexyl)pyrrolidine-1-carboxamide (1) was performed via preparatory SFC (stationary phase: Chiralpak Diacel AS 20×250 mm, mobile phase: CO₂, ethanol with 0.2% isopropylamine). The best fractions were collected and the solvent was removed under reduced pressure to afford the titled compound (9).

Preparation of (2S*,3S*)-3-((2-(5,7-difluoro-1H-indol-3-yl)-5-fluoropyrimidin-4-yl)-amino)bicyclo [2.2.2]octane-2-carboxylic Acid (10)

Purification of (+/−)-(trans)-3-((2-(5,7-difluoro-1H-indol-3-yl)-5-fluoropyrimidin-4-yl)-amino)bicyclo[2.2.2]octane-2-carboxylic acid(5) was performed via preparatory SFC (stationary phase: Chiralpak Diacel AS 20×250 mm, mobile phase: CO₂, 2-propanol with 0.2% isopropylamine). The best fractions were pooled, and the solvent was removed under reduced pressure. The crude salt was purified via preparatory HPLC (stationary phase: Uptisphere C18 ODB—10 μm, 200 g, 5 cm, mobile phase: 0.25% NH₄HCO₃ solution in water, CH₃CN). The best fractions were pooled, and the solvent was removed under reduced pressure to afford the titled compound (10) as a white solid.

Preparation of (+)-benzyl Tert-Butyl ((1R*,3S*)-cyclohexane-1,3-diyl)dicarbamate

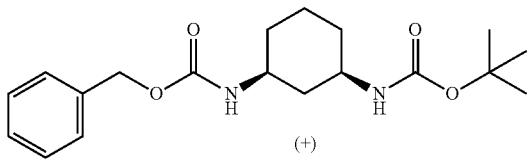 [SMILES: CC(C)(C)OC(=O)N[C@@H]1CCC[C@H](NC(=O)OCc2ccccc2)C1]

(+)

Triethylamine (35 mL, 251.6 mmol) and diphenylphosphoryl azide (39.056 mL, 181.086 mmol) were added to a stirred solution of cis-3-[(tert-butoxycarbonyl)-amino]cyclohexanecarboxylic acid (39 g, 160.25 mmol) in toluene (600 mL), and the resulting mixture was stirred at rt for 3 h. Benzyl alcohol (33.167 mL, 320.51 mmol) was added, and the mixture was heated to 100° C. After 12 h, the reaction mixture was cooled to rt, diluted with EtOAc, was washed with brine, dried (Na₂SO₄), the solids were removed by filtration and the filtrate concentrated in vacuo. A purification was performed via normal phase chiral separation (stationary phase: Daicel Chiralpak AD 2 kg, mobile phase: gradient from 80% heptane, 20% ethanol to 80% heptane, 20% ethanol) to afford (+)-benzyl tert-butyl ((1R*,3S*)-cyclohexane-1,3-diyl)dicarbamate, $[\alpha]_D^{20}$+10.9 (c 0.52, DMF) and (−)-benzyl tert-butyl ((1R*,3S*)-cyclohexane-1, 3-diyl)dicarbamate, $[\alpha]_D^{20}$−10.9 (c 0.47, DMF).

Synthesis of Tert-Butyl ((1R*,3S*)-3-aminocyclohexyl)carbamate

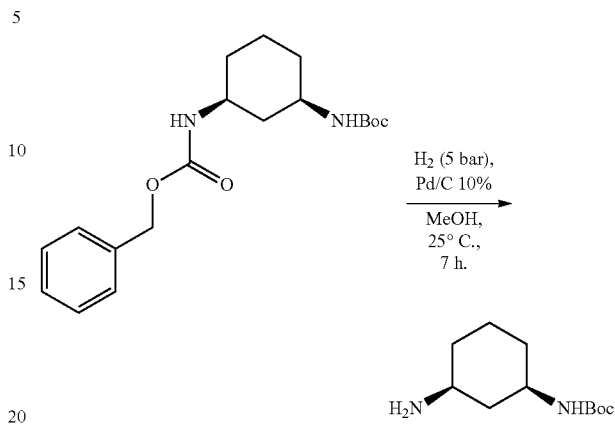

A mixture of benzyl tert-butyl ((1R*,3S*)-cyclohexane-1,3-diyl)dicarbamate (6.50 g, 18.65 mmol), Pd/C 10% (0.79 g) in methanol (55 mL) was stirred under hydrogen atmosphere (5 bar) at 25° C. for 7 h. The mixture was filtered through a pad of Celite and the solvent was removed under reduced pressure to yield tert-butyl ((1R*,3S*)-3-aminocyclohexyl)carbamate (3.88 g, 18.09 mmol) that was used without further purification. LC-MS ES⁺ m/z=215.1; Rt: 0.40 min, method E.

Synthesis of Tert-Butyl ((1R*,3S*)-3-((2-chloro-5-fluoropyrimidin-4-yl)amino)cyclohexyl)carbamate

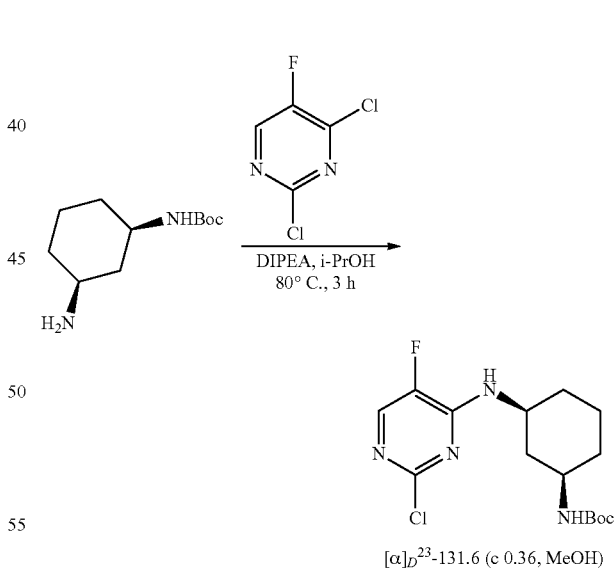

$[\alpha]_D^{23}$-131.6 (c 0.36, MeOH)

To a solution of tert-butyl ((1R*3S*)-3-aminocyclohexyl) carbamate (2.75 g, 12.83 mmol) in isopropyl alcohol (20 mL) was added N,N-diisopropylethylamine (2.68 mL, 15.39 mmol) and 2,4-dichloro-5-fluoropyrimidine (2.25 g, 13.47 mmol). The mixture was heated at 80° C. for 3 hours. The reaction mixture was evaporated to dryness and the crude was dissolved in CH₂Cl₂. The organic solution was washed with water and dried over MgSO₄. The organic layer was removed under reduced pressure to give a crude that was purified by flash chromatography on silica gel to yield tert-butyl ((1R*,3S*)-3-((2-chloro-5-fluoropyrimidin-4-yl)amino)cyclohexyl)-carbamate (2.70 g, 7.83 mmol).

LC-MS ES+ m/z=345.0; Rt: 1.42 min, method G. $[\alpha]_D^{23}$ −131.6 (c 0.36, MeOH).

$^1$H NMR (300 MHz, CDCl$_3$) δ ppm 0.97-1.26 (m, 3H), 1.44 (s, 9H), 1.50 (m, 1H), 1.84 (m, 1H), 1.96-2.14 (m, 2H), 2.39 (d, J=11.6 Hz, 1H), 3.55 (m, 1H), 4.07 (m, 1H), 4.40 (m, 1H), 5.04 (d, J=7.4 Hz, 1H), 7.86 (d, J=2.25 Hz, 1H).

Synthesis of N-((1R*,3S*)-3-((2-(5-chloro-7-fluoro-1H-indol-3-yl)-5-fluoropyrimidin-4-yl)amino)cyclohexyl)-5-methylpyrazine-2-carboxamide (11)

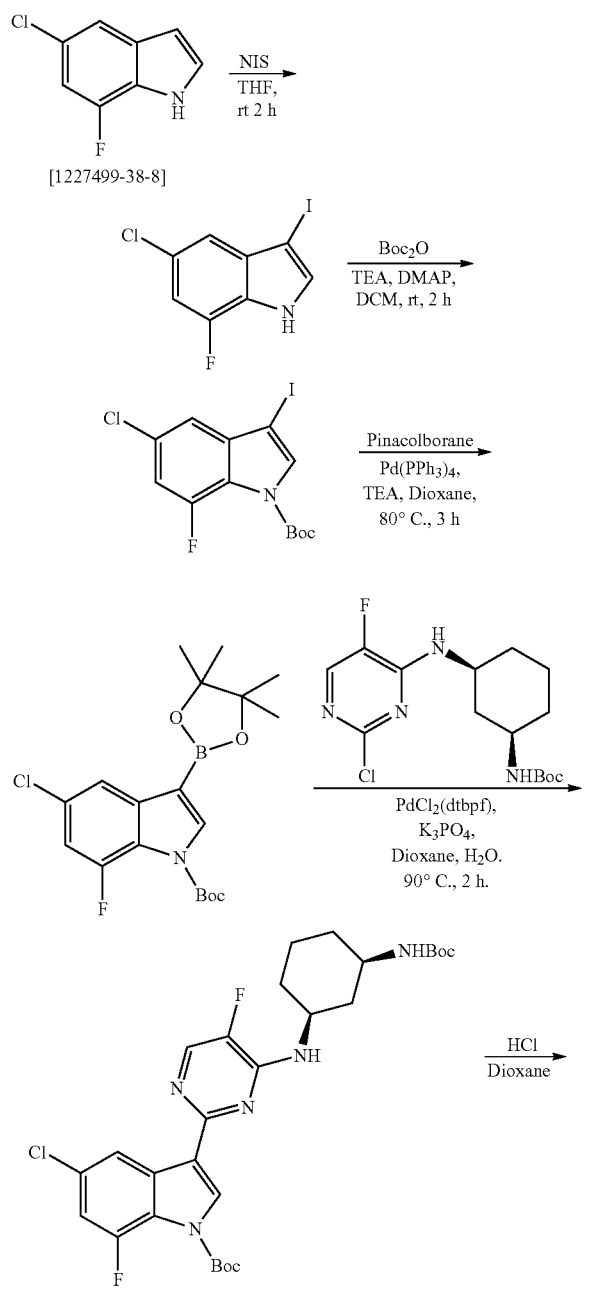

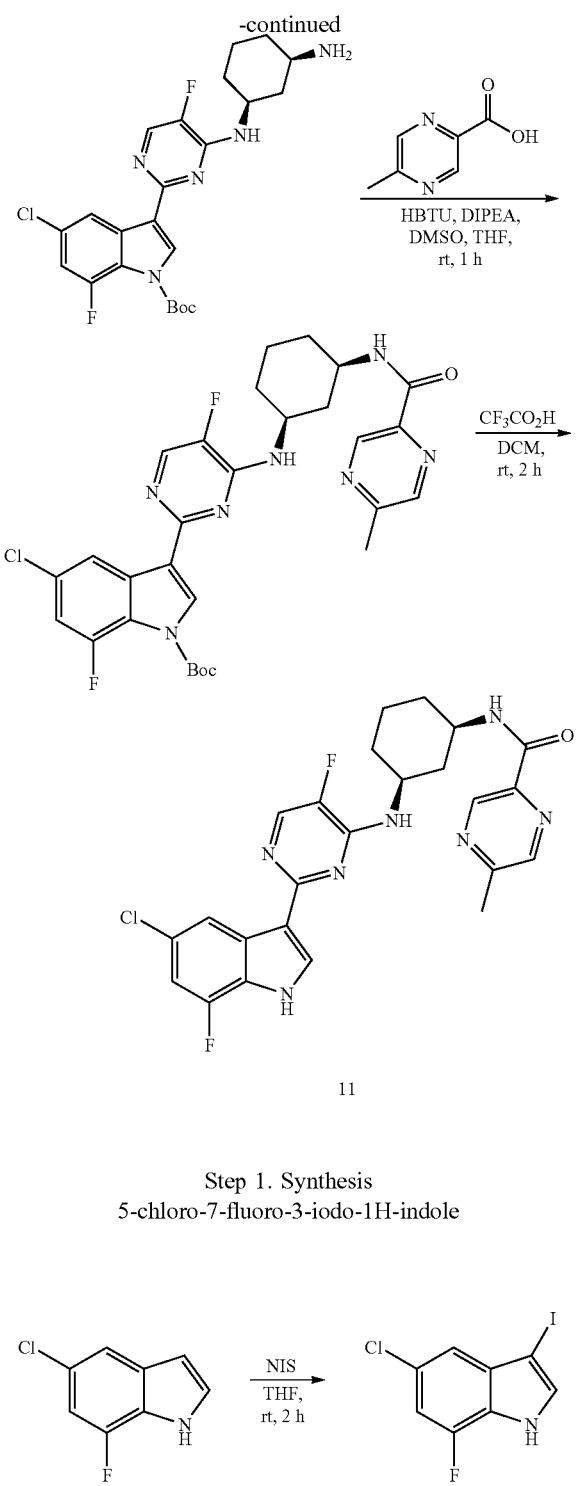

Step 1. Synthesis 5-chloro-7-fluoro-3-iodo-1H-indole

To a solution of 5-chloro-7-fluoro-1H-indole (500 mg, 2.94 mmol) in THF (15 mL) was added drop wise a solution of N-iodosuccinimide (729 mg, 3.24 mmol) in THF (15 mL) and the resulting suspension was stirred at room temperature for 2 hours. The reaction mixture was evaporated to dryness and dissolved in CH$_2$Cl$_2$. The organic solution was washed with saturated Na$_2$S$_2$O$_5$ solution. The organic layer was dried over MgSO$_4$ and evaporated to dryness to give a crude that was purified by column chromatography on silica gel to yield 5-chloro-7-fluoro-3-iodo-1H-indole (580 mg, 1.96 mmol). $^1$H NMR (300 MHz, CD$_3$OD) δ ppm 6.98 (dd, J=10.7, 1.4 Hz, 1H), 7.13 (d, J=1.4 Hz, 1H), 7.43 (s, 1H).

Step 2. Synthesis of Tert-Butyl 5-chloro-7-fluoro-3-iodo-1H-indole-1-carboxylate

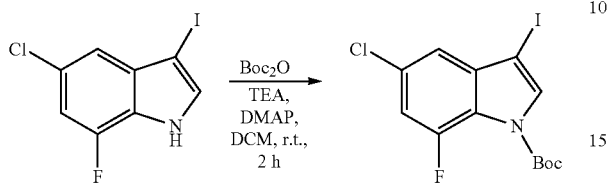

Di-tert-butyl dicarbonate (0.54 mL, 2.35 mmol) in CH$_2$Cl$_2$ (10 mL) was added to a stirred solution of 5-chloro-7-fluoro-3-iodo-1H-indole (580 mg, 1.96 mmol), triethylamine (0.41 mL, 2.94 mmol) and DMAP (2.32 mg, 0.02 mmol) in DCM (10 mL) at room temperature. After stirring for 2 hours the reaction mixture was washed with a saturated NaHCO$_3$ solution and water. The organic layer was evaporated to dryness and the crude was purified by column chromatography on silica gel eluting with heptane-EtOAc to yield tert-butyl 5-chloro-7-fluoro-3-iodo-1H-indole-1-carboxylate (700 mg, 1.77 mmol). $^1$H NMR (300 MHz, CDCl$_3$) δ ppm 1.64 (s, 9H), 7.12 (dd, J=11.8, 1.6 Hz, 1H), 7.21 (d, J=1.6 Hz, 1H), 7.77 (s, 1H).

Step 3. Synthesis of Tert-Butyl 5-chloro-7-fluoro-3-(4,4,5,5-tetramethyl-1,3,2-dioxaborolan-2-yl)-1H-indole-1-carboxylate

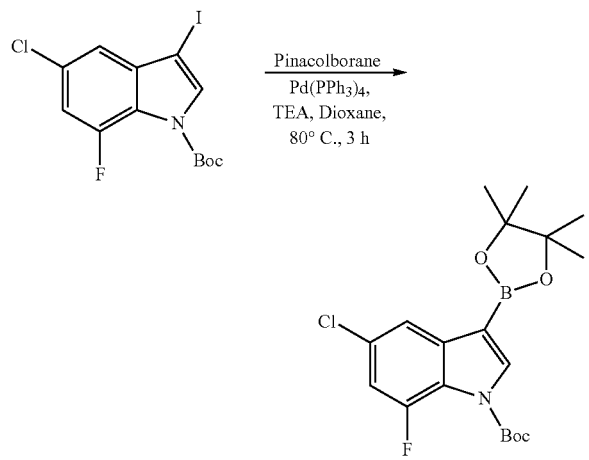

4,4,5,5-Tetramethyl-1,3,2-dioxaborolane (19.96 mL, 126.39 mmol) and triethylamine (10.19 mL, 75.83 mmol) were added to a degassed solution of tert-butyl 5-chloro-7-fluoro-3-iodo-1H-indole-1-carboxylate (10.0 g, 25.27 mmol) in dioxane (250 mL). Then, tetrakis(triphenylphosphine)palladium(0) (2.92 g, 2.52 mmol) was added and the mixture was degassed for 5 minutes and stirred at 80° C. for 3 hours. The reaction mixture was filtered through a pad of Celite and the solvent was evaporated to dryness. The crude was purified by column chromatography on silica gel eluting with heptane-EtOAc to yield tert-butyl 5-chloro-7-fluoro-3-(4,4,5,5-tetramethyl-1,3,2-dioxaborolan-2-yl)-1H-indole-1-carboxylate (5.7 g, 14.4 mmol). $^1$H NMR (300 MHz, CDCl$_3$) δ ppm 1.36 (s, 12H), 1.63 (s, 9H), 7.03 (dd, J=11.9, 1.7 Hz, 1H), 7.76 (d, J=1.7 Hz, 1H), 8.02 (s, 1H).

Step 4. Synthesis of Tert-Butyl 3-(4-(((1S*,3R*)-3-((tert-butoxycarbonyl)amino)cyclo-hexyl)amino)-5-fluoropyrimidin-2-yl)-5-chloro-7-fluoro-1H-indole-1-carboxylate

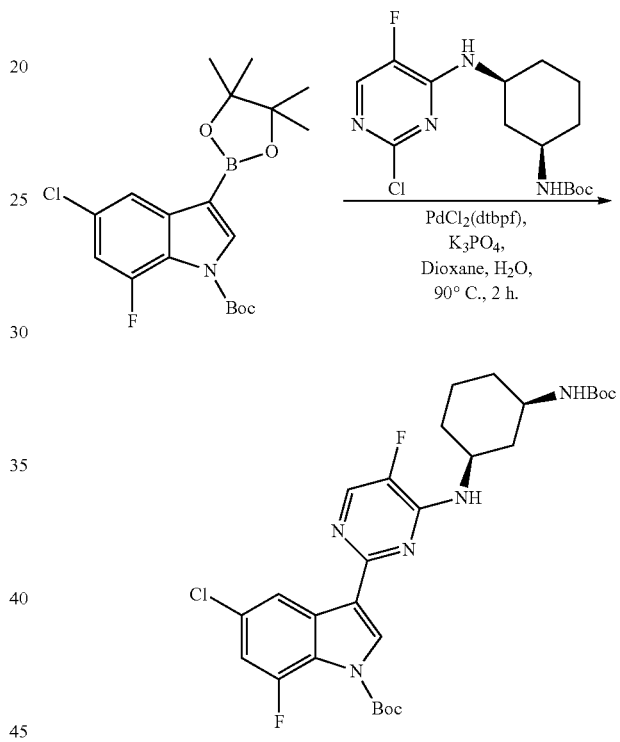

A mixture of tert-butyl 5-chloro-7-fluoro-3-(4,4,5,5-tetramethyl-1,3,2-dioxaborolan-2-yl)-1H-indole-1-carboxylate (1.5 g, 3.79 mmol), tert-butyl ((1R*,3S*)-3-((2-chloro-5-fluoropyrimidin-4-yl)amino)cyclohexyl)carbamate (1.30 g, 3.79 mmol), [1,1'-bis(di-tert-butylphosphino)ferrocene] dichloropalladium(II) (247 mg, 0.38 mmol) and tripotassium phosphate (2.41 g, 11.37 mmol) in dioxane (30 mL) and water (3 mL) was purged with nitrogen and stirred at 90° C. for 2 hours. The reaction mixture was filtered through a pad of Celite and the solvent was evaporated to dryness, diluted in CH$_2$Cl$_2$ and washed with water. The organic layer was removed under reduced pressure to give a crude that was purified by column chromatography on silica gel to yield tert-butyl 3-(4-(((1S*,3*R*)-3-((tert-butoxycarbonyl)amino)cyclohexyl)-amino)-5-fluoropyrimidin-2-yl)-5-chloro-7-fluoro-1H-indole-1-carboxylate (1.30 g, 2.25 mmol). LC-MS ES$^+$ m/z=578.3; Rt: 1.64 min, method E. $[α]_D^{23}$ −75.1 (c 0.26, MeOH).

Step 5. Synthesis of Tert-Butyl 3-(4-(((1S*,3R*)-3-aminocyclohexyl)amino)-5-fluoropyrimidin-2-yl)-5-chloro-7-fluoro-1H-indole-1-carboxylate

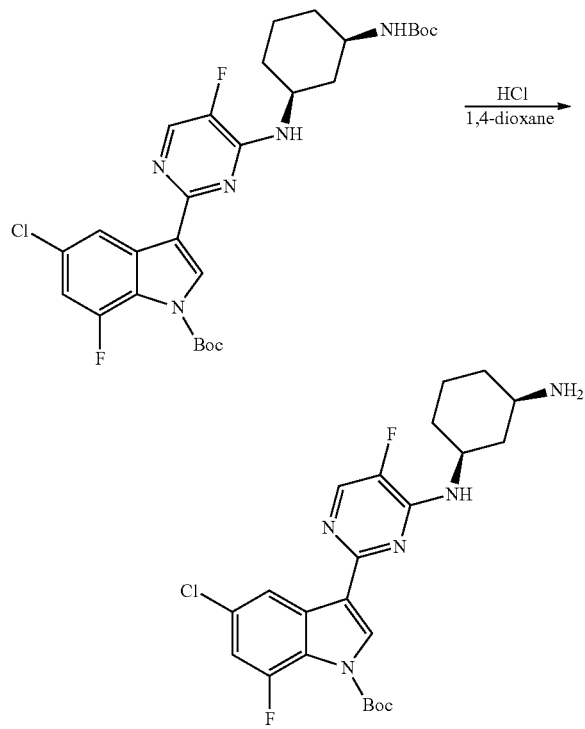

HCl (4.0 M in dioxane, 0.75 mL, 3.01 mmol) was added slowly to a solution of (tert-butyl 3-(4-(((1 S, 3R*)-3-((tert-butoxycarbonyl)amino)cyclohexyl)amino)-5-fluoropyrimidin-2-yl)-5-chloro-7-fluoro-1H-indole-1-carboxylate (290 mg, 0.50 mmol) in 1,4-dioxane (2 mL) and then concentrated HCl (0.1 mL, 0.19 mmol) was added. The resulting solution was stirred at room temperature for 2 hours. The reaction mixture was quenched with a saturated NaHCO$_3$ solution and extracted with CH$_2$Cl$_2$. The organic layer was dried over MgSO$_4$ and evaporated to dryness and the crude was purified by column chromatography on silica gel eluting with DCM-MeOH (92:8) to yield tert-butyl 3-(4-(((1S*,3R*)-3-aminocyclohexyl)amino)-5-fluoropyrimidin-2-yl)-5-chloro-7-fluoro-1H-indole-1-carboxylate (120 mg, 0.25 mmol). LC-MS ES$^+$ m/z=478.1; Rt: 1.27 min, method E. [α]$_D^{23}$ −54.9 (c 0.26, MeOH).

Step 6. Synthesis of Tert-Butyl 5-chloro-7-fluoro-3-(5-fluoro-4-(((1S*,3R*)-3-(5-methylpyrazine-2-carboxamido)cyclohexyl)amino)pyrimidin-2-yl)-1H-indole-1-carboxylate

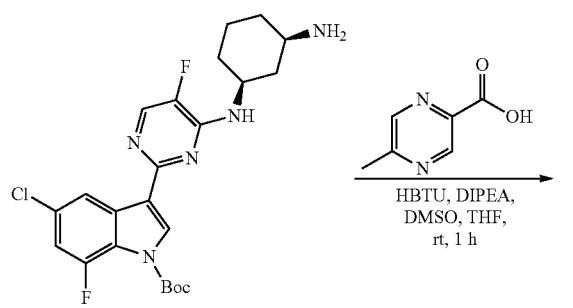

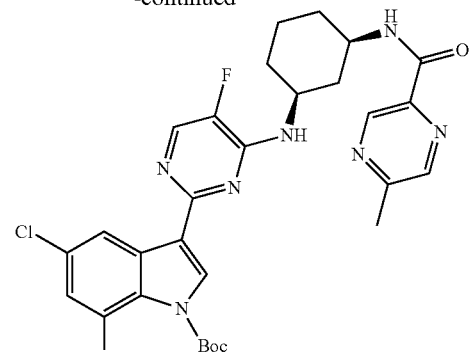

HBTU (396 mg, 1.04 mmol) was added to a solution of 5-methylpyrazine-2-carboxylic acid (75.8 mg, 0.54 mmol) in THF (2 mL) at room temperature for 5 minutes under inert atmosphere. Then, a solution of tert-butyl 3-(4-(((1S*,3R*)-3-aminocyclohexyl)amino)-5-fluoropyrimidin-2-yl)-5-chloro-7-fluoro-1H-indole-1-carboxylate (250 mg, 0.52 mmol) and N,N-diisopropylethylamine (0.22 mL, 1.30 mmol) in DMSO (0.25 mL) was added and the stirring continued at room temperature for 1 hour. The reaction mixture was diluted with water and extracted with DCM. The organic layers were concentrated under reduced pressure and the crude was purified by column chromatography on silica gel eluting with heptane-EtOAc to yield of tert-butyl 5-chloro-7-fluoro-3-(5-fluoro-4-(((1S*,3R*)-3-(5-methylpyrazine-2-carboxamido)cyclohexyl)amino)pyrimidin-2-yl)-1H-indole-1-carboxylate (160 mg, 0.26 mmol). LC-MS ES$^+$ m/z=598.2; Rt: 1.43 min, method E.

Step 7. Synthesis of N-((1R*,3S*)-3-((2-(5-chloro-7-fluoro-1H-indol-3-yl)-5-fluoropyrimidin-4-yl)amino)cyclohexyl)-5-methylpyrazine-2-carboxamide (11)

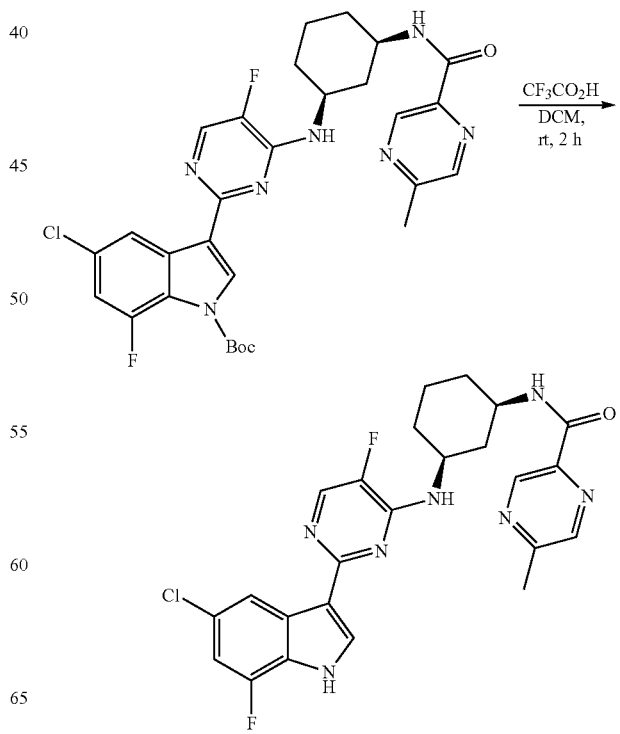

Trifluoroacetic acid (2 mL) was added to a solution of tert-butyl 5-chloro-7-fluoro-3-(5-fluoro-4-(((1S*,3R*)-3-(5-methylpyrazine-2-carboxamido)cyclohexyl)amino)-pyrimidin-2-yl)-1H-indole-1-carboxylate (150 mg, 0.25 mmol) in DCM (2 mL) and the resulting mixture was stirred at room temperature for 2 hours. The reaction mixture was basified with a 5% aq. NaOH solution and the precipitate was filtered and washed with CH$_2$Cl$_2$ to yield N-((1R*,3S*)-3-((2-(5-chloro-7-fluoro-1H-indol-3-yl)-5-fluoropyrimidin-4-yl)amino)cyclohexyl)-5-methylpyrazine-2-carboxamide (11) (45 mg, 0.09 mmol). LC-MS ES$^+$ m/z=498.1; Rt 2.86 min, method D. [α]$_D^{23}$ −159.3 (c 0.22, MeOH). mp 251.5° C. $^1$H NMR (300 MHz, DMSO-d$_6$) δ ppm 1.28-1.78 (m, 4H), 1.89 (m, 2H), 2.04 (m, 1H), 2.17 (m, 1H), 2.58 (s, 3H), 4.05 (m, 1H), 4.26 (m, 1H), 7.24 (d, J=5.4 Hz, 1H), 8.30 (m, 4H), 8.60 (s, 1H), 8.76 (d, J=8.2 Hz, 1H), 9.02 (s, 1H), 12.58 (br s, 1H).

Synthesis of N-((1R*,3S*)-3-((2-(5,7-difluoro-1H-indol-3-yl)-5-fluoropyrimidin-4-yl)-amino)cyclohexyl)-1-methyl-1H-imidazole-5-carboxamide

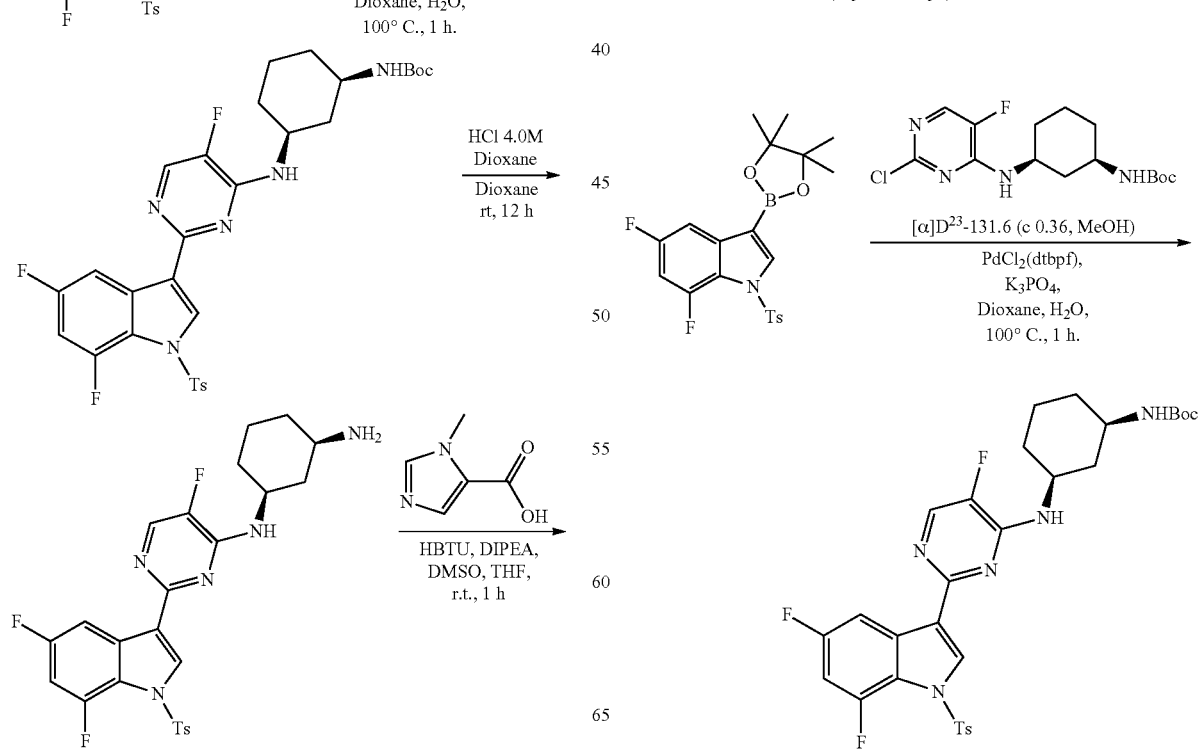

-continued

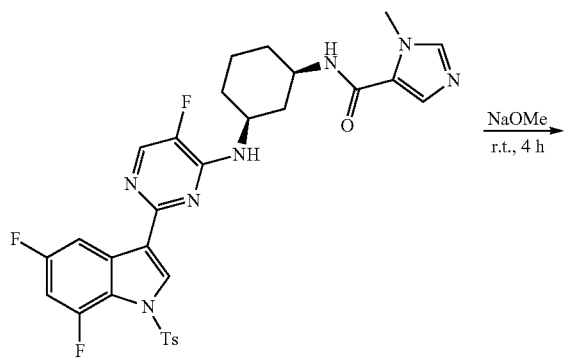

Synthesis of Tert-Butyl ((1R*,3S*)-3-((2-(5,7-difluoro-1-tosyl-1H-indol-3-yl)-5-fluoropyrimidin-4-yl)amino)cyclohexyl)carbamate

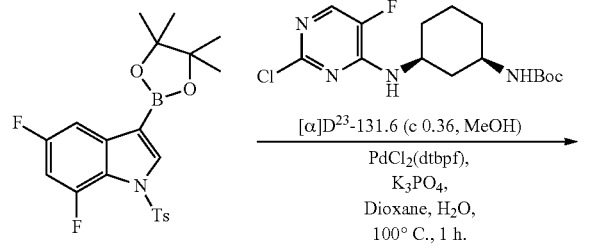

Step 1. 5,7-difluoro-3-(4,4,5,5-tetramethyl-1,3,2-dioxaborolan-2-yl)-1-tosyl-1H-indole (3.0 g, 6.92 mmol), tert-butyl ((1R*3S*)-3-((2-chloro-5-fluoropyrimidin-4-yl)amino)cyclohexyl)carbamate (2.86 g, 8.30 mmol, $[\alpha]_D^{23}$ −131.6 (c 0.36, MeOH)), tripotassium phosphate (4.41 g, 20.77 mmol) and [1,1'-bis(di-tert-butylphosphino)ferrocene]dichloropalladium(II) (0.45 g, 0.69 mmol) were added to a degassed mixture of dioxane (90 mL) and water (9 mL) under inert atmosphere. The mixture was stirred at 100° C. for 1 h. The reaction mixture was filtered through a pad of Celite and the solvent was evaporated to dryness to give a crude that was purified by column chromatography on silica gel to yield tert-butyl ((1R*,3S*)-3-((2-(5,7-difluoro-1-tosyl-1H-indol-3-yl)-5-fluoropyrimidin-4-yl)amino)cyclohexyl)carbamate (3.0 g, 4.87 mmol). LC-MS ES+ m/z=616.2; Rt: 1.38 min, method E.

Step 2. Synthesis of (1S*,3R*)—N-(2-(5,7-difluoro-1-tosyl-1H-indol-3-yl)-5-fluoropyrimidin-4-yl)cyclohexane-1,3-diamine

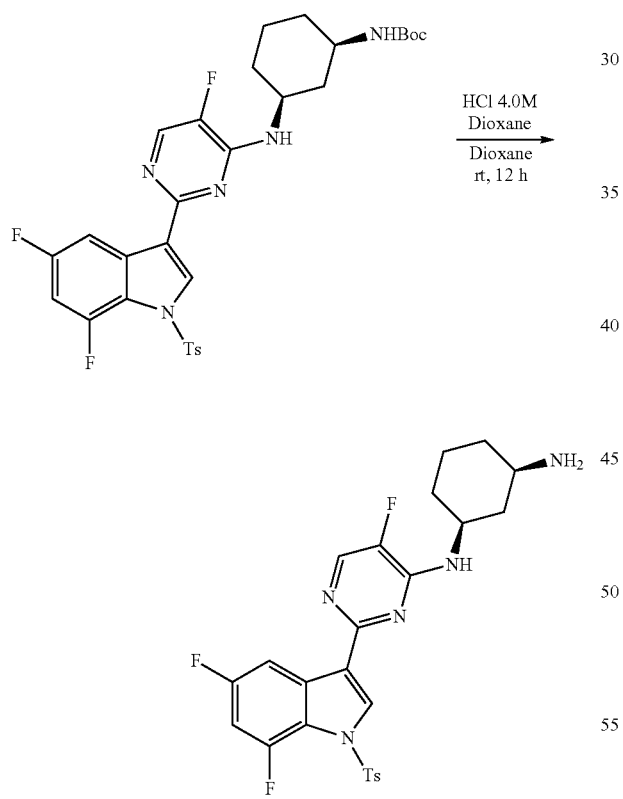

HCl 4.0 M in dioxane (34.1 mL, 136.43 mmol) was added slowly to a solution of tert-butyl ((1R*3S*)-3-((2-(5,7-difluoro-1-tosyl-1H-indol-3-yl)-5-fluoropyrimidin-4-yl)amino)cyclohexyl)carbamate (7.0 g, 11.37 mmol) in dioxane (20 mL) and stirred at room temperature for 12 hours. The reaction mixture was quenched with a saturated NaHCO₃ solution and extracted with CH₂Cl₂. The organic layer was dried over MgSO₄ and evaporated to yield (1S*3R*)—N-(2-(5,7-difluoro-1-tosyl-1H-indol-3-yl)-5-fluoropyrimidin-4-yl)cyclohexane-1,3-diamine (3.63 g, 7.05 mmol). LC-MS ES+ m/z=516.2; Rt: 0.90 min, method E. $[\alpha]_D^{23}$ −80.9 (c 0.23, MeOH).

Step 3. Synthesis of N-((1R*,3S*)-3-((2-(5,7-difluoro-1-tosyl-1H-indol-3-yl)-5-fluoropyrimidin-4-yl)amino)cyclohexyl)-1-methyl-1H-imidazole-5-carboxamide

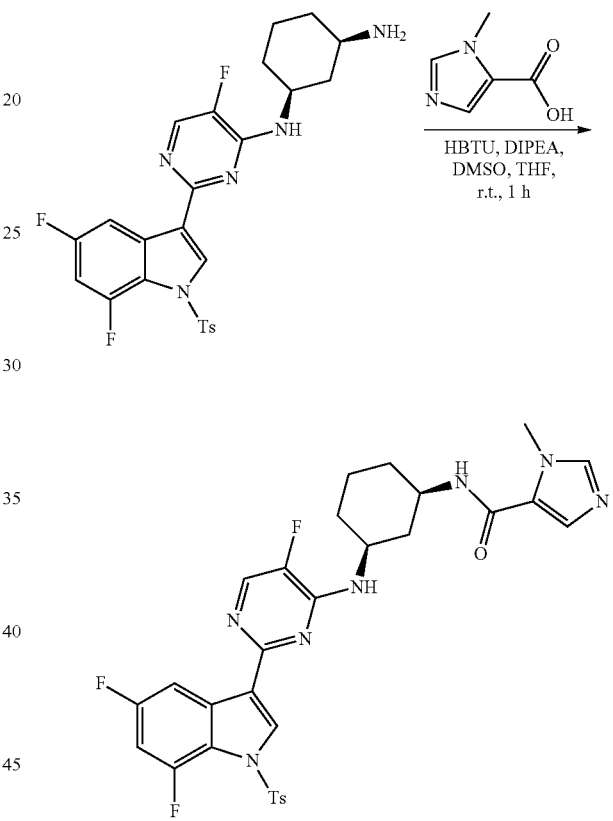

1-Methyl-1H-imidazole-5-carboxylic acid (55 mg, 0.43 mmol) was added to a mixture of HBTU (331 mg, 0.87 mmol) in THF (2 mL) and stirred at room temperature for 5 min. Then, a solution of (1S*3R*)—N-(2-(5,7-difluoro-1-tosyl-1H-indol-3-yl)-5-fluoropyrimidin-4-yl)cyclohexane-1,3-diamine (150 mg, 0.29 mmol) and N,N-diisopropylethylamine (0.15 mL, 0.87 mmol) in DMSO (2 mL) was added and the stirring continued at room temperature for 1 hour. The reaction mixture was diluted with water and extracted with CH₂Cl₂. The organic layer was concentrated under reduced pressure to yield N-((1R*,3S*)-3-((2-(5,7-difluoro-1-tosyl-1H-indol-3-yl)-5-fluoropyrimidin-4-yl)amino)cyclohexyl)-1-methyl-1H-imidazole-5-carboxamide (142 mg, 0.23 mmol). LC-MS ES+ m/z=624.2; Rt: 0.99 min, method E.

Step 4. Synthesis of N—((R*,3S*)-3-((2-(5,7-difluoro-1H-indol-3-yl)-5-fluoropyrimidin-4-yl)amino)cyclohexyl)-1-methyl-1H-imidazole-5-carboxamide

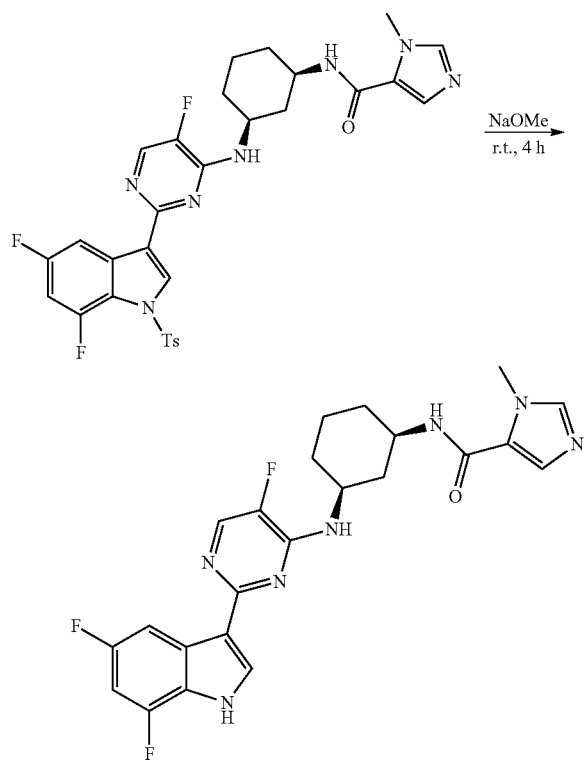

Sodium methoxide (0.62 mL of 25% w/v solution, 2.71 mmol) was added to a suspension of N-((1R*3S*)-3-((2-(5,7-difluoro-1-tosyl-1H-indol-3-yl)-5-fluoropyrimidin-4-yl)amino)cyclohexyl)-1-methyl-1H-imidazole-5-carboxamide (141 mg, 0.23 mmol) in CH₃OH (1 mL) and the mixture was stirred at room temperature for 4 hours. The solvent was removed under reduced pressure to give a crude that was purified by reverse phase chromatography to yield N-((1R*3S*)-3-((2-(5,7-difluoro-1H-indol-3-yl)-5-fluoropyrimidin-4-yl)amino)cyclohexyl)-1-methyl-1H-imidazole-5-carboxamide (12) (41 mg, 0.09 mmol).

Preparation of N-((1R*,3S*)-3-((2-(5,7-difluoro-1H-indol-3-yl)-5-fluoropyrimidin-4-yl)-amino)cyclohexyl)-cis-2,5-dimethylpyrrolidine-1-carboxamide (13) and N—((R*,3S*)-3-((2-(5,7-difluoro-1H-indol-3-yl)-5-fluoropyrimidin-4-yl)amino)cyclohexyl)-trans-2,5-dimethylpyrrolidine-1-carboxamide (14)

-continued

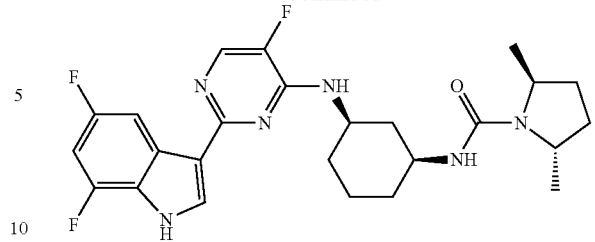

Step 1. A solution of (1S*3R*)—N¹-(2-(5,7-difluoro-1-tosyl-1H-indol-3-yl)-5-fluoropyrimidin-4-yl)cyclohexane-1,3-diamine (160 mg, 0.31 mmol) and Et₃N (0.086 mL, 0.728 g/mL, 0.621 mmol) in 1,4-dioxane (8 mL) was stirred at ambient temperature. A mixture of phenyl chloroformate (39 μL. 0.31 mmol) in 1,4-dioxane (2 mL) was added drop wise at rt. The reaction mixture was stirred for 16 h at ambient temperature. The reaction was complete and the solvent was removed under reduced pressure. The residual fraction was solved in CH₂Cl₂ and washed with brine. The organic layer was dried (MgSO₄), and concentrated under reduced pressure. The resulting product was used as such in the next step.

Step 2. In a 50 mL round bottom flask a mixture of phenyl ((1R*,3S*)-3-((2-(5,7-difluoro-1-tosyl-1H-indol-3-yl)-5-fluoropyrimidin-4-yl)amino)cyclohexyl)carbamate (150 mg, 0.236 mmol), 2,5-dimethylpyrrolidine (33 μL. 0.271 mmol), Et₃N (37.72 μL. 0.271 mmol) and DMAP (9 mg, 0.07 mmol) in 1,4-dioxane (15 mL) was heated to reflux and stirred for 16 h. The solvent was removed under reduced pressure. The crude was used without purification in the next step.

Step 3. In a 100 mL flask N-((1R*,3S*)-3-((2-(5,7-difluoro-1-tosyl-1H-indol-3-yl)-5-fluoropyrimidin-4-yl)amino)cyclohexyl)-2,5-dimethylpyrrolidine-1-carboxamide (170 mg, 0.266 mmol) was stirred in 1,4-dioxane (9 mL) at 60° C., while a solution of LiOH (63.7 mg, 2.7 mmol) in water, distilled (1 mL) was added. The mixture was brought to reflux for 1 h and was allowed to stir overnight at ambient temperature. 1,4-dioxane was evaporated and the residue was taken in 20 mL CH₃OH, stirred and neutralized with conc. HCl. The solution was purified via preparatory HPLC (stationary phase: RP XBridge Prep C18 ODB-5 μm, 30×250 mm, mobile phase: 0.25% NH₄HCO₃ solution in water, CH₃OH). The desired fractions were collected and evaporated to dryness to afford white solids, N-((1R*3S*)-3-((2-(5,7-difluoro-1H-indol-3-yl)-5-fluoropyrimidin-4-yl)amino)cyclohexyl)-cis-2,5-dimethylpyrrolidine-1-carboxamide (13) and N-((1R*3S*)-3-((2-(5,7-difluoro-1H-indol-3-yl)-5-fluoropyrimidin-4-yl)amino)cyclohexyl)-trans-2,5-dimethylpyrrolidine-1-carboxamide (14)

Preparation of 1-((1R*,3S*)-3-((2-(5,7-difluoro-1H-indol-3-yl)-5-fluoropyrimidin-4-yl)-amino)cyclohexyl)-3-(tetrahydrofuran-3-yl)urea(15)

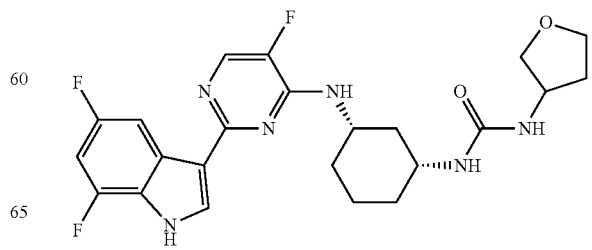

A mixture of (1S*3R*)—N¹-(2-(5,7-difluoro-1-tosyl-1H-indol-3-yl)-5-fluoropyrimidin-4-yl)cyclohexane-1,3-diamine (150 mg, 0.291 mmol) in CH₃CN (8 mL) was stirred at room temperature. 3-isocyanatooxolane (33 mg, 0.291 mmol) in CH₃CN (2 mL) was added and the mixture was stirred for 16 h at ambient temperature. The reaction was complete and the solvent was removed under reduced pressure. The crude was used without purification in the next step. The subsequent tosyl group deprotection was according to the procedure to deprotect the tosyl group for compounds 13 and 14. The crude was purified via preparatory HPLC (stationary phase: RP XBridge Prep C18 ODB-5 µm, 30×250 mm, mobile phase: 0.25% aq. NH₄HCO₃, CH₃OH). The desired fractions were collected and evaporated to dryness to afford a white solid (15).

Preparation of (cis)-N¹-(6-(5,7-difluoro-1-tosyl-1H-indol-3-yl)-3-fluoro-5-(trifluoro-methyl)pyridin-2-yl)cyclohexane-1,3-diamine

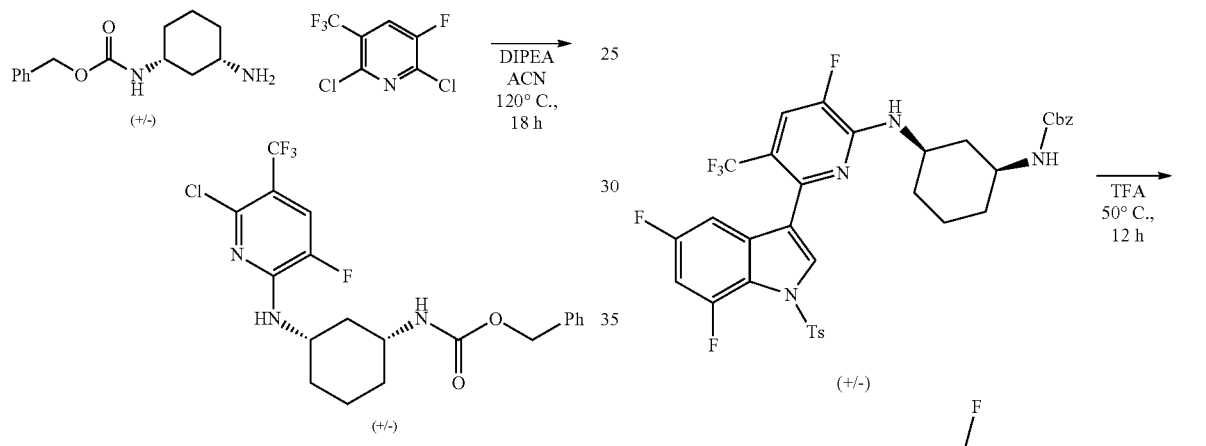

Step 1. A mixture of benzyl (cis)-3-aminocyclohexylcarbamate (3.55 g, 12.47 mmol), 2,6-dichloro-3-fluoro-5-(trifluoromethyl)-pyridine (2916.674 mg, 12.47 mmol) and N,N-diisopropylethylamine (4.3 mL, 24.93 mmol) in CH₃CN (35 mL) was heated in an autoclave at 120° C. for 18 h. The solvent was removed under reduced pressure. The residual fraction was purified by silica flash column chromatography using a heptane to dichloromethane gradient. The desired fractions were collected and evaporated to dryness to afford a white solid, benzyl ((cis)-3-((6-chloro-3-fluoro-5-(trifluoromethyl)pyridin-2-yl)amino)cyclohexyl)carbamate. LC-MS ES⁺ m/z=446.1; Rt: 1.36 min, method A

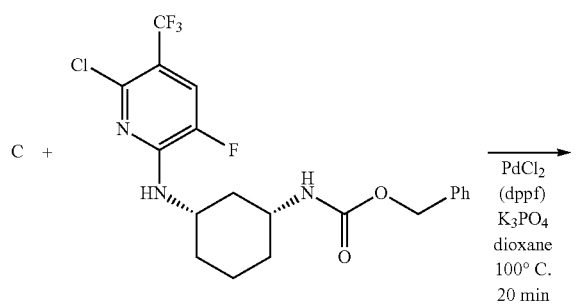

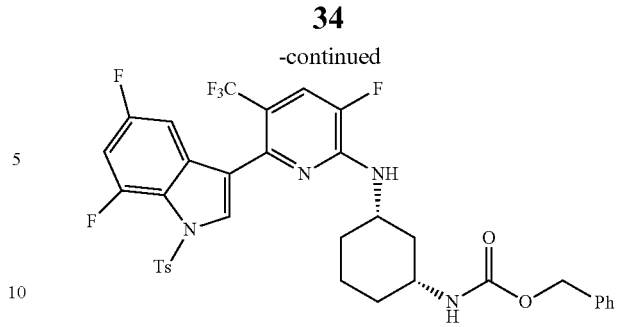

Step 2. A mixture of C (350 mg, 0.808 mmol), benzyl ((cis)-3-((6-chloro-3-fluoro-5-(trifluoromethyl)pyridin-2-yl)amino)cyclohexyl)carbamate (191.31 mg, 0.61 mmol), [1,1'-bis(di-tert-butylphosphino)ferrocene]dichloropalladium (52.6 mg, 0.08 mmol) and K₃PO₄ (514.4 mg, 2.423 mmol) in 1,4-dioxane (10 mL) and H₂O (1 mL) was heated to 100° C. for 20 minutes in an autoclave. The reaction was complete and the mixture was concentrated. The residual fraction was used as such in the next step. LC-MS ES⁺ m/z=717.2; Rt: 1.55 min, method A

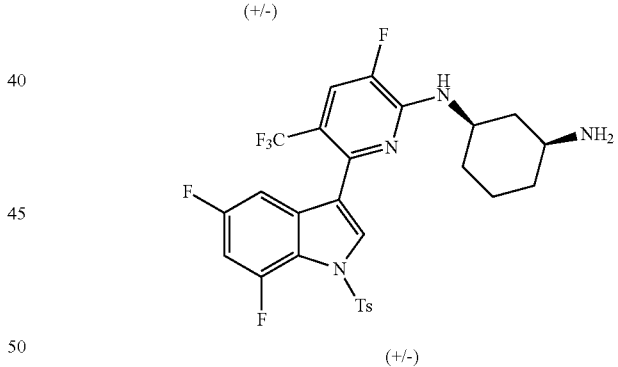

Step 3. To a 100 mL round bottom flask containing benzyl ((cis)-3-((6-(5,7-difluoro-1-tosyl-1H-indol-3-yl)-3-fluoro-5-(trifluoromethyl)pyridin-2-yl)amino)cyclohexyl)-carbamate (8.6 g, 8.4 mmol) was added TFA (25 mL) at 50° C. and stirring was continued for 12 h. Water (5 mL) was added and stirred for 3 h at ambient temperature. The mixture was reduced in volume under reduced pressure and extracted with CH₂Cl₂. The organic layer was washed with a saturated solution of NaHCO₃ and brine. The organic layer was separated, dried over MgSO₄, the solids were removed by filtration, and the filtrate was concentrated under reduced pressure to afford an oil, (cis)-N¹-(6-(5,7-difluoro-1-tosyl-1H-indol-3-yl)-3-fluoro-5-(trifluoromethyl)pyridin-2-yl)cyclohexane-1,3-diamine. LC-MS ES⁺ m/z=583.2; Rt: 1.29 min, method A

General Procedure Toward the Synthesis of N-((cis)-3-((6-(5,7-difluoro-1-tosyl-1H-indol-3-yl)-3-fluoro-5-(trifluoromethyl)pyridin-2-yl)amino)cyclohexyl) Amides

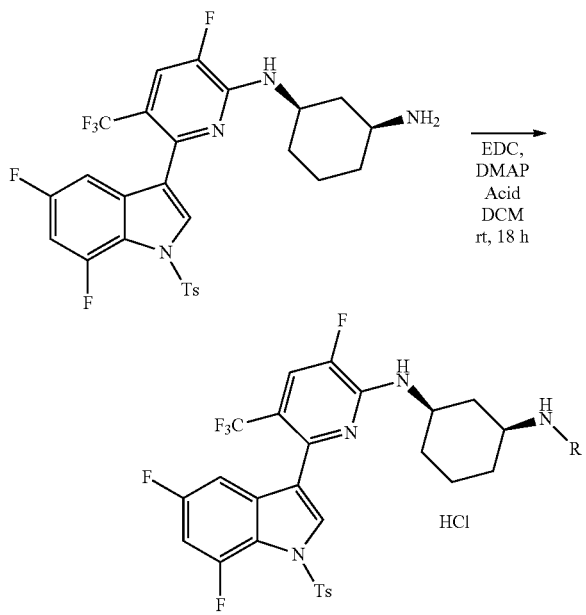

A mixture of (cis)-N$^1$-(6-(5,7-difluoro-1-tosyl-1H-indol-3-yl)-3-fluoro-5-(trifluoromethyl)pyridin-2-yl)cyclohexane-1,3-diamine (0.5 g, 0.858 mmol) and DMAP (0.262 g, 2.146 mmol) in CH$_2$Cl$_2$ (15 mL) was stirred at room temperature, then 1 eq. of the carboxylic acid derivative was added and the mixture stirred for 10 minutes. EDC (0.247 g, 1.287 mmol) was added and stirred for 18 h at room temperature. The reaction mixture was washed with HCl (aq., 1N) and the organic phase was concentrated to give the crude compound.

Example Procedure for Tosyl Group Deprotection of N-((cis)-3-((6-(5,7-difluoro-1-tosyl-1H-indol-3-yl)-3-fluoro-5-(trifluoromethyl)pyridin-2-yl)amino)cyclohexyl) Amides

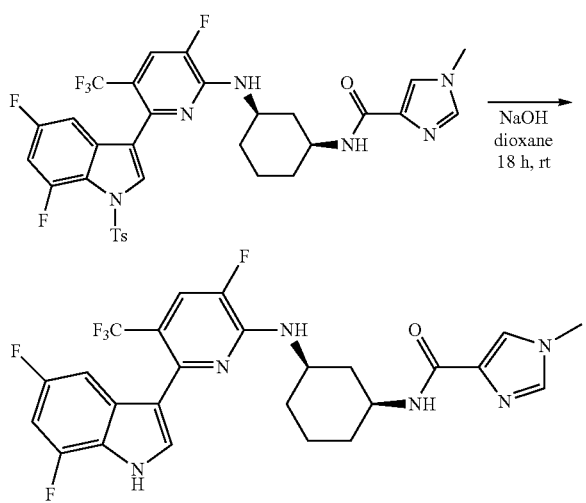

N-((cis)-3-((6-(5,7-difluoro-1-tosyl-1H-indol-3-yl)-3-fluoro-5-(trifluoromethyl)pyridin-2-yl)amino)cyclohexyl)-1-methyl-1H-imidazole-4-carboxamide (500 mg, 0.724 mmol) was added to a solution of NaOH (290 mg, 7.2 mmol) in water (5 mL), and 1,4-dioxane (15 mL). The mixture was stirred overnight at ambient temperature. The reaction was neutralized with 1N HCl (aq., 10 mL) and then evaporated to dryness. The purification was performed via preparatory HPLC (stationary phase: Uptisphere C18 ODB—10 μm, 200 g, 5 cm, mobile phase: 0.25% NH$_4$HCO$_3$ solution in water, CH$_3$CN). The desired fractions were collected and evaporated to dryness to afford a solid, N-((1S*,3R*)-3-((6-(5,7-difluoro-1H-indol-3-yl)-3-fluoro-5-(trifluoromethyl)pyridin-2-yl)amino)cyclohexyl)-1-methyl-1H-imidazole-4-carboxamide (16).

Preparation of 3-((6-(5,7-difluoro-1H-indol-3-yl)-3-fluoro-5-(trifluoromethyl)pyridin-2-yl)amino)-4,4-dimethylpentanoic Acid

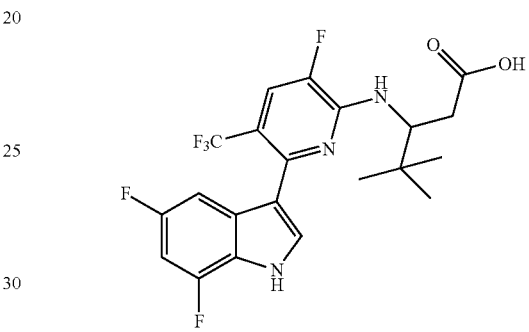

Step 1. A solution of 2,6-dichloro-3-fluoro-5-(trifluoromethyl)pyridine (1 g, 4.15 mmol) and methyl 3-amino-4,4-dimethylpentanate HCl (973.5 mg, 4.975 mmol) in DMA (5 mL) was added N,N-diisopropylethylamine (2.89 mL, 16.58 mmol). The mixture was heated at 140° C. for 45 min in a sealed tube, under microwave irradiation. The reaction mixture was quenched in ice water and extracted twice with EtOAc. The organic layer was separated, dried over MgSO$_4$, the solids were removed by filtration and the solvent of the filtrate was removed under reduced pressure. The crude was purified by flash column chromatography (silica; 100% CH$_2$Cl$_2$). The desired fractions were collected and evaporated in vacuo to afford a solid, methyl 3-((6-chloro-3-fluoro-5-(trifluoromethyl)pyridin-2-yl)amino)-4,4-dimethylpentanoate.

Step 2. Subsequent Suzuki reaction and tosyl group deprotection proceeded according to the method to prepare 1.

Step 3. A mixture of crude methyl 3-((6-(5,7-difluoro-1H-indol-3-yl)-3-fluoro-5-(trifluoromethyl)pyridin-2-yl)amino)-4,4-dimethylpentanoate (110 mg, 0.232 mmol) and LiOH (55.6 mg, 2.32 mmol) in a solution of 1,4-dioxane (20 mL) and water (2 mL) was stirred at ambient temperature for 18 h. The reaction neutralized with conc. HCl. The solvent was removed under reduced pressure and the crude was purified via preparatory HPLC (stationary phase: RP XBridge Prep C18 OBD-10 μm, 30×150 mm, mobile phase: 0.25% NH$_4$HCO$_3$ solution in water, CH$_3$CN), followed by a second purification was performed via preparatory HPLC (stationary phase: XBridge Prep C18 ODB-5 μm, 30×250 mm, mobile phase: 0.25% aq. NH$_4$HCO$_3$, CH$_3$OH). The desired fractions were collected and the solvent was removed under reduced pressure. Enatiomer separation was performed via preparatory SFC (stationary phase: Chiralpak Diacel AS 20×250 mm, mobile phase: CO$_2$, ethanol with 0.2% isopropylamine). The desired fractions were collected and the solvent removed under reduced pressure to afford (S*)-3-((6-(5,7-difluoro-1H-indol-3-yl)-3-fluoro-5-(trifluoromethyl)pyridin-2-yl)amino)-4,4-dimethylpentanoic acid (17) and (R*)-3-((6-(5,7-difluoro-1H-indol-3-yl)-3-fluoro-5-(trifluoromethyl)pyridin-2-yl)amino)-4,4-dimethylpentanoic acid(18).

Synthesis of 2-(5,7-difluoro-1H-indol-3-yl)-N-(3,3-dimethyl-1-(1H-tetrazol-5-yl)butan-2-yl)-5-fluoropyrimidin-4-amine (19)

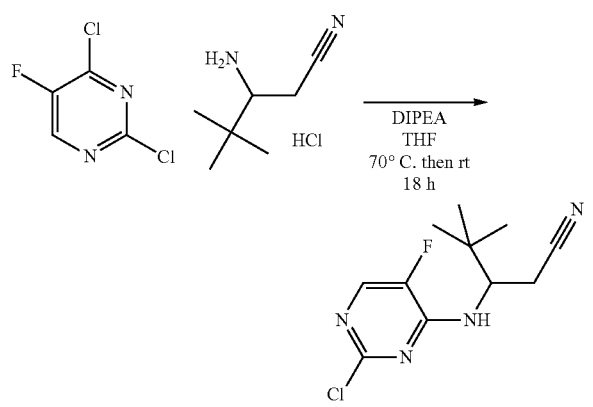

Step 1. In a round bottom flask a solution of 2,4-dichloro-5-fluoro-pyrimidine (1.5 g, 8.98 mmol) was stirred at room temperature in THF (36 mL). 3-amino-4,4-dimethylpentanenitrile hydrochloride (1.85 g, 11.38 mmol) and N,N-diisopropylethylamine (4.64 mL, 26.95 mmol) was added dropwise to the reaction mixture and stirred for one hour at 70° C. and continued overnight at ambient temperature. The solids were removed by filtration, washed with THF and evaporated under reduced pressure. The crude was purified by silica flash column chromatography (gradient: CH$_2$Cl$_2$ to CH$_2$Cl$_2$/CH$_3$OH 100-90/10). The desired fractions were collected and evaporated to dryness to afford 3-((2-chloro-5-fluoropyrimidin-4-yl)amino)-4,4-dimethylpentanenitrile, as a solid. LC-MS ES$^+$ m/z=257.2; Rt: 1.76 min, method B.

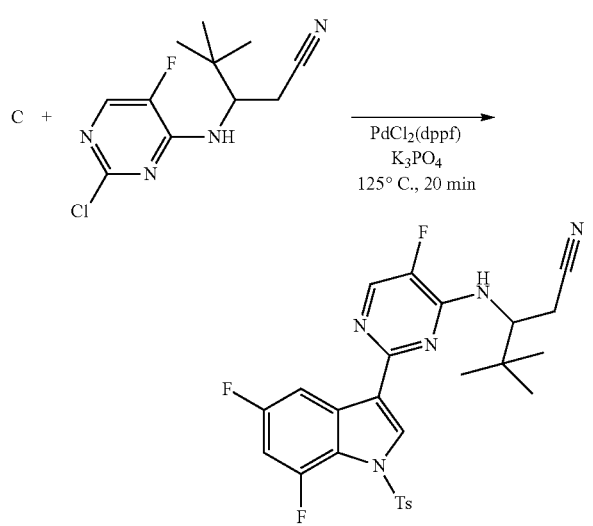

Step 2. A mixture of C (750 mg, 0.865 mmol), 3-((2-chloro-5-fluoropyrimidin-4-yl)-amino)-4,4-dimethylpentanenitrile (1739 mg, 4.616 mmol), [1,1'-bis(di-tert-butylphosphino)ferrocene] dichloropalladium (56.41 mg, 0.087 mmol) and K$_3$PO$_4$ (551 mg, 2.596 mmol) in 1,4-dioxane (9 mL) and H$_2$O (1.2 mL) was heated to 125° C. for 20 minutes under microwave irradiation. The solvent was removed under reduced pressure and the residue was dissolved in CH$_2$Cl$_2$. The mixture was filtered over decalite and the filtrate was washed twice with brine. The organic layer was dried over MgSO$_4$, the solids were removed by filtration, and the solvent of the filtrate was removed under reduced pressure. The crude 3-((2-(5,7-difluoro-1-tosyl-1H-indol-3-yl)-5-fluoropyrimidin-4-yl)amino)-4,4-dimethylpentanenitrile was used without further purification in the next step. LC-MS ES$^+$ m/z=528.4; Rt: 2.47 min, method B.

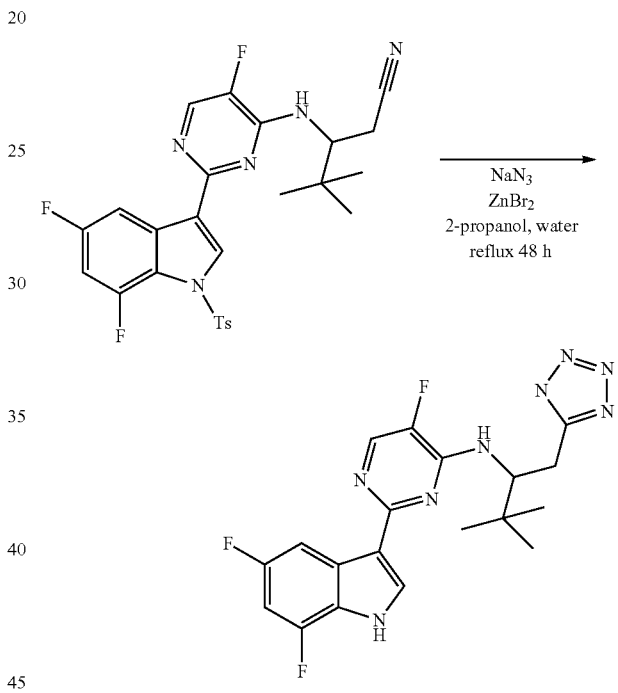

Step 3. To a solution of 3-((2-(5,7-difluoro-1-tosyl-1H-indol-3-yl)-5-fluoropyrimidin-4-yl)amino)-4,4-dimethylpentanenitrile (100 mg, 0.19 mmol) in 2-propanol (1.5 mL) and water (3 mL) was added sodium azide (24.6 mg, 0.38 mmol), zinc bromide (21 mg, 0.095 mmol). The reaction mixture was stirred at reflux for 48 h. To the reaction mixture was added HCl (3 N, 3 mL) and EtOAc (15 mL). The organic layer was isolated and the aqueous layer was extracted with EtOAc (2×20 mL). The combined organic layers were evaporated. The purification was performed via prep HPLC (Stationary phase: RP XBridge Prep C18 OBD-10 μm, 30×150 mm, mobile phase: 0.25% aq. NH$_4$HCO$_3$, CH$_3$CN). The desired fractions were collected and evaporated to dryness to afford a white solid, (19). LC-MS ES$^+$ m/z=417.4; Rt: 1.50 min, method B.

$^1$H NMR (400 MHz, DMSO-d$_6$) δ ppm 1.06 (s, 9H) 3.21-3.32 (m, 2H) 4.76 (td, J=9.85, 3.41 Hz, 1H) 6.77 (d, J=10.78 Hz, 1H) 6.85-6.95 (m, 1H) 7.96-8.01 (m, 2H) 8.03 (d, J=3.74 Hz, 1H) 11.75 (s, 1H)

Preparation of 7-fluoro-5-methyl-3-(4,4,5,5-tetramethyl-1,3,2-dioxaborolan-2-yl)-1-tosyl-1H-indole (C2)

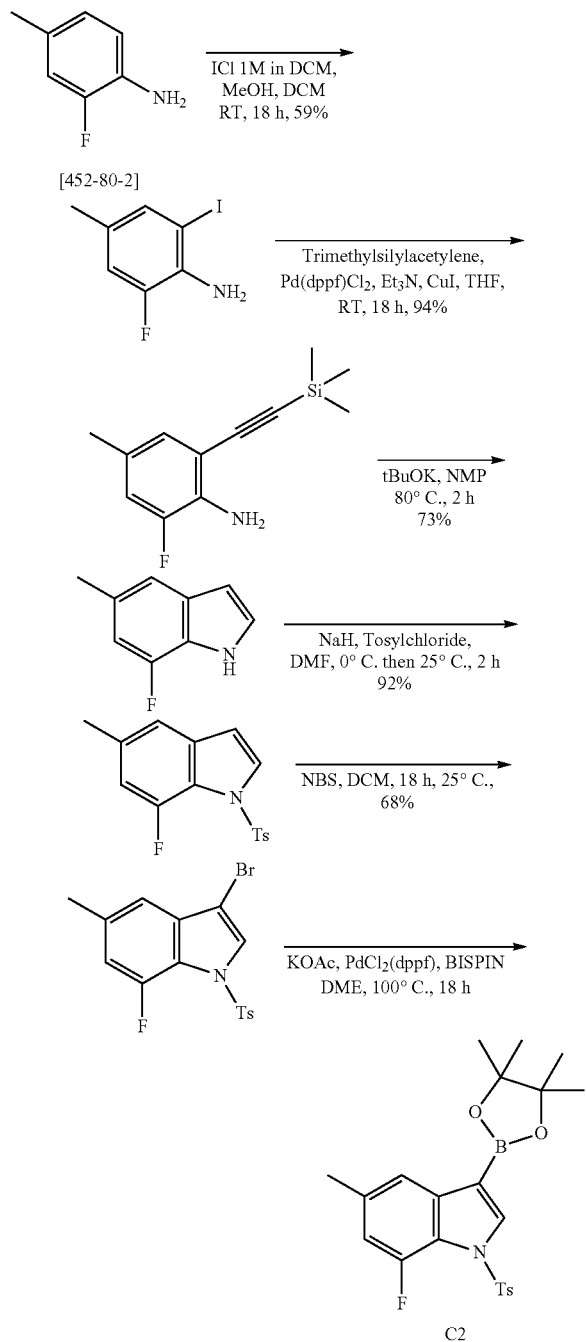

Preparation of 2-fluoro-6-iodo-4-methylaniline

Iodine monochloride (8.9 mL, 1 M in DCM, 8.9 mmol) was added drop wise over 20 min to a solution of 2-fluoro-4-methylaniline (0.5 mL, 4.45 mmol) in MeOH (5 mL) and CH$_2$Cl$_2$ (10 mL) at room temperature then the mixture was stirred at room temperature overnight. NaOH (1N) was added slowly at 5° C., the organic layer was separated, washed with aq. Na$_2$SO$_3$, then water, dried over MgSO$_4$, the solids were removed by filtration and the solvent of the filtrate was removed under reduced pressure. Purification was carried out by flash chromatography over silica gel (silica, 15-35 μm, Heptane/EtOAc 95/5). Pure fractions were collected and evaporated to give 2-fluoro-6-iodo-4-methylaniline as colorless oil (0.662 g, 95%).

Preparation of 2-fluoro-4-methyl-6-((trimethylsilyl)ethynyl)aniline

A solution of 2-fluoro-6-iodo-4-methylaniline (8.66 g, 34.5 mmol), Bis(triphenyl-phosphine)palladium(II) dichloride (1.21 g, 1.72 mmol), copper iodide (0.33 g, 1.72 mmol) and triethylamine (19.4 mL, 138 mmol) in THF (98 mL) was purged with N$_2$ gas for 5 min, then trimethylsylilacetylene (7.64 mL, 55.19 mmol) was added and the resulting solution was stirred at room temperature overnight. The reaction mixture was diluted with CH$_2$Cl$_2$, washed with water/NH$_3$ (30% aq.) then water. The organic layer was dried (MgSO$_4$), the solids were removed by filtration and the solvent of the filtrate was removed under reduced pressure. Purification was carried out by silica flash chromatography (15-35 μm, heptane/EtOAc from 100/0 to 95/5). Pure fractions were collected and the solvent was evaporated to give 2-fluoro-4-methyl-6-((trimethylsilyl)ethynyl)aniline (7.47 g, 94%).

Preparation of 7-fluoro-5-methyl-1H-indole

A solution of 2-fluoro-4-methyl-6-((trimethylsilyl)ethynyl)aniline (5.77 g, 24.76 mmol) and potassium t-butoxide (8.34 g, 74.29 mmol) in NMP (100 mL) was stirred and heated at 80° C. for 2 hours. The reaction mixture was cooled to room temperature, then poured into ice/water and extracted with EtOAc, the organic layer was separated, washed twice with water and brine, dried (MgSO$_4$), the solids were removed by filtration and the solvent of the filtrate was removed under reduced pressure. Purification was carried out by flash chromatography over silica gel (heptane/EtOAc from 95/5 to 85/15). Pure fractions were collected and the solvent was evaporated to give 7-fluoro-5-methyl-1H-indole (2.70 g, 73%) which crystallized on standing.

Preparation of 7-fluoro-5-methyl-1-tosyl-1H-indole

NaH (60% dispersion in mineral oil) (0.87 g, 21.72 mmol) was added portionwise to a solution of 7-fluoro-5-methyl-1H-indole (2.7 g, 18.1 mmol) in DMF (30 mL) at 0° C. purged with N$_2$ flow, and then the mixture was stirred for 30 min at 0° C. Tosyl chloride (3.62 g, 19.01 mmol) was added portion wise at 0° C. then the reaction mixture was stirred for 2 hours at room temperature. The reaction mixture was poured into ice-water (90 mL) then the mixture was stirred for 10 min. EtOAc was added and the organic layer was extracted, dried over MgSO$_4$, the solids were removed by filtration and the solvent of the filtrate was removed under reduced pressure to afford 7-fluoro-5-methyl-1-tosyl-1H-indole (5.08 g, 92%).

Preparation of 3-bromo-7-fluoro-5-methyl-1-tosyl-1H-indole

N-bromosuccinimide (2.27 g, 12.75 mmol) was added to a solution of 7-fluoro-5-methyl-1-tosyl-1H-indole (4.07 g, 12.75 mmol) in CH$_2$Cl$_2$ (66 mL) at room temperature. The reaction mixture was stirred at room temperature for 18 hours. The mixture was treated with a saturated aq. NaHCO$_3$ and the mixture was stirred for 5 min. The organic layer separated, dried over MgSO$_4$, the solids were removed by filtration and the solvent of the filtrate was removed under reduced pressure. Purification was carried out by silica flash chromatography (heptane/EtOAc from 95/5 to 80/20). Pure fractions were collected and the solvent was evaporated. The residue was crystallized from EtOH, filtered off and dried under vacuum to give 3-bromo-7-fluoro-5-methyl-1-tosyl-1H-indole (3.30 g, 68%) as pale beige powder.

Preparation of 7-fluoro-5-methyl-3-(4,4,5,5-tetramethyl-1,3,2-dioxaborolan-2-yl)-1-tosyl-1H-indole (C2)

A mixture of 3-bromo-7-fluoro-5-methyl-1-tosyl-1H-indole (0.7 g, 1.83 mmol), Bis(pinacolato)diboron (0.7 g, 2.75 mmol), dichloro[1,1'-bis(diphenylphosphino)-ferrocene]palladium(II):CH$_2$Cl$_2$ (0.075 g, 0.092 mmol) and potassium acetate (0.54 g, 5.49 mmol) in DME (16 mL) was purged with N$_2$ flow for 5 min and then was stirred and heated at 100° C. for 18 hours. EtOAc (40 mL) and brine (10 mL) were added, the reaction mixture was filtered through a short pad of Celite, the filtrate was washed with brine, dried (MgSO$_4$) and evaporated to dryness affording 7-fluoro-5-methyl-3-(4,4,5,5-tetramethyl-1,3,2-dioxaborolan-2-yl)-1-tosyl-1H-indole (C2), 1.27 g, 96%. Used without purification in the next step.

Synthesis of N-((cis)-3-((5-fluoro-2-(7-fluoro-5-methyl-1H-indol-3-yl)pyrimidin-4-yl)-amino)cyclohexyl)pyrrolidine-1-carboxamide (20)

clohexyl)pyrrolidine-1-carboxamide. A solution of C2 (1.27 g, 1.77 mmol), D (0.43 g, 1.27 mmol), K$_2$CO$_3$ (2M, 2.54 mL, 5.07 mmol) in DME (16 mL) was purged with N$_2$ gas for 5 min, then dichloro[1,1'-bis(diphenyl-phosphino)ferrocene]palladium II, complex with CH$_2$Cl$_2$ (0.1 g, 0.13 mmol) was added. The solution was heated to 100° C. in the microwave for 20 min. The mixture was poured out into water and CH$_2$Cl$_2$, the organic layer was separated with a hydrophobic frit and evaporated to dryness. Purification was carried out by silica flash chromatography (CH$_2$Cl$_2$/MeOH/NH$_4$OH, from 100/0/0 to 97/3/0.1). Pure fractions were collected and the solvent was evaporated to give N-((cis)-3-((5-fluoro-2-(7-fluoro-5-methyl-1-tosyl-1H-indol-3-yl)pyrimidin-4-yl)amino)-cyclohexyl)pyrrolidine-1-carboxamide, as a beige foam (0.14 g, 18%).

Step 2. A solution of N-((cis)-3-((5-fluoro-2-(7-fluoro-5-methyl-1-tosyl-1H-indol-3-yl)pyrimidin-4-yl)amino)cyclohexyl)pyrrolidine-1-carboxamide (0.14 g, 0.23 mmol) and sodium methoxide (30 wt % solution in MeOH) (0.13 mL, 0.69 mmol) in MeOH (2.8 mL) was stirred at room temperature for 30 min. Water and EtOAc were added. The organic layer was extracted, dried over MgSO$_4$, filtered and evaporated to give 0.1 g of crude product. A purification was performed via preparative LC (Stationary phase: spherical bare silica 5 μm 150×30.0 mm, Mobile phase: gradient from 0.2% NH$_4$OH, 98% CH$_2$Cl$_2$, 2% CH$_3$OH to 0.8% NH$_4$OH, 92% CH$_2$Cl$_2$, 8% MeOH). Pure fractions were collected and evaporated to give 0.025 g. The residue was freeze dried with acetonitrile/water 2/8 overnight to give 20 as a white powder (0.023 g, 22%).

General Procedure Toward the Synthesis of N-((cis)-3-((5-fluoro-2-(7-fluoro-5-methyl-1H-indol-3-yl)pyrimidin-4-yl)amino)cyclohexyl) Amides

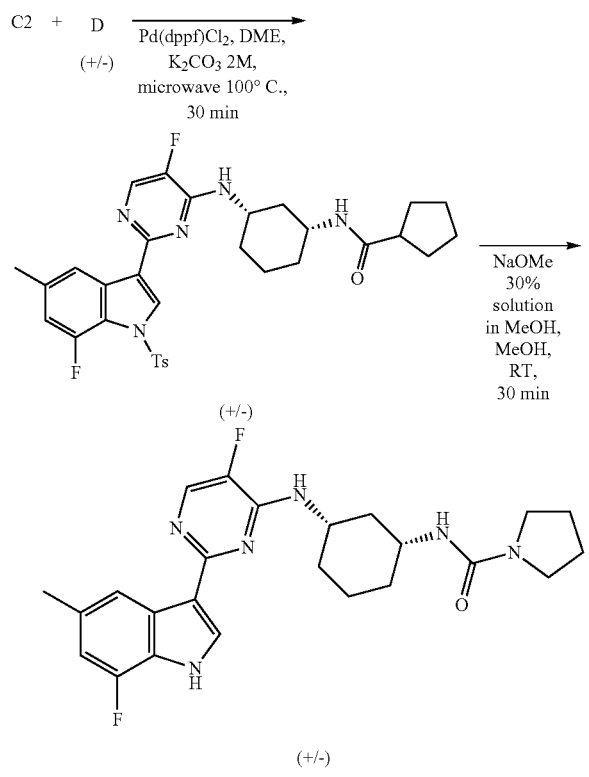

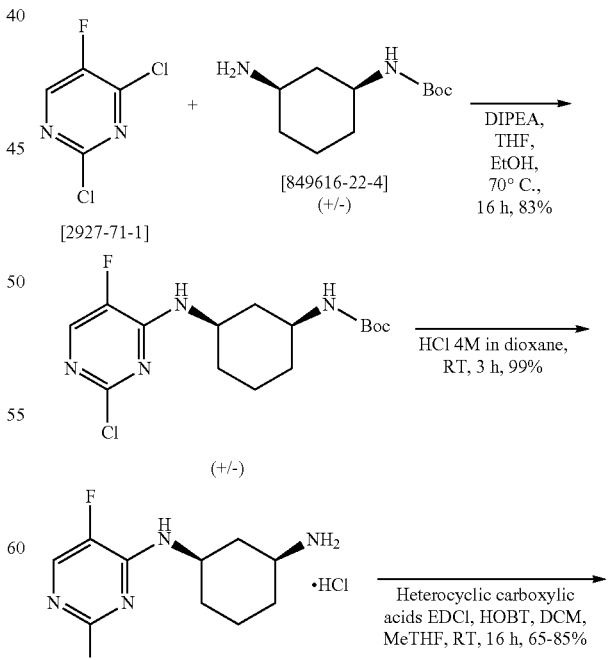

Step 1. Preparation of N-((cis)-3-((5-fluoro-2-(7-fluoro-5-methyl-1-tosyl-1H-indol-3-yl)pyrimidin-4-yl)amino)cy-

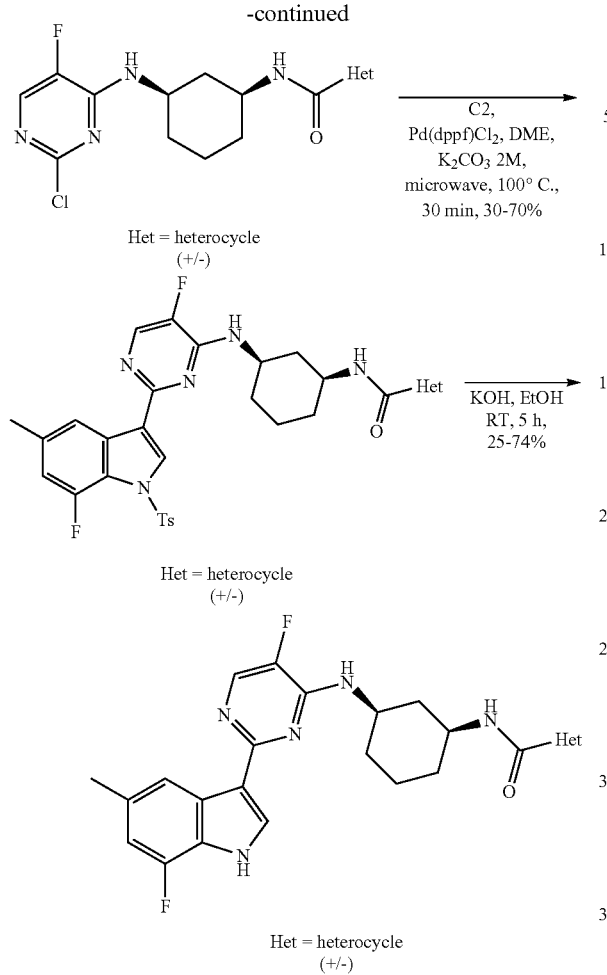

Het = heterocycle
(+/-)

Het = heterocycle
(+/-)

Het = heterocycle
(+/-)

Preparation of tert-butyl ((cis)-3-((2-chloro-5-fluoropyrimidin-4-yl)amino)cyclohexyl)-carbamate A solution of 2,4-dichloro-5-fluoro-pyrimidine (2.14 g, 12.83 mmol), tert-butyl ((cis)-3-aminocyclohexyl)carbamate (3.3 g, 15.4 mmol), diisopropyethylamine (13.3 mL, 76.99 mmol) in EtOH (21 mL) and THF (21 mL) was stirred at 70° C. for 16 hours. The reaction mixture was evaporated, the residue was taken up in water, extracted twice with EtOAc. The combined organic layers were washed with water, dried over MgSO$_4$, filtered and evaporated. The residue was crystallized from DIPE, filtered off and dried under vacuum at 60° C. affording tert-butyl ((cis)-3-((2-chloro-5-fluoropyrimidin-4-yl)amino)cyclohexyl)carbamate as a white powder, 3.67 g, 83%.

Preparation of (cis)-N$^1$-(2-chloro-5-fluoropyrimidin-4-yl)cyclohexane-1,3-diamine hydrochloride A solution of tert-butyl ((cis)-3-((2-chloro-5-fluoropyrimidin-4-yl)amino)cyclohexyl)-carbamate (3.67 g, 10.64 mmol) in HCl (4M in 1,4-dioxane, 58.5 mL, 234.15 mmol) was stirred at room temperature for 3 hours. The solution was concentrated under reduced pressure at 50° C. to give a white solid (cis)-N$^1$-(2-chloro-5-fluoropyrimidin-4-yl)cyclohexane-1,3-diamine hydrochloride, 3.3 g, 99%.

Preparation of N-((cis)-3-((2-chloro-5-fluoropyrimidin-4-yl)amino)cyclohexyl)-picolinamide

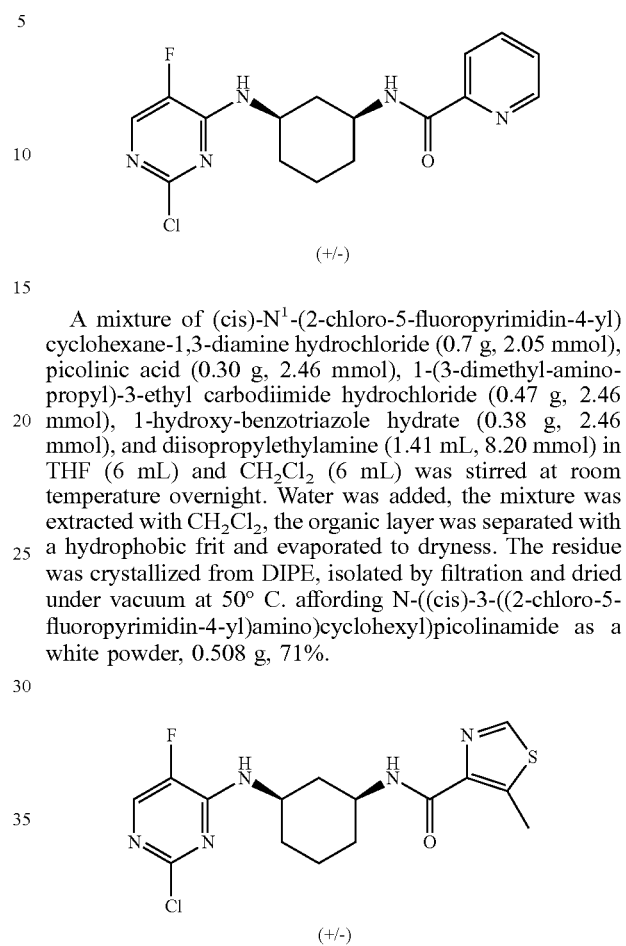

A mixture of (cis)-N$^1$-(2-chloro-5-fluoropyrimidin-4-yl) cyclohexane-1,3-diamine hydrochloride (0.7 g, 2.05 mmol), picolinic acid (0.30 g, 2.46 mmol), 1-(3-dimethyl-aminopropyl)-3-ethyl carbodiimide hydrochloride (0.47 g, 2.46 mmol), 1-hydroxy-benzotriazole hydrate (0.38 g, 2.46 mmol), and diisopropylethylamine (1.41 mL, 8.20 mmol) in THF (6 mL) and CH$_2$Cl$_2$ (6 mL) was stirred at room temperature overnight. Water was added, the mixture was extracted with CH$_2$Cl$_2$, the organic layer was separated with a hydrophobic frit and evaporated to dryness. The residue was crystallized from DIPE, isolated by filtration and dried under vacuum at 50° C. affording N-((cis)-3-((2-chloro-5-fluoropyrimidin-4-yl)amino)cyclohexyl)picolinamide as a white powder, 0.508 g, 71%.

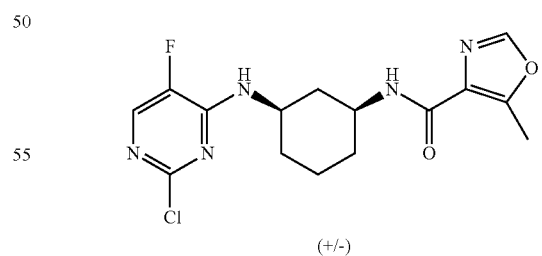

N-((cis)-3-((2-chloro-5-fluoropyrimidin-4-yl)amino)cyclohexyl)-5-methylthiazole-4-carboxamide was prepared according to the method to prepare N-((cis)-3-((2-chloro-5-fluoropyrimidin-4-yl)amino)cyclohexyl)picolinamide, starting from (cis)-N-(2-chloro-5-fluoropyrimidin-4-yl)cyclohexane-1,3-diamine hydrochloride and 5-methyl-4-thiazolecarboxylicacid.

N-((cis)-3-((2-chloro-5-fluoropyrimidin-4-yl)amino)cyclohexyl)-5-methyloxazole-4-carboxamide was prepared according to the method to prepare N-((cis)-3-((2-chloro-5-fluoropyrimidin-4-yl)amino)cyclohexyl)picolinamide, starting from (cis)-N$^1$-(2-chloro-5-fluoropyrimidin-4-yl)cyclohexane-1,3-diamine hydrochloride and 5-methyl-1,3-oxazole-4-carboxylic acid.

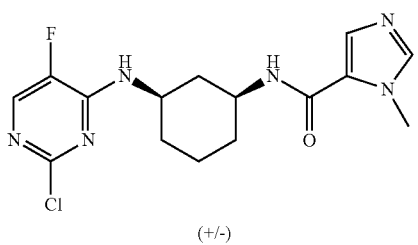 [SMILES: Cn1cncc1C(=O)N[C@H]1CCC[C@@H](Nc2nc(Cl)ncc2F)C1]

(+/-)

N-((cis)-3-((2-chloro-5-fluoropyrimidin-4-yl)amino)cyclohexyl)-1-methyl-1H-imidazole-5-carboxamide was prepared according to the method to prepare N-((cis)-3-((2-chloro-5-fluoropyrimidin-4-yl)amino)cyclohexyl)picolinamide, starting from (cis)-$N^1$-(2-chloro-5-fluoropyrimidin-4-yl)cyclohexane-1,3-diamine hydrochloride and 1-methyl-1H-imidazole-5-carboxylic acid.

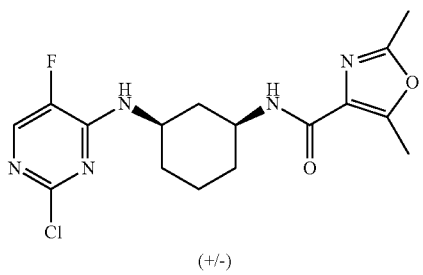 [SMILES: Cc1nc(C(=O)N[C@H]2CCC[C@@H](Nc3nc(Cl)ncc3F)C2)c(C)o1]

(+/-)

N-((cis)-3-((2-chloro-5-fluoropyrimidin-4-yl)amino)cyclohexyl)-2,5-dimethyloxazole-4-carboxamide was prepared according to the method to prepare N-((cis)-3-((2-chloro-5-fluoropyrimidin-4-yl)amino)cyclohexyl)picolinamide, starting from (cis)-$N^1$-(2-chloro-5-fluoropyrimidin-4-yl)cyclohexane-1,3-diamine hydrochloride and 2,5-dimethyl-1,3-oxazole-4-carboxylic acid.

Preparation of N-((cis)-3-((5-fluoro-2-(7-fluoro-5-methyl-1-tosyl-1H-indol-3-yl)-pyrimidin-4-yl)amino)cyclohexyl)picolinamide (21)

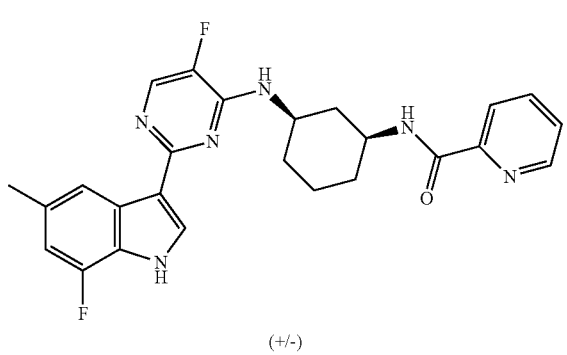 [SMILES: Cc1cc(F)c2[nH]cc(-c3ncc(F)c(N[C@@H]4CCC[C@H](NC(=O)c5ccccn5)C4)n3)c2c1]

(+/-)

Step 1. A solution of C2 (1.03 g, 1.2 mmol), N-((cis)-3-((2-chloro-5-fluoropyrimidin-4-yl)amino)cyclohexyl)picolinamide (0.23 g, 0.67 mmol) and $K_2CO_3$ (2 M, 1.33 mL, 2.67 mmol) in DME (15 mL) was purged with $N_2$ gas for 5 min and then dichloro[1,1'-bis(diphenylphosphino)ferrocene]palladium II complex with $CH_2Cl_2$ (0.055 g, 0.067 mmol) was added. The resulting mixture was stirred and heated at 100° C. in the microwave for 30 min. The mixture was poured into water and $CH_2Cl_2$, the organic layer was separated with a hydrophobic frit and evaporated to dryness. Purification was carried out by flash chromatography over silica gel ($CH_2Cl_2/CH_3OH$ from 100/0 to 98/2). Pure fractions were collected and evaporated to give N-((cis)-3-((5-fluoro-2-(7-fluoro-5-methyl-1-tosyl-1H-indol-3-yl)pyrimidin-4-yl)amino)-cyclohexyl)picolinamide.

Step 2. A solution of N-((cis)-3-((5-fluoro-2-(7-fluoro-5-methyl-1-tosyl-1H-indol-3-yl)-pyrimidin-4-yl)amino)cyclohexyl)picolinamide (0.3 g, 0.49 mmol) and potassium hydroxide (0.14 g, 2.43 mmol) in ethanol (7 mL) was stirred at room temperature for 5 hours. Water was added, the mixture was extracted with $CH_2Cl_2$, the organic layer was separated, washed with water then brine, dried ($MgSO_4$) and evaporated to dryness. Purification was performed via preparative LC (stationary phase: silica, mobile phase: 99% $CH_2Cl_2$, 1% $CH_3OH$). Pure fractions were collected and evaporated to give 0.08 g, 35%. The crude was crystallized from diisopropylether, isolated by filtration and dried under vacuum at 70° C. to afford 21 as a white powder, 0.058 g, 26%.

General Procedure Toward the Synthesis of N-((cis)-3-((5-cyano-3-fluoro-6-(7-fluoro-5-methyl-1H-indol-3-yl)pyridin-2-yl)amino)cyclohexyl) Amides

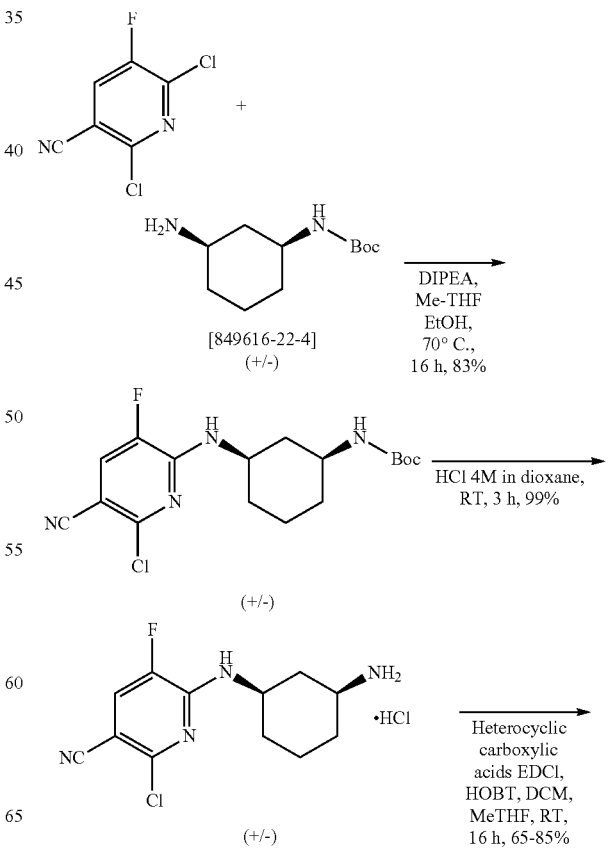

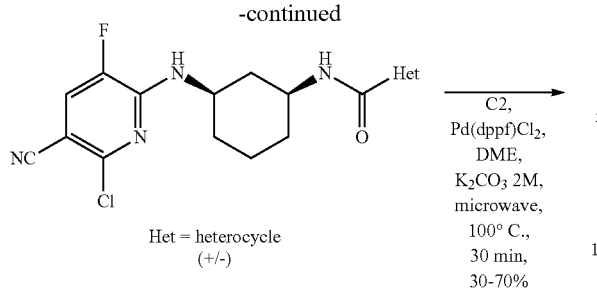

Het = heterocycle
(+/−)

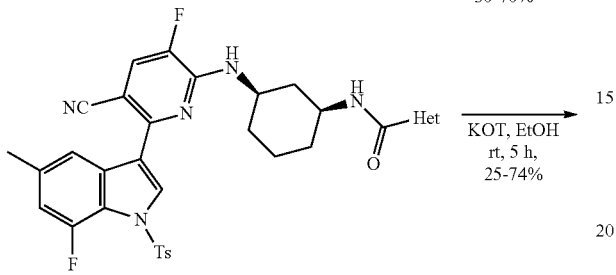

Het = heterocycle
(+/−)

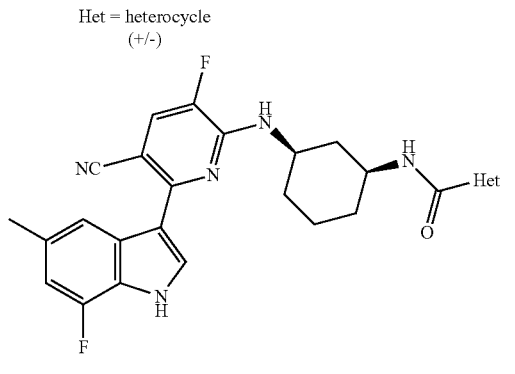

Het = heterocycle
(+/−)

Preparation of tert-butyl ((cis)-3-((6-chloro-5-cyano-3-fluoropyridin-2-yl)amino)-cyclohexyl)carbamate A solution of 2,6-dichloro-5-fluoro-3-pyridinecarbonitrile (0.45 g, 2.33 mmol), tert-butyl-3-aminocyclohexylcarbamate (0.6 g, 2.8 mmol), N,N-diisopropylethylamine (2.41 mL, 14 mmol) in ethanol (5 mL) and Me-THF (5 mL) was stirred and refluxed at 80° C. for 5 hours. The reaction mixture was concentrated under reduced pressure. The residue was taken up in water, and extracted twice with EtOAc. The combined organic layers were washed with water, dried over MgSO$_4$, filtered and evaporated. The residue was crystallized from DIPE, filtered off and dried under vacuum at 60° C. affording tert-butyl ((cis)-3-((6-chloro-5-cyano-3-fluoropyridin-2-yl)amino)cyclohexyl)carbamate as a white powder, 0.718 g, 83%.

Preparation of 6-(((cis)-3-aminocyclohexyl)amino)-2-chloro-5-fluoronicotinonitrile hydrochloride A solution of tert-butyl ((cis)-3-((6-chloro-5-cyano-3-fluoropyridin-2-yl)amino)-cyclohexyl)carbamate (3.92 g, 10.63 mmol) in HCl (4 M in dioxane, 58.5 mL, 233.82 mmol) was stirred at room temperature for 3 hours. The solution was concentrated under reduced pressure to give a white solid which was dried under reduced pressure at 50° C. affording 6-(((cis)-3-aminocyclohexyl)amino)-2-chloro-5-fluoronicotinonitrile hydrochloride as a beige foam, 3.39 g, 99%.

The Following Intermediates were Prepared According to the Method to Prepare N-((cis)-3-((2-chloro-5-fluoropyrimidin-4-yl)amino)cyclohexyl) picolinamide

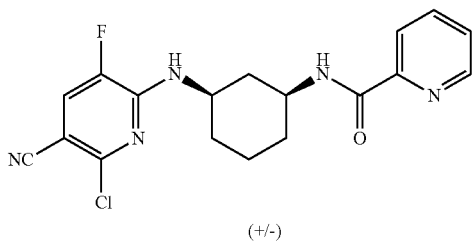 [SMILES: N#Cc1cc(F)c(N[C@@H]2CCC[C@H](NC(=O)c3ccccn3)C2)nc1Cl]

(+/−)

N-((cis)-3-((6-chloro-5-cyano-3-fluoropyridin-2-yl)amino)cyclohexyl)picolinamide was prepared according to the method to prepare N-((cis)-3-((2-chloro-5-fluoropyrimidin-4-yl)amino)cyclohexyl)picolinamide, starting from 6-(((cis)-3-amino-cyclohexyl)amino)-2-chloro-5-fluoronicotinonitrile hydrochloride and 2-picolinic acid.

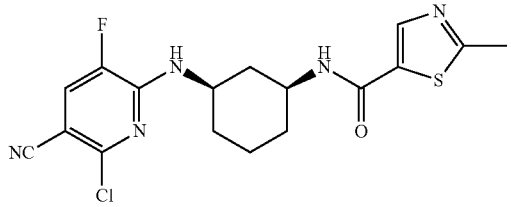

(+/−)

N-((cis)-3-((6-chloro-5-cyano-3-fluoropyridin-2-yl)amino)cyclohexyl)-2-methylthiazole-5-carboxamide was prepared according to the method to prepare N-((cis)-3-((2-chloro-5-fluoropyrimidin-4-yl)amino)cyclohexyl)picolinamide, starting from 6-(((cis)-3-aminocyclohexyl)amino)-2-chloro-5-fluoronicotinonitrile hydrochloride and 2-methyl-5-thiazolecarboxylicacid.

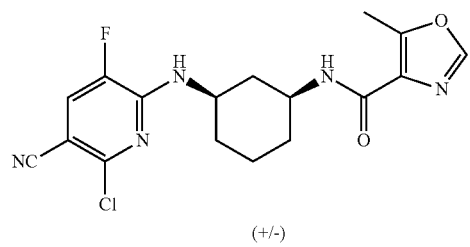

(+/−)

N-((cis)-3-((6-chloro-5-cyano-3-fluoropyridin-2-yl)amino)cyclohexyl)-5-methyloxazole-4-carboxamide was prepared according to the method to prepare N-((cis)-3-((2-chloro-5-fluoropyrimidin-4-yl)amino)cyclohexyl)picolinamide, starting from 6-(((cis)-3-aminocyclohexyl)amino)-2-chloro-5-fluoronicotinonitrile hydrochloride and 5-methyl-1,3-oxazole-4-carboxylic acid.

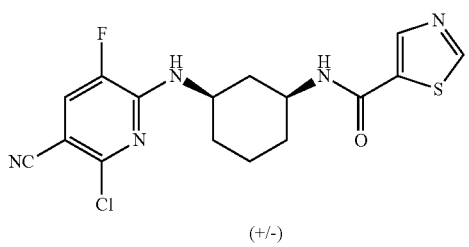 [SMILES: N#Cc1cc(F)c(N[C@@H]2CCC[C@H](NC(=O)c3cncs3)C2)nc1Cl]

(+/-)

N-((cis)-3-((6-chloro-5-cyano-3-fluoropyridin-2-yl)amino)cyclohexyl)thiazole-5-carboxamide was prepared according to the method to prepare N-((cis)-3-((2-chloro-5-fluoropyrimidin-4-yl)amino)cyclohexyl)picolinamide, starting from 6-(((cis)-3-aminocyclohexyl)amino)-2-chloro-5-fluoronicotinonitrile hydrochloride and 5-thiazolecarboxylicacid.

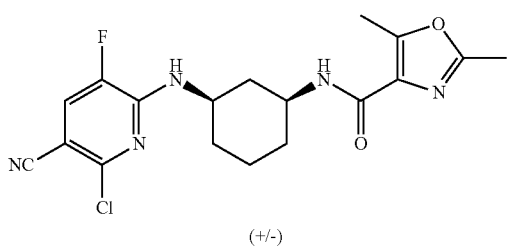 [SMILES: Cc1nc(C(=O)N[C@H]2CCC[C@@H](Nc3nc(Cl)c(C#N)cc3F)C2)c(C)o1]

(+/-)

N-((cis)-3-((6-chloro-5-cyano-3-fluoropyridin-2-yl)amino)cyclohexyl)-2,5-dimethyloxazole-4-carboxamide was prepared according to the method to prepare N-((cis)-3-((2-chloro-5-fluoropyrimidin-4-yl)amino)cyclohexyl)picolinamide, starting from 6-(((cis)-3-aminocyclohexyl)amino)-2-chloro-5-fluoronicotinonitrile hydrochloride and 2,5-dimethyl-1,3-oxazole-4-carboxylic acid.

Preparation of N-((cis)-3-((5-cyano-3-fluoro-6-(7-fluoro-5-methyl-1-tosyl-1H-indol-3-yl)pyridin-2-yl)amino)cyclohexyl)picolinamide

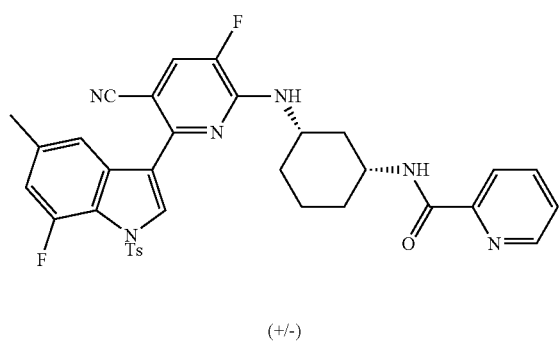 [SMILES: Cc1ccc(S(=O)(=O)n2cc(-c3nc(N[C@H]4CCC[C@@H](NC(=O)c5ccccn5)C4)c(F)cc3C#N)c3cc(C)cc(F)c32)cc1]

(+/-)

N-((cis)-3-((5-cyano-3-fluoro-6-(7-fluoro-5-methyl-1-tosyl-1H-indol-3-yl)-pyridin-2-yl)-amino)cyclohexyl)picolinamide was prepared employing an analogous method as the one to prepare N-((cis)-3-((5-fluoro-2-(7-fluoro-5-methyl-1-tosyl-1H-indol-3-yl)-pyrimidin-4-yl)amino)cyclohexyl)picolinamide yielding the titled compound, 0.630 g, 92%.

Preparation of N-((cis)-3-((5-cyano-3-fluoro-6-(7-fluoro-5-methyl-1H-indol-3-yl)-pyridin-2-yl)amino)cyclohexyl)picolinamide (22)

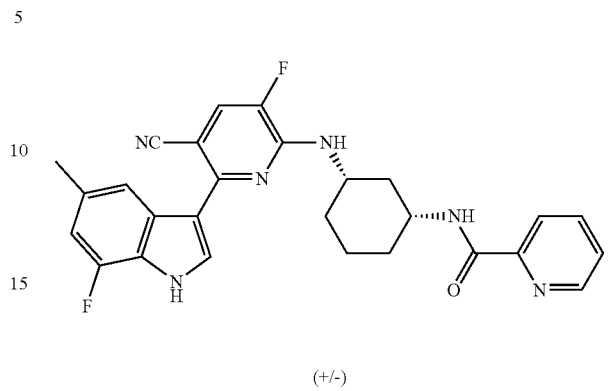

(+/-)

The titled compound was prepared employing an analogous method as the one to prepare N-((cis)-3-((5-fluoro-2-(7-fluoro-5-methyl-1-tosyl-1H-indol-3-yl)pyrimidin-4-yl)amino)cyclohexyl)picolinamide(21) 0.068 g, 43%

Preparation of 23

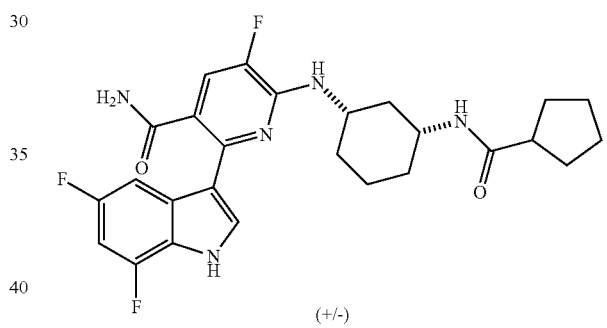

(+/-)

In a sealed tube a mixture of N-((cis)-3-((5-cyano-6-(5,7-difluoro-1-tosyl-1H-indol-3-yl)-3-fluoropyridin-2-yl)amino)cyclohexyl)pyrrolidine-1-carboxamide (200 mg, 314 μmol) and hydrido(dimethylphosphinous acid-kP)[hydrogen bis(dimethyl-phosphinito-kP)]platinum(II)[173416-05-2] (27 mg, 62.8 μmol) in THF (10 mL) and H$_2$O (2 mL) was stirred at 95° C. for 3 h, then at rt for 18 h. The reaction mixture was heated at 95° C. for 3 h. Water, brine and EtOAc were added to the reaction mixture, the aqueous layer was extracted with EtOAc (twice). The combined organic layers were dried over MgSO$_4$, filtered and evaporated in vacuo. The crude was purified by preparative silica LC (mobile phase gradient: from CH$_2$Cl$_2$/CH$_3$OH/aqNH$_3$ 100/0/0 to 90/10/1) to give 156 mg of 2-(5,7-difluoro-1-tosyl-1H-indol-3-yl)-5-fluoro-6-(((cis)-3-(pyrrolidine-1-carboxamido)cyclohexyl)amino)nicotinamide (76%).

Step 2. In a sealed tube, NaOH (3 N aq., 0.397 mL, 1.19 mmol) was added to a mixture of 2-(5,7-difluoro-1-tosyl-1H-indol-3-yl)-5-fluoro-6-(((cis)-3-(pyrrolidine-1-carboxamido)cyclohexyl)amino)nicotinamide (156 mg, 0.238 mmol) in MeOH (3 mL) at rt. The mixture was stirred at rt for 1 day. Water, brine and EtOAc were added to reaction mixture. The aqueous layer was extracted with EtOAc (twice). The combined organic layers were dried over MgSO₄, filtered and evaporated in vacuo. Et₂O was added to the residue, the solid was filtered and treated by EtOAc and NaHCO₃. The organic layer was washed with NaHCO₃ (twice), dried over MgSO₄, filtered and evaporated in vacuo. Acetone was added to the residue and the solvent was evaporated in vacuo, then dried under high vacuum (36 h at 50° C.) to give 82 mg of 23 as an off-white solid (69%).

Preparation of 24

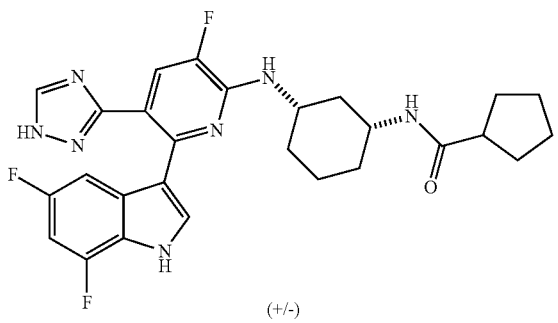

(+/-)

Step 1. A mixture of 2-(5,7-difluoro-1-tosyl-1H-indol-3-yl)-5-fluoro-6-(((cis)-3-(pyrrolidine-1-carboxamido)cyclohexyl)amino)nicotinamide (71 mg, 0.108 mmol) in DMFDMA (2.8 mL) was stirred at 105° C. for 2 h. The reaction mixture was evaporated until dryness. The crude material was diluted in AcOH (2.8 mL) and hydrazine monohydrate (37 µL. 0.759 mmol) was added. The mixture was heated at 100° C. for 1 h. The reaction mixture was evaporated until dryness. The residue was purified by preparative silica LC (mobile phase gradient: from DCM/MeOH/aq NH₃ 100/0/0 to 95/5/0.5) to give 41 mg of N-((cis)-3-((6-(5,7-difluoro-1-tosyl-1H-indol-3-yl)-3-fluoro-5-(1H-1,2,4-triazol-3-yl)pyridin-2-yl)amino)cyclohexyl)pyrrolidine-1-carboxamide as a white solid (56%).

Step 2. In a sealed tube, KOH (13 mg; 236 µmol) was added to a mixture of N-((cis)-3-((6-(5,7-difluoro-1-tosyl-1H-indol-3-yl)-3-fluoro-5-(1H-1,2,4-triazol-3-yl)-pyridin-2-yl)amino)cyclohexyl)pyrrolidine-1-carboxamide (16 mg, 23.6 µmol) in EtOH (1 mL) at rt. The mixture was stirred at rt for 5 h. Water, brine, NaHCO₃ (aq., sat.) and EtOAc were added to reaction mixture, the aqueous layer was extracted with EtOAc (twice). The combined organic layers were dried over MgSO₄, filtered and evaporated in vacuo. The residue was purified by preparative silica LC (mobile phase gradient: from DCM/MeOH/aq NH₃ 100/0/0 to 95/5/0.5) to give 7 mg of 24 (57%).

Synthesis of 25

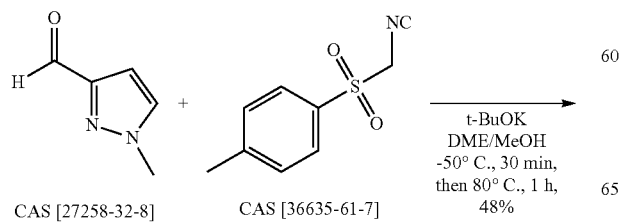

CAS [27258-32-8]   CAS [36635-61-7]

t-BuOK
DME/MeOH
-50° C., 30 min,
then 80° C., 1 h,
48%

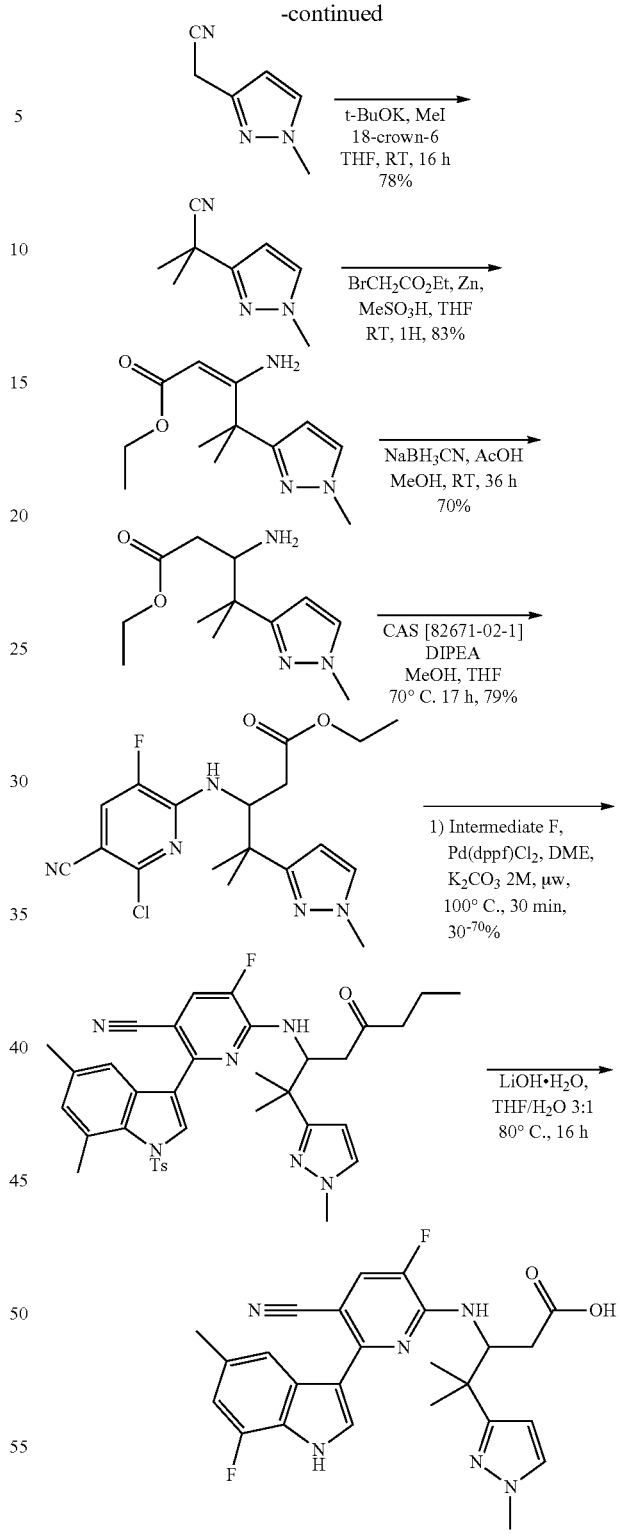

(+/-) 25

Preparation of 2-(1-methyl-1H-pyrazol-3-yl)acetonitrile

A solution of tosylmethyl isocyanide (17.8 g, 91.2 mmol) in DME (110 mL) under N₂ was added to a suspension of t-BuOK (19.5 g, 174 mmol) in MeOH (110 mL) dropwise at −50° C. A solution of 1-methyl-1H-pyrazole-3-carboxaldehyde (9.57 g, 86.9 mmol) in DME (110 mL) was added drop wise and the reaction mixture was stirred at −50° C. for 30 min. Then MeOH (110 mL) was added and the reaction mixture was heated to 80° C. for 1 h. The mixture was cooled to rt and the solvents were evaporated. Water and AcOH (approx. 10 mL) were added until pH=5-6. $CH_2Cl_2$ was added and the layers were separated. The organic layer was washed with water, dried over $MgSO_4$, filtered and evaporated in vacuo. Purification was performed by preparative silica chromatography (mobile phase gradient: from heptane/EtOAc 80/20 to 40/60) to give 2-(1-methyl-1H-pyrazol-3-yl)acetonitrile as a colorless oil.

Preparation of 2-methyl-2-(1-methyl-1H-pyrazol-3-yl)propanenitrile t-BuOK (14.5 g, 130 mmol) was added portionwise to a solution of 2-(1-methyl-1H-pyrazol-3-yl) 18-crown-6 (6.28 g, 51.8 mmol) in THF (200 mL) at 0° C. The mixture was stirred at 0° C. for 15 min before the slow addition of $CH_3I$ (9.7 mL, 156 mmol). The mixture was stirred at 0° C. for 15 min, then at rt for 16 h. The reaction mixture was quenched with aq. $NH_4Cl$ and extracted with EtOAc (twice). The combined organic layers were washed with brine, dried over $MgSO_4$, filtered and evaporated in vacuo. Purification was performed by preparative silica LC (mobile phase gradient: from heptane/EtOAc 80/20 to 0/100) to give 2-methyl-2-(1-methyl-1H-pyrazol-3-yl)propanenitrile as a colorless oil, 6 g, 78%.

Preparation of 3-amino-4-methyl-4-(1-methyl-1H-pyrazol-3-yl)pent-2-enoate

A suspension of activated zinc (10.5 g, 161 mmol) and methanesulfonic acid (800 μL. 12.3 mmol) in THF (65 mL) was heated at reflux for 15 min then 2-methyl-2-(1-methyl-1H-pyrazol-3-yl)propanenitrile (4.8 g, 32.2 mmol) in THF (15 mL) was added. Then ethylbromoacetate (10.7 mL, 96.7 mmol) in THF (50 mL) was added dropwise over 45 min. The mixture was stirred at reflux for 1 h then cooled down to rt then treated with $NaHCO_3$ (aq., sat.) filtered through a pad of celite and washed with EtOAc. The layers were separated. The organic layer was washed with brine, dried over $MgSO_4$, filtered and concentrated in vacuo. Purification was performed by preparative silica LC (mobile phase gradient: from heptane/EtOAc 80/20 to 50/50) to give ethyl 3-amino-4-methyl-4-(1-methyl-1H-pyrazol-3-yl)pent-2-enoate as a colorless oil.

Preparation of 3-amino-4-methyl-4-(1-methyl-1H-pyrazol-3-yl)pentanoate

Sodium cyanoborohydride (1.86 g, 29.6 mmol) was added to a solution of ethyl 3-amino-4-methyl-4-(1-methyl-1H-pyrazol-3-yl)pent-2-enoate (2.94 g, 12.4 mmol) in methanol (80 mL) and acetic acid (15 mL). The resulting mixture was stirred at rt for 56 h. The mixture was quenched by addition of water and the solvent was concentrated in vacuo. The resulting mixture was basify by addition of a solution of NaOH (1N) until pH=10-14, then extracted with $CH_2Cl_2$. The combined organic layers were washed with brine, dried over $MgSO_4$, filtered and concentrated in vacuo. Purification was performed by preparative silica LC (mobile phase gradient: from $CH_2Cl_2$/MeOH: 100/0 to 90/10) to give ethyl 3-amino-4-methyl-4-(1-methyl-1H-pyrazol-3-yl)pentanoate as a colorless oil 2.09 g, 70%.

Preparation of 3-((6-chloro-5-cyano-3-fluoropyridin-2-yl)amino)-4-methyl-4-(1-methyl-1H-pyrazol-3-yl)pentanoate A solution of 2,6-dichloro-5-fluoro-3-pyridinecarbonitrile (0.33 g, 1.74 mmol), ethyl 3-amino-4-methyl-4-(1-methyl-1H-pyrazol-3-yl)pentanoate (0.5 g, 2.09 mmol), N,N-diisopropylethylamine (1.8 mL, 10.45 mmol) in MeOH (5 mL) and THF (5 mL) was stirred and heated at 70° C. for 17 hours. The reaction mixture was concentrated under reduced pressure, the residue was taken up in water, extracted twice with EtOAc. The combined organic layers were washed with water, dried over $MgSO_4$, filtered and evaporated. Purification was carried out by flash chromatography over silica gel (heptane/EtOAc from 85/15 to 70/30). Pure fractions were collected and the solvent was evaporated to give ethyl 3-((6-chloro-5-cyano-3-fluoropyridin-2-yl)amino)-4-methyl-4-(1-methyl-1H-pyrazol-3-yl)pentanoate as colorless oil, 0.544 g, 79%.

Preparation of ethyl 3-((5-cyano-3-fluoro-6-(7-fluoro-5-methyl-1H-indol-3-yl)pyridin-2-yl)amino)-4-methyl-4-(1-methyl-1H-pyrazol-3-yl)pentanoate A solution of F (0.79 g, 1.01 mmol), ethyl 3-((6-chloro-5-cyano-3-fluoropyridin-2-yl)-amino)-4-methyl-4-(1-methyl-1H-pyrazol-3-yl)pentanoate (0.21 g, 0.56 mmol) and $K_2CO_3$ (1.12 mL, 2.23 mmol) in DME (12 mL) was purged with $N_2$ gas for 5 min and then Pd(dppf)$Cl_2$ (0.046 g, 0.056 mmol) was added. The resulting mixture was stirred and heated at 100° C. in the microwave for 30 min. The mixture was poured into water and $CH_2Cl_2$, the organic layer was separated with a hydrophobic frit and evaporated to dryness. Purification was carried out by flash chromatography over silica gel ($CH_2Cl_2$/MeOH from 100/0 to 98/2). Pure fractions were collected and evaporated to afford ethyl 3-((5-cyano-3-fluoro-6-(7-fluoro-5-methyl-1H-indol-3-yl)pyridin-2-yl)amino)-4-methyl-4-(1-methyl-1H-pyrazol-3-yl)pentanoate as a colorless oil, 0.363 g, 55%.

Preparation of 3-((5-cyano-3-fluoro-6-(7-fluoro-5-methyl-1H-indol-3-yl)pyridin-2-yl)-amino)-4-methyl-4-(1-methyl-1H-pyrazol-3-yl)pentanoic acid (25)

LiOH.$H_2O$ (0.12 g, 2.75 mmol) was added to a solution of ethyl 3-((5-cyano-3-fluoro-6-(7-fluoro-5-methyl-1H-indol-3-yl)pyridin-2-yl)amino)-4-methyl-4-(1-methyl-1H-pyrazol-3-yl)pentanoate (0.363 g, 0.55 mmol) in a mixture of THF/Water (3/1, 12 mL). The resulting solution was stirred and heated at 60° C. for 24 hours. LiOH.$H_2O$ (0.12 g, 2.75 mmol) was added and the resulting solution was heated to 60° C. for 18 hours. The solution was cooled down to room temperature. Water was added, the aqueous layer was acidified until pH=2 with 3N aq. HCl. The organic layer was extracted with EtOAc, separated, dried over $MgSO_4$, the solids were removed by filtration and the solvent of the filtrate was removed under reduced pressure. Purification was performed via preparative silica chromatography (mobile phase: 96% CH₂Cl₂, 4% MeOH). Pure fractions were collected and evaporated to give 25, 0.012 g, 4.6%.

Synthesis of 164

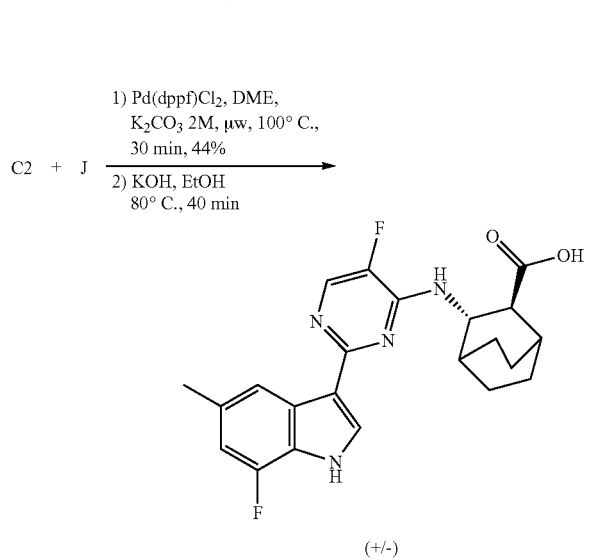

(+/-)

A solution of C2 (1.13 g, 1.58 mmol), J (0.41 g, 1.32 mmol) and K₂CO₃ (2 M aq., 2.63 mL, 5.26 mmol) in DME (14 mL) was purged with N₂ flow for 5 min and then dichloro[1,1'-bis(diphenylphosphino)ferrocene]palladium (II): complex with CH₂Cl₂ (0.11 g, 0.13 mmol) was added. The resulting mixture was stirred and heated at 100° C. in the microwave. The mixture was poured into water and CH₂Cl₂, the organic layer was separated with a hydrophobic frit and evaporated to dryness. Purification was carried out by flash chromatography over silica gel (heptane/EtOAc 70/30). Pure fractions were collected and evaporated to give 0.412 g, 51%.

A solution of (trans)-methyl 3-((5-fluoro-2-(7-fluoro-5-methyl-1-tosyl-1H-indol-3-yl)-pyrimidin-4-yl)amino)bicyclo[2.2.2]octane-2-carboxylate (0.34 g, 0.59 mmol) and potassium hydroxide (0.33 g, 5.89 mmol) in EtOH (8.5 mL) was stirred at 80° C. for 40 min. The solvent was evaporated under reduced pressure. H₂O and then HCl (3N aq., 1.96 mL, 5.89 mmol) was added. The solution was stirred at room temperature for 5 min. CH₂Cl₂ was added, and the organic layer was separated with a hydrophobic frit, a precipitate was isolated, washed with acetone and dried under vacuum at 50° C. for 16 hours. Purification was performed via reverse phase (stationary phase: X-Bridge-C18 5 μm 30×150 mm, mobile phase: gradient from 65% water (containing 0.05% TFA), 35% ACN to 25% water (containing 0.05% TFA), 75% ACN. Pure fractions were collected and the solvent was evaporated to give 0.083 g. The crude was crystallized from DIPE, isolated by filtration and dried under vacuum at 60° C. affording a white powder 164, as a TFA salt. Chiral separation via chiral SFC (stationary phase: Chiralpak AD-H 5 μm 250×30 mm, mobile phase: 60% CO₂, 40% isopropanol (0.3% isopropylamine)). Pure fractions were collected and the solvent was evaporated to afford two fractions. EtOAc was added, the organic layer was washed with KHSO₄ (aq. 10%×2), dried over MgSO₄, the solids were removed by filtration and the solvent of the filtrate was concentrated to dryness. The crude solids were freeze-dried with acetonitrile/water 2/8 overnight affording white powders, 165 and 166.

Synthesis of 167

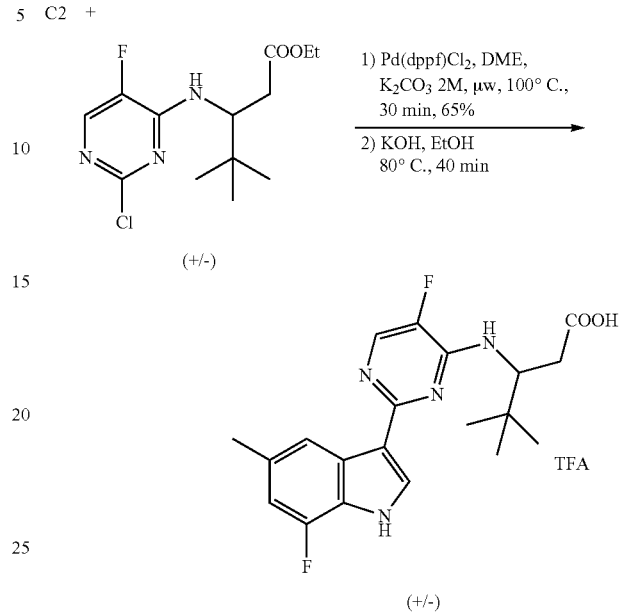

(+/-)

Step 1. A solution of C2 (1.23 g, 1.58 mmol), ethyl 3-((2-chloro-5-fluoropyrimidin-4-yl)amino)-4,4-dimethyl-pentanoate (0.4 g, 1.31 mmol) and K₂CO₃ (2 M aq., 2.63 mL, 5.26 mmol) in DME (14 mL) was purged with N₂ gas for 5 min, then dichloro[1,1'-bis(diphenylphosphino)ferrocene]palladium(III), complex with CH₂Cl₂ (0.11 g, 0.13 mmol) was added. The resulting mixture was stirred and heated at 100° C. in the microwave. The mixture was poured into water and CH₂Cl₂, the organic layer was separated with a hydrophobic frit and evaporated to dryness. Purification was carried out by flash chromatography over silica gel (heptane/EtOAc from 95/5 to 80/20). Pure fractions were collected and evaporated to give ethyl 3-((5-fluoro-2-(7-fluoro-5-methyl-1-tosyl-1H-indol-3-yl)pyrimidin-4-yl)amino)-4,4-dimethylpentanoate 0.485 g, 65%.

Step 2. To the product of step 1 was added potassium hydroxide (0.47 g, 8.32 mmol) in EtOH (12 mL) and the mixture was stirred at 80° C. for 40 min. The solvent was evaporated under reduced pressure. H₂O and then HCl 3N (2.77 mL, 8.32 mmol) was added. The solution was stirred at room temperature for 5 min. The precipitate was filtered off, washed with H₂O (2 mL) and dried under vacuum at 50° C. for 16 hours. Purification was performed via reverse phase chromatography (stationary phase: X-Bridge-C18 5 μm 30×150 mm, mobile phase: gradient from 65% water (containing 0.05% TFA), 35% ACN to 25% water (containing 0.05% TFA), 75% ACN). Pure fractions were collected and the solvent was evaporated to give 0.078 g. The residue was crystallized from DIPE, isolated by filtration and dried under vacuum at 60° C. affording 167 as a white powder, 0.060 g, 18%. Separation via chiral SFC (stationary phase: Chiralcel OJ-H 5 μm 250×20 mm, mobile phase: 90% CO₂, 10% CH₃OH (0.3% iPrNH₂)). The fractions were washed with KHSO₄ 10%, extracted with EtOAc, dried (MgSO₄), the solids removed by filtration, the solvent was evaporated to dryness, the solid lyophilized with CH₃CN/H₂O (80/20) to afford 0.062 g of 168, and 0.058 g of 169, 13%, m.p.=gum 144° C., OR=−34.61° (589 nm, c 0.27 w/v %, DMF, 20° C.).

Synthesis of N-((1R*,3S*)-3-((2-(5-cyano-7-fluoro-1H-indol-3-yl)-5-fluoropyrimidin-4-yl)amino)cyclohexyl)-1-methyl-1H-imidazole-4-carboxamide (170)

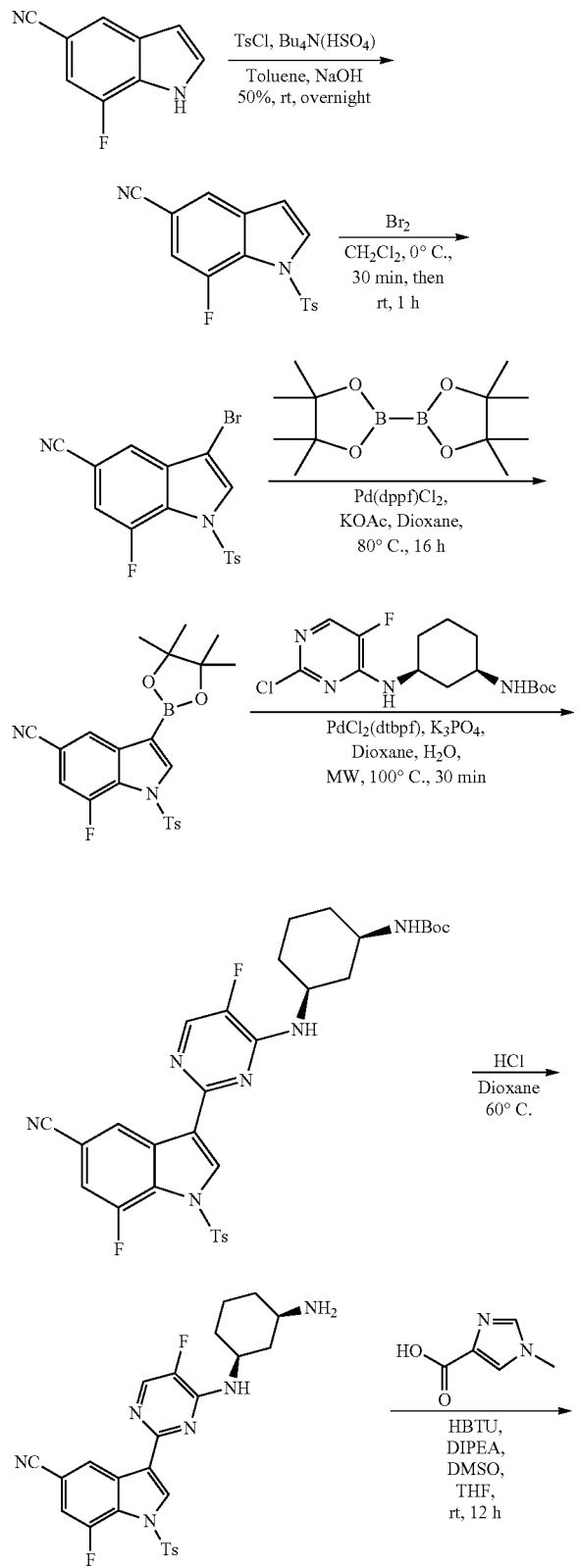

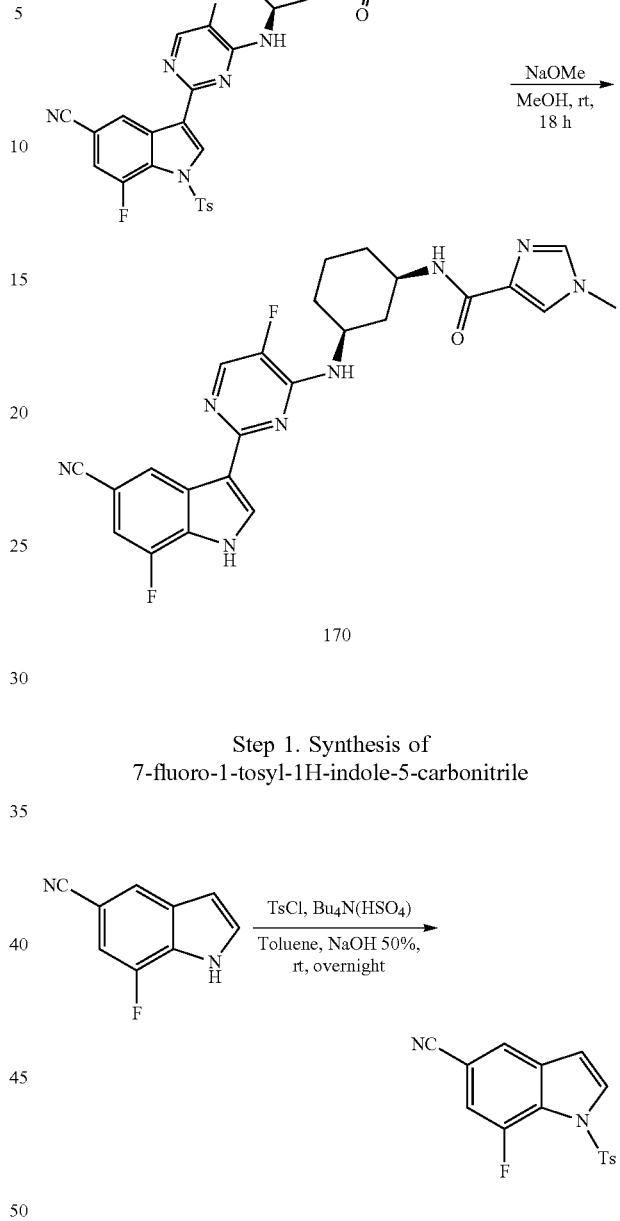

170

Step 1. Synthesis of 7-fluoro-1-tosyl-1H-indole-5-carbonitrile

7-Fluoro-1H-indole-5-carbonitrile (300 mg, 1.87 mmol) was added to toluene (3 mL) under nitrogen atmosphere. Tetrabutylammonium hydrogen sulphate (63.5 mg, 0.18 mmol) was added followed by NaOH (50% aq., 2 mL) and the mixture was stirred vigorously. Then, a solution of p-toluenesulfonyl chloride (535 mg, 2.81 mmol) in toluene (3 mL) was added and the mixture was stirred overnight. The reaction mixture was diluted with water and extracted with EtOAc. The organic layer was separated, dried and removed under reduced pressure to give a crude that was purified by silica flash column chromatography to yield 7-fluoro-1-tosyl-1H-indole-5-carbonitrile (360 mg, 1.14 mmol). LC-MS ES$^+$ m/z=315.0; Rt: 1.02 min, method E. $^1$H NMR (300 MHz, CDCl$_3$) δ 2.40 (s, 3H), 6.74 (m, 1H), 7.19 (d, J=11.4 Hz, 1H), 7.31 (d, J=8.1 Hz, 2H), 7.69 (br s, 1H), 7.81 (d, J=8.1 Hz, 2H), 7.91 (d, J=3.6 Hz, 1H).

Step 2. Synthesis of 3-bromo-7-fluoro-1-tosyl-1H-indole-5-carbonitrile

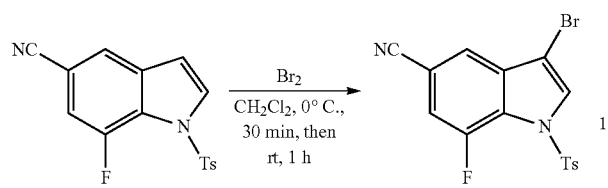

Bromine (0.05 mL, 0.99 mmol) was added slowly to a solution of 7-fluoro-1-tosyl-1H-indole-5-carbonitrile (260 mg, 0.82 mmol) in CH$_2$Cl$_2$ (3 mL) stirred at 0° C. for 30 min and then at room temperature for an additional hour. The reaction mixture was poured into water and treated with 5% sodium bisulfite solution and extracted with DCM. The organic layer was dried over MgSO$_4$ and removed under reduced pressure to yield 3-bromo-7-fluoro-1-tosyl-1H-indole-5-carbonitrile (300 mg, 0.76 mmol). LC-MS ES$^+$ m/z=392.9; Rt: 1.15 min, method E.

Step 3. Synthesis of 7-fluoro-3-(4,4,5,5-tetramethyl-1,3,2-dioxaborolan-2-yl)-1-tosyl-1H-indole-5-carbonitrile

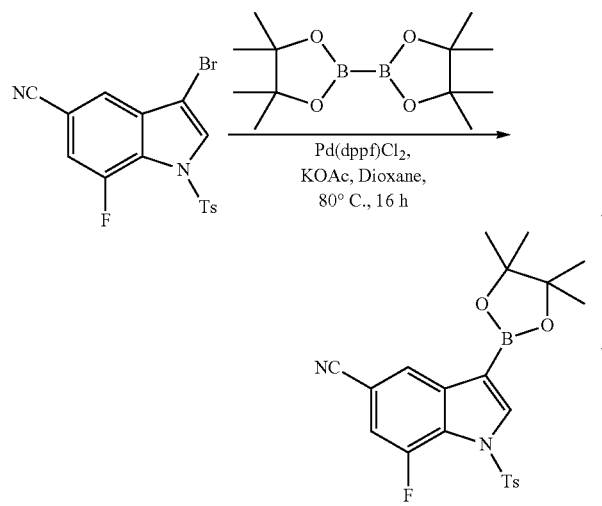

1,4-Dioxane (5 mL) was degassed for 10 minutes and then 3-bromo-7-fluoro-1-tosyl-1H-indole-5-carbonitrile (400 mg, 1.01 mmol), bis(pinacolato)diboron (774.9 mg, 3.05 mmol), [1,1'-bis(diphenylphosphino)ferrocene]dichloropalladium(II) (74.4 mg, 0.10 mmol) and potassium acetate (449.2 mg, 4.57 mmol) under inert atmosphere and the mixture stirred at 80° C. for 16 h. The mixture was filtered through a pad of Celite and further washed with EtOAc. The solvents were removed under reduced pressure to give a crude that was purified by column chromatography on silica gel to yield 7-fluoro-3-(4,4,5,5-tetramethyl-1,3,2-dioxaborolan-2-yl)-1-tosyl-1H-indole-5-carbonitrile (300 mg, 0.68 mmol). LC-MS ES$^+$ m/z=441.1; Rt: 1.32 min, method E.

Step 4. Synthesis of tert-butyl ((1R*,3S*)-3-((2-(5-cyano-7-fluoro-1-tosyl-1H-indol-3-yl)-5-fluoropyrimidin-4-yl)amino)cyclohexyl)carbamate

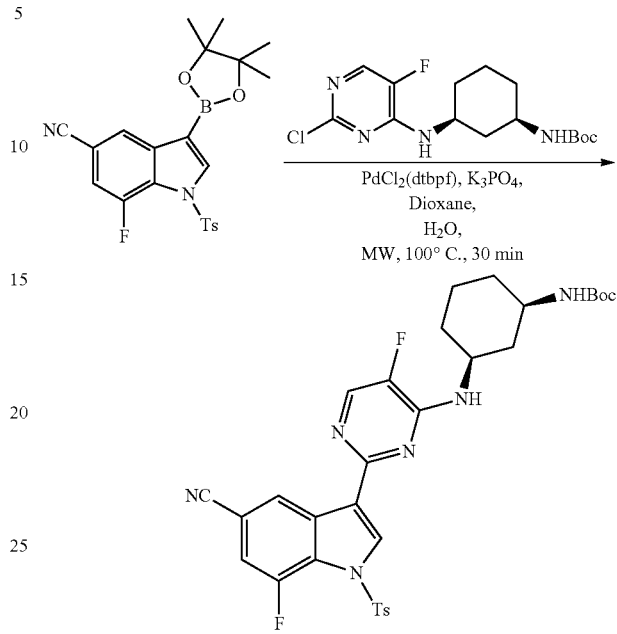

A mixture of 7-fluoro-3-(4,4,5,5-tetramethyl-1,3,2-dioxaborolan-2-yl)-1-tosyl-1H-indole-5-carbonitrile (300 mg, 0.68 mmol), tert-butyl ((1R*,3S*)-3-((2-chloro-5-fluoropyrimidin-4-yl)amino)cyclohexyl)carbamate (234 mg, 0.68 mmol), [1,1'-bis(di-tert-butylphosphino)ferrocene]dichloropalladium(II) (44.4 mg, 0.068 mmol) and tripotassium phosphate (434 mg, 2.04 mmol) in water (0.2 mL) and dioxane (2 mL) was purged with nitrogen and heated to 100° C. for 30 minutes under microwave irradiation. The reaction mixture was filtered through a pad of Celite and the solvent was evaporated. The residue was dissolved in DCM and washed with water. The organic layer was dried over MgSO$_4$ and removed under reduced pressure to give a crude that was purified by column chromatography on silica gel to yield tert-butyl ((1R*,3S*)-3-((2-(5-cyano-7-fluoro-1-tosyl-1H-indol-3-yl)-5-fluoropyrimidin-4-yl)amino)cyclohexyl)carbamate (200 mg, 0.32 mmol). LC-MS ES$^+$ m/z=623.2; Rt: 1.34 min, method E.

Step 5. Synthesis of 3-(4-(((1S*,3R*)-3-aminocyclohexyl)amino)-5-fluoropyrimidin-2-yl)-7-fluoro-1-tosyl-1H-indole-5-carbonitrile

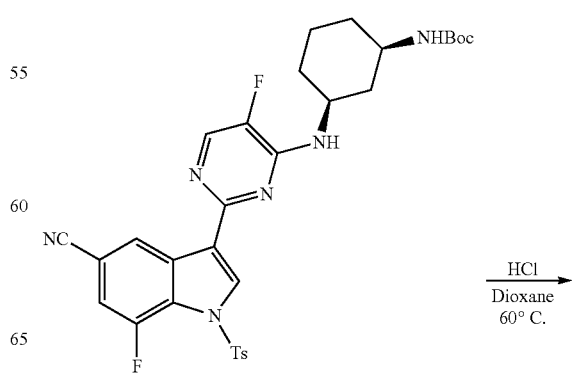

-continued

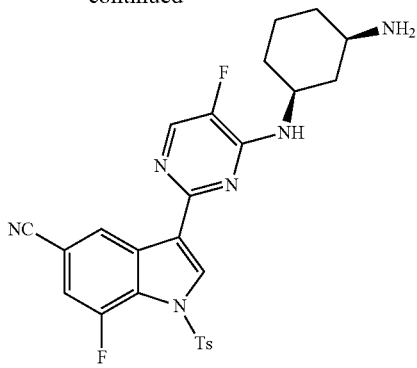

HCl 4M in dioxane (1.2 mL, 4.8 mmol) was added slowly to a solution of tert-butyl ((1R*,3S*)-3-((2-(5-cyano-7-fluoro-1-tosyl-1H-indol-3-yl)-5-fluoropyrimidin-4-yl)amino)cyclohexyl)carbamate (300 mg, 0.48 mmol) dissolved in dioxane (1.2 mL). The resulting solution was stirred at 60° C. overnight. The reaction mixture was quenched with a saturated NaHCO₃ solution and extracted with DCM. The organic layer was dried over MgSO₄ and evaporated to dryness to yield 3-(4-(((1S*,3R*)-3-aminocyclohexyl)amino)-5-fluoropyrimidin-2-yl)-7-fluoro-1-tosyl-1H-indole-5-carbonitrile (200 mg, 0.38 mmol). LC-MS ES⁺ m/z=523.2; Rt: 0.83 min, method E.

Step 6. Synthesis of N-((1R*,3S*)-3-((2-(5-cyano-7-fluoro-1-tosyl-1H-indol-3-yl)-5-fluoropyrimidin-4-yl)amino)cyclohexyl)-1-methyl-1H-imidazole-4-carboxamide

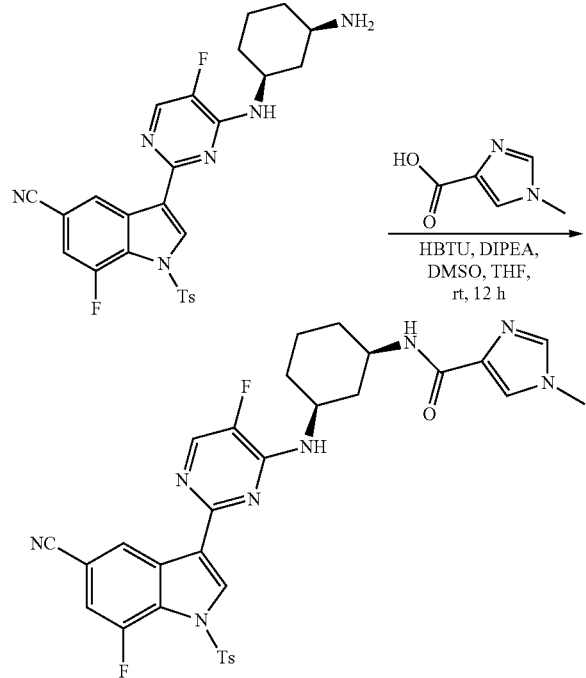

HBTU (522 mg, 1.38 mmol) was added to a solution of 1-methyl-1H-imidazole-4-carboxylic acid (50.7 mg, 0.40 mmol) in THF (2.5 mL) at room temperature for 5 minutes under inert atmosphere. Then, a solution of 3-(4-(((1S*,3R*)-3-amino-cyclohexyl)amino)-5-fluoropyrimidin-2-yl)-7-fluoro-1-tosyl-1H-indole-5-carbonitrile (200 mg, 0.38 mmol) and N,N-diisopropylethylamine (0.24 mL, 1.38 mmol) in DMSO (0.5 mL) was added and the stirring continued at room temperature for 12 hours. The reaction mixture was diluted with water and extracted with DCM. The organic layers were concentrated under reduced pressure to give a crude that was purified by column chromatography eluting with heptane-EtOAc to yield N-((1R*,3S*)-3-((2-(5-cyano-7-fluoro-1-tosyl-1H-indol-3-yl)-5-fluoropyrimidin-4-yl)amino)cyclohexyl)-1-methyl-1H-imidazole-4-carboxamide (150 mg, 0.23 mmol). LC-MS ES⁻ m/z=631.2; Rt: 1.09 min, method E.

Step 7. Synthesis of N-((1R*,3S*)-3-((2-(5-cyano-7-fluoro-1H-indol-3-yl)-5-fluoropyrimidin-4-yl)amino)cyclohexyl)-1-methyl-1H-imidazole-4-carboxamide (170)

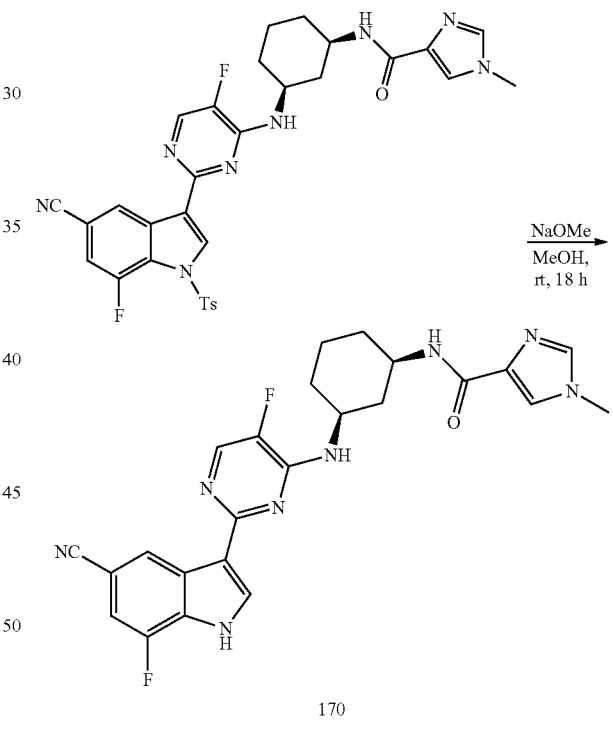

170

Sodium methoxide (0.54 mL of 25% w/v solution, 2.38 mmol) was added to a suspension of N-((1R*,3S*)-3-((2-(5-cyano-7-fluoro-1-tosyl-1H-indol-3-yl)-5-fluoropyrimidin-4-yl)amino)cyclohexyl)-1-methyl-1H-imidazole-4-carboxamide (150 mg, 0.24 mmol) in MeOH (3 mL) and the mixture was stirred at room temperature for 18 hours. The solvent was removed under reduced pressure to give a crude that was purified by reverse phase chromatography to yield N-((1R*,3S*)-3-((2-(5-cyano-7-fluoro-1H-indol-3-yl)-5-fluoropyrimidin-4-yl)amino)cyclohexyl)-1-methyl-1H-imidazole-4-carboxamide (170)(80 mg, 0.16 mmol).

Synthesis of N-(5-((2-(5,7-difluoro-1H-indol-3-yl)-5-fluoropyrimidin-4-yl)amino)-3,3-dimethylcyclohexyl)-1-methyl-1H-imidazole-4-carboxamide (202)

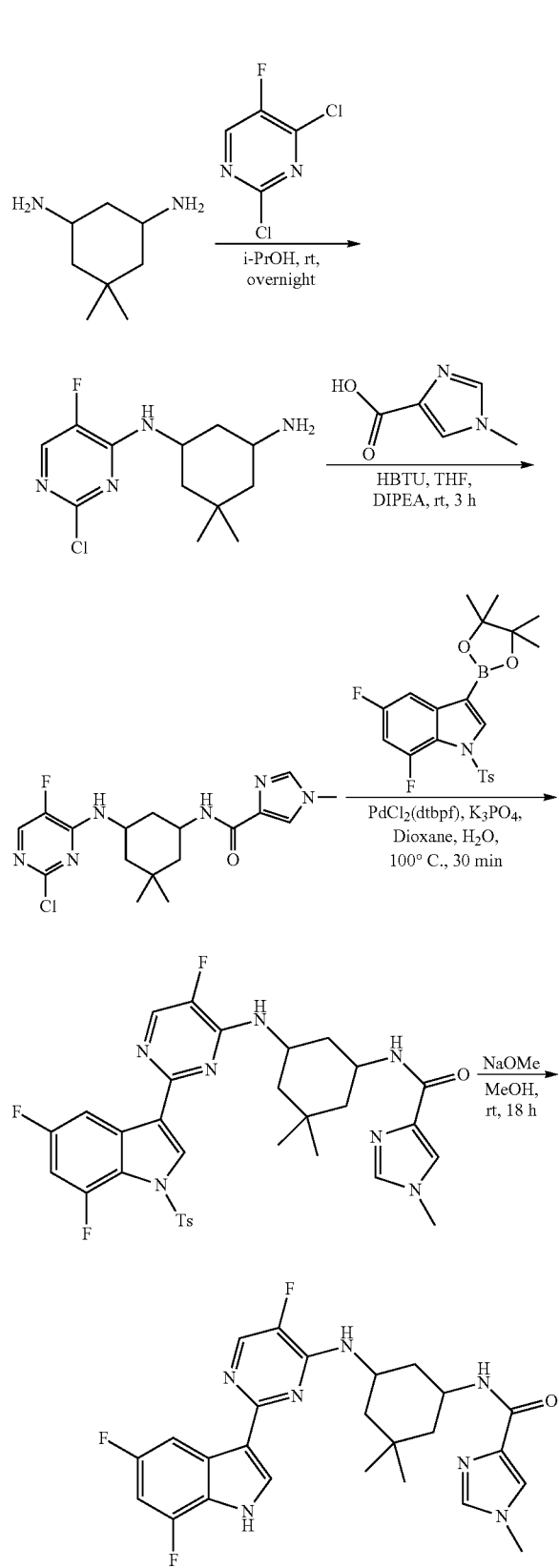

Step 1. Synthesis of $N^1$-(2-chloro-5-fluoropyrimidin-4-yl)-5,5-dimethylcyclohexane-1,3-diamine

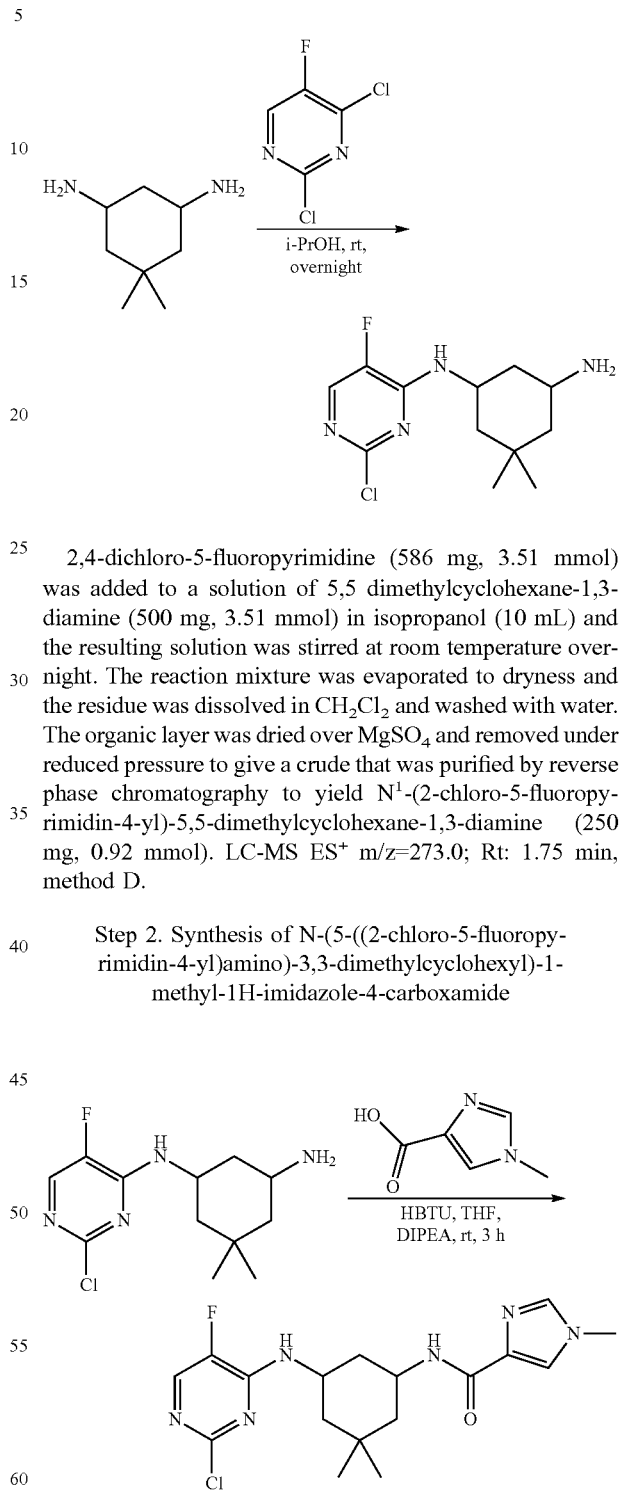

2,4-dichloro-5-fluoropyrimidine (586 mg, 3.51 mmol) was added to a solution of 5,5 dimethylcyclohexane-1,3-diamine (500 mg, 3.51 mmol) in isopropanol (10 mL) and the resulting solution was stirred at room temperature overnight. The reaction mixture was evaporated to dryness and the residue was dissolved in $CH_2Cl_2$ and washed with water. The organic layer was dried over $MgSO_4$ and removed under reduced pressure to give a crude that was purified by reverse phase chromatography to yield $N^1$-(2-chloro-5-fluoropyrimidin-4-yl)-5,5-dimethylcyclohexane-1,3-diamine (250 mg, 0.92 mmol). LC-MS $ES^+$ m/z=273.0; Rt: 1.75 min, method D.

Step 2. Synthesis of N-(5-((2-chloro-5-fluoropyrimidin-4-yl)amino)-3,3-dimethylcyclohexyl)-1-methyl-1H-imidazole-4-carboxamide HBTU (428 mg, 1.13 mmol) was added to a solution of 1-methyl-1H-imidazole-4-carboxylic acid (258 mg, 2.05 mmol) in THF (1 mL) at room temperature for 5 minutes under inert atmosphere. Then, a solution of $N^1$-(2-chloro-5-fluoropyrimidin-4-yl)-5,5-dimethylcyclohexane-1,3-diamine (280 mg, 1.03 mmol) and N,N-diisopropylethylamine (0.45 mL, 2.57 mmol) in THF (1 mL) was added and the stirring continued at room temperature for 3 hours. The reaction mixture was diluted with water and extracted with CH₂Cl₂. The organic layers were separated, dried over MgSO₄ and concentrated under reduced pressure to give a crude that was purified by column chromatography on silica gel eluting with CH₂Cl₂—CH₃OH to yield N-(5-((2-chloro-5-fluoropyrimidin-4-yl)amino)-3,3-dimethyl cyclohexyl)-1-methyl-1H-imidazole-4-carboxamide (350 mg, 0.92 mmol). LC-MS ES⁺ m/z=381.1; Rt: 0.630 and 0.65 min, method E.

Step 3. Synthesis of a Cis/Trans Mixture of N-(5-((2-(5,7-difluoro-1-tosyl-1H-indol-3-yl)-5-fluoropyrimidin-4-yl)amino)-3,3-dimethylcyclohexyl)-1-methyl-1H-imidazole-4-carboxamide

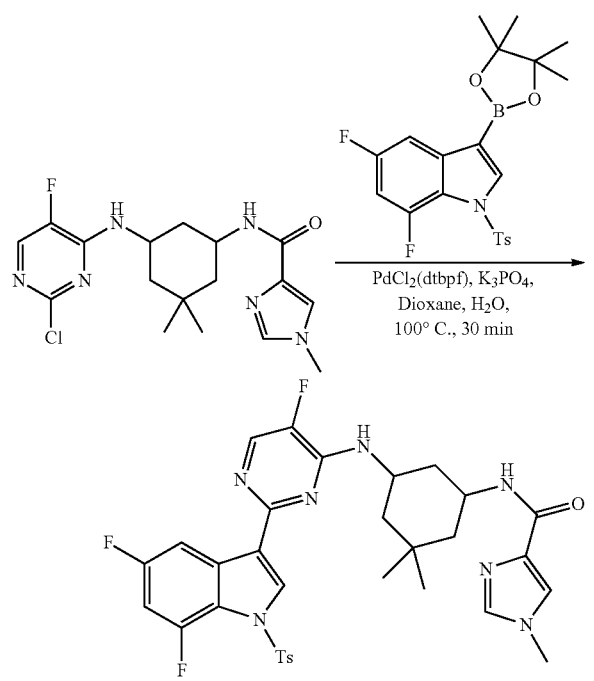

5,7-difluoro-3-(4,4,5,5-tetramethyl-1,3,2-dioxaborolan-2-yl)-1-tosyl-1H-indole (300 mg, 0.69 mmol), N-(5-((2-chloro-5-fluoropyrimidin-4-yl)amino)-3,3-dimethylcyclohexyl)-1-methyl-1H-imidazole-4-carboxamide (316 mg, 0.83 mmol), tripotassium phosphate (440 mg, 2.08 mmol) and [1,1'-bis(di-tert-butylphosphino)ferrocene]dichloropalladium(II) (45 mg, 0.07 mmol) were added to a degassed mixture of dioxane (4 mL) and water (1 mL) under inert atmosphere. The mixture was stirred at 100° C. for 30 min. The reaction mixture was filtered through a pad of Celite, washed with EtOAc and the solvents were evaporated to dryness to give a crude that was purified by column chromatography on silica gel to yield N-(5-((2-(5,7-difluoro-1-tosyl-1H-indol-3-yl)-5-fluoropyrimidin-4-yl)amino)-3,3-dimethylcyclohexyl)-1-methyl-1H-imidazole-4-carboxamide (250 mg, 0.38 mmol). LC-MS ES⁺ m/z=652.2; Rt: 1.24 min, method E.

Step 4. Synthesis of a Cis/Trans Mixture of N-(5-((2-(5,7-difluoro-1H-indol-3-yl)-5-fluoropyrimidin-4-yl)amino)-3,3-dimethylcyclohexyl)-1-methyl-1H-imidazole-4-carboxamide (202)

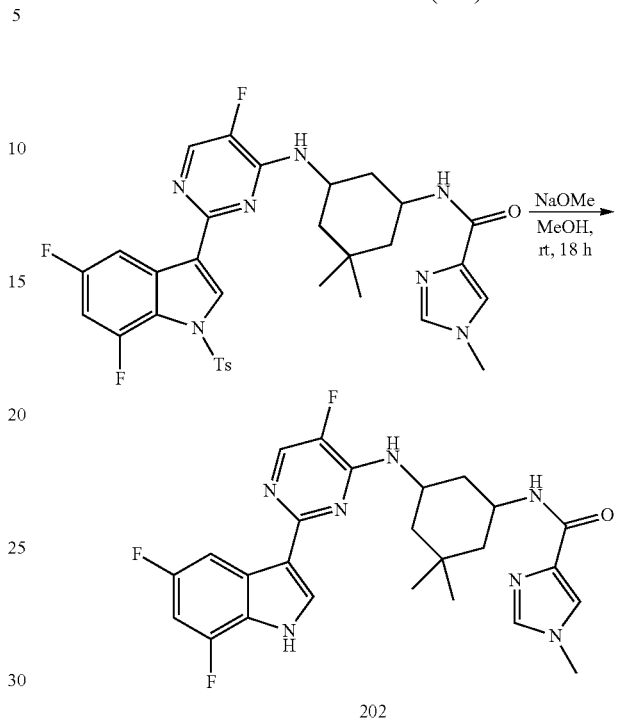

Sodium methoxide (0.87 mL of 25% w/v solution, 3.84 mmol) was added to a suspension of a cis/trans mixture of N-(5-((2-(5,7-difluoro-1-tosyl-1H-indol-3-yl)-5-fluoropyrimidin-4-yl)amino)-3,3-dimethylcyclohexyl)-1-methyl-1H-imidazole-4-carboxamide (250 mg, 0.38 mmol) in MeOH (4 mL) and the mixture was stirred at room temperature for 18 hours. The solvent was removed under reduced pressure to give a crude that was purified by reverse phase chromatography to yield a cis/trans mixture of N-(5-((2-(5,7-difluoro-1H-indol-3-yl)-5-fluoropyrimidin-4-yl)amino)-3,3-dimethylcyclohexyl)-1-methyl-1H-imidazole-4-carboxamide (202) (100 mg, 0.19 mmol).

Synthesis of (+/−)-(2-exo, 3-endo)-3-((2-(5,7-difluoro-1H-indol-3-yl)-5-fluoropyrimidin-4-yl)amino)bicyclo[2.2.1]heptane-2-carboxylic Acid

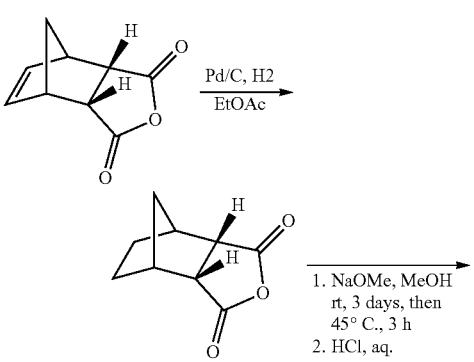

-continued

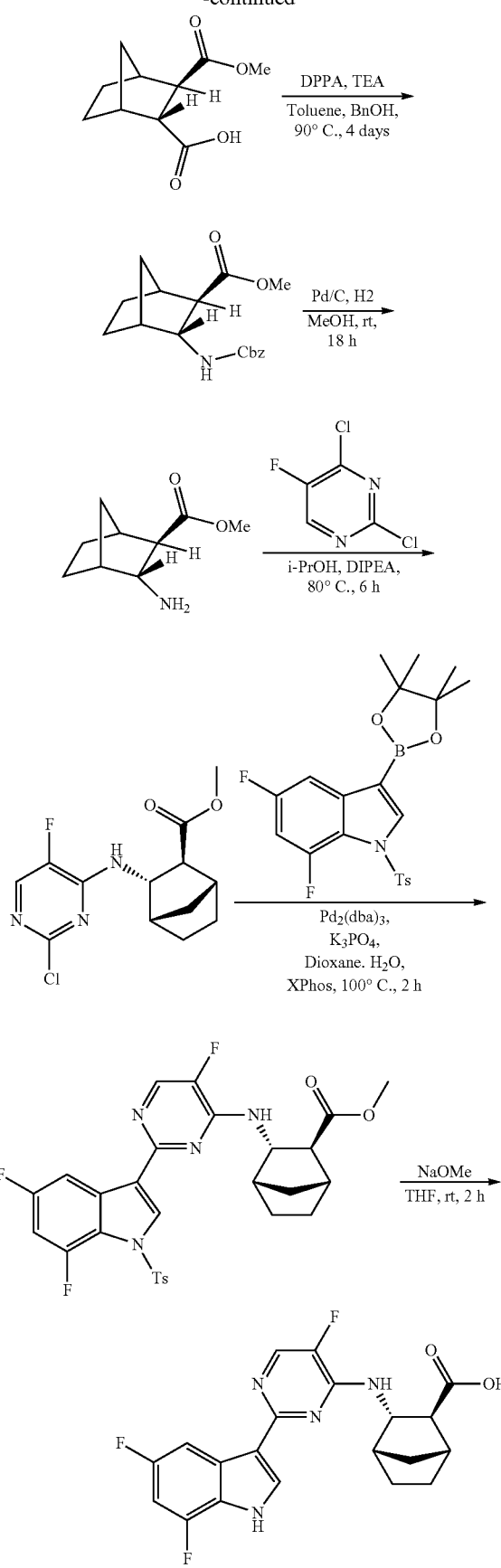

Step 1. Synthesis of bicyclo[2.2.1]heptane-2,3-endo-dicarboxylic Anhydride

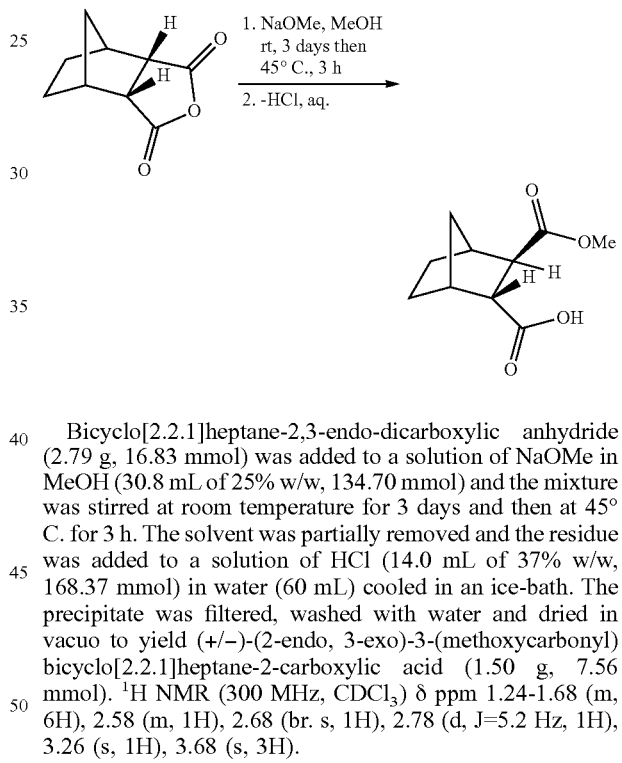

The compound bicyclo[2.2.1]heptane-2,3-endo-dicarboxylic anhydride was prepared in accordance to the procedure described in Birney, David et al., *J. Am. Chem. Soc.*, 2002, 124 (18), 5091-5099.

Step 2. Synthesis of (+/−)-(2-endo, 3-exo)-3-(methoxycarbonyl)bicyclo[2.2.1]-heptane-2-carboxylic Acid

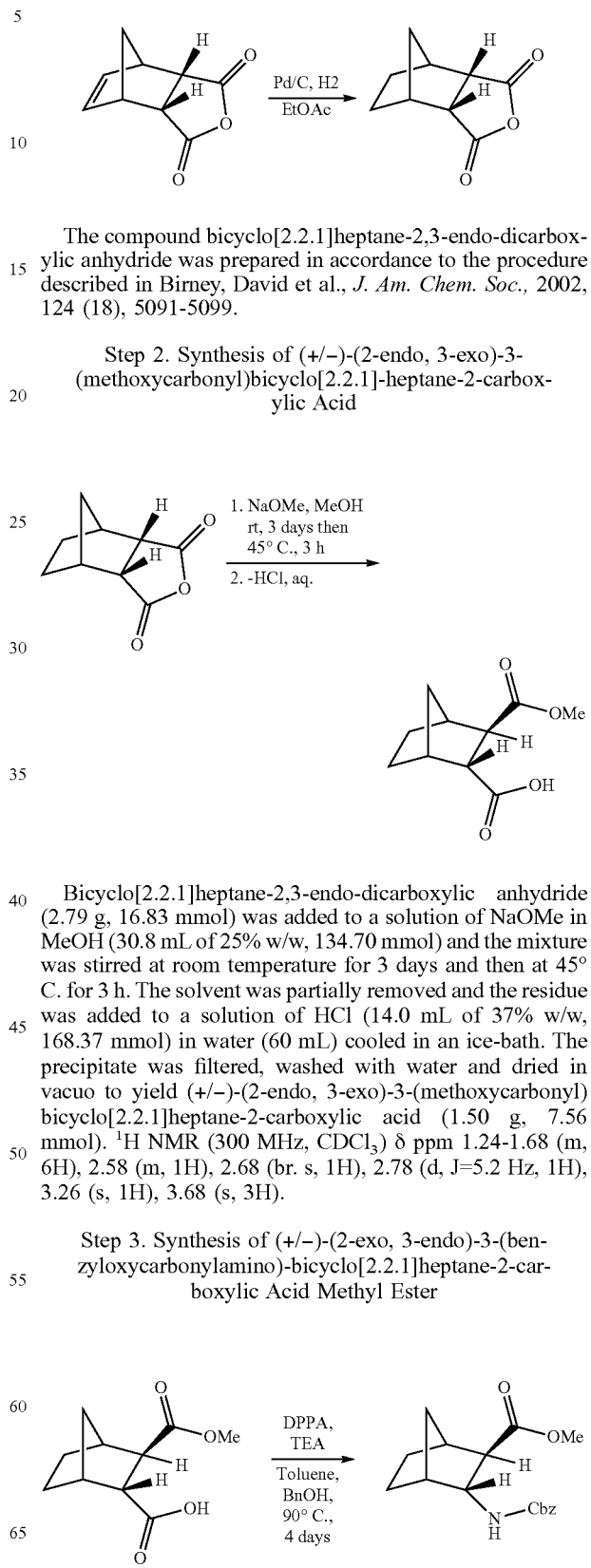

Bicyclo[2.2.1]heptane-2,3-endo-dicarboxylic anhydride (2.79 g, 16.83 mmol) was added to a solution of NaOMe in MeOH (30.8 mL of 25% w/w, 134.70 mmol) and the mixture was stirred at room temperature for 3 days and then at 45° C. for 3 h. The solvent was partially removed and the residue was added to a solution of HCl (14.0 mL of 37% w/w, 168.37 mmol) in water (60 mL) cooled in an ice-bath. The precipitate was filtered, washed with water and dried in vacuo to yield (+/−)-(2-endo, 3-exo)-3-(methoxycarbonyl)bicyclo[2.2.1]heptane-2-carboxylic acid (1.50 g, 7.56 mmol). $^1$H NMR (300 MHz, CDCl$_3$) δ ppm 1.24-1.68 (m, 6H), 2.58 (m, 1H), 2.68 (br. s, 1H), 2.78 (d, J=5.2 Hz, 1H), 3.26 (s, 1H), 3.68 (s, 3H).

Step 3. Synthesis of (+/−)-(2-exo, 3-endo)-3-(benzyloxycarbonylamino)-bicyclo[2.2.1]heptane-2-carboxylic Acid Methyl Ester

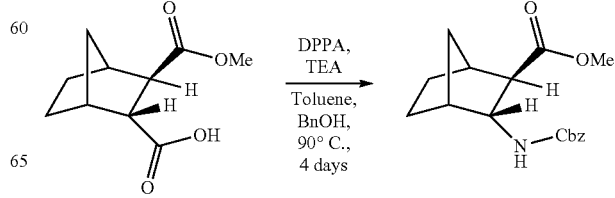

Diphenylphosphoryl azide (1.73 mL, 8.04 mmol) was added to a solution of (+/−)-(2-endo, 3-exo)-3-(methoxycarbonyl)bicyclo[2.2.1]heptane-2-carboxylic acid (1.45 g, 7.31 mmol) and triethylamine (1.02 mL, 7.31 mmol) in toluene (15 mL). The reaction mixture was stirred at 90° C. for 2 hours. Then, benzyl alcohol (0.75 mL, 7.31 mmol) was added and the mixture was stirred at 90° C. for 4 days. The mixture was cooled to room temperature, diluted with EtOAc and washed with NaHCO$_3$ (aq., sat.). The organic layer was separated, dried and removed under reduced pressure to give a crude that was purified eluting with heptane-EtOAc (100:0 to 80:20) to yield (+/−)-(2-exo, 3-endo)-3-(benzyloxycarbonylamino)bicyclo[2.2.1]heptane-2-carboxylic acid methyl ester (1.78 g, 5.86 mmol). LC-MS ES$^+$ m/z=304.1; Rt: 0.87 min, method E.

Step 4. Synthesis of (+/−)-(2-exo, 3-endo)-3-aminobicyclo[2.2.1]heptane-2-carboxylic Acid Methyl Ester

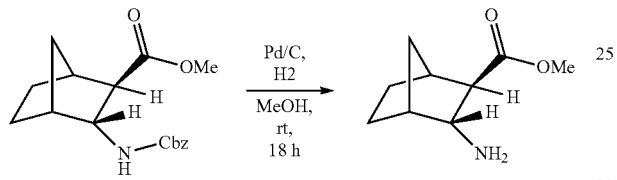

Pd/C 10% (248 mg) was added to a solution of (+/−)-(2-exo, 3-endo)-3-(benzyloxy-carbonylamino)bicyclo[2.2.1]heptane-2-carboxylic acid methyl ester (1.77 g, 5.83 mmol,) in MeOH (20 mL) and the suspension was stirred at room temperature under hydrogen atmosphere (5 bar) at 25° C. for 24 h. The reaction mixture was filtered through a pad of Celite and the solvent was removed under reduced pressure to yield (+/−)-(2-exo, 3-endo)-3-aminobicyclo[2.2.1]heptane-2-carboxylic acid methyl ester (920 mg, 5.43 mmol) that was used without further purification. LC-MS ES$^+$ m/z=170.1; Rt: 0.13 min, method E Step 5. Synthesis of (+/−)-(2-exo, 3-endo)-3-((2-chloro-5-fluoropyrimidin-4-yl)-amino)bicyclo[2.2.1]heptane-2-carboxylic Acid Methyl Ester

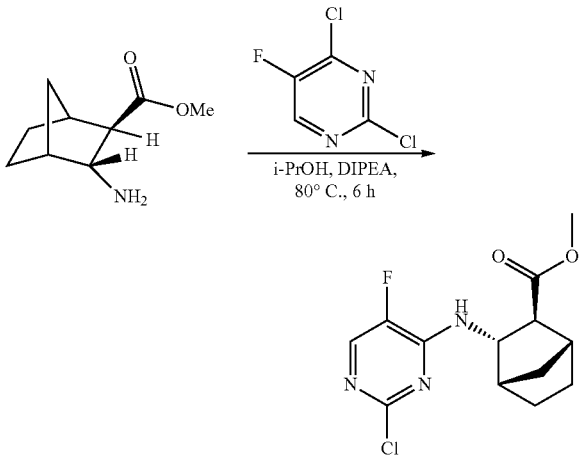

A mixture of (+/−)-(2-exo, 3-endo)-3-aminobicyclo[2.2.1]heptane-2-carboxylic acid methyl ester (861 mg, 5.08 mmol), 2,4-dichloro-5-fluoropyrimidine (1.02 g, 6.10 mmol) and N,N-diisopropylethylamine (1.77 mL, 10.17 mmol) in isopropyl alcohol (15 mL) was stirred at 80° C. for 6 hours. The mixture was diluted in EtOAc and washed with water and brine. The organic layer was dried with MgSO$_4$ and removed under reduced pressure to give a crude that was purified by flash column chromatography eluting with heptane-EtOAc (100:0 to 80:20) to yield (+/−)-(2-exo, 3-endo)-3-((2-chloro-5-fluoropyrimidin-4-yl)amino)bicyclo[2.2.1]heptane-2-carboxylic acid methyl ester (739 mg, 2.46 mmol). $^1$H NMR (300 MHz, CDCl$_3$) δ ppm 1.31-1.42 (m, 2H), 1.50-1.62 (m, 2H), 1.64-1.77 (m, 1H), 1.91 (d, J=10.4 Hz, 1H), 2.02 (d, J=3.4 Hz, 1H), 2.50 (m, 1H), 2.63 (br. s, 1H), 3.75 (s, 3H), 4.44 (q, J=4.8 Hz, 1H), 5.34 (br. signal, 1H), 7.87 (d, J=2.7 Hz, 1H).

Step 6. Synthesis of (+/−)-(2-exo, 3-endo)-3-((2-(5,7-difluoro-1-tosyl-1H-indol-3-yl)-5-fluoropyrimidin-4-yl)amino)bicyclo[2.2.1]heptane-2-carboxylic Acid Methyl Ester

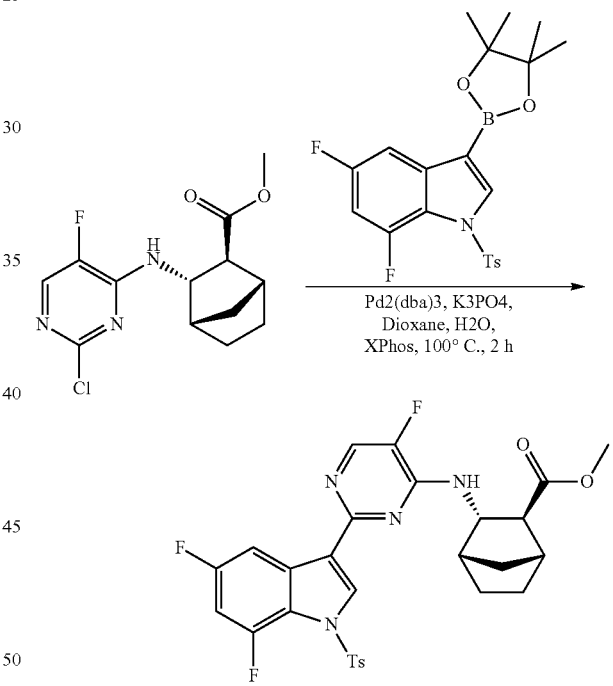

A mixture of 5,7-difluoro-3-(4,4,5,5-tetramethyl-[1,3,2]dioxaborolan-2-yl)-1-tosyl-1H-indole (100 mg, 0.23 mmol) and (+/−)-(2-exo, 3-endo)-3-((2-chloro-5-fluoropyrimidin-4-yl)amino)bicyclo[2.2.1]heptane-2-carboxylic acid methyl ester (76 mg, 0.25 mmol) in dioxane (4 mL) and water (1 mL) was purged with nitrogen at room temperature for 10 min. Then, Pd$_2$(dba)$_3$ (11 mg, 0.012 mmol), tripotassium phosphate (147 mg, 0.69 mmol) and XPhos (11 mg, 0.023 mmol) were added and the mixture was stirred at 100° C. for 2 hours. The mixture was filtered through a pad of Celite and washed with EtOAc. The solvent was removed under reduced pressure and the crude was purified by flash column chromatography on silica gel eluting with heptane-EtOAc (100:0 to 65:35) to yield (+/−)-(2-exo, 3-endo)-3-((2-(5,7-difluoro-1-tosyl-1H-indol-3-yl)-5-fluoropyrimidin-4-yl)

amino)bicyclo[2.2.1]heptane-2-carboxylic acid methyl ester (54 mg, 0.095 mmol). LC-MS ES⁻ m/z=571.2; Rt: 1.42 min, method E.

Step 7. Synthesis of (+/−)-(2-exo, 3-endo)-3-((2-(5, 7-difluoro-1H-indol-3-yl)-5-fluoropyrimidin-4-yl) amino)bicyclo[2.2.1]heptane-2-carboxylic Acid (217)

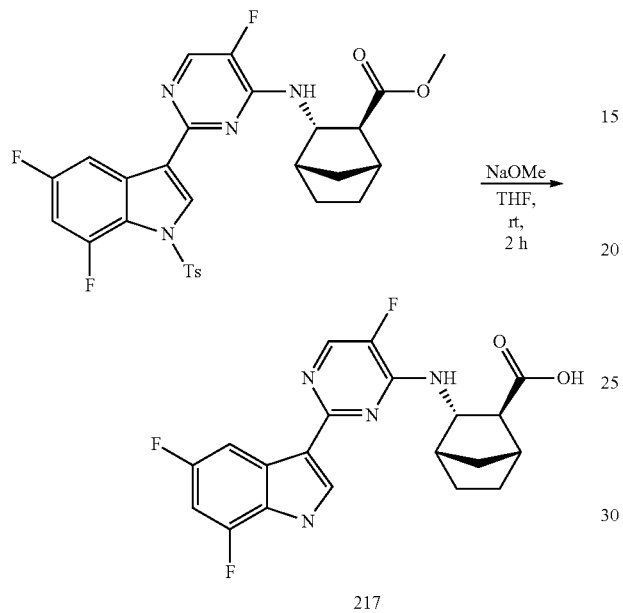

217

NaOCH₃ (3 mL, 25% w/w in CH₃OH, 13.12 mmol) was added to a solution of (+/−)-(2-exo, 3-endo)-3-((2-(5,7-difluoro-1-tosyl-1H-indol-3-yl)-5-fluoropyrimidin-4-yl) amino)bicyclo[2.2.1]heptane-2-carboxylic acid methyl ester (326 mg, 0.57 mmol) in THF (3 mL) and the mixture was stirred at room temperature for 2 hours under inert atmosphere. The solvent was removed under reduced pressure and the crude was purified by reverse phase chromatography to yield (+/−)-(2-exo, 3-endo)-3-((2-(5,7-difluoro-1H-indol-3-yl)-5-fluoropyrimidin-4-yl)amino)bicyclo[2.2.1]heptane-2-carboxylic acid (217)(105 mg, 0.26 mmol).

Synthesis of 2-(((1R*,3S*)-3-((2-(5,7-difluoro-1H-indol-3-yl)-5-fluoropyrimidin-4-yl)amino)cyclohexyl)carbamoyl)benzoic Acid

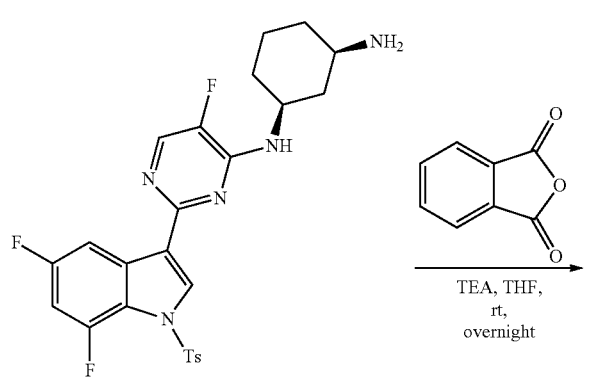

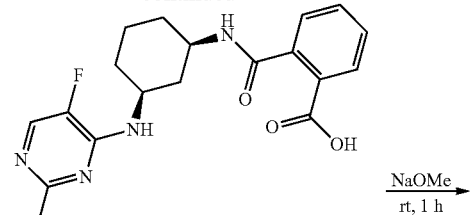

Step 1. Synthesis of 2-(((1R*,3S*)-3-((2-(5,7-difluoro-1-tosyl-1H-indol-3-yl)-5-fluoropyrimidin-4-yl)amino)cyclohexyl)carbamoyl)benzoic Acid

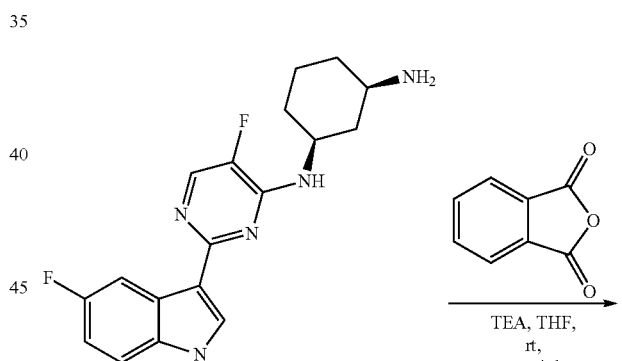

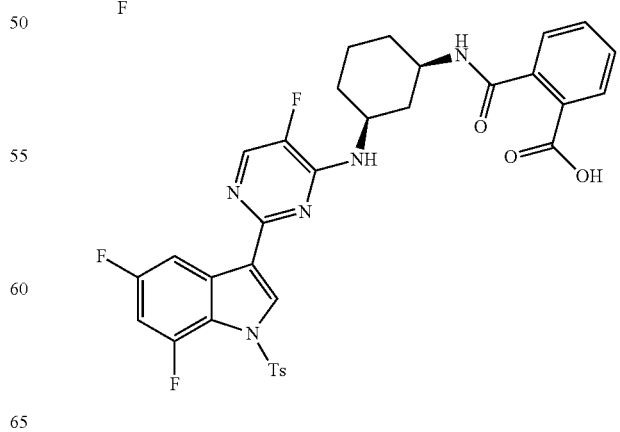

Phthalic anhydride (15 mg, 0.097 mmol) was added to a solution of (1S*,3R*)—N¹-(2-(5,7-difluoro-1-tosyl-1H-indol-3-yl)-5-fluoropyrimidin-4-yl)cyclohexane-1,3-diamine (50 mg, 0.097 mmol), triethylamine (0.014 mL, 0.097 mmol) in THF (4 mL) and the mixture was stirred at room temperature overnight. The reaction mixture was evaporated to dryness under reduced pressure to give 2-(((1R*,3S*)-3-((2-(5,7-difluoro-1-tosyl-1H-indol-3-yl)-5-fluoropyrimidin-4-yl)amino)cyclohexyl)carbamoyl)-benzoic acid (64 mg, 0.097). LC-MS ES+ m/z=663.9; Rt: 1.67 min, method G.

Step 2. Synthesis of 2-(((1R*,3S*)-3-((2-(5,7-difluoro-1H-indol-3-yl)-5-fluoropyrimidin-4-yl)amino)cyclohexyl)carbamoyl)benzoic Acid(224)

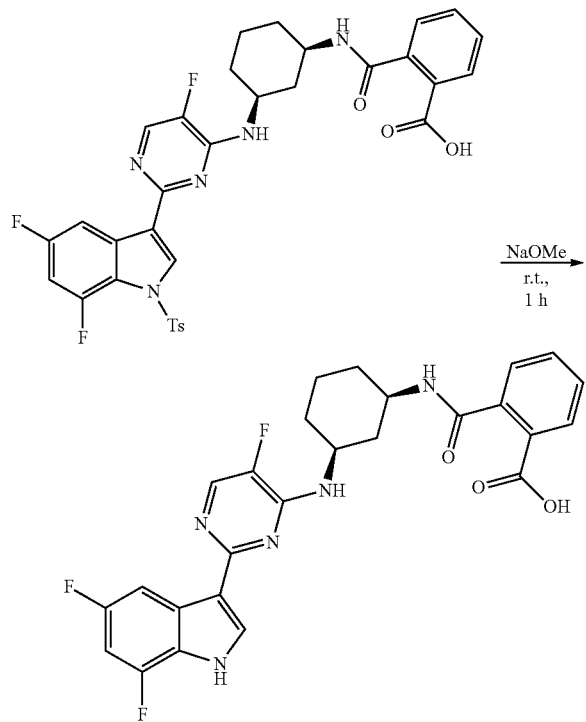

Sodium methoxide (0.22 mL of 25% w/v solution, 0.97 mmol) was added to a solution of 2-(((1R*,3S*)-3-((2-(5,7-difluoro-1-tosyl-1H-indol-3-yl)-5-fluoropyrimidin-4-yl)amino)cyclohexyl)carbamoyl)benzoic acid (129 mg, 0.19 mmol) was dissolved in methanol (5 mL) and the mixture was stirred at room temperature for 12 h. The solvent was removed under reduced pressure to give a crude that was purified by reverse phase chromatography to yield 2-(((1R*,3S*)-3-((2-(5,7-difluoro-1H-indol-3-yl)-5-fluoropyrimidin-4-yl)amino)cyclohexyl)carbamoyl)benzoic acid (224) (58 mg, 0.11 mmol).

Preparation of N-((1R*,3S*)-3-((2-(5,7-difluoro-1H-indol-3-yl)-5-fluoropyrimidin-4-yl)-amino)cyclohexyl)-1-methyl-3-(methylsulfonamido)-1H-pyrazole-5-carboxamide (226)

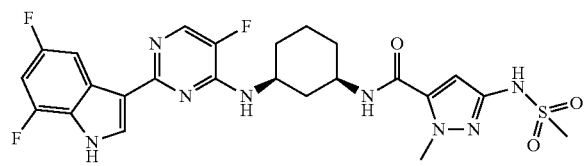 [SMILES: Cn1nc(NS(C)(=O)=O)cc1C(=O)N[C@@H]1CCC[C@H](Nc2nc(-c3c[nH]c4c(F)cc(F)cc34)ncc2F)C1]

3-amino-N-((1R*,3S*)-3-((2-(5,7-difluoro-1-tosyl-1H-indol-3-yl)-5-fluoropyrimidin-4-yl)amino)cyclohexyl)-1-methyl-1H-pyrazole-5-carboxamide (350 mg, 0.548 mmol) and N,N-diisopropylethylamine (0.472 mL, 2.74 mmol) were stirred in anhydrous 1,2-dichloroethane (6 mL) at room temperature, then MsCl (0.085 mL, 1.09 mmol) in 1,2-dichloroethane (1 mL) was added drop-wise. The mixture was stirred at room temperature for 3 h, then partitioned between CH$_2$Cl$_2$ and water. The organic layers were combined, washed with brine, dried over sodium sulfate, the solids were removed by filtration, and the solvent of the filtrate was removed under reduced pressure. To the resulting solid was added tetrabutylammonium fluoride (1M THF, 10 mL) and the mixture was heated at reflux for 4 h, then concentrated under reduced pressure and reconstituted in CH$_2$Cl$_2$ (40 mL), washed with water (4×25 mL), followed by brine (25 mL). The organic layers were dried over sodium sulfate, the solids were removed by filtration, and the solvent of the filtrate was concentrated under reduced pressure. The crude was purified via preparatory HPLC (stationary phase: RP XBridge Prep C18 ODB-5 µm, 30×250 mm, mobile phase: 0.5% aq. NH$_4$Ac+10% CH$_3$CN, MeOH). The desired fractions were collected and reduced in volume under reduced pressure. The aqueous layer was basified with aq. NaHCO$_3$ and extracted with EtOAc. The organic layer was dried with MgSO$_4$, the solids were removed by filtration and the solvent of the filtrate was removed under reduced pressure to afford N-((1R*3S*)-3-((2-(5,7-difluoro-1H-indol-3-yl)-5-fluoropyrimidin-4-yl)amino)cyclohexyl)-1-methyl-3-(methylsulfonamido)-1H-pyrazole-5-carboxamide (226).

Preparation of N-((1R*,3S*)-3-((2-(5,7-difluoro-1H-indol-3-yl)-5-fluoropyrimidin-4-yl)-amino)cyclohexyl)-1-methyl-3-(sulfamoylamino)-1H-pyrazole-5-carboxamide (227)

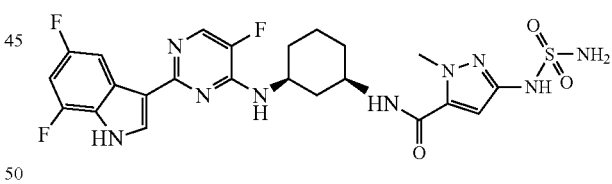

Step 1. To a solution of 3-amino-N-((1R*,3S*)-3-((2-(5,7-difluoro-1-tosyl-1H-indol-3-yl)-5-fluoropyrimidin-4-yl)amino)cyclohexyl)-1-methyl-1H-pyrazole-5-carboxamide (350 mg, 0.548 mmol) and pyridine (40 µL. 0.49 mmol) in 1,2-dichloroethane (3.5 mL) was added a solution of sulfamoyl chloride (89 µL. 1.37 mmol) in 1,2-dichloroethane (0.5 mL). The reaction was heated to 60° C. for one hour. Upon cooling, the reaction mixture was concentrated in vacuo, diluted with EtOAc and washed with 1 M HCl and water. The organic layer was dried over MgSO$_4$, filtered, concentrated in vacuo. The crude was used without further purification in the next step.

Step 2. In a 100 mL flask N-((1R*,3S*)-3-((2-(5,7-difluoro-1-tosyl-1H-indol-3-yl)-5-fluoropyrimidin-4-yl)amino)cyclohexyl)-1-methyl-3-(sulfamoylamino)-1H-pyrazole-5-carboxamide (300 mg, 0.418 mmol) was stirred in 1,4-dioxane (9 mL) at rt, while a solution of LiOH (200 mg, 8.36 mmol) in water (1 mL) was added. The mixture was brought between 80 and 90° C. for approximately 4 hours. 1,4-dioxane was evaporated and the residue was purified via preparatory HPLC (stationary phase: RP XBridge Prep C18 ODB-5 µm, 30×250 mm, mobile phase: 0.25% aq. NH$_4$HCO$_3$, CH$_3$OH). The desired fractions were collected and evaporated to dryness to afford a solid, 227.

Preparation of 3-acetamido-N-((1R*,3S*)-3-((2-(5,7-difluoro-1H-indol-3-yl)-5-fluoropyrimidin-4-yl)amino)cyclohexyl)-1-methyl-1H-pyrazole-5-carboxamide(228)

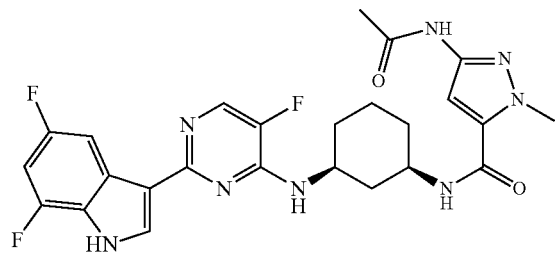 [SMILES: CC(=O)Nc1cc(C(=O)N[C@@H]2CCC[C@H](Nc3nc(-c4c[nH]c5c(F)cc(F)cc45)ncc3F)C2)n(C)n1]

Step 1. A mixture of 3-amino-N-((1R*,3S*)-3-((2-(5,7-difluoro-1-tosyl-1H-indol-3-yl)-5-fluoropyrimidin-4-yl)amino)cyclohexyl)-1-methyl-1H-pyrazole-5-carboxamide (350 mg, 0.548 mmol) in Ac$_2$O (2 mL) was stirred at 40° C. for 2 h. The solvent was removed under reduced pressure. The crude was used without purification in the next step.

Step 2. Deprotection of the tosyl group occurred according to the method used in step 2 to prepare 227. The crude was purified via preparatory HPLC (stationary phase: RP XBridge Prep C18 ODB-5 µm, 30×250 mm, mobile phase: 0.5% aq. NH$_4$Ac+10% CH$_3$CN, MeOH). The desired fractions were collected and reduced in volume under reduced pressure. The water layer was basified with aq. NaHCO$_3$ and extracted with EtOAc. The organic layer was dried over MgSO$_4$, the solids were removed by filtration, and the solvent of the filtrate evaporated to dryness to afford the titled compound, 228, as a solid.

Preparation of 3-((5-cyano-6-(5,7-difluoro-1H-indol-3-yl)-3-fluoropyridin-2-yl)amino)-4-methyl-4-(thiophen-2-yl)pentanoic Acid(229)

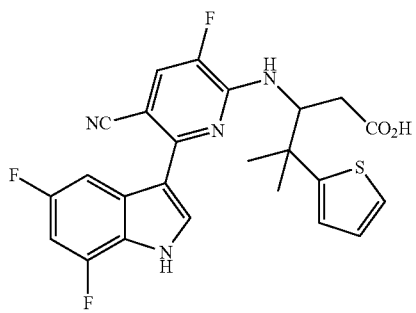 [SMILES: CC(C)(c1cccs1)C(CC(=O)O)Nc1nc(-c2c[nH]c3c(F)cc(F)cc23)c(C#N)cc1F]

The titled compound was prepared employing an analogous method as the one to prepare 3-((5-cyano-3-fluoro-6-(7-fluoro-5-methyl-1H-indol-3-yl)pyridin-2-yl)amino)-4-methyl-4-(1-methyl-1H-pyrazol-3-yl)pentanoic acid (25) starting from 2-methyl-2-(thiophen-2-yl)propanenitrile.

Preparation of 3-((5-cyano-6-(5,7-difluoro-1H-indol-3-yl)-3-fluoropyridin-2-yl)amino)-4-methyl-4-(thiazol-2-yl)pentanoic Acid (242)

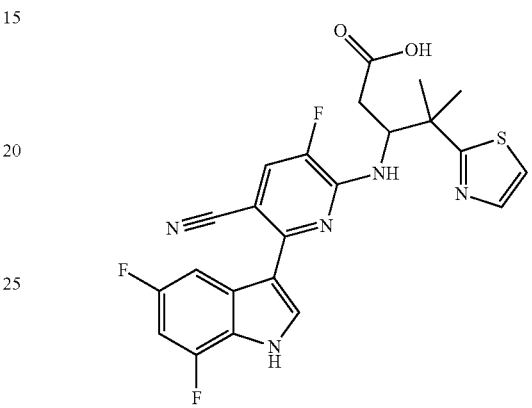

The titled compound was prepared employing an analogous method as the one to prepare 3-((5-cyano-6-(5,7-difluoro-1H-indol-3-yl)-3-fluoropyridin-2-yl)amino)-4-methyl-4-(thiophen-2-yl)pentanoic acid(229) starting from 2-methyl-2-(thiazol-2-yl)-propanenitrile.

Preparation of 2-methyl-2-(thiazol-2-yl)propanenitrile

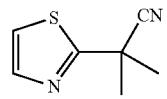

t-BuOK (4.74 g, 42.3 mmol) was added to a solution of 2-(thiazol-2-yl)acetonitrile (2.10 g, 16.9 mmol) in THF (65 mL), at 0° C. 18-crown-6 (0.670 g, 2.50 mmol) was added to the mixture. The mixture was stirred at 0° C. for 15 minutes and iodomethane (2.57 mL, 50.7 mmol) was added drop-wise at 0° C. The reaction mixture was stirred at 0° C. for 15 minutes then at rt overnight. NH$_4$Cl (aq., sat.) was added. The reaction mixture was extracted with ethyl acetate (2×150 mL), dried over Na$_2$SO$_4$, the solids removed by filtration and the solvent of the filtrate was concentrated under reduced pressure. The residue was purified by preparative silica LC (mobile phase: cyclohexane/EtOAc gradient: from 90/10 to 70/30) to give 1.64 g of the titled compound as a yellow liquid (64%).

Preparation of 3-((5-cyano-6-(5,7-difluoro-1H-indol-3-yl)-3-fluoropyridin-2-yl)amino)-4-methyl-4-(pyridin-2-yl)pentanoic Acid (237)

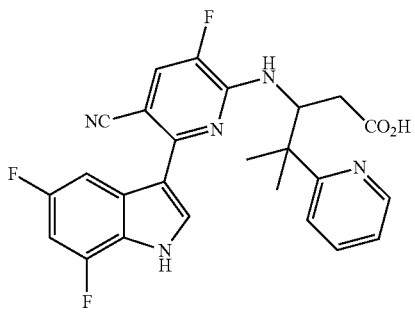 [SMILES: CC(C)(c1ccccn1)C(CC(=O)O)Nc1nc(-c2c[nH]c3c(F)cc(F)cc23)c(C#N)cc1F]

The titled compound was prepared employing an analogous method as the one to prepare 3-((5-cyano-3-fluoro-6-(7-fluoro-5-methyl-1H-indol-3-yl)pyridin-2-yl)amino)-4-methyl-4-(1-methyl-1H-pyrazol-3-yl)pentanoic acid (25) starting from 2-methyl-2-(pyridin-2-yl)propanenitrile.

Preparation of 3-((5-cyano-6-(5,7-difluoro-1H-indol-3-yl)-3-fluoropyridin-2-yl)amino)-4-methoxy-4-methylpentanoic Acid (240)

Preparation of Intermediate E2

(Carbethoxymethylene)triphenylphosphorane (12 g, 34 mmol) was added in one portion to a mixture of compound E1 (2.3 g, 22 mmol) in dry DCM (144 mL) and stirred at rt overnight. The mixture was concentrated and purified by preparative silica LC (mobile phase gradient: heptane/EtOAc from 90/10 to 80/20) to give 0.82 g of intermediate E2 as colorless oil (21%).

Preparation of Intermediate E3

Et$_3$N (0.99 mL, 7.1 mmol) was added to a mixture of intermediate E2 (820 mg, 4.8 mmol) and N-benzylhydroxylamine hydrochloride (0.99 g, 6.2 mmol) in dry DCM (30 mL) and stirred at rt overnight. The mixture was concentrated and purified by preparative silica LC (mobile phase gradient: heptane/EtOAc from 90/10 to 70/30) to give 0.64 g of E3 as colorless oil (54%).

Preparation of Intermediate E4

A solution of intermediate E3 (640 mg, 2.6 mmol) in EtOH (30 mL) was hydrogenated under 5 bar with B (721 mg; 0.52 mmol) as catalyst for 18 h. The mixture was diluted with MeOH and filtered through a pad of Celite®. The solvent was removed in vacuo to give 457 mg of E4 as a grey solid (97%, purity 88%).

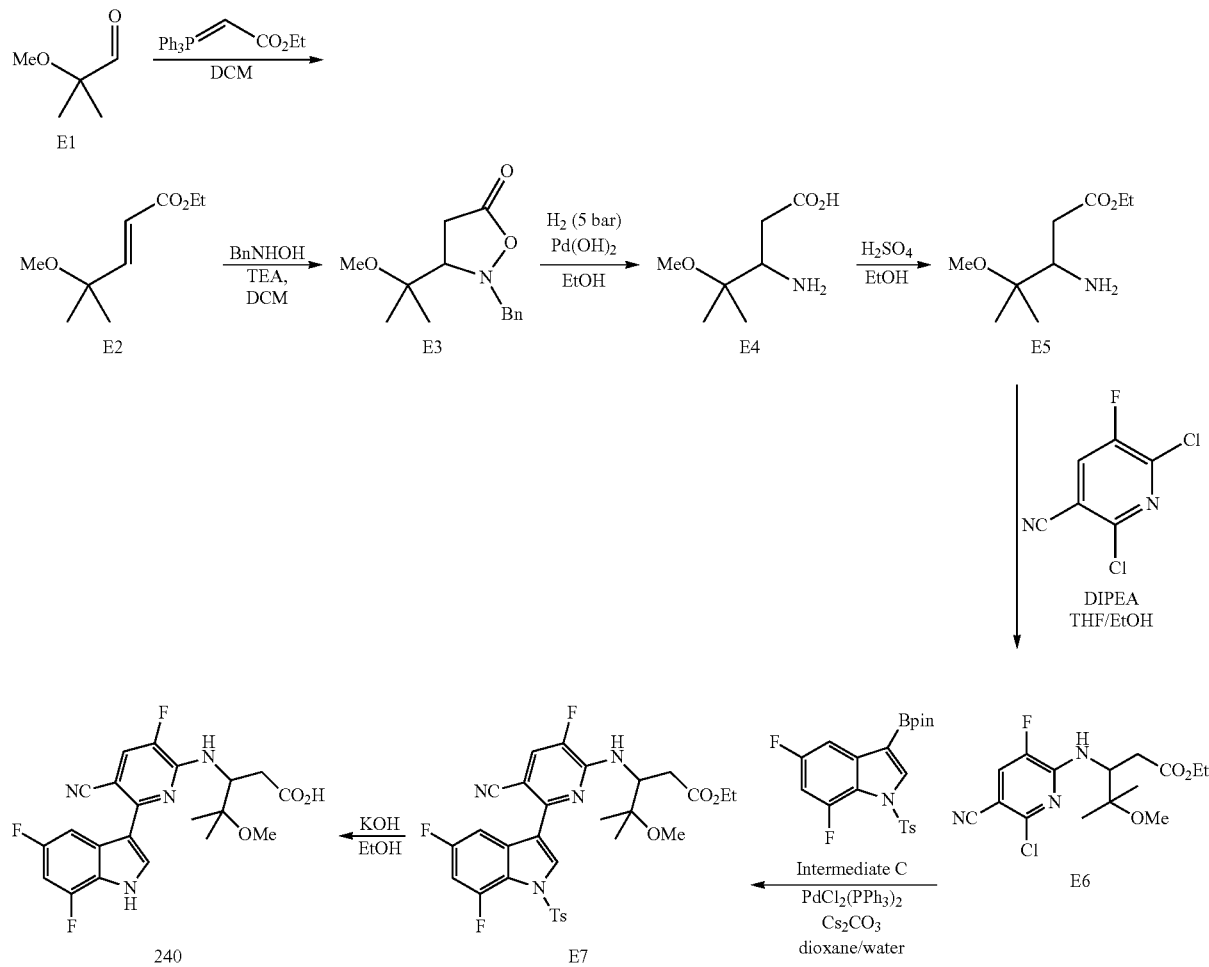

Preparation of Intermediate E5

Concentrated H$_2$SO$_4$ (0.27 mL; 5.0 mmol) was added to a solution of intermediate E4 (0.457 g; 2.50 mmol) in EtOH (17 mL). The reaction mixture was heated at 70° C. for 1 h30. The mixture was concentrated, reconstituted in EtOAc and NaHCO$_3$ (aq., sat). The aqueous layer was extracted with DCM (3 times). The combined organic layers were dried over MgSO$_4$, filtered and evaporated in vacuo to give 230 mg of E5 as a colorless oil (49%).

Preparation of Intermediate E6

2,6-Dichloro-3 cyano-5 fluoropyridine (0.23 g; 1.2 mmol), DIPEA (1.1 mL, 6.1 mmol), intermediate E5 (0.23 g, 1.2 mmol) in THF (3.0 mL) and EtOH (3.0 mL) were heated at 90° C. for 18 h in a sealed tube. EtOAc was added and washed twice with brine. The organic layer was dried over MgSO$_4$, filtered and evaporated in vacuo and was purified by preparative silica LC (mobile phase gradient: from heptane/AcOEt 80/20 to 70/30) to give 0.195 g of E6 as a white solid (47%).

Preparation of Intermediate E7

Under N$_2$, in a sealed tube, a mixture of C (144 mg; 0.33 mmol), E6 (95 mg; 0.28 mmol) and Cs$_2$CO$_3$ (0.32 g; 0.97 mmol) in dioxane (2.4 mL) and distilled water (0.75 mL) was degassed with N$_2$ for 5 min. PdCl$_2$(PPh$_3$)$_2$ (19 mg, 28 μmol) was added and the reaction mixture was degassed again with N$_2$ for 2 min. The reaction mixture was heated at 90° C. for 2 h. The reaction mixture was cooled down to rt. DCM and brine were added to the reaction mixture. The aqueous layer was extracted with DCM. The combined organic layers were washed with brine, dried over MgSO$_4$, filtered off, concentrated to dryness and purified by preparative silica LC (mobile phase gradient: from Heptane/EtOAc 90/10 to 70/30) to give 71 mg of E7 as a white solid.

Preparation of 3-((5-cyano-6-(5,7-difluoro-1H-indol-3-yl)-3-fluoropyridin-2-yl)amino)-4-methoxy-4-methylpentanoic Acid (240)

A solution of LiOH.H$_2$O (24 mg, 0.58 mmol) in distilled water (0.22 mL) was added to a mixture of intermediate E7 (71 mg, 0.12 mmol) in THF (0.64 mL). The mixture was stirred for 18 h at 60° C. The solution was evaporated in vacuo and purified by preparative silica LC (mobile phase: DCM/MeOH/AcOH 98/2/0.2) to give a colorless oil which was freeze-dried in MeCN/H2O to give 28 mg as a white solid. This solid was taken up in CH$_3$CN and washed 3 times with pentane, CH$_3$CN was evaporated in vacuo and the residue was freeze-dried in CH$_3$CN/H$_2$O to give 25 mg of 3-((5-cyano-6-(5,7-difluoro-1H-indol-3-yl)-3-fluoropyridin-2-yl)amino)-4-methoxy-4-methylpentanoic acid (240) as a white solid (50%).

Preparation of 3-((5-cyano-6-(5,7-difluoro-1H-indol-3-yl)-3-fluoropyridin-2-yl)amino)-4,4-dimethyl-hept-6-enoic Acid 241

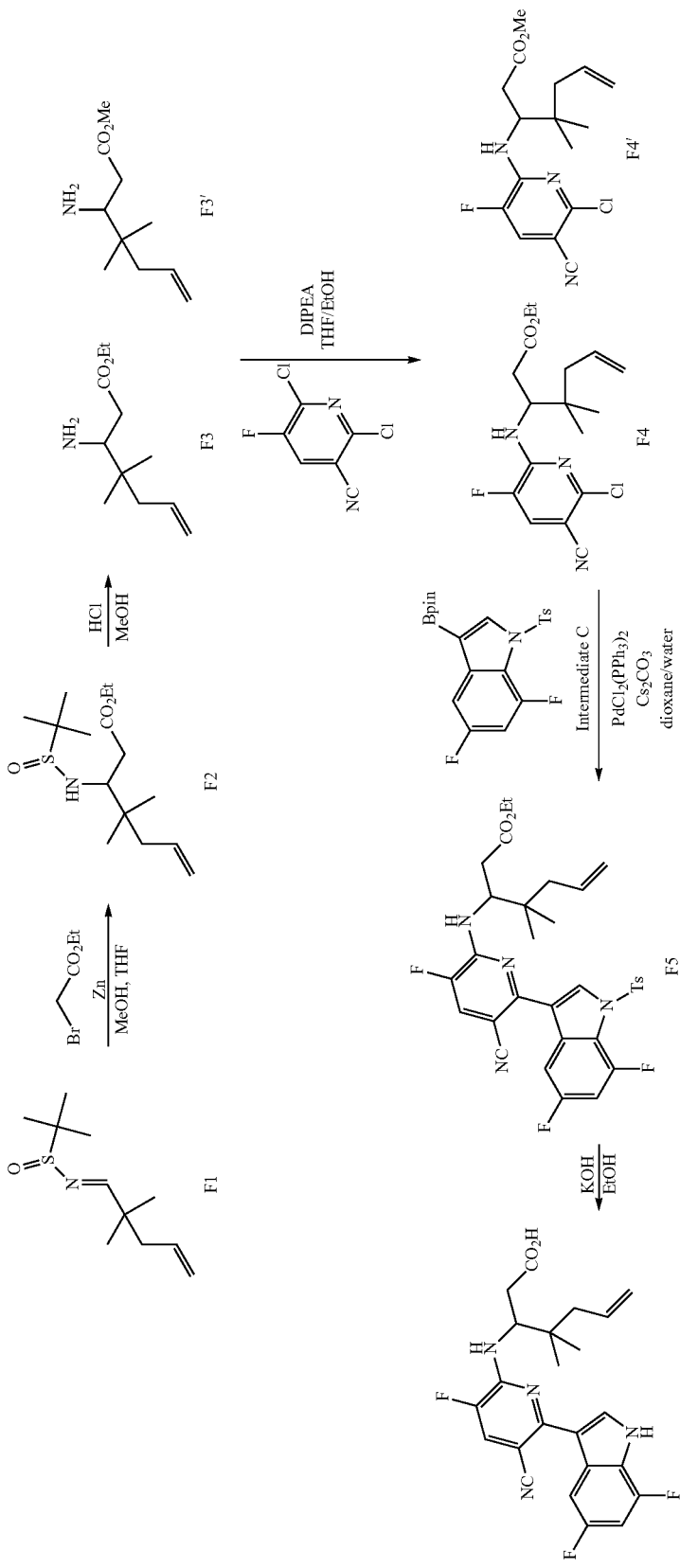

Preparation of Intermediate F1

To a mixture of 2,2-dimethyl-4-pentanal (3.68 g, 32.8 mmol) and 2-methyl-2-propanesulfinamide (4.77 g, 39.4 mmol) in anhydrous $CH_2Cl_2$ (225 mL) was added drop-wise titanium(IV) ethoxide (9.8 mL, 39.4 mmol) at rt. The resulting mixture was stirred at rt for 18 h. Water was added portion-wise until all precipitation of $TiO_2$ and the mixture was filtered over celite. The filtrate was decanted and the organic layer was washed with water (once). The organic layer was dried over $MgSO_4$, filtered and the solvent was removed in vacuo. The crude was purified by preparative silica LC (mobile phase gradient: heptane/EtOAc: 95/5 to 70/30) to give 4.89 g of F1 as a colorless oil (69%).

Preparation of Intermediate F2

A suspension of activated Zn (1.41 g; 21.6 mmol) and methanesulfonic acid (107 µL. 1.65 mmol) in dry THF (10 mL) was heated at reflux for 15 min then compound F1 (930 mg; 4.32 mmol) in dry THF (5 mL) was added. Then ethylbromoacetate (1.4 mL, 13.0 mmol) in dry THF (5 mL) was added dropwise over 10 min. The mixture was stirred at reflux for 1 h then cooled down to rt, then treated with $NaHCO_3$ (aq., sat.), filtered through a pad of celite and washed with EtOAc. The layers were separated. The organic layer was washed with brine, dried over $MgSO_4$, filtered, concentrated in vacuo and purified by preparative silica LC (gradient: from heptane/EtOAc 90/10 to 50/50) to give 672 mg of intermediate F2 as a colorless oil (51%).

Preparation of Intermediate F3/F3'

A mixture of F2 (670 mg; 2.21 mmol) and HCl (3 M in CPME, 2.2 mL, 6.62 mmol) in MeOH (20 mL) was stirred at rt for 56 h. The mixture was evaporated to dryness then reconstituted in $Et_2O$ and pentane and the solvents were evaporated to give 510 mg of a mixture of intermediates F3 and F3' (70/30) as a colorless oil (98%).

Preparation of Intermediate F4/F4'

2,6-Dichloro-3 cyano-5 fluoropyridine (457 mg, 2.39 mmol), N,N-diisopropylamine (2.1 mL, 12.0 mmol), intermediates F3/F3' (510 mg, 2.56 mmol) in THF (6.4 mL) and EtOH (6.4 mL) were heated at 90° C. for 2 h in a sealed tube. Solvents were evaporated. EtOAc was added and the resulting solution was washed twice with water. The organic layer was dried over $MgSO_4$, filtered, evaporated and purified by preparative silica LC (mobile phase gradient: from heptane/EtOAc 90/10 to 50/50) to give 304 mg of intermediate F4 as a yellow solid (36%), and 76 mg of intermediate F4' as a yellow oil (9%).

Preparation of Intermediate F5

Under $N_2$, in a sealed tube, a mixture of C (462 mg, 821 µmol), F4 (264 mg, 746 µmol) and $Cs_2CO_3$ (851 mg, 2.61 mmol) in dioxane (6.5 mL) and distilled water (2 mL) was degassed with $N_2$ (twice). $PdCl_2(PPh_3)_2$ (52.4 mg, 74.6 µmol) was added and the reaction mixture was degassed again with $N_2$ (twice). The reaction mixture was heated at 90° C. for 2 h, then at rt for 16 h. The reaction mixture was cooled to rt, then EtOAc was added and the organic layer was washed with water (twice) and brine. The organic layer was dried over $MgSO_4$, filtered, evaporated in vacuo and purified by preparative LC (silica, mobile phase gradient: from heptane/EtOAc 90/10 to 60/40) to give 188 mg of impure F5 as a brown solid. The solid was purified again by preparative silica LC (mobile phase gradient: from heptane/EtOAc 90/10 to 70/30) to give 153 mg of F5 as a yellow foam.

Preparation of 3-((5-cyano-6-(5,7-difluoro-1H-indol-3-yl)-3-fluoropyridin-2-yl)amino)-4,4-dimethylhept-6-enoic Acid 241

To a solution of F5 (153 mg, 0.245 mmol) in THF (4.7 mL) and distilled water (1.6 mL) was added $LiOH.H_2O$ (52.4 mg, 1.22 mmol) and the reaction mixture was stirred at 60° C. for 16 h. The solvent was evaporated in vacuo. Then the residue was acidified with HCl (aq., 1M) and the resulting precipitate was filtered and washed with water to give a green solid. This solid was diluted in diethyl ether. Pentane was added and the resulting precipitate was filtered and washed with pentane and purified via reverse phase chromatography (stationary phase: X-Bridge-C18 5 µm 30×150 mm, mobile phase gradient: from $H_2O$ ($NH_4HCO_3$ 0.5%)/$CH_3CN$ 75/25 to 35/65) to give 11 mg of 241 (10%).

Preparation of 3-((5-cyano-6-(5,7-difluoro-1H-indol-3-yl)-3-fluoropyridin-2-yl)amino)-3-(1-methylcyclopentyl)propanoic Acid (244)

-continued

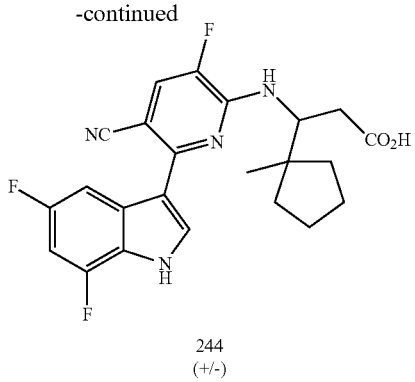

244
(+/-)

Preparation of Intermediate H1

Step 1. Under nitrogen, LiHMDS (1M in THF) (189 mL, 189 mmol) was added dropwise to a solution of cyclopentanecarbonitrile (15 g, 158 mmol) in THF (64 mL) at −78° C. The mixture was then stirred at 30 min and $CH_3I$ (14.7 mL, 240 mmol) was added in one portion and the mixture was slowly warmed to rt overnight. EtOAc (250 mL) was added and $NH_4Cl$ 10% (200 mL) was slowly added at 0° C. Then water (100 mL) was added to form a solution and the organic layer was separated and washed with brine, dried and concentrated to give 1-methylcyclopentanecarbonitrile (16.8 g, yellow oil) that was used without purification in the next step.

Step 2. At −78° C. under nitrogen, DIBAL (37 mL, 37 mmol) was added dropwise to a solution of 1-methylcyclopentanecarbonitrile (2.0 g, 18 mmol) in $CH_2Cl_2$ (117 mL) and the mixture was stirred 15 min at −78° C. after the end of addition. $CH_3OH$ (37 mL) was added slowly at −78° C. and the reaction warmed to rt. NaOH (1M) 200 mL was added and the aqueous solution was extracted twice with $CH_2Cl_2$, dried over $MgSO_4$ and concentrated. This mixture was stirred for 1 h in HCl aq. (3M), extracted with $CH_2Cl_2$, dried over $MgSO_4$ and concentrated to give 1-methylcyclopentanecarbaldehyde (1.4 g, yellow oil).

Step 3. 1-methylcyclopentanecarbaldehyde (1.4 g, 12 mmol), malonic acid (1.0 g, 9.6 mmol), NH4OAc (1.5 g, 19 mmol) in EtOH (5.6 mL) was stirred overnight at 80° C. in a sealed tube. The mixture was cooled to rt, filtered and washed with EtOH. $H_2SO_4$ (0.51 mL, 9.6 mmol) was added to the filtrate and the mixture was stirred for 2 h at 80° C. The mixture was concentrated, taken in water and washed with DCM (3×). The organic mixture was discarded and the aqueous layer was basified with NaOH (3N) and extracted with DCM thrice. The organic layer was dried over $MgSO_4$, filtered and concentrated to give H1 (0.75 g, colorless oil).

Preparation of Intermediate H2

2,6-Dichloro-3 cyano-5-fluoropyridine (0.3 g, 1.6 mmol), N,N-diisopropylethylamine (1.4 mL, 7.9 mmol), H1 (0.47 g, 2.4 mmol) in THF (3.9 mL) and EtOH (3.9 mL) were heated at 90° C. for 3 h. The mixture was cooled to rt, concentrated and purified by preparative silica LC (mobile phase gradient: heptane/EtOAc from 90/10 to 70/30) to give 295 mg of H2 as colorless oil (53%).

Preparation of Intermediate H3

$PdCl_2(PPh_3)_2$ (58 mg, 0.083 mmol) was added to a degassed solution of H2 (0.295 g, 0.83 mmol), C (0.39 g, 0.83 mmol) and $Cs_2CO_3$ (0.95 g, 2.9 mmol) in 1,4-dioxane (11 mL) and $H_2O$ (3.8 mL) and the mixture was stirred 1 h at 90° C. Water and EtOAc were added and the organic layer was washed with brine, dried over $MgSO_4$, filtered, evaporated and purified by preparative silica LC (mobile phase: heptane/EtOAc from 90/10 to 80/20) to give 320 mg of H3 as a beige solid.

Preparation of 244

KOH (287 mg; 5.12 mmol) was added to a mixture of H3 (320 mg; 0.512 mmol) in EtOH (7.4 mL) and the mixture was stirred at rt for 3 days. The solvent was removed under reduced pressure and reconstituted in water, acidified with 3N HCl until the formation of a precipitate. The solution was filtered, and the solid was reconstituted in $CH_2Cl_2$, dried over $MgSO_4$, filtered and concentrated to give a beige solid which was purified via reverse phase chromatography (stationary phase: X-Bridge-C18 5 µm 30×150 mm, mobile phase: Gradient from 75% $H_2O(NH_4HCO_3$ 0.5%), 25% $CH_3CN$ to 35% $H_2O$ ($NH_4HCO_3$ 0.5%), 65% $CH_3CN$) to give 137 mg of the titled compound(244) as a solid (60%). Separation via chiral SFC (stationary phase: Lux cellulose 25 µm 250×21.2 mm, mobile phase: 80% $CO_2$, 20% $CH_3OH$) afforded 98 mg of 245 as a white solid.

Preparation of 246

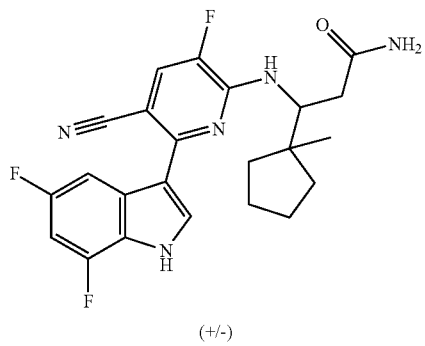 [SMILES: CC1(C(CC(N)=O)Nc2nc(-c3c[nH]c4c(F)cc(F)cc34)c(C#N)cc2F)CCCC1]

(+/-)

A mixture of H4 (30.0 mg; 67.8 µmol), HMDS (28.8 µL. 0.136 mmol), EDCl.HCl (15.6 mg, 0.0814 mmol), HOBT (11.0 mg, 0.081 mmol) and TEA (14.1 µL. 0.102 mmol) in THF (1.4 mL) and $CH_2Cl_2$ (1.3 mL) was stirred at rt for 16 h. Water and DCM were added, the aqueous layer was extracted with $CH_2Cl_2$ (twice). The combined organic layers were washed with brine (twice), dried over $MgSO_4$, filtered and evaporated in vacuo. This residue was purified by preparative silica LC (mobile phase: $CH_2Cl_2/CH_3OH/$aq.$NH_3$ from 98:2:0.2 to 96:4:0.4) to give 246 (12 mg, white solid, 43%).

Preparation of (trans)-2-((5-cyano-6-(5,7-difluoro-1H-indol-3-yl)-3-fluoropyridin-2-yl)-amino)-1-ethyl-cyclohexanecarboxylic Acid (247)

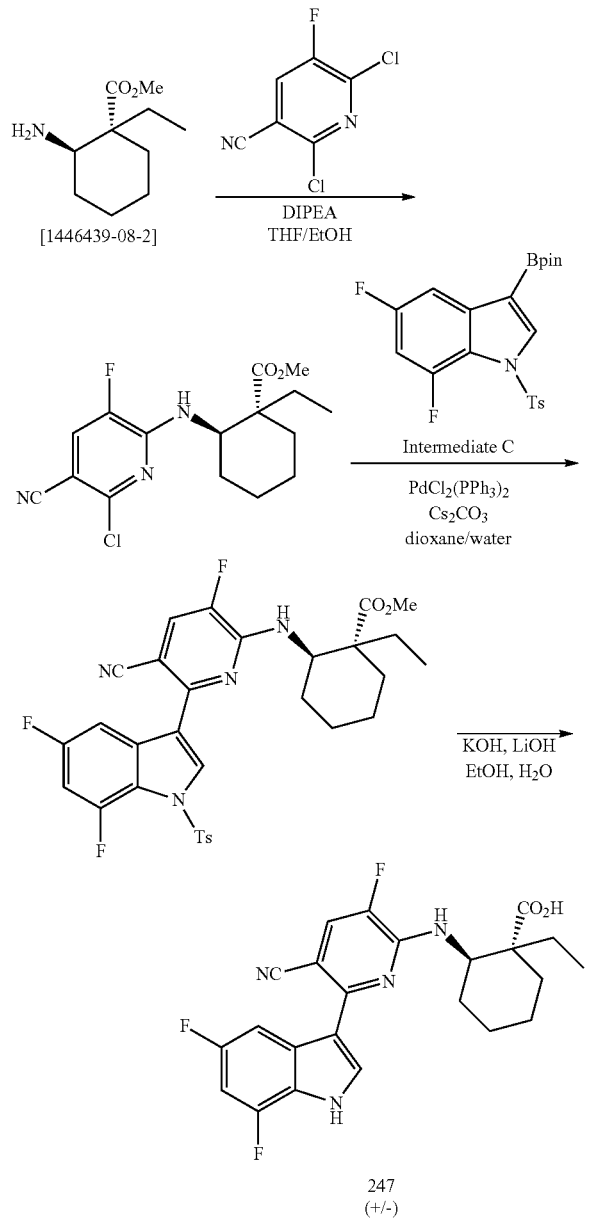

Preparation of (trans)-methyl 2-((6-chloro-5-cyano-3-fluoropyridin-2-yl)amino)-1-ethylcyclohexanecarboxylate 2,6-Dichloro-3 cyano-5-fluoropyridine (400 mg, 2.09 mmol), N,N-diisopropylamine (1.8 mL, 10.5 mmol), (trans)-methyl 2-amino-1-ethylcyclohexanecarboxylate [1446439-08-2] (616 mg, 3.32 mmol) in THF (5 mL) and EtOH (5 mL) were heated at reflux for 2 h. The mixture was cooled to rt, then the solvent was evaporated in vacuo. Water, brine and EtOAc were added. The organic layer was removed, washed with brine, dried over MgSO₄, filtered, evaporated in vacuo and purified by preparative silica LC (mobile phase gradient: from heptane/EtOAc 90/10 to 50/50) to give 600 mg of (trans)-methyl 2-((6-chloro-5-cyano-3-fluoropyridin-2-yl)amino)-1-ethylcyclohexanecarboxylate as a white solid (84%).

Preparation of (trans)-methyl 2-((5-cyano-6-(5,7-difluoro-1-tosyl-1H-indol-3-yl)-3-fluoropyridin-2-yl)amino)-1-ethylcyclohexanecarboxylate Under N₂, in a sealed tube, a mixture of C (250 mg, 0.346 mmol), (trans)-methyl 2-((6-chloro-5-cyano-3-fluoropyridin-2-yl)amino)-1-ethylcyclohexanecarboxylate (176 mg; 0.519 mmol) and Cs₂CO₃ (395 mg, 1.21 mmol) in 1,4-dioxane (7.5 mL) and distilled water (2.5 mL) was degassed with N₂ (3 times). PdCl₂(PPh₃)₂ (24.3 mg, 34.6 μmol) was added and the reaction mixture was degassed again with N2 (3 times). The reaction mixture was heated at 90° C. for 1 h. The reaction mixture was cooled down to rt and the solvent was evaporated in vacuo. The residue was taken up in EtOAc and the organic layer was washed with brine (twice), dried over MgSO₄, filtered off, concentrated to dryness and purified by preparative LC (silica, mobile phase gradient: from heptane/EtOAc 95/5 to 70/30) to give 196 mg of the titled compound as a blue solid (93%).

Preparation of (trans)-2-((5-cyano-6-(5,7-difluoro-1H-indol-3-yl)-3-fluoropyridin-2-yl)-amino)-1-ethyl-cyclohexanecarboxylic Acid (247)

KOH (101 mg; 1.80 mmol) was added to a mixture of (trans)-methyl 2-((5-cyano-6-(5,7-difluoro-1-tosyl-1H-indol-3-yl)-3-fluoropyridin-2-yl)amino)-1-ethylcyclohexanecarboxylate (165 mg, 0.361 mmol) in EtOH (5.2 mL) and the mixture was stirred at rt for 6 h. Then a solution of LiOH.H₂O (30.3 mg, 0.722 mmol) in distilled water (1 mL) was added and the reaction mixture was stirred at rt overnight. Then the mixture was heated at 50° C. for 6 h then at 80° C. for 16 h. The reaction mixture was evaporated to dryness. The residue was taken up in water HCl (aq. 1N) was added until pH=1. The resulting precipitate was filtered to afford 89 mg of a beige solid. This solid was purified by preparative silica LC (mobile phase gradient: from CH₂Cl₂/MeOH 98/2 to 90/10) to afford 55 mg of a white solid purified via reverse phase (stationary phase: X-Bridge-C18 5 μm 30×150 mm, mobile phase gradient: H₂O (containing TFA 0.05%)/CH₃CN 60/40 to 0/100) to give 25 mg of the titled compound as a beige solid (16%).

Preparation of 248

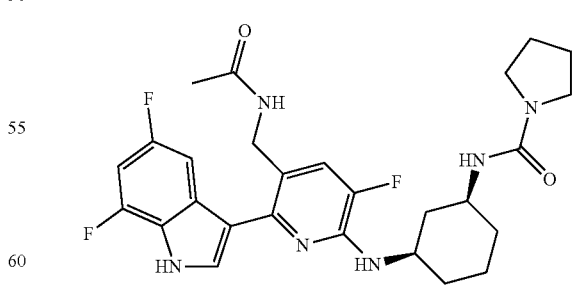

A chiral separation on 82 mg of 6 via chiral SFC (stationary phase: CHIRALCEL OJ-H 5 μm 250×20 mm, mobile phase: 80% CO₂, 20% CH₃OH (0.3% isopropylamine)) afforded 29 mg of the titled compound after freeze-drying of collected fractions.

Preparation of N-((cis)-3-((6-(5,7-difluoro-1H-indol-3-yl)-3-fluoro-5-(methylsulfonamidomethyl)pyridin-2-yl)amino)cyclohexyl)pyrrolidine-1-carboxamide (250)

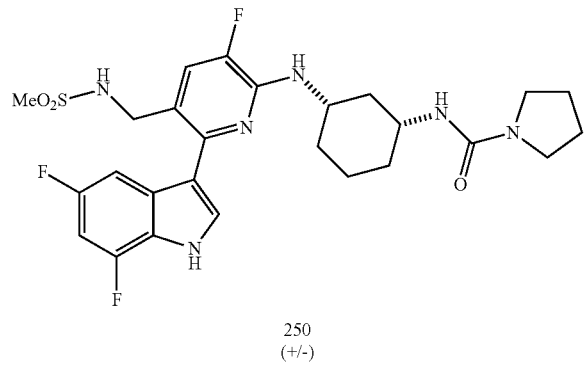

250
(+/-)

In sealed tube, methanesulfonyl chloride (26 μL 0.331 mmol) was added to a solution of N-((cis)-3-((5-(aminomethyl)-6-(5,7-difluoro-1H-indol-3-yl)-3-fluoropyridin-2-yl)amino)cyclohexyl)pyrrolidine-1-carboxamide (115 mg, 0.165 mmol) and Et$_3$N (81 μL. 0.579 mmol) in DCM (2 mL). The reaction mixture was stirred at rt for 18 h. Water, brine and EtOAc were added to the reaction mixture. The aqueous layer was extracted with EtOAc (twice). The combined organic layers were dried over MgSO$_4$, filtered and evaporated in vacuo. The residue was purified by preparative silica LC (mobile phase gradient: from DCM/MeOH/aqNH$_3$ 100/0/0 to 90/10/1). The pure fractions were collected and evaporated to dryness. The residue was taken-up with acetone and evaporated in vacuo and the solid was dried under high vacuum (36 h at 50° C.) to give 50 mg of 250 as an off-white solid (54%).

Preparation of 251

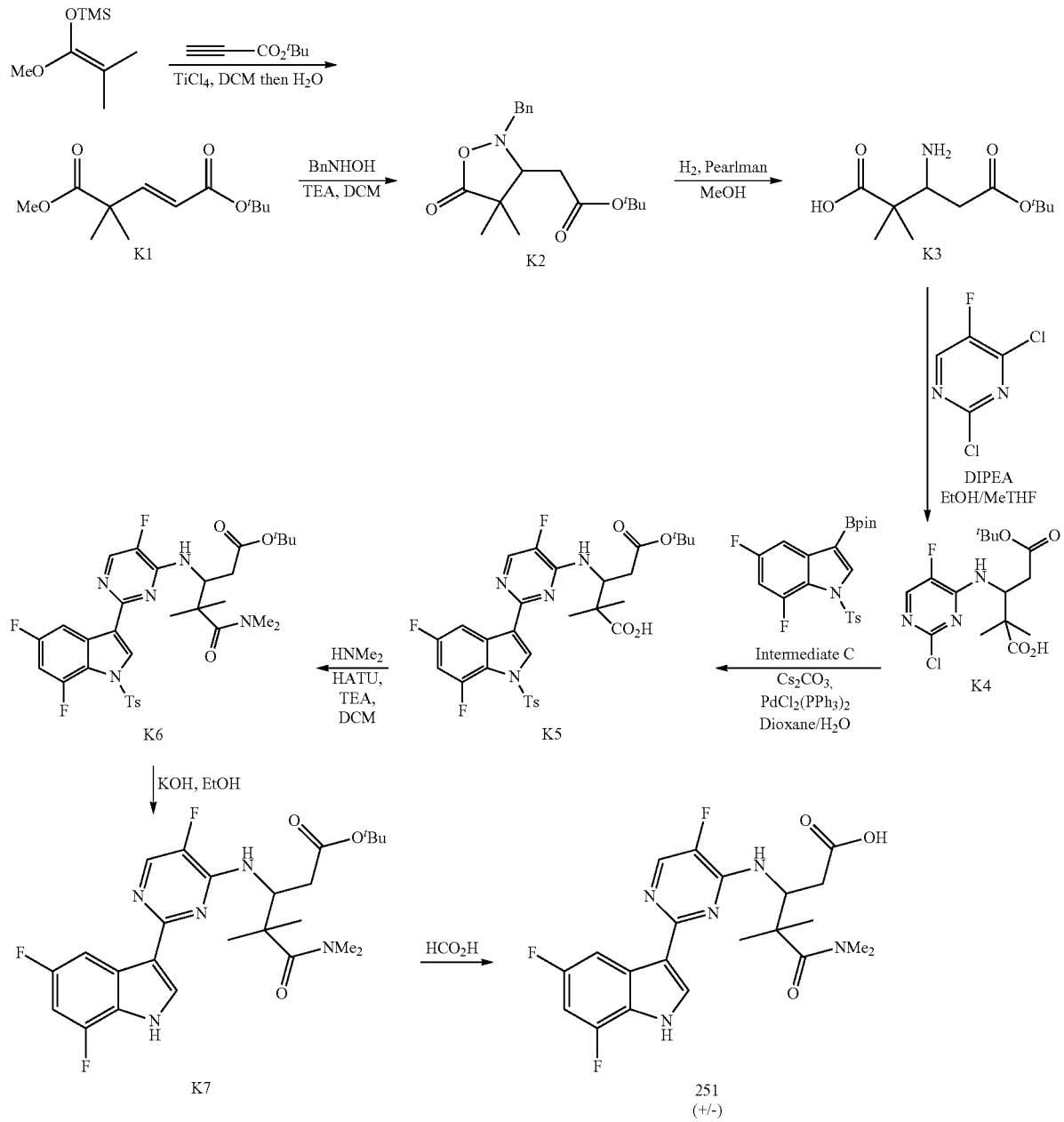

Preparation of K1

Under N$_2$, at −78° C., TiCl$_4$ (10.8 µL. 98.7 mmol) was added to a solution of 1-methoxy-2-methyl-1-(trimethylsiloxy)propene (20 mL; 98.7 mmol) and tert-butyl propiolate (13.5 µL. 98.7 mmol) in E (340 mL). The reaction mixture was stirred at −78° C. for 30 min. H$_2$O (65 mL) was added at −78° C. The mixture was allowed to warm to rt and water and DCM were added. The aqueous layer was extracted with CH2Cl2. The combined organic layer were washed with water, dried over MgSO$_4$, filtered and evaporated in vacuo to give K1(79%).

Preparation of K2

Under N2, Et$_3$N (16.3 mL, 117 mmol, 1.5 eq) was added to a mixture of 01 (22.3 g, 78.1 mmol) and benzylhydroxylamine hydrochloride (16.2 g, 102 mmol, 1.3 eq) in dry DCM (400 mL) and stirred at rt 4 h. The reaction mixture was heated at reflux for 2 days and 6 h. DCM and water were added to the reaction mixture. The aqueous layer was extracted with DCM. The combined organic layers were dried over MgSO$_4$, filtered and evaporated in vacuo. The residue was purified by preparative silica LC (mobile phase gradient: from heptane/EtOAc 80/20 to 50/50) to give 16.5 g of K2 (62%).

Preparation of K3

A solution of K2 (16.5 g, 51.7 mmol) in MeOH (245 mL) was hydrogenated at rt under 15 bars with Pearlman catalyst (7.36 g, 5.17 mmol) as catalyst in a pressure vessel reactor at rt for 2 h. The reaction mixture was filtered over a pad of celite and rinsed with MeOH. The solvent was evaporated in vacuo to give 15.5 g of K3.

Preparation of K4

2,4-dichlorofluoropyrimidine (263 mg, 1.58 mmol), K3 (490 mg, 1.13 mmol), DIPEA (1.15 mL, 6.57 mmol) in Me-THF (5 mL) and EtOH (5 mL) were heated at 80° C. for 18 h. The mixture was concentrated to dryness. Water and brine were added. The aqueous layer was extracted with EtOAc (twice). The combined organic layers were dried over MgSO$_4$, filtered and evaporated in vacuo. The residue was purified by preparative silica LC (mobile phase gradient: from DCM/MeOH/AcOH: 100/0/0 to 95/5/0.5) to give 373 mg of K4 (72%).

Preparation of K5

Under N$_2$, in a microwave tube, a mixture of C (594 mg, 1.14 mmol, 83% purity), K4 (373 mg; 0.948 mmol; 92% purity) and Cs$_2$CO$_3$ (1.08 g, 3.32 mmol) in dioxane (8 mL) and H$_2$O (2.5 mL) was degassed with N$_2$ for 5 min. PdCl$_2$(PPh$_3$)$_2$ (67 mg, 94.9 µmol) was added and the reaction mixture was degassed again with N$_2$ for 2 min. The reaction mixture was heated at 100° C. in the microwave. The reaction mixture was filtered over Celite and rinsed with a mixture of DCM/MeOH 80/20. The filtrate was purified by preparative silica LC (mobile phase gradient: from heptane/EtOAc 80/20 to 60/40) to give 419 mg of K5 (57%).

Preparation of K6

HN(CH$_3$)$_2$ (2M in THF 0.402 mL, 0.805 mmol) was added to a solution of K5 (419 mg, 0.536 mmol), HATU (408 mg, 1.07 mmol) and Et$_3$N (0.186 mL, 1.34 mmol) in DCM (10 mL). The reaction mixture was stirred for 18 h at rt. NaHCO$_3$ (sat., aq.) and DCM were added to reaction mixture. The aqueous layer was extracted with DCM (twice). The combined organic layers were dried over MgSO$_4$, filtered and evaporated in vacuo. The residue was purified by preparative silica LC (mobile phase gradient: from DCM/MeOH/AcOH 100/0/0 to 99/1/0.1) to give 240 mg of K6 (68%).

Preparation of K7

KOH (102 mg; 1.82 mmol) was added to K6 (240 mg, 0.364 mmol) in EtOH (10 mL). The reaction mixture was stirred at rt for 18 h. NaHCO$_3$ (sat., aq.) and EtOAc were added. The aqueous layer was extracted with EtOAc (twice). The combined organic layers were washed with a mixture of NaHCO$_3$ (sat., aq.) and water (9/1), dried over MgSO$_4$, filtered and evaporated in vacuo to give 207 mg of K7.

Preparation of 251

Formic acid (2 mL) was added to K7 (90 mg; 0.178 mmol), the reaction mixture was stirred at rt for 14 h. Toluene was added and the reaction mixture was evaporated in vacuo. The residue was purified via reverse phase (stationary phase: X-Bridge-C18 5 µm 30×150 mm, mobile phase: gradient from aq. NH$_4$HCO$_3$ (0.5%)/MeCN 85/15 to 45/55). The pure fraction was collected and evaporated in vacuo to give 10 mg of the titled compound.

Preparation of 3-((5-cyano-6-(5,7-difluoro-1H-indol-3-yl)-3-fluoropyridin-2-yl)amino)-3-(4-methyltetrahydro-2H-pyran-4-yl)propanoic Acid 255

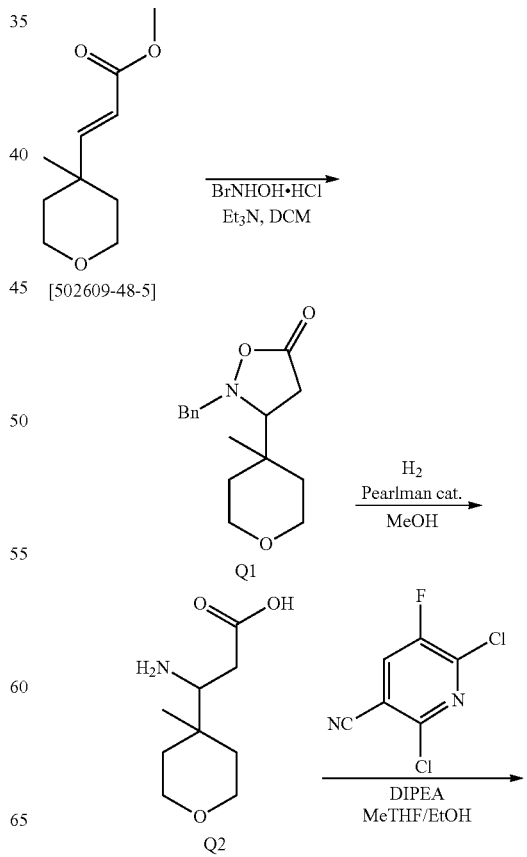

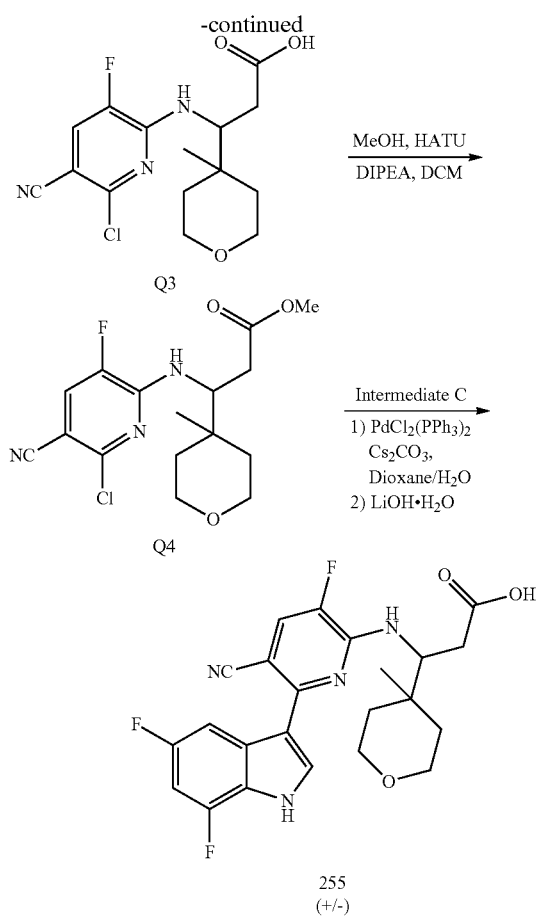

Preparation of Intermediate Q1

Under nitrogen, Et₃N (1.5 mL, 10.8 mmol) was added to a mixture of [502609-48-5](1.4 g, 7.60 mmol) and N-benzylhydroxylamine HCl (1.5 g, 9.40 mmol) in DCM (50 mL) and stirred at rt overnight. The mixture was concentrated in vacuo. The residue was purified by preparative silica LC (mobile phase gradient: from heptane/EtOAc 90:10 to 50:50). The fractions containing product were combined and the solvent was removed in vacuo to give 960 mg of Q1 (46%) as a colorless oil.

Preparation of Q2

In an autoclave, a solution of Q1 (960 mg; 3.49 mmol) and Pearlman catalyst (979 mg, 0.697 mmol) in MeOH (30 mL) was stirred under an atmosphere of H₂ (5 bar) at rt overnight. The reaction mixture was filtered on a pad of celite, washed with MeOH and the filtrate was evaporated in vacuo to give 670 mg of Q2 as a white solid.

Preparation of Q3

2,6-dichloro-3 cyano-5 fluoropyridine (820 mg, 4.29 mmol), Q2 (670 mg, 3.58 mmol), N,N-diisopropylethylamine (3.12 mL, 17.9 mmol) in MeTHF (14 mL) and EtOH (14 mL) were heated at 80° C. overnight. The mixture was evaporated and the residue was reconstituted in water, then acidified HCl (aq. 1M) until pH=1. The aqueous layer was extracted with EtOAc (×2). The combined organic layers were dried over MgSO₄, filtered and evaporated in vacuo to give 1.09 g of Q3 as a brown solid (89%).

Preparation of Q4

MeOH (401 µL; 9.90 mmol) was added to a solution of Q3 (1.09 g; 3.19 mmol), HATU (1.82 g; 4.78 mmol) and N,N-diisopropylethylamine (989 µL; 5.74 mmol) in DCM (31 mL). The reaction mixture was stirred at rt for 3 h. Water and CH₂Cl₂ were added and the layers were separated. The organic layer was washed with brine, then dried over MgSO₄, filtered and concentrated in vacuo. The residue was purified by preparative silica LC (mobile phase gradient: from CH₂Cl₂/EtOAc 100/0 to 90/10). The fractions containing product were combined and the solvent was removed in vacuo to give 255 mg of Q4 (22%) as a colorless oil.

Preparation of 255

A solution of Q4 (255 mg, 0.717 mmol), C (405 mg; 0.860 mmol) and Cs₂C03 (701 mg, 2.15 mmol) in 1,4-dioxane (8 mL) and H₂O (3.2 mL) was degassed by N₂ bubbling for 10 min before the addition of PdCl₂(PPh₃)₂ (50 mg, 71.7 µmol). The resulting mixture was degassed by N₂ bubbling for 10 min then stirred at 90° C. overnight. Lithium hydroxide monohydrate (153 mg, 3.58 mmol) was added and the mixture was stirred at 60° C. overnight. The mixture was evaporated in vacuo. The residue was reconstituted in MeOH/AcOH (90:10) filtered through Celite, and the solvent of the filtrate was evaporated in vacuo. The crude was purified by preparative silica LC (mobile phase gradient: from CH2Cl₂/MeOH/AcOH 100:0:0 to 90:10:1). The fractions containing product were combined and the solvent was removed in vacuo to give a brown oil which was azeotroped with toluene (twice). The solid was triturated in MeCN, then isolated by filtration to give 60 mg of 255 (18%) as a white solid.

Preparation of 256

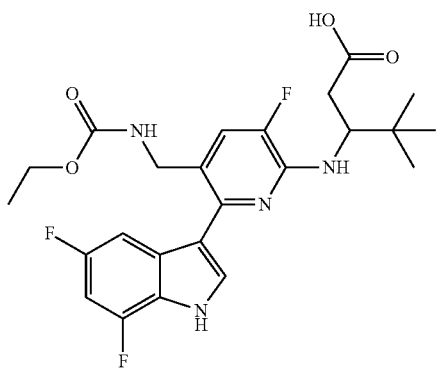 [SMILES: CCOC(=O)NCc1cc(F)c(NC(CC(=O)O)C(C)(C)C)nc1-c1c[nH]c2c(F)cc(F)cc12]

Step 1. The reduction of the nitrile group was performed by employing an analogous method as the one to prepare 6.

Step 2. In a sealed tube ethyl chloroformate (26.6 µL. 279 µmol) was added to a mixture of methyl 3-((5-(aminomethyl)-6-(5,7-difluoro-1H-indol-3-yl)-3-fluoropyridin-2-yl)amino)-4,4-dimethylpentanoate (55 mg, 127 µmol), DMAP (2 mg, 13 µmol) and Et₃N (53 µL. 380 µmol) in DCM (2.75 mL). The reaction mixture was stirred at rt for 18 h. NaOH (51 mg, 1.27 mmol, 10 eq), EtOH (1 mL), H₂O (1 mL) were added and the reaction mixture was stirred at rt for 18 h.

NaOH (203 mg, 5.06 mmol, 40 eq) was added and the reaction mixture was stirred at rt for 18 h. Lithium hydroxide monohydrate (108 mg, 2.53 mmol) was added and the reaction mixture was stirred at rt for 18 h. KHSO$_4$ (aq. 10%) and EtOAc were added to the reaction mixture. The aqueous layer was extracted with EtOAc (twice). The combined organic layers were dried over MgSO$_4$, the solids were removed by filtration and the solvent of the filtrate was evaporated in vacuo. The crude was purified by reverse phase (stationary phase: X-Bridge-C18 5 μm 30×150 mm, mobile phase: gradient from MeCN/H$_2$O (NH$_4$HCO$_3$ 0.5%) 85/15 to 55/40). The pure fraction was collected, evaporated to dryness, dissolved in MeCN and to it was added water. The resulting mixture was freeze-dried to yield the titled compound as a white solid (11 mg, 18%).

Preparation of (S)-2-(5,7-difluoro-1H-indol-3-yl)-5-fluoro-6-((1-hydroxy-3,3-dimethyl-butan-2-yl)amino)nicotinonitrile (257)

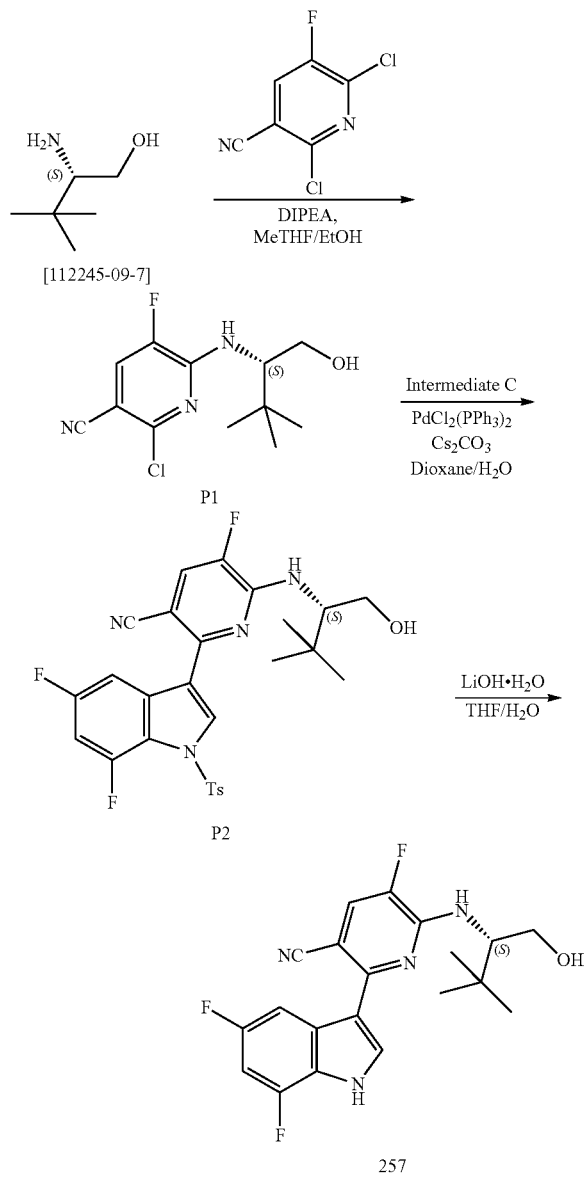

Preparation of P1

2,6-dichloro-3-cyano-5-fluoropyridine (0.518 g, 2.71 mmol), N,N-diisopropylethylamine (2.37 mL, 13.6 mmol), [112245-09-7] (318 mg, 2.71 mmol) in MeTHF (6.5 mL) and EtOH (6.5 mL) were heated at reflux for 20 hours. The mixture was evaporated to dryness. The residue was purified by preparative silica LC (mobile phase gradient: from heptane/EtOAc 85/15 to 60/40) to give 0.5 g of P1 (68%).

Preparation of P2

A solution of C (450 mg, 1.66 mmol), P1 (936 mg, 1.99 mmol) and Cs$_2$CO$_3$ (1.62 g, 4.97 mmol) in 1,4-dioxane (18 mL) and H$_2$O (7.3 mL) was degassed by N$_2$ bubbling for 10 min before the addition of PdCl$_2$(PPh$_3$)$_2$ (116 mg, 166 μmol). The resulting mixture was degassed by N$_2$ bubbling for 10 min then stirred at 90° C. for 3 h. Water and EtOAc were added and the layers were separated. The organic layer was washed with brine, dried over MgSO$_4$, filtered and evaporated in vacuo. The residue was purified by preparative silica LC (mobile phase gradient: from Heptane/DCM 50:50 to 100:0). The best fractions were combined and the solvent was removed in vacuo to give 274 mg of P2 (30%) as a white solid.

Preparation of 257

A mixture of P2 (50 mg, 92.2 μmol) and lithium hydroxide monohydrate (19 mg, 0.461 mmol) in THF (0.7 mL) and H$_2$O (173 μL) was stirred at 60° C. overnight. The solution was evaporated in vacuo. The residue was reconstituted in MeOH/AcOH (90:10), evaporated in vacuo and purified by preparative silica LC (mobile phase gradient: from DCM/MeOH/AcOH 100:0:0 to 95:5:0.5). The fractions containing product were combined and the solvent was removed in vacuo to give a white solid, azeotroped with toluene (twice) to give 20 mg of an impure white solid which was purified via reverse phase (stationary phase: X-Bridge-C18 5 μm 30×150 mm, mobile phase gradient: from H$_2$O(NH$_4$HCO$_3$ 0.5%)/MeCN 65:35 to 25:75) to give 10 mg of 257 (28%) as a yellow solid.

N-((cis)-3-((5-(acetamidomethyl)-6-(5,7-difluoro-1H-indol-3-yl)pyridin-2-yl)amino)-cyclohexyl)pyrrolidine-1-carboxamide (260) was isolated as a side product during the process to form compound 6.

Preparation of N-(5-((2-(5,7-difluoro-1H-indol-3-yl)-5-fluoropyrimidin-4-yl)amino)-tetrahydro-2H-pyran-3-yl)-1H-1,2,3-triazole-5-carboxamide (261)

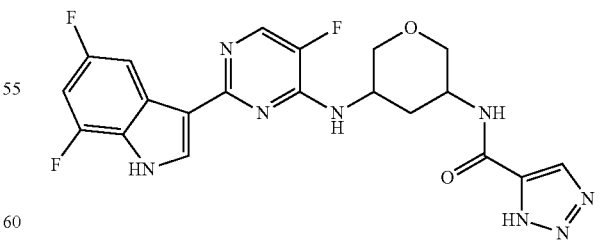

The titled compound was prepared employing an analogous method as the one to prepare N-(5-((2-(5,7-difluoro-1H-indol-3-yl)-5-fluoropyrimidin-4-yl)amino)-3,3-dimethylcyclohexyl)-1-methyl-1H-imidazole-4-carboxamide (202), starting from 2H-pyran-3,5(4H,6H)-dione, which was converted to tetrahydro-2H-pyran-3,5-diamine according to Preparation of N-((1R*,3S*)-3-((2-(5,7-difluoro-1H-indol-3-yl)-5-fluoropyrimidin-4-yl)-amino)cyclohexyl)-3-(hydroxymethyl)-1-methyl-1H-pyrazole-5-carboxamide(262)

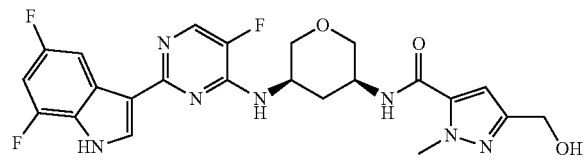 [SMILES: Cn1nc(CO)cc1C(=O)N[C@@H]1COC[C@H](Nc2nc(-c3c[nH]c4c(F)cc(F)cc34)ncc2F)C1]

To a solution of 5-(((1R*,3S*)-3-((2-(5,7-difluoro-1H-indol-3-yl)-5-fluoropyrimidin-4-yl)amino)cyclohexyl)carbamoyl)-1-methyl-1H-pyrazole-3-carboxylic acid(159) (350 mg, 0.663 mmol) in THF (10 mL) was added LAH (1M in THF) (0.995 mL, 1 M, 0.995 mmol) at 0-5° C. in an ice/salt bath. Then the mixture was warmed to room temperature and after an additional 2 hours, the reaction was quenched with ice/water (1 mL) and extracted with dichloromethane (3×10 mL). The combined organic layers were dried over anhydrous sodium sulfate and concentrated in vacuo. The crude was purified via preparatory HPLC (stationary phase: RP XBridge Prep C18 OBD-10 μm, 30×150 mm, mobile phase: 0.5% aq. NH₄Ac+10% CH₃CN, CH₃OH). The desired fractions were collected and concentrated under reduced pressure. The crude was dissolved in methanol and concentrated under reduced pressure to afford the titled compound as a solid.

the procedures described in Faming Zhuanli Shenqing (2015), Chinese patent 104592038 and Yingyong Huaxue (1992), 9(6), 57-60.

TABLE 1

Compounds of formula (I) and corresponding analytical data.

| # | STRUCTURE | $^1$H NMR | Rt (min) | LC Method | LC-MS Mass Found [M + H]$^+$ | MP (° C.) |
|---|---|---|---|---|---|---|
| 1 | 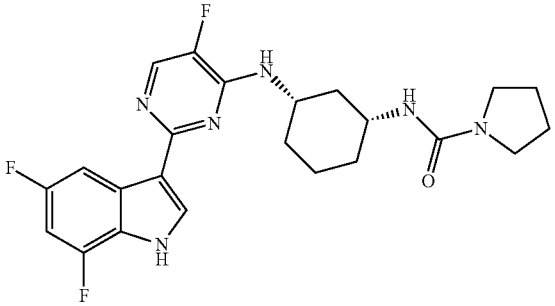 (+/−) | $^1$H NMR (400 MHz, DMSO-d$_6$) δ ppm 1.17-1.31 (m, 2H) 1.37-1.51 (m, 2H) 1.74-1.87 (m, 6H) 2.01 (d, J = 11.44 Hz, 1H) 2.11 (d, J = 11.66 Hz, 1H) 3.14-3.23 (m, 4H) 3.56-3.68 (m, 1H) 4.05-4.17 (m, 1H) 5.82 (d, J = 7.92 Hz, 1H) 7.04 (ddd, J = 11.33, 9.46, 2.31 Hz, 1H) 7.47 (d, J = 7.48 Hz, 1H) 8.01 (dd, J = 10.12, 2.20 Hz, 1H) 8.13 (dd, J = 5.17, 3.41 Hz, 2H) 12.17 (s, 1H) | 0.99 | A | 459.2 | |
| 2 | 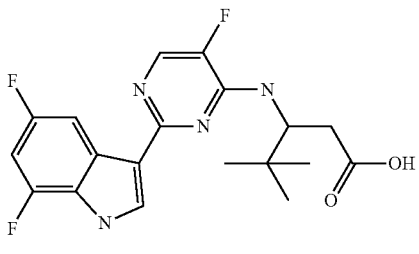 (+/−) | $^1$H NMR (400 MHz, DMSO-d$_6$) δ ppm 0.97 (s, 9H) 2.52-2.70 (m, 2H) 4.81 (t, J = 8.36 Hz, 1H) 6.92-7.16 (m, 1H) 7.43 (d, J = 8.80 Hz, 1H) 8.08 (s, 1H) 8.11 (d, J = 3.96 Hz, 1H) 8.16 (dd, J = 10.34, 2.20 Hz, 1H) 12.15 (br. s., 1H) | 0.83 | A | 393.1 | |
| 3 | 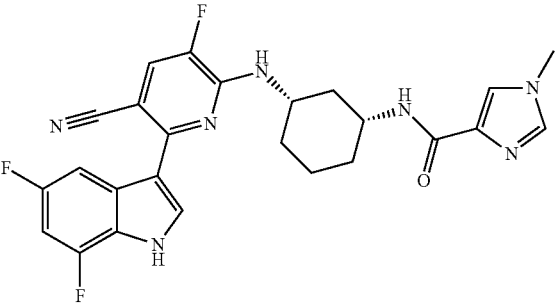 (+/−) | $^1$H NMR (400 MHz, DMSO-d$_6$) δ ppm 1.28-1.71 (m, 4H) 1.84 (m, J = 9.90 Hz, 2H) 1.98-2.13 (m, 2H) 3.67 (s, 3H) 3.75-3.88 (m, 1H) 4.11-4.26 (m, 1H) 7.02-7.20 (m, 2H) 7.61 (dd, J = 19.04, 1.21 Hz, 2H) 7.65-7.73 (m, 2H) 7.83 (d, J = 11.22 Hz, 1H) 7.89 (dd, J = 10.12, 2.20 Hz, 1H) 8.29 (s, 1H) 9.68-14.83 (m, 1H) 12.32 (s, 1H) | 1.81 | B | 494.4 | |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 4 | (+/-) | ¹H NMR (400 MHz, DMSO-d₆) δ ppm 12.3 (s br, 1H), 8.28 (s, 1H), 7.87 (dd, J = 2.0, 10.1 Hz, 1H), 7.83 (d, J = 11.6 Hz, 1H), 7.65 (d, J = 7.6 Hz, 1H), 7.11 (ddd, J = 2.0, 9.6, 11.6 Hz, 1H), 5.81 (d, J = 5.8 Hz, 1H), 4.13 (m, 1H), 3.50 (m, 1H), 3.17 (m, 4H), 2.02 (m, 2H), 1.81 (m, 2H), 1.76 (m, 4H), 1.16-1.53 (m, 4H) | 2.87 | C | 483.1 | |
| 5 | (+/-) | ¹H NMR (400 MHz, DMSO-d₆) δ ppm 1.16-1.65 (m, 6H), 1.68-1.91 (m, 3H), 1.96 (br. s., 1H), 2.01 (br. s., 1H), 2.82 (d, J = 6.9 Hz, 1H), 4.70 (t, J = 6.7 Hz, 1H), 7.04 (ddd, J = 11.3, 9.5, 2.2 Hz, 1H), 7.50 (d, J = 6.9 Hz, 1H), 8.06-8.11 (m, 2H), 8.13 (d, J = 4.0 Hz, 1H), 12.19 (br. s., 1H) | 0.87 | A | 417.1 | |
| 6 | (+/-) | ¹H NMR (400 MHz, DMSO-d₆) δ ppm 1.09-1.45 (m, 4H) 1.68-1.81 (m, 6H) 1.87 (s, 3H) 1.95-2.05 (m, 2H) 3.11-3.20 (m, 4H) 3.40-3.51 (m, 1H) 3.94-4.06 (m, 1H) 4.22-4.35 (m, 2H) 5.75 (d, J = 7.6 Hz, 1H) 6.39 (d, J = 8.1 Hz, 1H) 7.02 (ddd, J = 10.9, 10.1, 2.0 Hz, 1H) 7.30 (d, J = 12.1 Hz, 1H) 7.65 (dd, J = 10.1, 2.0 Hz, 1H) 7.72 (s, 1H) 8.26 (t, J = 5.3 Hz, 1H) 11.98 (br. s., 1H) | 2.51 | C | 529.3 | |
| 7 | (+/-) | ¹H NMR (300 MHz, CD₃OD) δ ppm 1.22-1.38 (m, 5H), 1.51 (m, 1H), 1.83-1.93 (m, 7H), 2.05 (m, 1H), 2.15 (s, 1H), 2.26 (m, 1H), 3.72 (m, 1H), 4.37 (m, 1H), 6.74 (m, 1H), 6.85 (m, 1H), 7.85 (s, 1H), 7.95 (d, J = 4.1 Hz, 1H). | 2.26 | D | 459 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 8 | 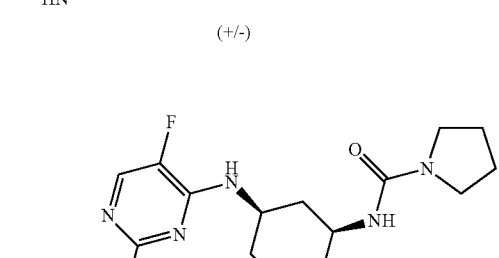 (+/−) | ¹H NMR (300 MHz, CDCl₃) δ ppm 1.15 (m, 3H), 1.51 (m, 2H), 1.90 (m, 5H), 2.07 (m, 1H), 2.22 (m, 1H), 2.63 (m, 1H), 3.32 (m, 4H), 3.85 (m, 1H), 3.99 (m, 1H), 4.08 (d, J = 7.4 Hz, 1H), 4.79 (m, 1H), 7.16 (m, 1H), 8.01 (m, 1H), 8.05 (m, 1H), 8.22 (m, 1H), 9.14 (br. s, 1H). | 2.45 | D | 459 | n.d. |
| 9 | 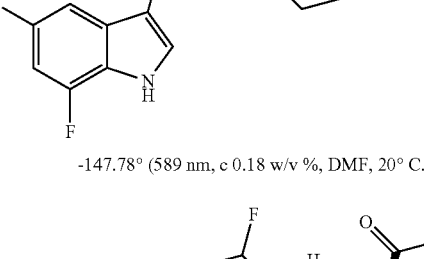 −147.78° (589 nm, c 0.18 w/v %, DMF, 20° C.) | ¹H NMR (400 MHz, DMSO-d₆) δ ppm 1.17-1.31 (m, 2H) 1.37-1.51 (m, 2H) 1.74-1.87 (m, 6H) 2.01 (m, 1H) 2.11 (m, 1H) 3.14-3.23 (m, 4H) 3.56-3.68 (m, 1H) 4.05-4.17 (m, 1H) 5.82 (m, 1H) 7.04 (m, 1H) 7.47 (m, 1H) 8.01 (m, 1H) 8.13 (m, 2H) 12.17 (s, 1H) | 1.00 | A | 459.2 | n.d. |
| 10 | 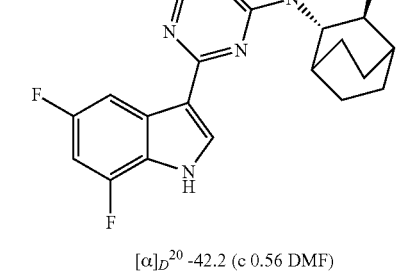 [α]_D²⁰ −42.2 (c 0.56 DMF) | ¹H NMR (360 MHz, DMSO-d₆) δ ppm 1.33-1.66 (m, 4H) 1.75 (m, 2H) 1.79-1.91 (m, 1H) 1.99 (m, 2H) 2.86 (d, J = 6.59 Hz, 1H) 4.69 (t, J = 6.95 Hz, 1H) 7.06 (m, 1H) 7.56 (d, J = 6.59 Hz, 1H) 8.01-8.20 (m, 3H) 12.12-12.29 (m, 1H) | 1.70 | B | 417.2 | 165 |
| 12 | 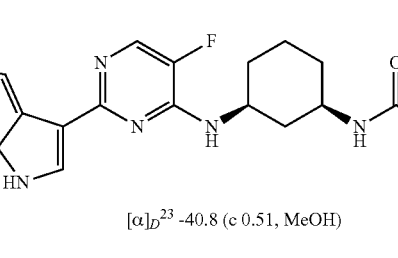 [α]_D²³ −40.8 (c 0.51, MeOH) | ¹H NMR (300 MHz, CD₃OD) δ 1.27-1.46 (m, 4H), 1.91-2.12 (m, 2H), 2.25 (m, 1H), 2.39 (m, 1H), 3.89 (s, 3H), 4.06 (m, 1H), 4.32 (m, 1H), 6.80 (m, 1H), 7.56 (m, 1H), 7.70 (s, 1H), 7.98 (m, 1H), 8.03 (m, 1H), 8.07 (s, 1H). | 2.04 | D | 469.9 | 283.0 |
| 13 | 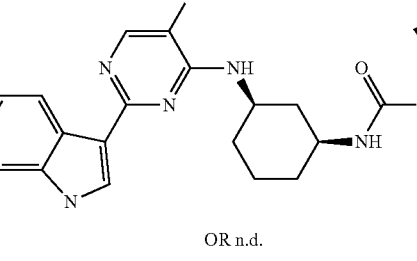 OR n.d. | ¹H NMR (400 MHz, DMSO-d₆) δ ppm 1.07-1.16 (m, 1H) 1.10-1.20 (m, 6H) 1.26 (m, 1H) 1.36-1.57 (m, 4H) 1.81 (m, 2H) 1.86-1.94 (m, 2H) 2.04 (m, 2H) 3.62 (m, 1H) 3.82 (m, 2H) 4.11 (m, 1H) 5.63 (m, 1H) 7.05 (t, J = 10.5 Hz, 1H) 7.47 (m, 1H) 8.01 (m, 1H) 8.10-8.15 (m, 2H) 12.17 (br s, 1H) | 1.12 | A | 487.3 | n.d. |

TABLE 1-continued
Compounds of formula (I) and corresponding analytical data.
| # | STRUCTURE | $^1$H NMR | Rt (min) | LC Method | LC-MS Mass Found [M + H]$^+$ | MP (° C.) |
|---|---|---|---|---|---|---|
| 14 | 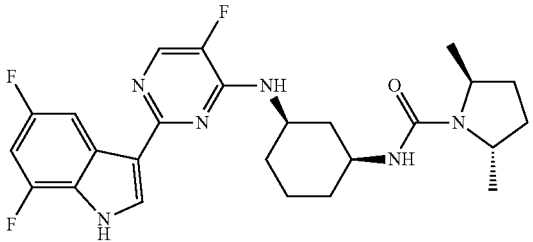<br>OR n.d. | $^1$H NMR (400 MHz, DMSO-d$_6$) δ ppm 1.00 (m, 6H) 1.16-1.30 (m, 2H) 1.38-1.51 (m, 4H) 1.81 (m, 2H) 1.98-2.09 (m, 4H) 3.52-3.75 (m, 1H) 3.93 (m, 2H) 4.06-4.22 (m, 1H) 5.74 (m, 1H) 7.05 (m, 1H) 7.48 (d, J = 8.1 Hz, 1H) 8.01 (m, 1H) 8.07-8.14 (m, 2H) 12.17 (br s, 1H) | 0.78 | B | 487.2 | n.d. |
| 15 | 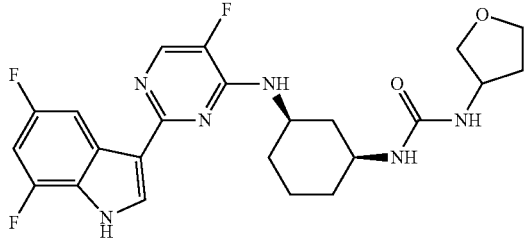<br>(+/-) | | 0.90 | A | 475.2 | n.d. |
| 16 | 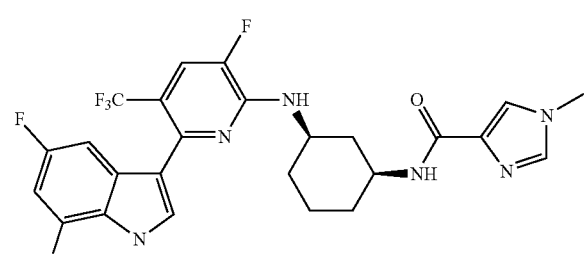<br>(+/-) | $^1$H NMR (400 MHz, DMSO-d$_6$) δ ppm 1.19-1.40 (m, 3H) 1.57 (m, 1H) 1.71-1.84 (m, 2H) 2.02 (m, m, 2H) 3.67 (s, 3H) 3.68-3.78 (m, 1H) 4.10 (m, 1H) 7.05 (m, 1H) 7.36 (m, 1H) 7.46 (m, 1H) 7.54-7.68 (m, 4H) 7.73 (m, 1H) 12.11 (br. s., 1H) | 2.00 | B | 537.4 | |
| 17 | 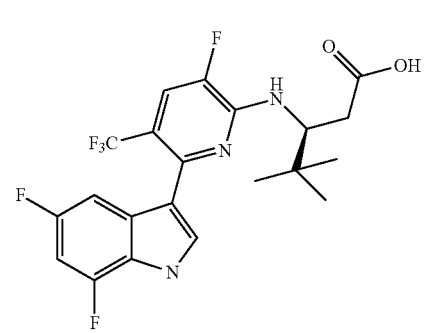<br>OR n.d. | | 1.90 | B | 560.3 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 18 | (structure) OR n.d. | | 1.89 | B | 560.3 | n.d. |
| 20 | (structure) (+/−) | ¹H NMR (500 MHz, DMSO-d₆) δ ppm 1.11-1.34 (m, 2H) 1.35-1.47 (m, 2H) 1.72-1.78 (m, 4H) 1.79-1.88 (m, 2H) 1.97 (m, 1H) 2.13 (m, 1H) 2.43 (s, 3H) 3.13-3.21 (m, 4H) 3.64 (m, 1H) 4.17 (m, 1H) 5.83 (m, 1H) 6.83 (m, 1H) 7.42 (m, 1H) 7.99 (s, 1H) 8.09 (s, 1H) 8.11 (m, 1H) 11.88 (br s, 1H) | 2.77 | C | 455.3 | 94 |
| 21 | (structure) (+/−) | ¹H NMR (500 MHz, DMSO-d₆) δ ppm 1.31-1.43 (m, 1H) 1.43-1.68 (m, 3H) 1.89 (m, 2H) 2.02 (m, 1H) 2.22 (m, 1H) 2.46 (br s, 3H) 3.97-4.13 (m, 1H) 4.19-4.33 (m, 1H) 6.84 (m, 1H) 7.50 (m, 1H) 7.55-7.63 (m, 1H) 7.95-8.07 (m, 3H) 8.11 (m, 2H) 8.57-8.72 (m, 2H) 11.91 (br s, 1H) | 3.03 | C | 463.1 | 208 |
| 22 | (structure) (+/−) | ¹H NMR (500 MHz, DMSO-d₆) δ ppm 1.36-1.50 (m, 3H) 1.68 (q, J = 11.8 Hz, 1H) 1.88 (br d, J = 8.8 Hz, 2H) 2.00 (m, 1H) 2.15 (m, 1H) 2.44 (s, 3H) 3.91-3.99 (m, 1H) 4.29 (m, 1H) 6.91 (d, J = 12.3 Hz, 1H) 7.59 (m, 1H) 7.69 (m, 1H) 7.83 (d, J = 11.3 Hz, 1H) 7.93 (s, 1H) 7.95-8.05 (m, 2H) 8.15 (s, 1H) 8.58-8.70 (m, 2H) 12.08 (br s, 1H) | 3.18 | C | 487.2 | 98 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 23 | (+/-) | ¹H NMR (500 MHz, DMSO-d₆) δ ppm 1.13-1.28 (m, 2H) 1.31-1.46 (m, 2H) 1.70-1.82 (m, 6H) 2.02 (t, J = 11.6 Hz, 2H) 2.08 (br, s, 2H) 3.14-3.18 (br m, 4H) 3.46-3.53 (m, 1H) 4.01-4.07 (br m, 1H) 5.79 (d, J = 7.88 Hz, 1H) 6.74 (m, 1H) 7.01 (ddd, J = 1.9, 9.5, 11.4 Hz, 1H) 7.35 (d, J = 11.0 Hz, 1H) 7.32 (s, 1H) 7.63 (m, 1H) 7.73 (m, 1H) 7.76 (d, J = 1.9 Hz, 1H) 11.95 (br s, 1H) | 2.40 | C | 501.2 | 249.2 |
| 24 | (+/-) | ¹H NMR (400 MHz, DMSO-d₆) δ ppm 1.14-1.30 (m, 3H) 1.32-1.48 (m, 2H) 1.69-1.83 (m, 6H) 2.06 (t, J = 13.1 Hz, 2H) 3.13-3.24 (m, 4H) 3.35-3.56 (m, 1H) 4.04-4.14 (m, 1H) 5.79 (d, J = 7.58 Hz, 1H) 6.76-7.03 (br s 2H) 6.99 (t, J = 9.6 Hz, 1H) 7.45 (d, J = 11.62 Hz, 1H) 7.50-7.57 (br s, 1H) 11.70-11.9 (br s, 1H) 13.71-14.07 (br s 1H) | 2.43 | C | 525.1 | n.d. |
| 25 | (+/-) | ¹H NMR (500 MHz, DMSO-d₆) δ ppm 1.25 (br s, 6H) 2.30 (m, 2H) 2.41 (s, 3H) 3.76 (s, 3H) 5.30 (br t, J = 7.9 Hz, 1H) 6.04 (s, 1H) 6.90 (br d, J = 12.0 Hz, 1H) 7.36-7.53 (m, 1H) 7.56 (br s, 1H) 7.83 (m, 1H) 8.08 (br s, 1H) 8.23 (br s, 1H) 12.04 (br s, 2H) | 2.45 | C | 479.1 | |
| 26 | [α]$_D^{20}$ -765.6 (c 0.25, CD₃OD) | ¹H NMR (360 MHz, DMSO-d₆) δ ppm 1.23-1.44 (m, 2H) 1.57 (m, 2H) 1.79-1.91 (m, 2H) 2.09 (m, 2H) 3.34 (s, 3H) 3.94 (m, 1H) 4.19 (m, 1H) 7.17 (m, 1H) 7.56 (m, 1H) 7.62 (m, 2H) 7.71 (m, 1H) 8.15 (m, 1H) 8.15 (s, 1H) 8.35 (m, 1H) 12.30 (s, 1H) | 0.99 | A | 486.2 | n.d. |

TABLE 1-continued
Compounds of formula (I) and corresponding analytical data.
| # | STRUCTURE | ¹H NMR | Rt (min) | LC Method | LC-MS Mass Found [M + H]⁺ | MP (° C.) |
|---|---|---|---|---|---|---|
| 27 | 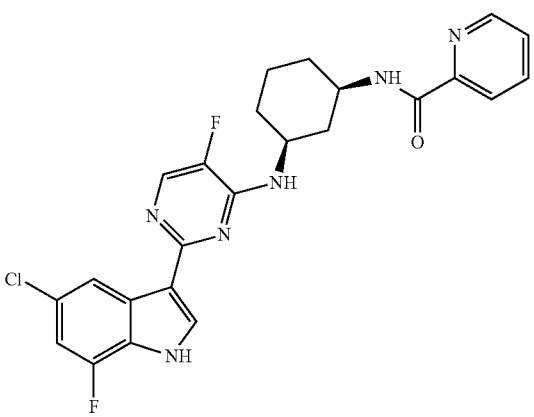 (+/−) | ¹H NMR (300 MHz, CD$_3$OD) δ ppm 1.38-1.60 (m, 2H), 1.66-1.88 (m, 2H), 2.04 (m, 1H), 2.14 (m, 1H), 2.24 (m, 1H), 2.44 (m, 1H), 4.17 (m, 1H), 4.40 (m, 1H), 7.16 (m, 1H), 7.55 (m, 1H), 7.96 (m, 1H), 8.10 (m, 1H), 8.17 (br. s, 1H), 8.24 (m, 1H), 8.33 (s, 1H), 8.63 (d, J = 4.1 Hz, 1H). | 3.02 | D | 483.1 | n.d. |
| 28 | 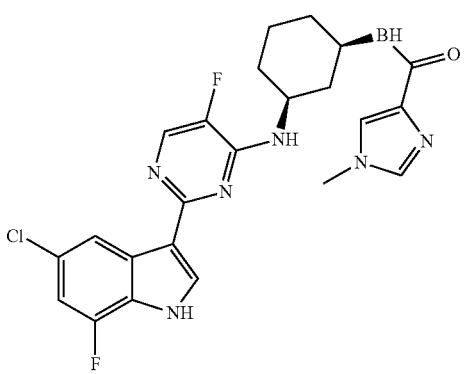 (+/−) | ¹H NMR (300 MHz, CD$_3$OD) δ ppm 1.34-1.53 (m, 2H), 1.54-1.86 (m, 2H), 2.02 (m, 1H), 2.12 (m, 1H), 2.21 (m, 1H), 2.45 (m, 1H), 3.81 (s, 3H), 4.11 (m, 1H), 4.36 (m, 1H), 7.08 (m, 1H), 7.72 (s, 1H), 7.93 (s, 1H), 8.16 (s, 1H), 8.21 (m, 1H), 8.30 (s, 1H). | 2.27 | D | 486.1 | n.d. |
| 29 | 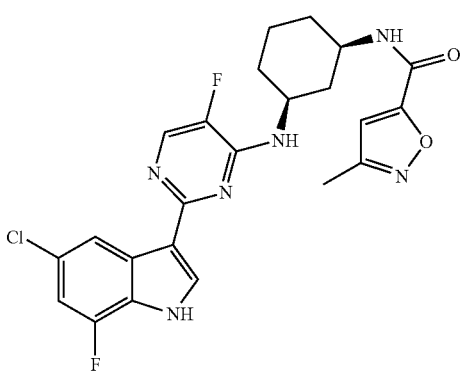 (+/−) | ¹H NMR (300 MHz, DMSO-d$_6$) δ ppm 1.19-1.43 (m, 2H), 1.46-1.68 (m, 2H), 1.79-1.94 (m, 2H), 2.01 (m, 1H), 2.15 (m, 1H), 2.27 (s, 3H), 3.97 (m, 1H), 4.20 (m, 1H), 6.89 (s, 1H), 7.15 (m, 1H), 7.56 (m, 1H), 8.15-8.18 (m, 2H), 8.33 (m, 1H), 8.83 (m, 1H), 12.28 (br s, 1H). | 2.81 | D | 487.0 | 246.7 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 30 | 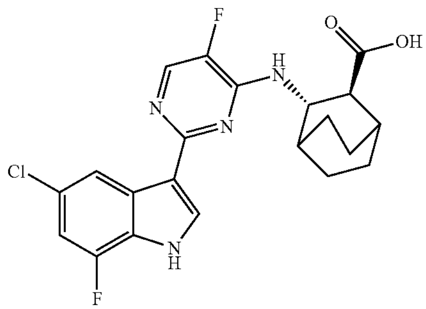 [SMILES: O=C(O)[C@H]1C2CCC(CC2)[C@@H]1Nc1nc(-c2c[nH]c3c(F)cc(Cl)cc23)ncc1F] | | 1.84 | B | 433.3 | n.d. |
| 31 | [α]$_D^{23}$ -251.0 (c 0.1, MeOH) | ¹H NMR (300 MHz, CD$_3$OD) δ ppm 1.41-1.63 (m, 2H), 1.68-1.89 (m, 2H), 1.99-2.18 (m, 2H), 2.24 (m, 1H), 2.45 (m, 1H), 3.99 (s, 3H), 4.14 (m, 1H), 4.42 (m, 1H), 6.96 (d, J = 8.1 Hz, 1H), 7.11 (m, 1H), 7.66 (d, J = 7.1 Hz, 1H), 7.80 (m, 1H), 8.17 (d, J = 1.2 Hz, 1H), 8.26 (d, J = 5.5 Hz, 1H), 8.35 (s, 1H). | 3.36 | D | 513.0 | 256.7 |
| 32 | [α]$_D^{23}$ -212.6 (c 0.21, MeOH) | ¹H NMR (300 MHz, CD$_3$OD) δ ppm 1.32-1.48 (m, 2H), 1.58 (m, 1H), 1.79 (m, 1H), 1.98 (m, 1H), 2.15 (m, 1H), 2.26 (m, 1H), 2.45 (m, 1H), 2.56 (s, 3H), 4.13 (m, 1H), 4.34 (m, 1H), 6.98 (m, 1H), 7.39 (m, 1H), 7.71 (d, J = 7.7 Hz, 1H), 7.99 (d, J = 4.3 Hz, 1H), 8.08 (s, 1H), 8.33 (m, 1H), 8.39 (m, 1H). | 3.05 | D | 497.0 | 226.5 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 33 | 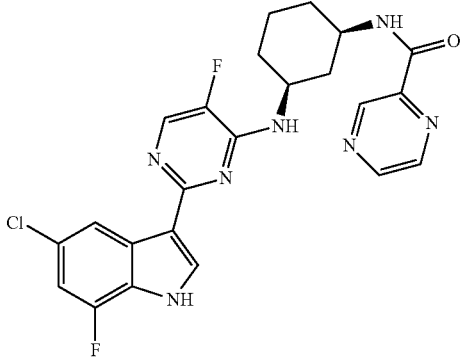<br>$[\alpha]_D^{23}$ -116.2 (c 0.23, DMF) | ¹H NMR (300 MHz, DMSO-d₆) δ ppm 1.24-1.72 (m, 4H), 1.80-1.93 (m, 2H), 2.03 (m, 1H), 2.18 (m, 1H), 4.06 (m, 1H), 4.21 (m, 1H), 7.12 (m, 1H), 7.54 (d, J = 7.5 Hz, 1H), 8.10-8.17 (m, 2H), 8.33 (d, J = 1.6 Hz, 1H), 8.71 (m, 1H), 8.81 (m, 1H), 8.85 (m, 1H), 9.16 (m, 1H). | 2.73 | D | 484.0 | 249.9 |
| 34 | 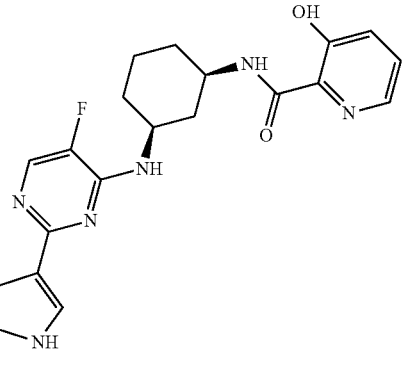<br>$[\alpha]_D^{23}$ -164.3 (c 0.17, MeOH) | ¹H NMR (300 MHz, CD₃OD) δ ppm 1.27-1.47 (m, 2H), 1.57 (m, 1H), 1.78 (m, 1H), 1.98 (m, 1H), 2.14 (m, 1H), 2.26 (m, 1H), 2.45 (m, 1H), 4.13 (m, 1H), 4.35 (m, 1H), 6.97 (m, 1H), 7.37 (m, 1H), 7.70 (m, 1H), 7.98 (m, 1H), 8.06 (s, 1H), 8.35-8.41 (m, 2H). | 3.09 | D | 499.0 | 242.2 |
| 35 | 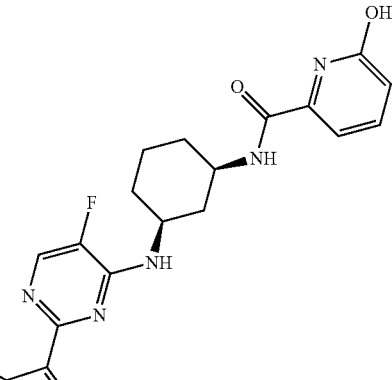<br>$[\alpha]_D^{23}$ -135.0 (c 0.17, MeOH) | ¹H NMR (300 MHz, CD₃OD) δ ppm 1.32-1.47 (m, 2H), 2.11 (m, 1H), 1.76 (m, 1H), 2.00 (m, 1H), 2.11 (m, 1H), 2.25 (m, 1H), 2.44 (m, 1H), 4.12 (m, 1H), 4.34 (m, 1H), 6.73 (d, J = 8.8 Hz, 1H), 6.98 (m, 1H), 7.17 (m, 1H), 7.67 (m, 1H), 7.99 (m, 1H), 8.07 (s, 1H), 8.38 (d, J = 1.5 Hz, 1H). | 2.47 | D | 499.0 | 253.4 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 36 | [α]$_D^{23}$ -143.2 (c 0.2, MeOH) | ¹H NMR (300 MHz, DMSO-d₆) δ ppm 1.22-1.46 (m, 2H), 1.57 (m, 2H), 1.84 (m, 2H), 2.03 (m, 1H), 2.13 (m, 1H), 2.26 (s, 3H), 3.76 (s, 3H), 3.95 (m, 1H), 4.18 (m, 1H), 6.39 (s, 1H), 7.17 (m, 1H), 7.55 (m, 1H), 7.82 (m, 1H), 8.15-8.18 (m, 2H), 8.35 (m, 1H), 12.29 (s, 1H). | 2.78 | D | 500.1 | 178.2 |
| 37 | [α]$_D^{23}$ -170.6 (c 0.2, DMF) | ¹H NMR (300 MHz, DMSO-d₆) δ ppm 1.22-1.40 (m, 2H), 1.45-1.65 (m, 2H), 1.80-1.96 (m, 2H), 2.04 (m, 1H), 2.17 (m, 1H), 3.96 (m, 1H), 4.21 (m, 1H), 7.15 (m, 1H), 7.46-7.60 (m, 3H), 8.08-8.19 (m, 4H), 8.34 (m, 1H), 12.29 (s, 1H). | 2.97 | D | 488.0 | >300 |
| 38 | [α]$_D^{23}$ -217.0 (c 0.13, DMF) | ¹H NMR (300 MHz, CD₃OD) δ ppm 1.31-1.49 (m, 2H), 2.12 (m, 1H), 1.78 (m, 1H), 1.99 (m, 1H), 2.11 (m, 1H), 2.27 (m, 1H) 2.41 (m, 1H) 4.10 (m, 1H), 4.36 (m, 1H), .67 (d, J = 8.2 Hz, 1H), 6.98 (m, 1H), 7.29 (d, J = 7.4 Hz, 1H), 7.53 (m, 1H), 7.98 (d, J = 4.1 Hz, 1H), 8.07 (s, 1H), 8.38 (d, J = 1.6 Hz, 1H). | 2.50 | D | 498.1 | 268.4 |
| 39 | (+/-) | ¹H NMR (400 MHz, DMSO-d₆) δ ppm 1.01 (s, 9H) 2.55-2.63 (m, 2H) 4.81 (m, 1H) 6.86 (m, 1H) 7.04 (m, 1H) 8.03 (s, 1H) 8.08 (d, J = 3.96 Hz, 1H) 8.45 (d, J = 1.76 Hz, 1H) 11.85 (s, 1H) | 1.70 | B | 409.2 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 40 | 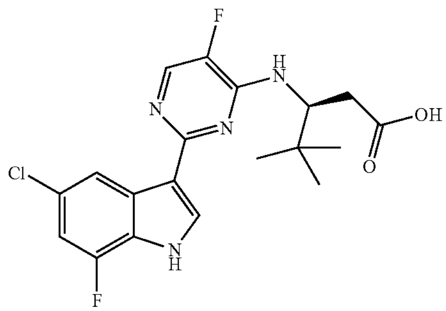 [SMILES: CC(C)(C)[C@H](CC(=O)O)Nc1nc(-c2c[nH]c3c(F)cc(Cl)cc23)ncc1F] | | 1.71 | B | 409.3 | n.d. |
| 41 | [α]$_D^{23}$ -153.0 (c 0.2, MeOH) | ¹H NMR (300 MHz, CD₃OD) δ ppm 1.28-1.45 (m, 2H), 1.54 (m, 1H), 1.75 (m, 1H), 1.98 (m, 1H), 2.08 (m, 1H), 2.21 (s, 3H), 2.25 (m, 1H), 2.40 (m, 1H), 4.00 (s, 3H), 4.09 (m, 1H), 4.34 (m, 1H), 6.53 (s, 1H), 6.98 (m, 1H), 7.99 (m, 1H), 8.07 (s, 1H), 8.38 (m, 1H). | 2.85 | D | 500.1 | 281.2 |
| 42 | [α]$_D^{23}$ -159.0 (c 0.2, MeOH) | ¹H NMR (300 MHz, CD₃OD) δ ppm 1.30-1.51 (m, 2H), 1.60 (m, 1H), 1.78 (m, 1H), 1.99 (m, 1H), 2.12 (m, 1H), 2.26 (m, 1H), 2.43 (m, 1H), 4.17 (m, 1H), 4.34 (m, 1H), 6.98 (m, 1H), 7.99 (d, J = 4.1 Hz, 1H), 8.07 (s, 1H), 8.19 (s, 1H), 8.39 (d, J = 1.6 Hz, 1H). | 2.45 | D | 473.0 | 280.1 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 43 | [α]$_D^{23}$ -133.0 (c 0.2, MeOH) | ¹H NMR (300 MHz, CD$_3$OD) δ ppm 1.28-1.46 (m, 2H), 1.55 (m, 1H), 1.76 (m, 1H), 1.98 (m, 1H), 2.10 (m, 1H), 2.25 (m, 1H), 2.30 (s, 3H), 2.43 (m, 1H), 4.11 (m, 1H), 4.35 (m, 1H), 6.48 (s, 1H), 6.98 (m, 1H), 7.98 (d, J = 4.1 Hz, 1H), 8.06 (s, 1H), 8.38 (d, J = 1.5 Hz, 1H). | 2.58 | D | 486.1 | 189.2 |
| 44 | [α]$_D^{23}$ -162.2 (c 0.17, DMF) | ¹H NMR (300 MHz, DMSO-d$_6$) δ ppm 1.28-1.43 (m, 2H), 1.47-1.69 (m, 2H), 1.81-1.94 (m, 2H), 2.03 (m, 1H), 2.15 (m, 1H), 2.28 (s, 3H), 3.97 (m, 1H), 4.23 (m, 1H), 6.90 (s, 1H), 7.21 (m, 1H), 8.06 (m, 1H), 8.19-8.32 (m, 3H), 18.85 (m, 1H), 12.49 (br s, H). | 2.85 | D | 487.1 | 255.1 |
| 45 | [α]$_D^{23}$ -3.8 (c 0.13, MeOH) | ¹H NMR (300 MHz, CD$_3$OD) δ ppm 1.28-1.47 (m, 2H), 1.55 (m, 1H), 1.77 (m, 1H), 1.98 (m, 1H), 2.11-2.28 (m, 2H), 2.34 (s, 3H), 2.49 (m, 1H), 3.77 (s, 3H), 4.11 (m, 1H), 4.36 (m, 1H), 7.00 (m, 1H), 7.84 (br s, 1H), 8.01 (d, J = 4.2 Hz, 1H), 8.10 (s, 1H), 8.38 (d, J = 1.4 Hz, 1H). | 2.18 | D | 500.1 | >300 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 46 | [α]$_D^{23}$ -134.3 (c 0.17, DMF) | ¹H NMR (300 MHz, DMSO-d$_6$) δ ppm 1.25-1.50 (m, 2H), 1.51-1.70 (m, 2H), 1.80-1.95 (m, 2H), 2.04 (m, 1H), 2.19 (m, 1H), 4.01 (m, 1H), 4.21 (m, 1H), 7.16 (m, 1H), 7.56 (d, J = 7.3 Hz, 1H), 7.66 (m, 1H), 8.12-8.17 (m, 2H), 8.35 (m, 1H), 8.75 (d, J = 8.1 Hz, 1H), 8.94 (m, 2H), 12.29 (br s, 1H). | 2.52 | D | 484.0 | 286.8 |
| 47 | [α]$_D^{23}$ -91.1 (c 0.16, MeOH) | ¹H NMR (300 MHz, CD$_3$OD) δ ppm 1.38-1.56 (m, 2H), 1.65-1.88 (m, 2H), 2.01-2.17 (m, 2H), 2.24 (m, 1H), 2.41 (m, 1H), 2.77 (s, 3H), 4.10 (m, 1H), 4.46 (m, 1H), 7.14 (m, 1H), 8.19 (d, J = 1.5 Hz, 1H), 8.28 (d, J = 5.6 Hz, 1H), 8.44 (s, 1H), 8.74 (s, 1H). | 3.17 | D | 503.0 | >300 |
| 48 | [α]$_D^{23}$ -124.0 (c 0.16, MeOH) | ¹H NMR (300 MHz, CD$_3$OD) δ ppm 1.24-1.46 (m, 2H), 1.57 (m, 1H), 1.76 (m, 1H), 1.96 (m, 1H), 2.08 (m, 1H), 2.25 (m, 1H), 2.37 (m, 1H), 2.59 (s, 3H), 4.10 (m, 1H), 4.32 (m, 1H), 6.96 (m, 1H), 7.96 (d, J = 4.1 Hz, 1H), 7.96 (s, 1H), 8.05 (s, 1H), 8.35 (d, J = 1.6 Hz, 1H). | 2.92 | D | 487.0 | 253.4 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 49 | [α]$_D^{23}$ -76.1 (c 0.22, DMF) | ¹H NMR (300 MHz, DMSO-d$_6$) δ ppm 1.25-1.41 (m, 2H), 1.46-1.65 (m, 2H), 1.82-2.09 (m, 3H), 2.19 (m, 1H), 3.97 (m, 1H), 4.18 (s, 3H), 4.21 (m, 1H), 7.16 (m, 1H), 7.73 (m, 1H), 8.15-8.23 (m, 3H), 8.33 (d, J = 1.3 Hz, 1H), 8.65 (m, 1H), 12.35 (br s, 1H). | 2.65 | D | 487.0 | 249.6 |
| 50 | [α]$_D^{23}$ -58.6 (c 0.17, DMF) | ¹H NMR (300 MHz, DMSO-d$_6$) δ ppm 1.21-1.48 (m, 2H), 1.50-1.68 (m, 2H), 1.80-1.91 (m, 2H), 2.01 (m, 1H), 2.14 (m, 1H), 2.64 (s, 3H), 4.01 (m, 1H), 4.18 (m, 1H), 7.16 (m, 1H), 7.57 (d, J = 7.4 Hz, 1H), 8.10-8.18 (m, 2H), 8.33 (m, 1H), 8.96 (d, J = 7.8 Hz, 1H), 12.29 (s, 1H). | 2.75 | D | 488.0 | 276.7 |
| 51 | [α]$_D^{23}$ -116.7 (c 0.16, DMF) | ¹H NMR (300 MHz, DMSO-d$_6$) δ ppm 1.26-1.47 (m, 2H), 1.49-1.71 (m, 2H), 1.82-1.94 (m, 2H), 2.05 (m, 1H), 2.15 (m, 1H), 3.98 (m, 1H), 4.25 (m, 1H), 6.66 (d, J = 1.5 Hz, 1H), 7.24 (m, 1H), 7.72 (m, 1H), 8.06 (m, 1H), 8.24-8.44 (m, 4H), 12.60 (br s, 1H). | 2.52 | D | 472.1 | 263.3 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 52 | 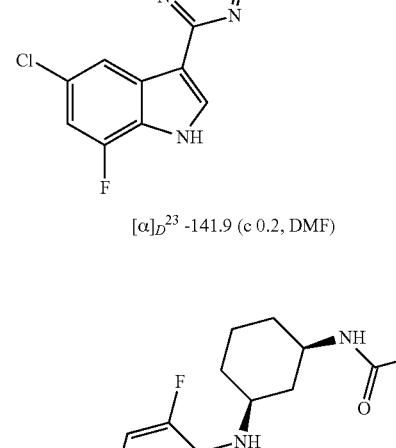 [α]$_D^{23}$ -141.9 (c 0.2, DMF) | ¹H NMR (300 MHz, DMSO-d$_6$) δ ppm 1.20-1.35 (m, 2H), 1.40-1.56 (m, 2H), 1.79-1.93 (m, 2H), 2.02 (m, 1H), 2.14 (m, 1H), 3.82 (s, 3H), 3.93 (m, 1H), 4.19 (m, 1H), 7.14 (d, J = 10.9 Hz, 1H), 7.53 (m, 1H), 7.82 (s, 1H), 7.90 (m, 1H), 8.09 (s, 1H), 8.11-8.17 (m, 2H), 8.33 (m, 1H), 12.33 (br s, 1H). | 2.50 | D | 486.1 | 286.8 |
| 53 | 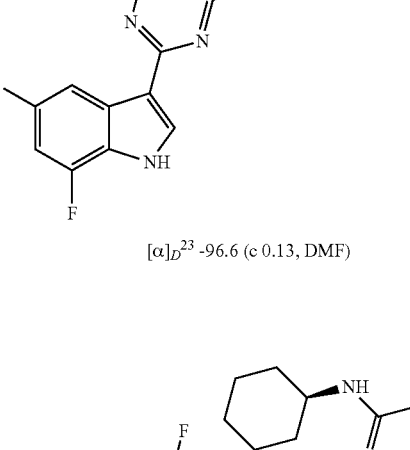 [α]$_D^{23}$ -96.6 (c 0.13, DMF) | ¹H NMR (300 MHz, DMSO-d$_6$) δ ppm 1.20-1.40 (m, 2H), 1.48-165 (m, 2H), 1.82-2.12 (m, 3H), 2.18-2.29 (m, 1H), 4.01 (m, 1H), 4.23 (m, 1H), 6.77 (m, 1H), 7.26 (m, 1H), 8.03 (br s, 1H), 8.10 (s, 1H), 8.17 (br s, 1H), 8.72 (d, J = 7.3 Hz, 1H), 9.14 (s, 2H), 9.29 (s, 1H). | 2.51 | D | 484.0 | >300 |
| 54 | 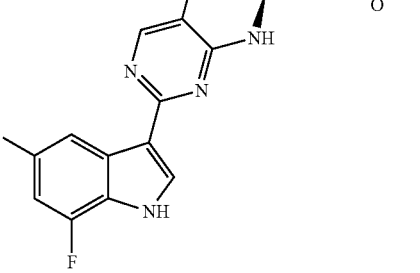 [α]$_D^{23}$ -85.0 (c 0.13, DMF) | ¹H NMR (300 MHz, DMSO-d$_6$) δ ppm 1.23-1.43 (m, 2H), 1.48-165 (m, 2H), 1.78-1.90 (m, 2H), 2.02 (m, 1H), 2.13 (m, 1H), 3.91 (m, 1H), 4.17 (m, 1H), 6.07 (br s, 2H), 7.15 (m, 1H), 7.53 (m, 1H), 7.80 (m, 1H), 8.10-8.17 (m, 2H), 8.34 (m, 1H), 12.28 (br s, 1H), 12.37 (br s, 1H). | 2.27 | D | 488.1 | 293.5 |

TABLE 1-continued

Compounds of formula (I) and corresponding analytical data.

| # | STRUCTURE | $^1$H NMR | Rt (min) | LC Method | LC-MS Mass Found $[M + H]^+$ | MP (° C.) |
|---|---|---|---|---|---|---|
| 55 | 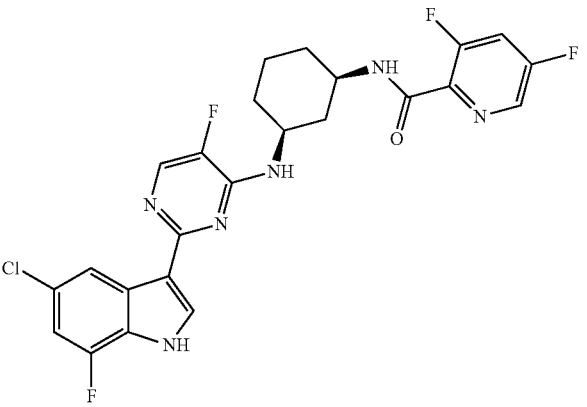<br>$[\alpha]_D^{23}$ -103.5 (c 0.13, DMF) | $^1$H NMR (300 MHz, DMSO-d$_6$) δ ppm 1.24-1.43 (m, 2H), 1.57 (m, 2H), 1.80-195 (m, 2H), 2.03 (m, 1H), 2.18 (m, 1H), 3.98 (m, 1H), 4.21 (m, 1H), 7.16 (m, 1H), 7.56 (d, 7.6 Hz, 1H), 8.06 (m, 1H), 8.12-8.18 (m, 2H), 8.35 (m, 1H), 8.54 (m, 1H), 8.59 (d, J = 8.0 Hz, 1H), 12.29 (s, 1H). | 3.09 | D | 519.0 | >300 |
| 56 | 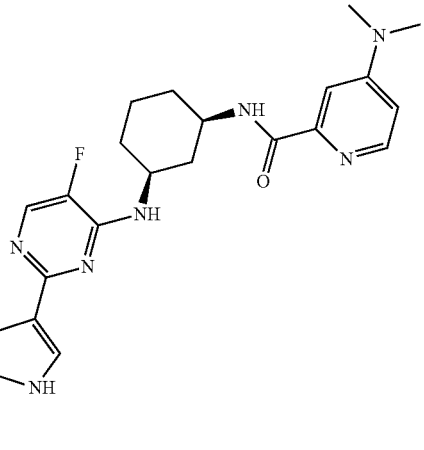<br>$[\alpha]_D^{23}$ -130.0 (c 0.17, DMF) | $^1$H NMR (300 MHz, DMSO-d$_6$) δ ppm 1.28-1.59 (m, 2H), 1.59 (m, 2H), 1.80-1.94 (m, 2H), 2.04 (m, 1H), 2.18 (m, 1H), 3.00 (s, 6H), 3.98 (m, 1H), 4.20 (m, 1H), 6.72 (m, 1H), 7.16 (m, 1H), 7.24 (d, J = 2.4 Hz, 1H), 7.55 (d, J = 7.3 Hz, 0.6H), 8.09-8.20 (m, 3H), 8.35 (m, 1H), 8.44 (m, 0.6H), 12.21 (s, 1H). | 2.32 | D | 526.0 | 281.8 |
| 57 | 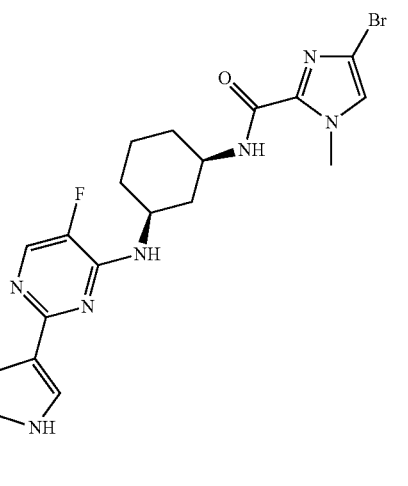<br>$[\alpha]_D^{23}$ -173.3 (c 0.14, DMF) | $^1$H NMR (300 MHz, CD$_3$OD) δ ppm 1.27-1.46 (m, 2H), 1.56 (m, 1H), 1.75 (m, 1H), 1.97 (m, 1H), 2.08 (m, 1H), 2.25 (m, 1H), 2.39 (m, 1H), 3.97 (s, 3H), 4.11 (m, 1H), 4.33 (m, 1H), 6.97 (m, 1H), 7.25 (s, 1H), 7.97 (d, J = 4.1 Hz, 1H), 8.06 (s, 1H), 8.36 (d, J = 1.6 Hz, 1H). | 3.36 | D | 563.9 | 214.9 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 58 | [α]$_D^{23}$ -137.3 (c 0.2, DMF) | ¹H NMR (300 MHz, DMSO-d₆) δ ppm 1.21-1.72 (m, 4H), 1.85 (m, 2H), 2.03 (m, 1H), 2.12 (m, 1H), 3.97 (m, 1H), 4.20 (m, 1H), 7.01 (m, 1H), 7.16 (m, 1H), 7.23 (m, 1H), 7.57 (d, J = 7.5 Hz, 1H), 8.12-8.16 (m, 2H), 8.30 (d, J = 8.3 Hz, 1H), 8.35 (m, 1H), 12.27 (m, 1H), 12.91 (br s, 1H). | 2.48 | D | 472.1 | >300 |
| 59 | [α]$_D^{23}$ -123.6 (c 0.16, DMF) | ¹H NMR (300 MHz, DMSO-d₆) δ ppm 1.22-1.40 (m, 2H), 1.44-1.65 (m, 2H), 1.78-1.92 (m, 2H), 2.03 (m, 1H), 2.14 (m, 1H), 3.90 (m, 1H), 4.17 (m, 1H), 7.15 (m, 1H), 7.53 (d, J = 7.3 Hz, 1H), 8.10-8.17 (m, 2H), 8.34 (d, J = 1.3 Hz, 1H), 11.73-12.09 (m, 1H), 12.26 (br s, 1H). | 2.33 | D | 487.1 | 245.2 |
| 60 | [α]$_D^{23}$ -135.7 (c 0.2, MeOH) | ¹H NMR (300 MHz, CD₃OD) δ ppm 1.29-1.46 (m, 5H), 1.56 (m, 1H), 1.76 (m, 1H), 1.98 (m, 1H), 2.10 (m, 1H), 2.25 (m, 1H), 2.42 (m, 1H), 4.11 (m, 1H), 4.34 (m, 1H), 4.52 (m, 2H), 6.75 (d, J = 2.0 Hz, 1H), 6.98 (m, 1H), 7.45 (d, J = 2.0 Hz, 1H), 7.99 (d, J = 4.1 Hz, 1H), 8.07 (s, 1H), 8.38 (m, 1H). | 2.96 | D | 500.0 | >300 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 61 | [α]$_D^{23}$ -139.2 (c 0.2, MeOH) | ¹H NMR (300 MHz, CD₃OD) δ ppm 1.27-1.47 (m, 2H), 1.56 (m, 1H), 1.76 (m, 1H), 1.99 (m, 1H), 2.10 (m, 1H), 2.25 (m, 1H), 2.42 (m, 1H), 4.08 (s, 3H), 4.11 (m, 1H), 4.34 (m, 1H), 6.77 (d, J = 2.0 Hz, 1H), 6.98 (m, 1H), 7.43 (d, J = 2.0 Hz, 1H), 7.98 (d, J = 4.1 Hz, 1H), 8.07 (s, 1H), 8.38 (d, J = 1.6 Hz, 1H). | 2.79 | D | 486.0 | >300 |
| 62 | [α]$_D^{23}$ -64.3 (c 0.14, DMF) | ¹H NMR (300 MHz, DMSO-d₆) δ ppm 1.19-1.86 (m, 9H), 1.96-2.13 (m, 3H), 2.16-2.29 (m, 4H), 2.65 (m, 1H), 3.01 (m, 1H), 3.77 (m, 1H), 4.15 (m, 1H), 7.16 (m, 1H), 7.51 (m, 1H), 7.57 (m, 1H), 8.09-8.17 (m, 2H), 8.33 (m, 1H), 12.28 (s, 1H). | 2.10 | D | 489.1 | 196.5 |
| 63 | [α]$_D^{23}$ -110.5 (c 0.13, DMF) | ¹H NMR (300 MHz, DMSO-d₆) δ ppm 1.16-1.43 (m, 2H), 1.48-1.67 (m, 2H), 1.78-1.92 (m, 2H), 2.01 (m, 1H), 2.14 (m, 1H), 3.94 (m, 1H), 4.18 (m, 1H), 7.16 (m, 1H), 7.54 (d, J = 7.4 Hz, 1H), 7.58 (s, 1H), 7.64-7.72 (m, 2H), 8.12-8.16 (m, 2H), 8.34 (d, J = 1.4 Hz, 1H), 12.28 (br s, 1H), 12.43 (br s, 1H). | 2.24 | D | 472.0 | 245 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 64 | [α]$_D^{23}$ -190.4 (c 0.16, DMF) | ¹H NMR (300 MHz, DMSO-d$_6$) δ ppm 1.21-1.38 (m, 2H), 1.44-1.61 (m, 2H), 1.80-1.94 (m, 2H), 2.03 (m, 1H), 2.15 (m, 1H), 3.78 (s, 3H), 3.93 (m, 1H), 4.19 (m, 1H), 7.16 (m, 1H), 7.51-7.60 (m, 2H), 7.69 (s, 1H), 8.09-8.18 (m, 3H), 8.34 (d, J = 1.4 Hz, 1H), 12.28 (s, 1H). | 2.21 | D | 486.0 | 291.8 |
| 65 | [α]$_D^{23}$ -188.8 (c 0.13, DMF) | ¹H NMR (300 MHz, DMSO-d$_6$) δ ppm 1.24-1.42 (m, 2H), 1.45-1.67 (m, 2H), 1.78-1.97 (m, 2H), 2.04 (m, 1H), 2.21 (m, 1H), 3.95 (m, 1H), 4.21 (m, 1H), 6.86 (br s, 2H), 7.03 (d, J = 4.8 Hz, 1H), 7.16 (m, 1H), 7.54 (d, J = 7.8 Hz, 1H), 8.12-8.17 (m, 2H), 8.20 (m, 1H), 8.34 (m, 1H), 8.44 (m, 1H), 12.29 (s, 1H). | 2.62 | D | 498.8 | 261.7 |
| 66 | [α]$_D^{23}$ -48.0 (c 0.15, DMF) | ¹H NMR (300 MHz, DMSO-d$_6$) δ ppm 1.23-1.69 (m, 4H), 1.77-1.91 (m, 2H), 2.03 (m, 1H), 2.13 (m, 1H), 3.96 (m, 1H), 4.19 (m, 1H), 7.00 (s, 1H), 7.16 (m, 1H), 7.21 (br s, 2H), 7.56 (m, 1H), 8.10-8.17 (m, 2H), 8.34 (m, 1H), 8.39 (s, 1H), 8.50 (m, 1H), 12.29 (d, J = 1.6 Hz, 1H). | 2.55 | D | 498.9 | 152.4 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 67 | 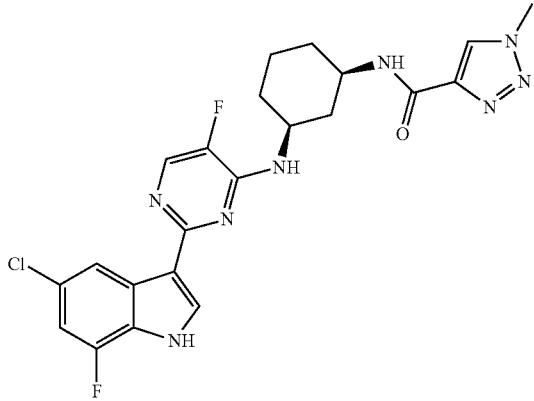<br>[α]$_D^{23}$ -170.0 (c 0.07, MeOH) | ¹H NMR (300 MHz, CD$_3$OD) δ ppm 1.33-1.50 (m, 2H), 1.59 (m, 1H), 1.76 (m, 1H), 1.98 (m, 1H), 2.11 (m, 1H), 2.25 (m, 1H), 2.42 (m, 1H) 4.13 (s, 3H), 4.16 (m, 1H), 4.35 (m, 1H), 6.97 (m, 1H), 7.98 (d, J = 4.1 Hz, 1H), 8.06 (s, 1H), 8.28 (s, 1H), 8.38 (m, 1H). | 2.55 | D | 486.9 | 283 |
| 68 | 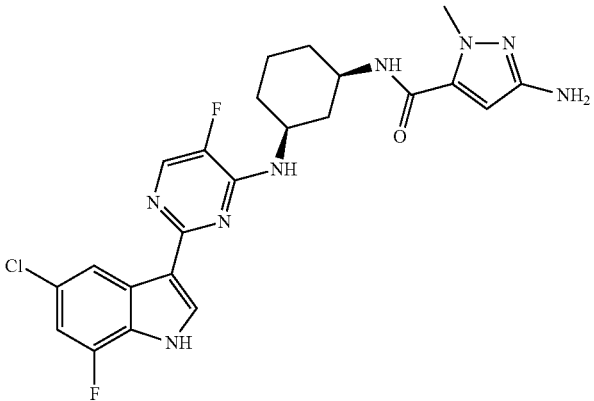<br>O.R. no data | ¹H NMR (300 MHz, CD$_3$OD) δ ppm 1.20-144 (m, 2H), 1.53 (m, 1H), 1.75 (m, 1H), 1.97 (m, 1H), 2.08 (m, 1H), 2.24 (m, 1H), 2.39 (m, 1H), 3.86 (s, 3H), 4.07 (m, 1H), 4.33 (m, 1H), 6.04 (s, 1H), 6.98 (m, 1H), 7.98 (d, J = 4.1 Hz, 1H), 8.07 (s, 1H), 8.37 (d, J = 1.4 Hz, 1H). | 2.45 | D | 500.8 | 267.2 |
| 69 | 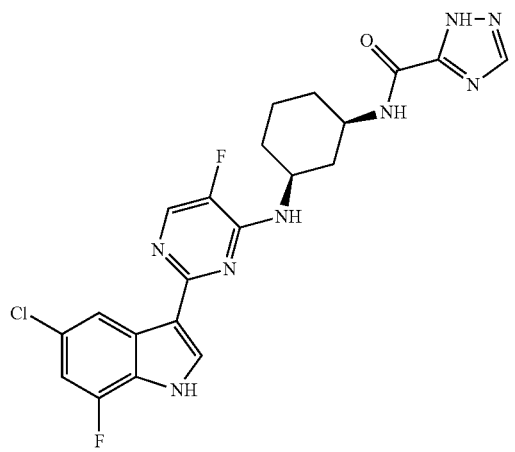<br>O.R. no data | ¹H NMR (300 MHz, CD$_3$OD) δ ppm 1.32-1.49 (m, 2H), 1.60 (m, 1H), 1.78 (m, 1H), 1.99 (m, 1H), 2.13 (m, 1H), 2.26 (m, 1H), 2.45 (m, 1H), 4.14 (m, 1H), 4.35 (m, 1H), 6.97 (m, 1H), 7.98 (d, J = 4.1 Hz, 1H), 8.07 (s, 1H), 8.23 (br s, 1H), 8.38 (d, J = 1.1 Hz, 1H). | 2.35 | D | 472.8 | 293.5 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 70 | O.R. no data | ¹H NMR (300 MHz, CD₃OD) δ ppm 1.30-1.48 (m, 2H), 1.58 (m, 1H), 1.76 (m, 1H), 1.98 (m, 1H), 2.10 (m, 1H), 2.25 (m, 1H), 2.44 (m, 1H), 3.97 (s, 3H), 4.15 (m, 1H), 4.33 (m, 1H), 6.97 (m, 1H), 7.98 (d, J = 4.1 Hz, 1H), 8.07 (s, 1H), 8.37 (m, 1H), 8.40 (s, 1H). | 2.43 | D | 486.8 | 291.9 |
| 71 | O.R. no data | ¹H NMR (300 MHz, CD₃OD) δ ppm 1.27-1.45 (m, 2H), 1.56 (m, 1H), 1.76 (m, 1H), 1.98 (m, 1H), 2.13 (m, 1H), 2.24 (s, 3H), 2.26 (m, 1H), 2.42 (m, 1H), 4.08 (m, 1H), 4.35 (m, 1H), 6.85 (s, 1H), 6.97 (m, 1H), 7.98 (d, J = 4.1 Hz, 1H), 8.06 (s, 1H), 8.37 (m, 1H). | 2.19 | F | 486.1 | 276.8 |
| 72 | [α]_D²³ -189.7 (c 0.11, MeOH) | ¹H NMR (300 MHz, CD₃OD) δ ppm 1.25-1.46 (m, 5H), 1.56 (m, 1H), 1.17 (m, 1H), 1.98 (m, 1H), 2.13 (m, 1H), 2.25 (m, 1H), 2.43 (m, 1H), 4.08 (m, 1H), 4.35 (m, 1H), 4.47 (m, 2H), 6.93-7.03 (m, 2H), 7.27 (m, 1H), 7.98 (d, J = 4.1 Hz, 1H), 8.06 (s, 1H), 8.37 (d, J = 1.6 Hz, 1H). | 2.94 | D | 499.9 | 156.4 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 73 | [α]$_D^{23}$ -175.9 (c 0.16, MeOH) | ¹H NMR (300 MHz, CD$_3$OD) δ ppm 1.26-1.45 (m, 2H), 1.56 (m, 1H), 1.76 (m, 1H), 1.96 (m, 1H), 2.10 (m, 1H), 2.23 (s, 3H), 2.26 (m, 1H), 2.38 (m, 1H), 3.85 (s, 3H), 4.09 (m, 1H), 4.34 (m, 1H), 6.97 (m, 1H), 7.37 (s, 1H), 7.98 (d, J = 4.1 Hz, 1H), 8.06 (s, 1H), 8.37 (d, J = 1.6 Hz, 1H). | 2.03 | D | 499.8 | 248.4 |
| 74 | [α]$_D^{23}$ -118.5 (c 0.22, MeOH) | ¹H NMR (300 MHz, DMSO-d$_6$) δ ppm 1.23-1.71 (m, 4H), 1.79-1.93 (m, 2H), 2.02 (m, 1H), 2.17 (m, 1H), 4.03 (m, 1H), 4.20 (m, 1H), 4.42 (s, 3H), 7.15 (m, 1H), 7.56 (m, 1H), 8.11-8.18 (m, 2H), 8.34 (m, 1H), 8.97 (m, 1H), 12.28 (br s, 1H). | 2.63 | D | 487.8 | 259.7 |
| 75 | O.R. no data | ¹H NMR (300 MHz, CD$_3$OD) δ ppm 1.36-1.53 (m, 2H), 1.57-1.86 (m, 2H), 2.02 (m, 1H), 2.13 (m, 1H), 2.25 (m, 1H), 2.44 (m, 1H), 4.14 (m, 1H), 4.20 (s, 3H), 4.42 (m, 1H), 7.06 (m, 1H), 7.92 (s, 1H), 8.10 (d, J = 4.6 Hz, 1H), 8.19 (s, 1H), 8.35 (d, J = 1.5 Hz, 1H). | 2.78 | D | 486.8 | >300 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 76 | 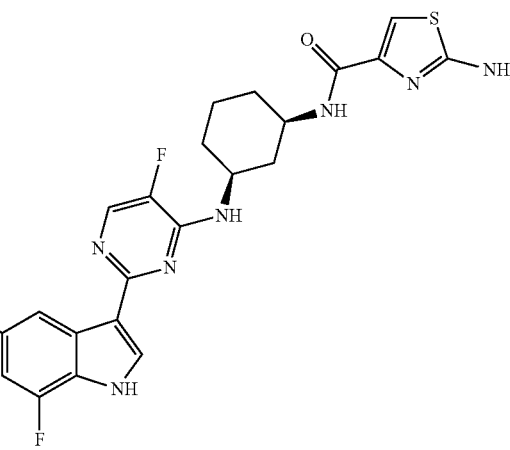<br>$[\alpha]_D^{23}$ -266.9 (c 0.2, MeOH) | ¹H NMR (300 MHz, CD₃OD) δ ppm 1.23-1.43 (m, 2H), 1.53 (m, 1H), 1.75 (m, 1H), 1.96 (m, 1H), 2.09 (m, 1H), 2.26 (m, 1H), 2.40 (m, 1H), 4.07 (m, 1H), 4.34 (m, 1H), 6.95 (m, 1H), 7.22 (s, 1H), 7.96 (d, J = 4.1 Hz, 1H), 8.05 (s, 1H), 8.36 (m, 1H). | 2.54 | D | 503.8 | 184.8 |
| 77 | 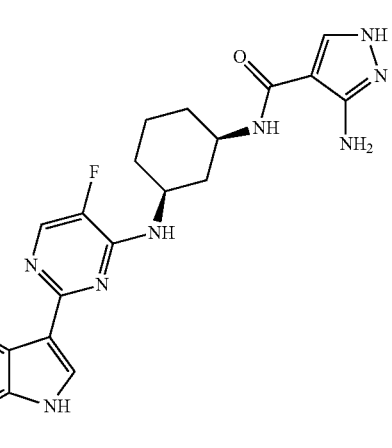<br>$[\alpha]_D^{23}$ -36.2 (c 0.2, MeOH) | ¹H NMR (300 MHz, CD₃OD) δ ppm 1.23-1.61 (m, 3H), 1.77 (m, 1H), 1.89-2.15 (m, 2H), 2.27 (m, 1H), 2.35 (m, 1H), 4.07 (m, 1H), 4.34 (m, 1H), 6.98 (m, 1H), 7.80 (s, 1H), 7.98 (d, J = 4.1 Hz, 1H), 8.07 (s, 1H), 8.38 (m, 1H). | 2.35 | D | 486.8 | 133 |
| 78 | 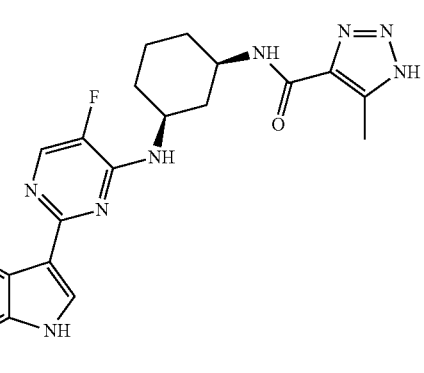<br>$[\alpha]_D^{23}$ -299.1 (c 0.2, MeOH) | ¹H NMR (300 MHz, CD₃OD) δ ppm 1.25-1.44 (m, 2H), 1.56 (m, 1H), 1.78 (m, 1H), 1.98 (m, 1H), 2.14 (m, 1H), 2.28 (m, 1H), 2.40 (m, 1H), 2.43 (s, 3H), 4.09 (m, 1H), 4.35 (m, 1H), 6.96 (m, 1H), 7.97 (d, J = 4.1 Hz, 1H), 8.06 (s, 1H), 8.37 (m, 1H). | 2.57 | D | 486.8 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|-----------|--------|----------|-----------|---------------------------|-----------|
| 79 | 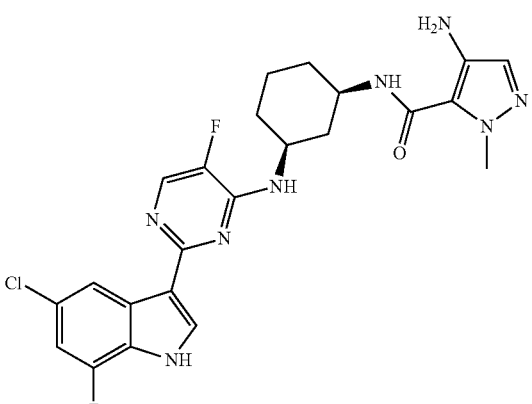<br>[α]$_D^{23}$ -2.3 (c 0.13, DMF) | ¹H NMR (300 MHz, CD$_3$OD) δ ppm 1.25-1.44 (m, 2H), 1.52 (m, 1H), 1.76 (m, 1H), 1.94-2.17 (m, 2H), 2.26 (m, 1H), 2.50 (m, 1H), 3.99 (s, 3H), 4.11 (m, 1H), 4.36 (m, 1H), 6.96 (m, 1H), 7.84 (s, 1H), 7.96 (d, J = 4.1 Hz, 1H), 8.06 (br s, 1H), 8.37 (d, J = 1.5 Hz, 1H). | 2.51 | D | 500.9 | 166.4 |
| 80 | 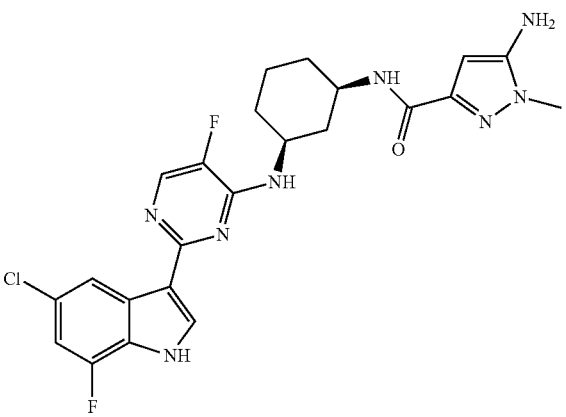<br>[α]$_D^{23}$ -159.3 (c 0.08, MeOH) | ¹H NMR (300 MHz, CD$_3$OD) δ ppm 1.25-1.42 (m, 2H), 1.51 (m, 1H), 1.73 (m, 1H), 1.94 (m, 1H), 2.07 (m, 1H), 2.23 (m, 1H), 2.38 (m, 1H), 3.63 (s, 3H), 4.07 (m, 1H), 4.26 (m, 1H), 5.87 (s, 1H), 6.93 (m, 1H), 7.93 (d, J = 4.1 Hz, 1H), 8.02 (s, 1H), 8.29 (d, J = 1.5 Hz, 1H). | 2.44 | D | 500.9 | 174.8 |
| 81 | 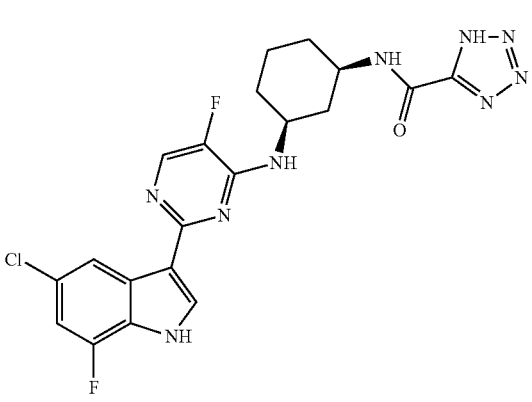<br>O.R. n.d. | ¹H NMR (300 MHz, CD$_3$OD) δ ppm 1.26-1.66 (m, 3H), 1.78 (m, 1H), 1.99 (m, 1H), 2.15 (m, 1H), 2.27 (m, 1H), 2.46 (m, 1H), 4.17 (m, 1H), 4.35 (m, 1H), 6.97 (m, 1H), 7.98 (d, J = 4.1 Hz, 1H), 8.08 (s, 1H), 8.38 (d, J = 1.5 Hz, 1H). | 2.47 | D | 473.8 | 275.1 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 82 | 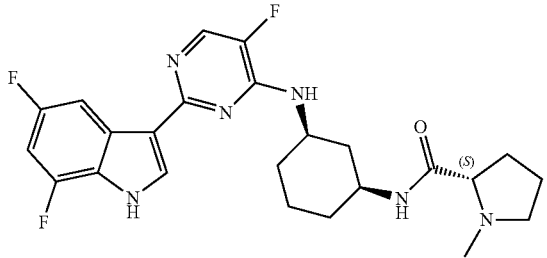<br>OR n.d. | ¹H NMR (360 MHz, DMSO-d₆) δ ppm 1.27 (m, J = 11.3 Hz, 2H) 1.37-1.54 (m, 2H) 1.57-1.71 (m, 4H) 1.78 (br d, J = 17.6 Hz, 2H) 1.96-2.10 (m, 3H) 2.23 (s, 3H) 2.18-2.29 (m, 1H) 2.63-2.70 (m, 1H) 2.99 (br d, J = 3.7 Hz, 1H) 3.70-3.80 (m, 1H) 4.09-4.19 (m, 1H) 7.04 (t, J = 10.4 Hz, 1H) 7.49 (d, J = 7.3 Hz, 1H) 7.59 (d, J = 8.4 Hz, 1H) 8.00 (m, 1H) 8.13 (d, J = 3.9 Hz, 2H) 12.24 (br s, 1H) | 1.01 | A | 473.3 | n.d. |
| 83 | 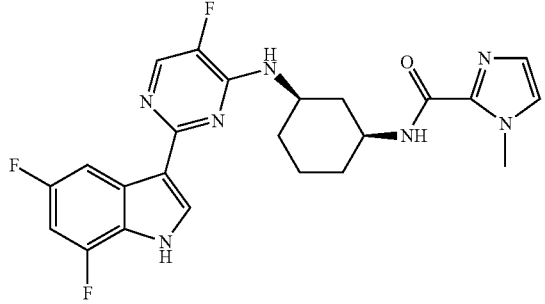<br>[α]$_D^{20}$ -172.2 (c 0.34, DMF) | ¹H NMR (360 MHz, DMSO-d₆) δ ppm 1.22-1.68 (m, 4H) 1.75-1.89 (m, 2H) 2.08 (m, 2H) 3.86-3.99 (m, 1H) 3.93 (s, 3H) 4.18 (m, 1H) 6.96 (d, J = 1.1 Hz, 1H) 7.04 (t, J = 10.4 Hz, 1H) 7.32 (d, J = 0.7 Hz, 1H) 7.55 (d, J = 7.7 Hz, 1H) 8.02 (m, 1H) 8.10-8.15 (m, 2H) 8.31 (d, J = 8.8 Hz, 1H) 12.35 (br s, 1H) | 1.03 | A | 470.2 | 166.6 |
| 84 | 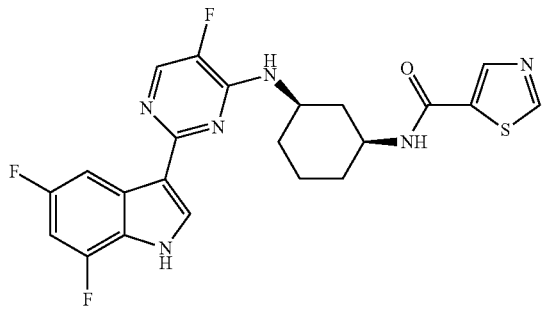<br>OR n.d. | ¹H NMR (360 MHz, DMSO-d₆) δ ppm 1.22-1.38 (m, 2H) 1.46-1.59 (m, 2H) 1.83-1.96 (m, 2H) 2.00-2.08 (m, 1H) 2.17-2.23 (m, 1H) 3.90-4.01 (m, 1H) 4.15-4.25 (m, 1H) 7.05 (m, 1H) 7.56 (m, 1H) 8.02 (m, 1H) 8.14-8.16 (m, 2H) 8.48 (s, 1H) 8.60 (m, 1H) 9.20 (d, J = 0.7 Hz, 1H) 12.21 (s, 1H) | 0.97 | A | 473.1 | 295.2 |
| 85 | 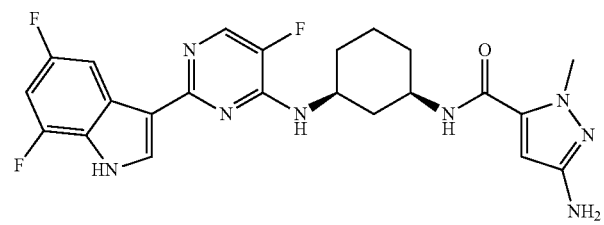<br>[α]$_D^{20}$ -212.7 (c 0.22, DMF) | ¹H NMR (360 MHz, DMSO-d₆) δ ppm 1.30 (m, 2H) 1.52 (m, 2H) 1.86 (m, 2H) 2.06 (m, 2H) 3.78 (s, 3H) 3.93 (m, 1H) 4.06-4.31 (m, 1H) 4.71 (m, 2H) 5.99 (s, 1H) 7.07 (m, 1H) 7.57 (d, J = 8.1 Hz, 1H) 7.98-8.04 (m, 1H) 8.11-8.20 (m, 3H) 12.17-12.23 (m, 1H) | 1.67 | L | 485.1 | |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 86 | 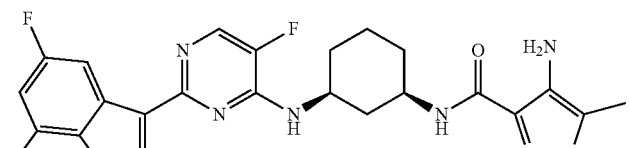 OR n.d. | ¹H NMR (400 MHz, DMSO-d₆) δ ppm 1.21 (m, 1H) 1.35 (m, 1H) 1.54 (m, 1H) 1.86 (m, 1H) 1.97 (m, 1H) 2.05 (m, 1H) 2.13 (s, 3H) 2.32 (m, 1H) 3.94-4.13 (m, 2H) 4.17 (m, 2H) 6.28 (s, 1H) 7.05 (t, J = 10.3 Hz, 1H) 7.20 (m, 1H) 7.50 (m, 1H) 8.04 (m, 1H) 8.13-8.22 (m, 2H) 8.25 (s, 1H) 12.23 (br s, 1H) | 1.70 | L | 485.1 | |
| 87 | 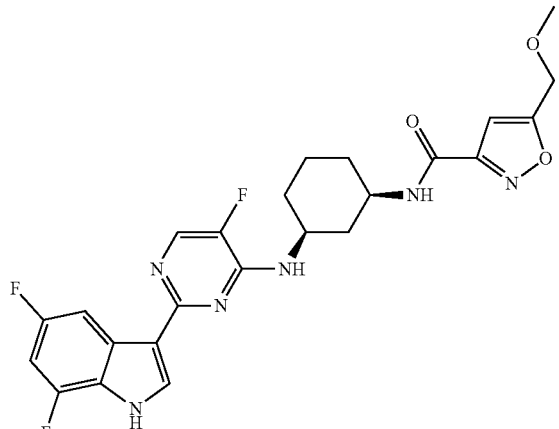 OR n.d. | ¹H NMR (400 MHz, DMSO-d₆) δ ppm 1.27-1.43 (m, 2H) 1.46-1.62 (m, 2H) 1.87 (m, J = 10.3 Hz, 2H) 2.03 (m, 1H) 2.17 (m, 1H) 3.31 (s, 3H) 3.98 (m, J = 8.1 Hz, 1H) 4.18 (m, 1H) 4.58 (s, 2H) 6.79 (s, 1H) 7.05 (t, J = 10.4 Hz, 1H) 7.54 (m, 1H) 8.02 (m, 1H) 8.14 (d, J = 3.7 Hz, 2H) 8.76 (m, 1H) 12.18 (s, 1H) | 1.47 | L | 502.1 | n.d. |
| 88 | 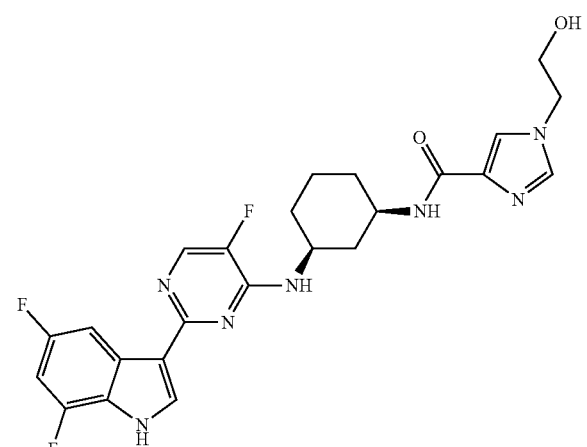 OR n.d. | ¹H NMR (400 MHz, DMSO-d₆) δ ppm 1.24-1.43 (m, 2H) 1.46-1.61 (m, 2H) 1.85 (m, J = 10.8 Hz, 2H) 2.04 (m, 1H) 2.14 (m, 1H) 3.65 (m, 2H) 3.93 (m, 1H) 4.02 (m, 2H) 4.12-4.23 (m, 1H) 4.96 (m, 1H) 7.05 (m, 1H) 7.51 (m, 1H) 7.65 (s, 1H) 7.65 (m, 1H) 7.68 (m, 1H) 8.02 (m, 1H) 8.13 (m, 2H) 12.17 (s, 1H) | 1.61 | L | 500.2 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 89 | (structure) OR n.d. | ¹H NMR (360 MHz, chloroform-d) δ ppm 1.20-1.36 (m, 3H) 1.58-1.70 (m, 1H) 1.95 (n, J = 13.9 Hz, 1H) 2.15 (m, J = 12.1 Hz, 1H) 2.29 (m, 1H) 2.66 (m, J = 11.7 Hz, 1H) 4.06-4.29 (m, 2H) 4.88 (m, 1H) 5.03 (m, 1H) 5.40 (m, 1H) 6.72-6.82 (m, 1H) 6.89 (m, 1H) 7.05 (m, 1H) 7.58 (m, 1H) 7.82 (m, 1H) 7.95-8.08 (m, 2H) 8.10 (s, 1H) 9.11-9.53 (m, 1H) | 1.21 | N | 482.2 | n.d. |
| 90 | (structure) (+/-) | ¹H NMR (300 MHz, CD₃OD) δ ppm 1.30-1.54 (m, 2H), 1.55-1.81 (m, 2H), 2.00 (m, 1H), 2.12 (m, 1H), 2.28 (m, 1H), 2.43 (m, 1H), 4.14 (m, 1H), 4.36 (m, 1H), 6.81 (m, 1H), 7.54 (m, 1H), 7.90-8.01 (m, 2H), 8.02-8.12 (m, 3H), 8.62 (d, J = 4.1 Hz, 1H). | 2.77 | D | 467.0 | n.d. |
| 91 | (structure) (+/-) | ¹H NMR (300 MHz, CDCl₃) δ ppm 1.25-1.37 (m, 3H), 1.67 (m, 1H), 2.00 (m, 1H), 2.18 (m, 1H), 2.29 (br. s, 1H), 2.35 (s, 3H), 2.68 (m, 1H), 4.15-4.29 (m, 2H), 4.87 (d, J = 7.1 Hz, 1H), 6.43 (d, J = 7.9 Hz, 1H), 6.74-6.82 (m, 2H), 8.04-8.10 (m, 3H), 8.63 (br. s, 1H). | 2.56 | D | 471.0 | n.d. |

151
152
TABLE 1-continued
Compounds of formula (I) and corresponding analytical data.
| # | STRUCTURE | ¹H NMR | Rt (min) | LC Method | LC-MS Mass Found [M + H]⁺ | MP (° C.) |
|---|---|---|---|---|---|---|
| 92 | 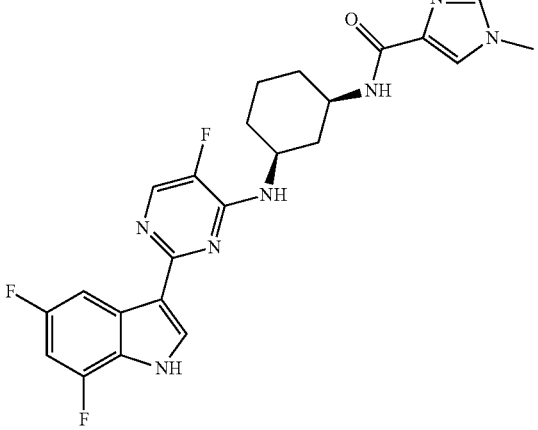<br>(+/−) | ¹H NMR (300 MHz, CDCl₃) δ ppm 1.11-1.68 (m, 4H), 1.89 (m, 1H), 2.07 (m, 1H), 2.23 (m, 1H), 2.59 (m, 1H), 3.65 (s, 3H), 4.13 (m, 2H), 4.79 (m, 1H), 6.71 (m, 1H), 6.92 (d, J = 7.8 Hz, 1H), 7.27 (s, 1H), 7.45 (s, 1H), 7.95-8.07 (m, 3H), 8.62 (br s, 1H). | 2.07 | D | 470.1 | n.d. |
| 93 | 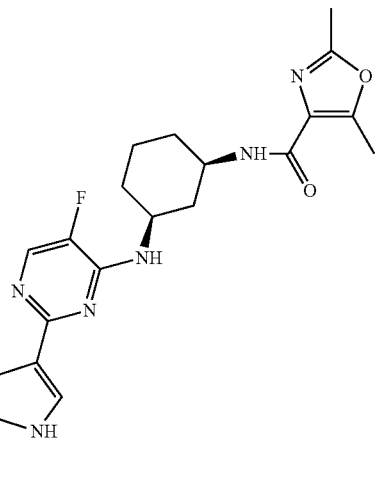<br>(+/−) | ¹H NMR (300 MHz, CDCl₃) δ ppm 1.19-1.35 (m, 4H), 1.62 (m, 1H), 1.94 (m, 1H), 2.12 (m, 1H), 2.28 (m, 1H), 2.39 (s, 3H), 2.58 (s, 3H), 4.08-4.20 (m, 2H), 4.86 (d, J = 7.3 Hz, 1H), 5.42 (br. s, 1H), 6.74 (t, J = 10.9 Hz, 1H), 6.82 (d, J = 8.0 Hz, 1H), 8.00 (m, 1H), 8.04 (d, J = 3.0 Hz, 1H), 8.08 (s, 1H). | 2.77 | D | 485.1 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 94 | (+/−) | ¹H NMR (300 MHz, CD₃OD) δ ppm 1.24-1.46 (m, 2H), 1.47-1.76 (m, 2H), 1.94-2.10 (m, 2H), 2.27 (m, 1H), 2.35 (m, 1H), 3.86 (s, 3H), 4.04 (m, 1H), 4.32 (m, 1H), 6.03 (m, 1H), 6.71-6.85 (m, 3H), 7.97 (d, J = 4.1 Hz, 1H), 8.04 (m, 1H), 8.07 (s, 1H). | 2.77 | D | 469.1 | n.d. |
| 95 | (+/−) | ¹H NMR (300 MHz, CD₃OD) δ ppm 1.29-153 (m, 2H), 1.54-1.79 (m, 2H), 2.00 (m, 1H), 2.09 (m, 1H), 2.27 (m, 1H), 2.41 (m, 1H), 4.12 (m, 1H), 4.34 (m, 1H), 6.80 (m, 1H), 7.74 (m, 1H), 7.98 (d, J = 4.1 Hz, 1H), 8.01-8.10 (m, 2H), 8.15 (m, 1H), 8.51 (m, 1H). | 2.91 | D | 485.1 | n.d. |
| 96 | (+/−) | ¹H NMR (300 MHz, DMSO-d₆) δ ppm 1.19-1.63 (m, 4H), 1.74-1.90 (m, 2H), 2.02 (m, 1H), 2.11 (m, 1H), 2.24 (s, 3H), 3.75 (s, 3H), 3.92 (m, 1H), 4.15 (m, 1H), 6.38 (s, 1H), 7.04 (m, 1H), 7.51 (d, J = 7.5 Hz, 1H), 7.81 (d, J = 8.2 Hz, 1H), 8.01 (m, 1H), 8.12 (s, 2H), 12.18 (br s, 1H). | 2.53 | D | 484.1 | n.d. |

TABLE 1-continued
Compounds of formula (I) and corresponding analytical data.
| # | STRUCTURE | ¹H NMR | Rt (min) | LC Method | LC-MS Mass Found [M + H]⁺ | MP (° C.) |
|---|---|---|---|---|---|---|
| 97 | 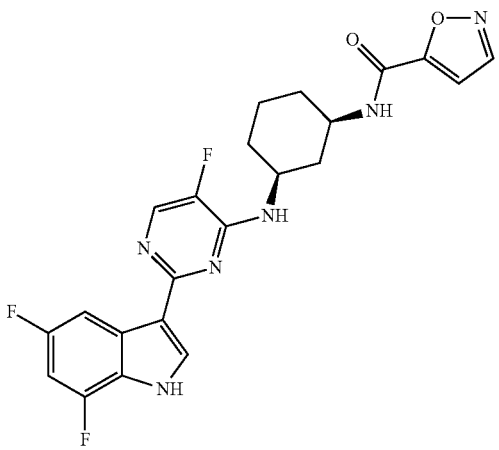 (+/−) | ¹H NMR (300 MHz, DMSO-d₆) δ ppm 1.25-1.64 (m, 4H), 1.78-1.94 (m, 2H), 2.03 (m, 1H), 2.18 (m, 1H), 3.97 (m, 1H), 4.19 (m, 1H), 6.96-7.12 (m, 2H), 7.55 (d, J = 7.3 Hz, 1H), 8.01 (m, 1H), 8.10-8.18 (m, 2H), 8.71 (d, J = 1.6 Hz, 1H), 8.90 (m, 1H), 12.18 (br s, 1H). | 2.48 | D | 457.0 | n.d. |
| 98 | 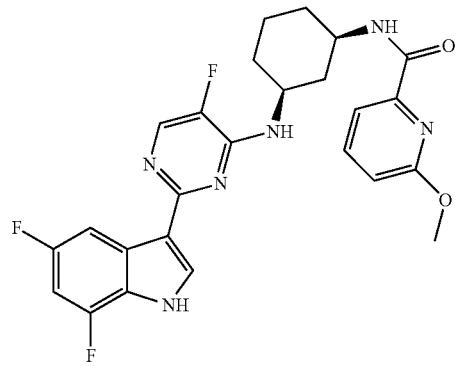 [α]$_D^{23}$ −202.8 (c 0.13, MeOH) | ¹H NMR (300 MHz, CDCl₃) δ ppm 1.22-1.74 (m, 4H), 2.04 (m, 1H), 2.18 (m, 1H), 2.27 (m, 1H), 2.86 (m, 1H), 3.97 (s, 3H), 4.04-4.22 (m, 2H), 5.79 (m, 1H), 6.76 (m, 1H), 6.90 (d, J = 8.0 Hz, 1H), 7.63-7.77 (m, 2H), 7.78-7.95 (m, 3H), 8.62 (br s, 1H), 10.37 (m, 1H). | 3.08 | D | 497.1 | 240 |
| 99 | 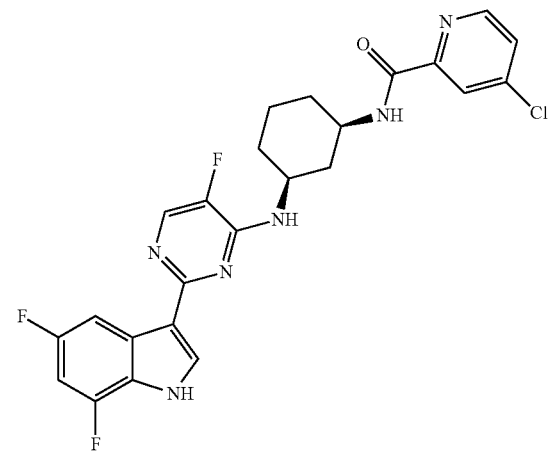 [α]$_D^{23}$ −195.7 (c 0.13, MeOH) | ¹H NMR (300 MHz, CD₃OD) δ ppm 1.24-1.82 (m, 4H), 2.01 (m, 1H), 2.11 (m, 1H), 2.29 (m, 1H), 2.43 (m, 1H), 4.15 (m, 1H), 4.36 (m, 1H), 6.80 (m, 1H), 7.62 (m, 1H), 7.94-8.16 (m, 4H), 8.57 (m, 1H). | 3.12 | D | 501.0 | 86 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 100 | [α]$_D^{23}$ -182.4 (c 0.21, MeOH) | ¹H NMR (300 MHz, CD₃OD) δ ppm 1.33-1.61 (m, 2H), 1.62-1.82 (m, 2H), 2.02 (m, 1H), 2.16 (m, 1H), 2.28 (m, 1H), 2.48 (d, J = 12.1 Hz, 1H), 4.02 (m, 1H), 4.36 (m, 1H), 6.80 (m, 1H), 7.83 (m, 1H), 7.97 (d, J = 4.1 Hz, 1H), 8.00-8.09 (m, 2H), 8.45 (m, 1H), 8.57 (m, 2H), 9.02 (d, J = 2.9 Hz, 1H). | 2.77 | D | 518.1 | 84.6 |
| 101 | [α]$_D^{23}$ -154.1 (c 0.22, MeOH) | ¹H NMR (300 MHz, CD₃OD) δ ppm 1.24-1.48 (m, 2H), 1.56 (m, 1H), 1.70 (m, 1H), 1.99 (m, 1H), 2.13 (m, 1H), 2.26 (m, 1H), 2.45 (m, 1H), 2.54 (s, 3H), 4.10 (m, 1H), 4.34 (m, 1H), 6.80 (m, 1H), 7.38 (m, 1H), 7.70 (m, 1H), 7.97 (d, J = 4.1 Hz, 1H), 8.01-8.08 (m, 2H), 8.38 (m, 1H). | 2.77 | D | 481.1 | 236 |
| 102 | [α]$_D^{23}$ -154.0 (c 0.07, MeOH) | ¹H NMR (300 MHz, CD₃OD) δ ppm 1.29-1.54 (m, 2H), 1.55-1.79 (m, 2H), 1.99 (m, 1H), 2.10 (m, 1H), 2.27 (m, 1H), 2.43 (m, 1H), 4.12 (m, 1H), 4.32 (m, 1H), 6.80 (m, 1H), 7.31 (m, 1H), 7.41 (m, 1H), 7.97 (d, J = 4.1 Hz, 1H), 8.03 (m, 1H), 8.06-8.13 (m, 2H). | 3.21 | D | 483.1 | 176 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 103 | [α]$_D^{23}$ -127.5 (c 0.16, MeOH) | ¹H NMR (300 MHz, CD₃OD) δ ppm 1.27-1.54 (m, 2H), 1.55-1.79 (m, 2H), 2.00 (m, 1H), 2.09 (m, 1H), 2.27 (m, 1H), 2.42 (m, 1H), 2.62 (s, 3H), 4.16 (m, 1H), 4.35 (m, 1H), 6.81 (m, 1H), 7.98 (d, J = 4.1 Hz, 1H), 8.01-8.11 (m, 2H), 8.56 (s, 1H), 9.07 (m, 1H). | 2.62 | D | 482.1 | 215 |
| 104 | [α]$_D^{23}$ -199.6 (c 0.22, MeOH) | ¹H NMR (300 MHz, CD₃OD) δ ppm 1.26-1.48 (m, 2H), 1.49-1.78 (m, 2H), 1.99 (m, 1H), 2.09 (m, 1H), 2.26 (m, 1H), 2.44 (m, 1H), 4.09 (m, 1H), 4.32 (m, 1H), 6.72 (d, J = 8.7 Hz, 1H), 6.80 (m, 1H), 7.16 (m, 1H), 7.67 (m, 1H), 7.98 (d, J = 4.1 Hz, 1H), 8.03 (m, 1H), 8.08 (s, 1H). | 2.17 | F | 483.2 | 226.6 |
| 105 | [α]$_D^{23}$ -181.5 (c 0.2, MeOH) | ¹H NMR (300 MHz, CD₃OD) δ ppm 1.29-1.52 (m, 2H), 1.53-1.79 (m, 2H), 1.99 (m, 1H), 2.10 (m, 1H), 2.27 (m, 1H), 2.42 (m, 1H), 3.91 (s, 3H), 4.12 (m, 1H), 4.34 (m, 1H), 6.80 (m, 1H), 7.06 (m, 1H), 7.63 (d, J = 2.4 Hz, 1H), 7.98 (d, J = 4.1 Hz, 1H), 8.02-8.10 (m, 2H), 8.41 (d, J = 5.7 Hz, 1H). | 2.52 | F | 497.2 | 233.8 |
| 106 | [α]$_D^{23}$ -97.4 (c 0.07, MeOH) | ¹H NMR (300 MHz, CD₃OD) δ ppm 1.28-1.50 (m, 2H), 1.51-1.79 (m, 2H), 1.99 (m, 1H), 2.10 (m, 1H), 2.28 (m, 1H), 2.41 (m, 1H), 4.08 (m, 1H), 4.35 (m, 1H), 6.67 (m, 1H), 6.81 (m, 1H), 7.28 (m, 1H), 7.53 (m, 1H), 7.98 (d, J = 4.1 Hz, 1H), 8.01-8.10 (m, 2H). | 2.28 | D | 482.1 | 190 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 107 | [α]$_D^{23}$ -80.5 (c 0.07, DMF) | ¹H NMR (300 MHz, DMSO-d$_6$) δ ppm 1.26-1.71 (m, 4H), 1.80-1.92 (m, 2H), 2.03 (m, 1H), 2.18 (m, 1H), 4.04 (m, 1H), 4.20 (m, 1H), 7.05 (m, 1H), 7.55 (d, J = 7.3 Hz, 1H), 8.02 (m, 1H), 8.10-8.18 (m, 2H), 8.71 (m, 1H), 8.75-8.88 (m, 2H), 9.17 (d, J = 1.2 Hz, 1H). | 2.52 | D | 468.0 | 269 |
| 108 | [α]$_D^{23}$ -154.0 (c 0.07, MeOH) | ¹H NMR (300 MHz, CD$_3$OD) δ ppm 1.29-1.82 (m, 4H), 2.03 (m, 1H), 2.12 (m, 1H), 2.27 (m, 1H), 2.48 (m, 1H), 4.17 (m, 1H), 4.34 (m, 1H), 6.80 (m, 1H), 7.61 (m, 1H), 7.99 (d, J = 4.1 Hz, 1H), 8.05 (m, 1H), 8.09 (s, 1H), 8.93 (d, J = 4.9 Hz, 2H). | 2.32 | D | 468.1 | >300 |
| 109 | No OR data | ¹H NMR (300 MHz, CD$_3$OD) δ ppm 1.27-1.54 (m, 2H), 1.56 (m, 2H), 1.99 (m, 1H), 2.10 (m, 1H), 2.27 (m, 1H), 2.43 (m, 1H), 4.11 (m, 1H), 4.34 (m, 1H), 6.81 (m, 1H), 7.82 (d, J = 3.0 Hz, 1H), 7.93 (d, J = 3.0 Hz, 1H), 7.98 (d, J = 4.1 Hz, 1H), 8.01-8.09 (m, 2H). | 2.73 | D | 473.0 | 277.0 |
| 110 | [α]$_D^{23}$ -167.0 (c 0.15, MeOH) | ¹H NMR (300 MHz, CD$_3$OD) δ ppm 1.26-1.52 (m, 2H), 1.54-1.79 (m, 2H), 1.99 (m, 1H), 2.10 (m, 1H), 2.28 (m, 1H), 2.4 (m, 1H), 2.43 (s, 3H), 4.12 (m, 1H), 4.34 (m, 1H), 6.80 (m, 1H), 7.36 (m, 1H), 7.92 (s, 1H), 7.97 (d, J = 4.1 Hz, 1H), 8.00-8.10 (m, 2H), 8.45 (d, J = 4.9 Hz, 1H). | 2.95 | D | 481.1 | 255 |
| 111 | [α]$_D^{20}$ -170 (c 0.2, DMF) | ¹H NMR (300 MHz, CD$_3$OD) δ ppm 1.26-1.79 (m, 4H), 1.99 (m, 1H), 2.10 (m, 1H), 2.26 (m, 1H), 2.43 (m, 1H), 4.14 (m, 1H), 4.33 (m, 1H), 6.80 (m, 1H), 7.98 (d, J = 4.1 Hz, 1H), 8.00-8.09 (m, 2H), 8.18 (s, 1H). | 2.28 | D | 457.0 | 265 |

TABLE 1-continued

Compounds of formula (I) and corresponding analytical data.

| # | STRUCTURE | $^1$H NMR | Rt (min) | LC Method | LC-MS Mass Found [M + H]$^+$ | MP (° C.) |
|---|---|---|---|---|---|---|
| 112 | [α]$_D^{23}$ -187.9 (c 0.07, MeOH) | $^1$H NMR (300 MHz, CD$_3$OD) δ ppm 1.25-1.78 (m, 4H), 1.97 (m, 1H), 2.08 (m, 1H), 2.28 (m, 1H), 2.30 (s, 3H), 2.40 (d, J = 11.6 Hz, 1H), 4.08 (m, 1H), 4.31 (m, 1H), 6.48 (s, 1H), 6.79 (m, 1H), 7.97 (d, J = 4.1 Hz, 1H), 8.03 (m, 1H), 8.07 (s, 1H). | 2.39 | D | 470.1 | 283 |
| 113 | [α]$_D^{23}$ -134.5 (c 0.12, MeOH) | $^1$H NMR (300 MHz, CD$_3$OD) δ ppm 1.28-1.46 (m, 2H), 1.54 (m, 1H), 1.69 (m, 1H), 1.98 (m, 1H), 2.12 (m, 1H), 2.25 (m, 1H), 2.31 (s, 3H), 2.48 (m, 1H), 3.73 (s, 3H), 4.08 (m, 1H), 4.33 (m, 1H), 6.80 (m, 1H), 7.55 (s, 1H), 7.99 (d, J = 4.1 Hz, 1H), 8.05 (m, 1H), 8.08 (s, 1H). | 2.02 | D | 484.1 | >300 |
| 114 | [α]$_D^{23}$ -213.5 (c 0.08, MeOH) | $^1$H NMR (300 MHz, DMSO-d$_6$) δ ppm 1.20-1.63 (m, 4H), 1.72-1.85 (m, 2H), 1.91 (m, 1H), 2.08 (m, 1H), 3.93 (m, 1H), 4.24 (m, 1H), 6.84 (m, 1H), 7.08 (m, 1H), 7.41 (m, 1H), 7.98 (s, 1H), 8.09 (d, J = 3.9 Hz, 1H), 8.36 (s, 1H), 8.49 (m, 1H), 11.81 (br s, 1H). | 1.98 | F | 457.1 | 289.8 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 115 | [α]$_D^{23}$ -210.9 (c 0.17, MeOH) | ¹H NMR (300 MHz, CD$_3$OD) δ ppm 1.26-1.50 (m, 6H), 1.57 (m, 1H), 1.87-2.13 (m, 3H), 2.37 (m, 1H), 4.04 (m, 1H), 4.39 (m, 1H), 4.53 (m, 2H), 6.65-6.76 (m, 2H), 6.98 (m, 1H), 7.45 (d, J = 2.0 Hz, 1H), 7.84 (s, 1H), 7.95 (m, 1H). | 2.44 | D | 484.1 | 266.8 |
| 116 | [α]$_D^{23}$ -184.5 (c 0.1, MeOH) | ¹H NMR (300 MHz, CD$_3$OD) δ ppm 1.25-1.45 (m, 2H), 1.46-1.77 (m, 2H), 1.90-2.11 (m, 2H), 2.21 (s, 3H), 2.25 (m, 1H), 2.40 (d, J = 11.8 Hz, 1H), 3.99 (s, 3H), 4.06 (m, 1H), 4.31 (m, 1H), 6.53 (s, 1H), 6.80 (m, 1H), 7.98 (d, J = 4.1 Hz, 1H), 8.03 (m, 1H), 8.07 (s, 1H). | 2.64 | D | 484.1 | 279 |
| 117 | [α]$_D^{23}$ -162.9 (c 0.12, MeOH) | ¹H NMR (300 MHz, CD$_3$OD) δ ppm 1.25-1.50 (m, 2H), 1.52-1.78 (m, 2H), 1.98 (m, 1H), 2.09 (m, 1H), 2.27 (m, 1H), 2.39 (m, 1H), 2.55 (s, 3H), 3.98 (s, 3H), 4.11 (m, 1H), 4.34 (m, 1H), 6.80 (m, 1H), 7.98 (d, J = 4.1 Hz, 1H), 8.00-8.09 (m, 2H). | 2.53 | D | 485.1 | 202 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 118 | [α]$_D^{23}$ -297.5 (c 0.07, MeOH) | ¹H NMR (300 MHz, CD$_3$OD) δ ppm 1.19-1.77 (m, 4H), 1.93-2.12 (m, 2H), 2.24 (m, 1H), 2.43 (m, 1H), 2.64 (s, 3H), 4.13 (m, 1H), 4.30 (m, 1H), 6.80 (m, 1H), 7.98 (d, J = 4.1 Hz, 1H), 8.02 (m, 1H), 8.07 (s, 1H). | 2.52 | D | 472.1 | 233 |
| 119 | [α]$_D^{23}$ -184.0 (c 0.07, MeOH) | ¹H NMR (300 MHz, CD$_3$OD) δ ppm 1.27-1.77 (m, 4H), 1.99 (m, 1H), 2.10 (m, 1H), 2.25 (m, 1H), 2.45 (m, 1H), 4.10 (m, 1H), 4.27 (s, 3H), 4.32 (m, 1H), 6.81 (m, 1H), 7.98 (d, J = 4.1 Hz, 1H), 8.03 (m, 1H), 8.08 (s, 1H), 8.11 (s, 1H). | 2.47 | D | 471.0 | 285 |
| 120 | [α]$_D^{23}$ -160.0 (c 0.12, MeOH) | ¹H NMR (300 MHz, CD$_3$OD) δ ppm 1.21-1.77 (m, 4H), 1.84-2.11 (m, 2H), 2.26 (m, 1H), 2.39 (m, 1H), 3.09 (s, 3H), 4.07 (m, 1H), 4.32 (m, 1H), 6.80 (m, 1H), 7.88 (s, 1H), 7.91-8.10 (m, 4H). | 2.33 | D | 470.2 | >300 |

TABLE 1-continued
Compounds of formula (I) and corresponding analytical data.
| # | STRUCTURE | ¹H NMR | Rt (min) | LC Method | LC-MS Mass Found [M + H]⁺ | MP (° C.) |
|---|---|---|---|---|---|---|
| 121 | 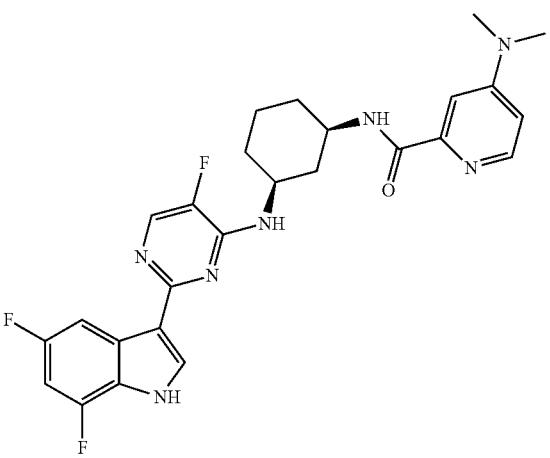 [α]$_D^{23}$ -136.6 (c 0.11, MeOH) | ¹H NMR (300 MHz, CD₃OD) δ ppm 1.27-1.49 (m, 2H), 1.50-1.79 (m, 2H), 1.99 (m, 1H), 2.11 (m, 1H), 2.27 (m, 1H), 2.43 (m, 1H), 3.06 (s, 6H), 4.11 (m, 1H), 4.35 (m, 1H), 6.71 (m, 1H), 6.81 (m, 1H), 7.37 (d, J = 2.6 Hz, 1H), 7.98 (d, J = 4.1 Hz, 1H), 8.01-8.10 (m, 2H), 8.13 (d, J = 5.9 Hz, 1H). | 2.18 | D | 510.1 | 282.8 |
| 122 | 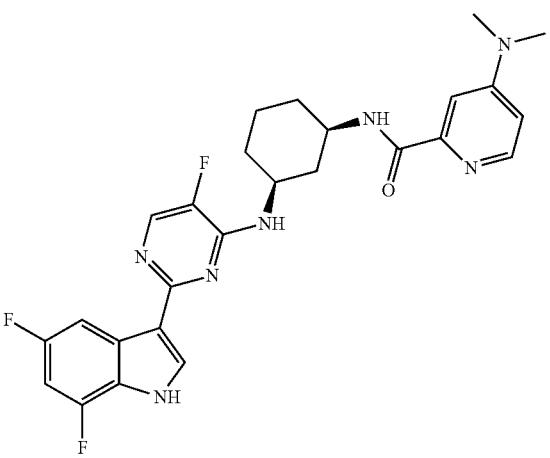 [α]$_D^{23}$ -69.0 (c 0.07, MeOH) | ¹H NMR (300 MHz, CD₃OD) δ ppm 1.25-1.78 (m, 4H), 1.91-2.13 (m, 2H), 2.26 (m, 1H), 2.41 (m, 1H), 4.09-4.15 (br s, 4H), 4.32 (m, 1H), 6.74-6.86 (m, 2H), 7.43 (d, J = 2.0 Hz, 1H), 7.98 (d, J = 4.1 Hz, 1H), 8.04 (m, 1H), 8.08 (s, 1H). | 2.56 | D | 469.8 | >300 |
| 123 | 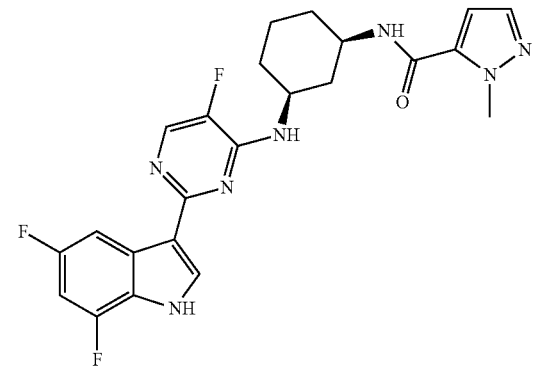 OR n.d. | ¹H NMR (300 MHz, CD₃OD) δ ppm 1.25-1.51 (m, 2H), 1.52-1.78 (m, 2H), 1.94-2.13 (m, 2H), 2.27 (m, 1H), 2.41 (m, 1H), 4.08 (m, 1H), 4.34 (m, 1H), 6.81 (m, 1H), 7.20 (d, J = 5.0 Hz, 1H), 7.99 (d, J = 4.1 Hz, 1H), 8.08-8.10 (m, 2H), 8.43 (d, J = 5.0 Hz, 1H). | 2.43 | D | 482.9 | 235 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 124 | 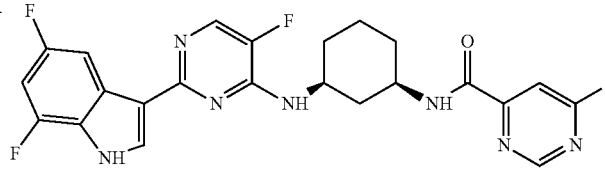<br>OR n.d. | ¹H NMR (300 MHz, CD₃OD) δ ppm 1.25-1.50 (m, 2H), 1.52-1.78 (m, 2H), 1.94-2.13 (m, 2H), 2.27 (m, 1H), 4.09 (m, 1H), 4.34 (m, 1H), 6.81 (m, 1H), 7.11 (d, J = 1.0 Hz, 1H), 7.98 (d, J = 4.1 Hz, 1H), 8.01-8.09 (m, 2H), 8.39 (d, J = 1.0 Hz, 1H). | 2.36 | D | 482.8 | 228 |
| 125 | 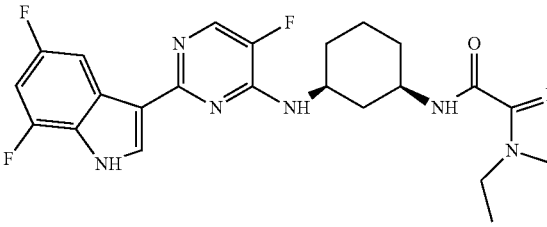<br>OR n.d. | ¹H NMR (300 MHz, CD₃OD) δ ppm 1.22-1.46 (m, 5H), 1.48-1.81 (m, 2H), 1.98 (m, 1H), 2.10 (m, 1H), 2.26 (d, J = 12.2 Hz, 1H), 2.42 (m, 1H), 4.05 (m, 1H), 4.32 (m, 1H), 4.47 (m, 2H), 6.80 (m, 1H), 7.00 (s, 1H), 7.27 (s, 1H), 7.97 (d, J = 4.1 Hz, 1H), 8.03 (m, 1H), 8.07 (s, 1H). | 2.67 | D | 483.9 | n.d. |
| 126 | 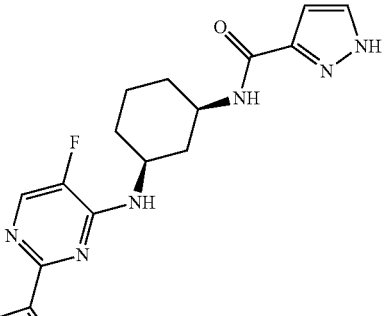<br>OR n.d. | ¹H NMR (300 MHz, DMSO-d₆) δ ppm 1.25-1.64 (m, 4H), 1.78-1.93 (m, 2H), 2.04 (m, 1H), 2.16 (m, 1H), 3.96 (m, 1H), 4.18 (m, 1H), 6.67 (m, 1H), 7.05 (m, 1H), 7.53 (m, 1H), 7.73 (br s, 1H), 8.02 (m, 1H), 8.10-8.17 (m, 3H), 12.18 (s, 1H), 13.14 (br s, 1H). | 2.33 | D | 456.1 | >300 |
| 127 | 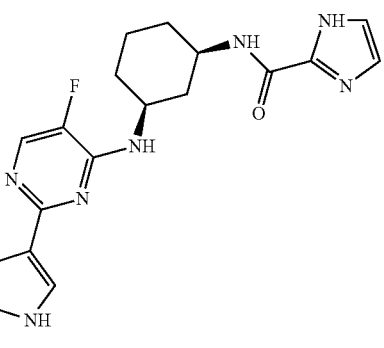<br>[α]$_D^{23}$ -209.2 (c 0.14, DMF) | ¹H NMR (300 MHz, CD₃OD) δ ppm 1.32-1.48 (m, 2H), 1.50-1.79 (m, 2H), 1.99 (m, 1H), 2.12 (m, 1H), 2.27 (m, 1H), 2.42 (m, 1H), 4.08 (m, 1H), 4.34 (m, 1H), 6.80 (m, 1H), 7.16 (s, 2H), 7.98 (m, 1H), 8.04 (m, 1H), 8.07 (s, 1H). | 2.34 | D | 455.9 | >300 |

TABLE 1-continued
Compounds of formula (I) and corresponding analytical data.
| # | STRUCTURE | ¹H NMR | Rt (min) | LC Method | LC-MS Mass Found [M + H]⁺ | MP (° C.) |
|---|---|---|---|---|---|---|
| 128 | 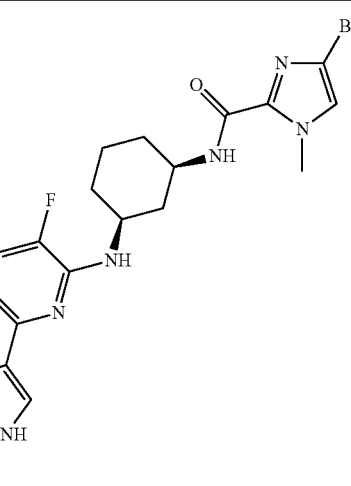<br>[α]$_D^{23}$ -179.0 (c 0.25, DMF) | ¹H NMR (300 MHz, CD$_3$OD) δ ppm 1.27-1.47 (m, 2H), 1.48-1.76 (m, 2H), 1.97 (m, 1H), 2.07 (m, 1H), 2.25 (m, 1H), 2.38 (m, 1H), 3.98 (s, 3H), 4.03 (m, 1H), 4.31 (m, H), 6.80 (m, 1H), 7.25 (s, 1H), 7.98 (d, J = 4.1 Hz, 1H), 8.03 (m, 1H), 8.07 (s, 1H). | 3.09 | D | 549.7 | 176 |
| 129 | 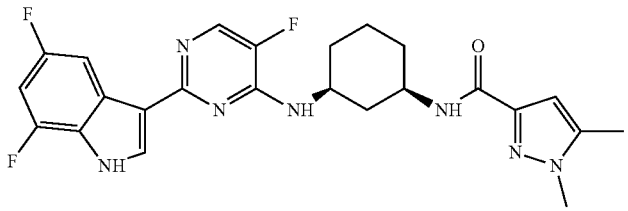<br>OR n.d. | ¹H NMR (300 MHz, DMSO-d$_6$) δ ppm 1.24-1.62 (m, 4H), 1.76-1.89 (m, 2H), 2.02 (m, 1H), 2.12 (m, 1H), 2.25 (s, 3H), 3.75 (s, 3H), 3.92 (m, 1H), 4.16 (m, 1H), 6.39 (s, 1H), 7.05 (m, 1H), 7.52 (d, J = 7.3 Hz, 1H), 7.81 (m, 1H), 8.02 (m, 1H), 8.10-8.17 (m, 2H), 12.18 (br s, 1H). | 2.58 | D | 483.9 | 158 |
| 130 | 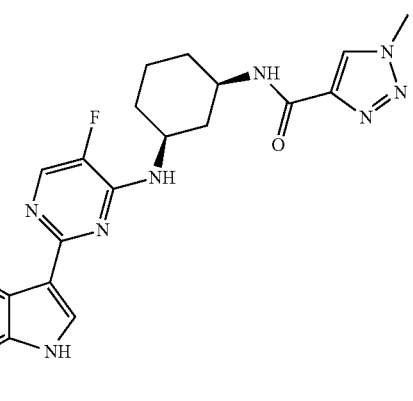<br>[α]$_D^{23}$ -162.0 (c 0.04, MeOH) | ¹H NMR (300 MHz, CD$_3$OD) δ ppm 1.27-1.76 (m, 4H), 1.99 (m, 1H), 2.09 (m, 1H), 2.26 (m, 1H), 2.41 (m, 1H), 4.05-4.19 (br s, 4H), 4.33 (m, 1H), 6.80 (m, 1H), 7.98 (d, J = 4.1 Hz, 1H) 8.00-8.10 (m, 2H), 8.28 (s, 1H). | 2.38 | D | 470.9 | >300 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 131 | [α]$_D^{23}$ -73.9 (c 0.14, MeOH) | ¹H NMR (300 MHz, CD₃OD) δ ppm 1.26-1.45 (m, 2H), 1.46-1.77 (m, 2H), 1.98 (m, 1H), 2.08 (m, 1H), 2.26 (m, 1H), 2.39 (m, 1H), 4.06 (m, 1H), 4.32 (m, 1H), 5.86 (m, 1H), 6.81 (m, 1H), 7.98 (d, J = 4.1 Hz, 1H), 8.04 (m, 1H), 8.07 (s, 1H). | 2.15 | D | 471.0 | 245.7 |
| 132 | OR n.d. | ¹H NMR (300 MHz, CD₃OD) δ ppm 1.26-1.47 (m, 2H), 1.49-1.77 (m, 2H), 1.91-2.12 (m, 2H), 2.27 (m, 1H), 2.36 (m, 1H), 2.59 (s, 3H), 4.07 (m, 1H), 4.33 (m, 1H), 6.80 (m, 1H), 7.94-8.00 (m, 2H), 8.03 (m, 1H), 8.07 (s, 1H). | 2.69 | D | 471.0 | 266.7 |
| 133 | [α]$_D^{23}$ -281.0 (c 0.11, MeOH) | ¹H NMR (300 MHz, CD₃OD) δ ppm 1.16-1.67 (m, 4H), 1.81-2.02 (m, 2H), 2.14 (m, 1H), 2.22 (s, 3H), 2.31 (m, 1H), 4.00 (m, 1H), 4.21 (m, 1H), 6.65-6.75 (m, 2H), 7.88 (d, J = 4.1 Hz, 1H), 7.93 (m, 1H), 7.97 (s, 1H). | 2.64 | D | 471.0 | 278.5 |

TABLE 1-continued
Compounds of formula (I) and corresponding analytical data.
| # | STRUCTURE | ¹H NMR | Rt (min) | LC Method | LC-MS Mass Found [M + H]⁺ | MP (° C.) |
|---|---|---|---|---|---|---|
| 134 | 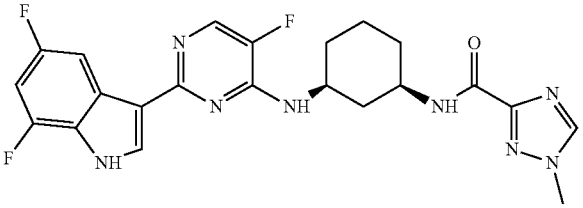<br>OR n.d. | ¹H NMR (300 MHz, CD₃OD) δ ppm 1.28-1.78 (m, 4H), 1.97 (m, 1H), 2.08 (m, 1H), 2.25 (m, 1H), 2.43 (m, 1H), 3.97 (s, 3H), 4.12 (m, 1H), 4.31 (m, 1H), 6.80 (m, 1H), 7.98 (d, J = 4.1 Hz, 1H), 8.03 (m, 1H), 8.08 (s, 1H), 8.40 (s, 1H). | 2.14 | F | 471.2 | 183.2 |
| 135 | 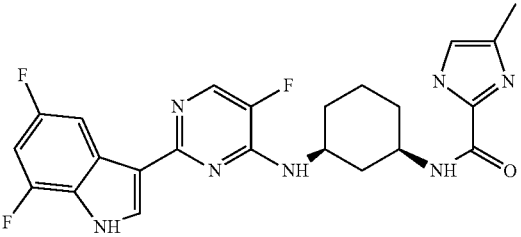<br>OR n.d. | ¹H NMR (300 MHz, CD₃OD) δ ppm 1.26-1.45 (m, 2H), 1.48-1.77 (m, 2H), 1.98 (m, 1H), 2.11 (m, 1H), 2.24 (s, 3H), 2.27 (m, 1H), 2.41 (m, 1H), 4.05 (m, 1H), 4.34 (m, 1H), 6.73-6.97 (m, 2H), 7.98 (d, J = 4.1 Hz, 1H), 8.04 (m, 1H), 8.07 (s, 1H). | 2.03 | F | 470.1 | 281.9 |
| 136 | 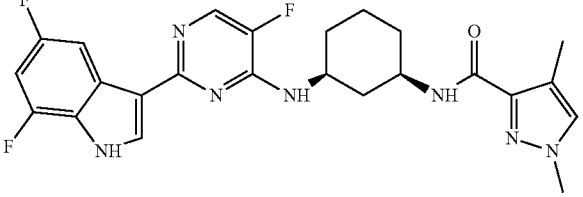<br>[α]$_D^{23}$ -203.6 (c 0.09, MeOH) | ¹H NMR (300 MHz, CD₃OD) δ ppm 1.25-1.46 (m, 2H), 1.48-1.75 (m, 2H), 1.97 (m, 1H), 2.08 (m, 1H), 2.23 (s, 3H), 2.27 (m, 1H), 2.37 (m, 1H), 3.85 (s, 3H), 4.06 (m, 1H), 4.33 (m, 1H), 6.80 (m, 1H), 7.37 (s, 1H), 7.98 (d, J = 4.1 Hz, 1H), 8.00-8.09 (m, 2H). | 2.69 | D | 484.9 | 265.1 |
| 137 | 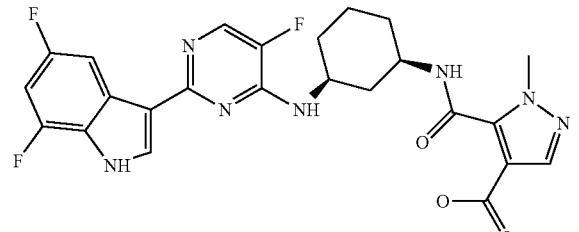<br>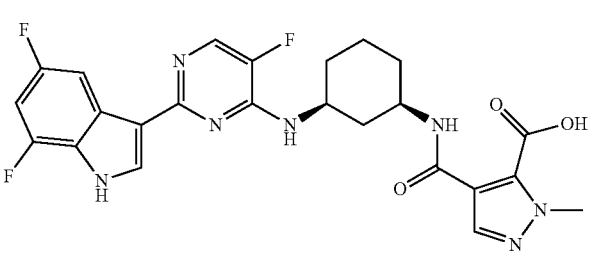 [SMILES: Cn1ncc(C(=O)N[C@@H]2CCC[C@H](Nc3nc(-c4c[nH]c5c(F)cc(F)cc45)ncc3F)C2)c1C(=O)O] | | 2.47, 2.63 | D | 513.8 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 138 | 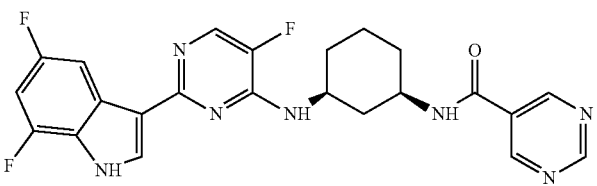 [α]$_D^{23}$ -183.5 (c 0.08, DMF) | ¹H NMR (300 MHz, CD₃OD) δ ppm 1.34-1.51 (m, 2H), 1.53-1.78 (m, 2H), 2.02 (m, 1H), 2.13 (m, 1H), 2.24 (m, 1H), 2.48 (m, 1H), 4.15 (m, 1H), 4.34 (m, 1H), 6.92 (m, 1H), 8.06-8.14 (m, 2H), 8.17 (s, 1H), 9.19 (s, 2H), 9.30 (br s, 1H). | 2.31 | D | 467.8 | >300 |
| 139 | 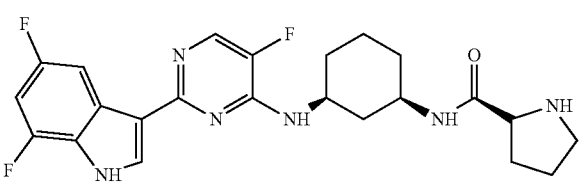 OR n.d. | ¹H NMR (300 MHz, CD₃OD) δ ppm 1.20-1.51 (m, 3H), 1.56-1.80 (m, 4H), 1.85-2.16 (m, 3H), 2.22 (m, 1H), 2.32 (m, 1H), 2.88 (m, 1H), 2.96 (m, 1H), 3.56 (m, 1H), 3.88 (m, 1H), 4.28 (m, 1H), 6.79 (m, 1H), 7.97 (d, J = 4.1 Hz, 1H), 8.01 (d, J = 9.8 Hz, 1H), 8.06 (s, 1H). | 1.93 | D | 459.0 | 208.1 |
| 140 | 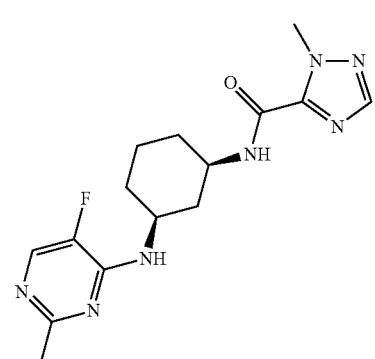 OR n.d. | ¹H NMR (300 MHz, CD₃OD) δ ppm 1.27-1.50 (m, 2H), 1.51-1.78 (m, 2H), 1.99 (m, 1H), 2.09 (m, 1H), 2.25 (m, 1H), 2.43 (m, 1H), 4.08 (m, 1H), 4.19 (s, 3H), 4.32 (m, 1H), 6.80 (m, 1H), 7.90 (s, 1H), 7.98 (d, J = 4.1 Hz, 1H), 8.03 (m, 1H), 8.08 (s, 1H). | 2.54 | D | 470.9 | 172.7 |
| 141 | 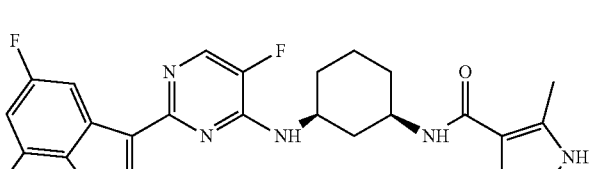 [α]$_D^{23}$ -164.8 (c 0.19, MeOH) | ¹H NMR (300 MHz, CD₃OD) δ ppm 1.24-1.49 (m, 2H), 1.51-1.79 (m, 2H), 1.98 (m, 1H) 2.10 (m, 1H) 2.27 (m, 1H), 2.39 (m, 1H), 2.51 (s, 3H), 4.10 (m, 1H), 4.33 (m, 1H), 6.80 (m, 1H), 7.97 (d, J = 4.0 Hz, 1H), 7.99-8.12 (m, 2H). | 2.37 | D | 470.8 | 256.6 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 142 | 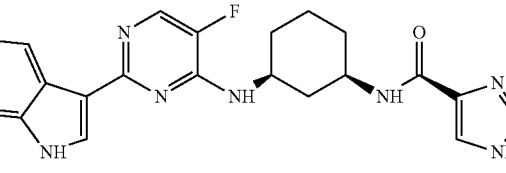 OR n.d. | ¹H NMR (300 MHz, CD₃OD) δ ppm 1.25-1.47 (m, 2H), 1.55 (m, 1H), 1.69 (m, 1H), 1.98 (m, 1H), 2.11 (m, 1H), 2.26 (m, 1H), 2.42 (m, 1H), 4.09 (m, 1H), 4.33 (m, 1H), 6.80 (m, 1H), 7.65 (s, 1H), 7.71 (s, 1H), 7.97 (m, 1H), 8.00-8.11 (m, 2H). | 2.02 | D | 455.8 | 219.9 |
| 143 | 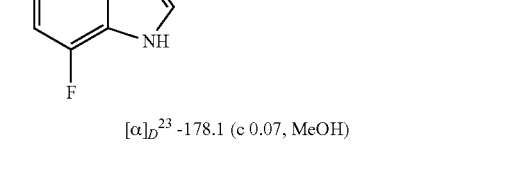 [α]$_D^{23}$ -178.1 (c 0.07, MeOH) | ¹H NMR (300 MHz, CD₃OD) δ ppm 1.26-1.51 (m, 2H), 1.52-1.79 (m, 2H), 1.99 (m, 1H), 2.11 (m, 1H), 2.26 (m, 1H), 2.44 (m, 1H), 3.97 (s, 3H), 4.11 (m, 1H), 4.33 (m, 1H), 6.81 (m, 1H), 7.99 (d, J = 4.1 Hz, 1H), 8.04 (m, 1H), 8.08 (s, 1H), 8.53 (s, 1H). | 2.31 | D | 470.9 | 169.8 |
| 144 | 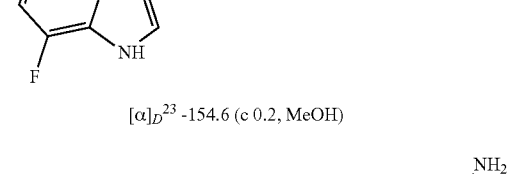 [α]$_D^{23}$ -154.6 (c 0.2, MeOH) | ¹H NMR (300 MHz, CD₃OD) δ ppm 1.26-1.44 (m, 2H), 1.54 (m, 1H), 1.68 (m, 1H), 1.99 (m, 1H), 2.02 (m, 1H), 2.24 (s, 3H), 2.26 (m, 1H), 2.41 (m, 1H), 3.89 (s, 3H), 4.04 (m, 1H), 4.33 (m, 1H), 6.74-6.86 (m, 2H), 7.98 (d, J = 4.1 Hz, 1H), 8.04 (m, 1H), 8.07 (s, 1H). | 2.42 | D | 483.9 | 204.9 |
| 145 | 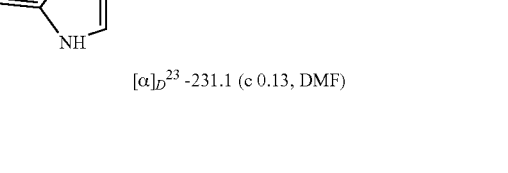 [α]$_D^{23}$ -231.1 (c 0.13, DMF) | ¹H NMR (300 MHz, CD₃OD) δ ppm 1.18-1.77 (m, 4H), 1.19 (m, 1H), 2.06 (m, 1H), 2.25 (m, 1H), 2.38 (m, 1H), 4.04 (m, 1H), 4.29 (m, 1H), 6.78 (m, 1H), 7.23 (s, 1H), 7.95 (d, J = 3.4 Hz, 1H), 8.00 (d, J = 10.3 Hz, 1H), 8.05 (s, 1H). | 2.34 | D | 487.8 | 178.1 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 146 | OR n.d. | ¹H NMR (300 MHz, CD₃OD) δ ppm 1.20-1.45 (m, 2H), 1.46-1.77 (m, 2H), 1.94-2.11 (m, 2H), 2.22-2.40 (m, 2H), 4.04 (m, 1H), 4.32 (m, 1H), 6.80 (m, 1H), 7.79 (m, 1H). | 2.20 | D | 470.9 | 169.7 |
| 147 | [α]$_D^{23}$ -205.5 (c 0.23, MeOH) | ¹H NMR (300 MHz, CD₃OD) δ ppm 1.23-1.46 (m, 2H), 1.50-1.79 (m, 2H), 1.96 (m, 1H), 2.15 (m, 1H), 2.30 (m, 1H), 2.42 (m, 1H), 4.07 (m, 1H), 4.33 (m, 1H), 6.80 (m, 1H), 7.96 (d, J = 4.1 Hz, 1H), 8.04 (m, 1H), 8.08 (s, 1H). | 2.34 | D | 500.9 | >300 |
| 148 | [α]$_D^{23}$ -114.1 (c 0.19, MeOH) | ¹H NMR (300 MHz, CD₃OD) δ ppm 1.18-1.50 (m, 3H), 1.55-1.82 (m, 4H), 1.88-2.16 (m, 3H), 2.22 (m, 1H), 2.33 (m, 1H), 2.89 (m, 1H), 2.97 (m, 1H), 3.57 (m, 1H), 3.88 (m, 1H), 4.27 (m, 1H), 6.80 (m, 1H), 7.97 (m, 1H), 8.01 (m, 1H), 8.06 (s, 1H). | 1.84 | D | 459.0 | 220.8 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 149 | [α]$_D^{23}$ -205.8 (c 0.19, MeOH) | ¹H NMR (300 MHz, CD₃OD) δ ppm 1.24-1.44 (m, 2H), 1.53 (m, 1H), 1.67 (m, 1H), 1.96 (m, 1H), 2.06 (m, 1H), 2.25 (m, 1H), 2.38 (m, 1H), 3.63 (s, 3H), 4.05 (m, 1H), 4.31 (m, 1H), 5.87 (s, 1H), 6.80 (m, 1H), 7.97 (d, J = 4.1 Hz, 1H), 8.03 (m, 1H), 8.07 (s, 1H). | 2.27 | D | 484.9 | 253.4 |
| 150 | [α]$_D^{23}$ -299.4 (c 0.13, MeOH) | ¹H NMR (300 MHz, CD₃OD) δ ppm 1.23-1.49 (m, 2H), 1.52 (m, 1H), 1.68 (m, 1H), 1.97 (m, 1H), 2.07 (m, 1H), 2.27 (m, 1H), 2.35 (m, 1H), 2.55 (s, 3H), 4.00 (m, 1H), 4.33 (m, 1H), 6.81 (m, 1H), 7.98 (d, J = 4.1 Hz, 1H), 8.03 (m, 1H), 8.07 (s, 1H). | 2.56 | D | 501.9 | 248.4 |
| 151 | OR n.d. | ¹H NMR (300 MHz, DMSO-d₆) δ ppm 1.18-1.63 (m, 4H), 1.76-1.90 (m, 2H), 2.03 (m, 1H), 2.13 (m, 1H), 3.90 (m, 1H), 4.16 (m, 1H), 5.94 (m, 2H), 7.04 (m, 1H), 7.53 (d, J = 7.2 Hz, 1H), 7.88 (m, 1H), 8.02 (m, 1H), 8.13 (m, 2H), 11.80-12.7 (br s, 1H). | 2.10 | D | 471.7 | >300 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 152 | [α]$_D^{23}$ -109.6 (c 0.06, MeOH) | ¹H NMR (300 MHz, CD$_3$OD) δ ppm 1.25-1.77 (m, 4H), 2.00 (m, 1H), 2.09 (m, 1H), 2.25 (m, 1H), 2.44 (m, 1H), 4.14 (m, 1H), 4.32 (s, 3H), 4.34 (m, 1H), 6.81 (m, 1H), 7.99 (d, J = 4.1 Hz, 1H), 8.04 (m, 1H), 8.08 (s, 1H). | 2.24 | D | 471.9 | 250.3 |
| 153 | [α]$_D^{23}$ -194.4 (c 0.06, MeOH) | ¹H NMR (300 MHz, CD$_3$OD) δ ppm 1.26-1.79 (m, 4H), 2.00 (m, 1H), 2.10 (m, 1H), 2.26 (m, 1H), 2.46 (m, 1H), 4.18 (m, 1H), 4.32 (m, 1H), 4.43 (s, 3H), 6.80 (m, 1H), 7.99 (d, J = 4.1 Hz, 1H), 8.04 (m, 1H), 8.08 (s, 1H). | 2.43 | D | 471.9 | 230.0 |
| 154 | [α]$_D^{23}$ -158.6 (c 0.13, MeOH) | ¹H NMR (300 MHz, CD$_3$OD) δ ppm 1.27-1.52 (m, 2H), 1.54-1.79 (m, 2H), 2.00 (m, 1H), 2.11 (m, 1H), 2.28 (m, 1H), 2.43 (m, 1H), 4.14 (m, 1H), 4.35 (m, 1H), 6.81 (m, 1H), 7.99 (d, J = 4.1 Hz, 1H), 8.02-8.10 (m, 2H), 8.24 (d, J = 1.9 Hz, 1H), 9.00 (d, J = 1.9 Hz, 1H). | 2.57 | D | 473.0 | 266.8 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 155 | (structure) OR n.d. | ¹H NMR (400 MHz, DMSO-d₆) δ ppm 1.27-1.39 (m, 1H) 1.42-1.69 (m, 3H) 1.88 (m, J = 7.0 Hz, 2H) 2.02-2.12 (m, 1H) 2.20 (m, J = 11.4 Hz, 1H) 3.95-4.06 (m, 1H) 4.19 (m, J = 7.5, 4.0 Hz, 1H) 7.01-7.19 (m, 1H) 7.55 (d, J = 7.5 Hz, 1H) 8.03 (m, 1H) 8.13-8.28 (m, 3H) 8.46 (s, 1H) 12.19 (br s, 1H) | 1.39 | L | 517.1 | 260.8 |
| 156 | (structure) OR n.d. | ¹H NMR (400 MHz, DMSO-d₆) δ ppm 1.21-1.35 (m, 2H) 1.40-1.54 (m, 2H) 1.86 (m, J = 11.4 Hz, 2H) 2.00-2.07 (m, 1H) 2.17 (m, J = 12.1 Hz, 1H) 3.49 (s, 3H) 3.85-3.94 (m, 1H) 4.11-4.20 (m, 1H) 6.11 (s, 2H) 7.05 (t, J = 10.1 Hz, 1H) 7.49-7.55 (m, 2H) 7.66 (s, 1H) 8.02 (m, 1H) 8.14 (s, 1H) 8.15 (s, 1H) 12.18 (br s, 1H) | 1.72 | L | 485.1 | 248.7 |
| 157 | (structure) OR n.d. | ¹H NMR (400 MHz, DMSO-d₆) δ ppm 1.32-1.48 (m, 2H) 1.52-1.66 (m, 2H) 1.95 (m, 2H) 2.09 (m, 1H) 2.23-2.34 (m, 1H) 4.00-4.14 (m, 1H) 4.18-4.30 (m, 1H) 7.02-7.10 (m, 1H) 7.57 (m, 1H) 8.04 (m, 1H) 8.15-8.29 (m, 5H) 9.04 (m, 1H) 12.19 (br s, 1H) 13.07 (br s, 1H). | 1.38 | L | 511.1 | n.d. |
| 158 | (structure) OR n.d. | ¹H NMR (400 MHz, DMSO-d₆) δ ppm 1.21-1.40 (m, 2H) 1.52 (m, J = 11.7 Hz, 2H) 1.80-1.93 (m, 2H) 1.99-2.09 (m, 1H) 2.11-2.22 (m, 1H) 3.89-3.99 (m, 1H) 4.03-4.25 (m, 1H) 5.94 (s, 1H) 7.01-7.09 (m, 1H) 7.52 (m, 1H) 8.02 (m, 2H) 8.08-8.18 (m, 2H) 12.16 (br s, 1H). | 1.56 | K | 472.2 | n.d. |
| 159 | (structure) OR n.d. | ¹H NMR (400 MHz, DMSOd₆) δ ppm 1.31 (m, J = 9.5 Hz, 2H) 1.45-1.58 (m, 2H) 1.89 (m, J = 10.8 Hz, 2H) 2.09 (m, 2H) 3.88-3.98 (m, 1H) 4.06 (s, 3H) 4.14-4.25 (m, 1H) 7.05 (t, J = 10.2 Hz, 1H) 7.26 (s, 1H) 7.53 (m, 1H) 8.02 (m, 1H) 8.13-8.17 (m, 2H) 8.45 (m, 1H) 12.19 (br s, 1H) | 0.72 | A | 514.2 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 160 | 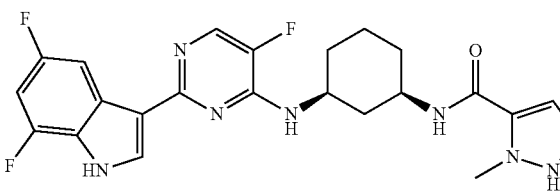<br>OR n.d. | ¹H NMR (400 MHz, DMSO-d₆) δ ppm 1.20-1.62 (m, 4H) 1.77-1.98 (m, 2H) 2.04 (m, 1H) 2.16 (m, 1H) 3.85-3.98 (m, 1H) 4.12-4.27 (m, 1H) 6.06 (s, 1H) 6.99-7.12 (m, 1H) 7.52 (d, J = 7.7 Hz, 1H) 8.02 (m, 1H) 8.14 (m, 3H) 8.20 (m, 1H) 12.00 (s, 1H) | 1.76 | K | 486.3 | n.d. |
| 161 | 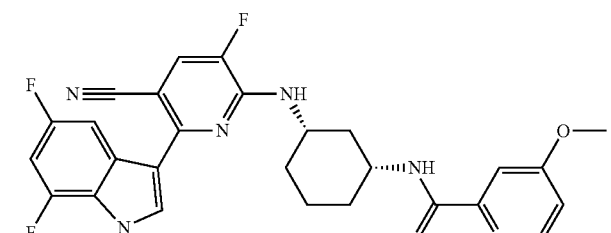<br>[α]$_D^{20}$ -217.8 (c 0.62, DMF) | ¹H NMR (360 MHz, DMSO-d₆) δ ppm 1.36 (m, 1H) 1.46 (m, 2H) 1.70 (m, 1H) 1.80-1.95 (m, 2H) 1.98-2.20 (m, 2H) 3.89 (s, 3H) 7.04-7.23 (m, 2H) 7.52 (m, 1H) 7.76 (m, 1H) 7.80-8.06 (m, 2H) 8.30 (s, 1H) 8.44 (m, 1H) 8.61 (m, 1H) 12.38 (br. s., 1H) | 1.76 | H | 521.4 | 285.5 |
| 162 | 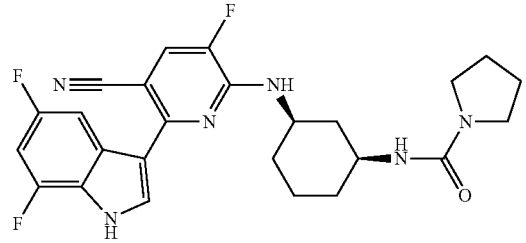<br>[α]$_D^{20}$ -214.9 (c 0.28, DMF) |  | 1.97 | B | 483.4 | n.d. |
| 163 | 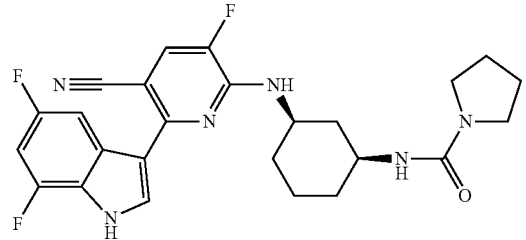<br>[α]$_D^{20}$ +224.2 (c 0.27, DMF) |  | 1.97 | B | 483.4 | n.d. |
| 164 | 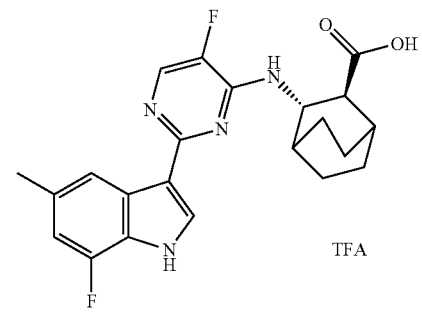<br>(+/-) | ¹H NMR (500 MHz, DMSO-d₆) δ ppm 1.35-1.69 (m, 5H) 1.71-1.85 (m, 3H) 1.92 (br s, 1H) 2.04 (m, 1H) 2.43 (s, 4H) 2.93 (m, 1H) 4.93 (m, 1H) 6.94 (m, 1H) 8.11 (s, 1H) 8.25 (br s, 1H) 8.39 (br s, 1H) 12.40 (br s, 2H) | 2.59 | C | 413.2 | >250 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 165 | [α]$_D^{20}$ +23.4 (c 0.26, DMF) | | 2.52 | C | 413.1 | n.d. |
| 166 | [α]$_D^{20}$ -27.3 (c 0.26, DMF) | ¹H NMR (500 MHz, DMSO-d$_6$) δ ppm 1.26-1.59 (m, 5H) 1.62-1.80 (m, 3H) 1.86 (br s, 1H) 1.93 (br s, 1H) 2.35 (s, 3H) 2.78 (br d, J = 6.6 Hz, 1H) 4.71 (br t, J = 6.8 Hz, 1H) 6.77 (d, J = 12.3 Hz, 1H) 7.44 (m, 1H) 7.90 (d, J = 2.5 Hz, 1H) 8.07 (d, 1 = 9.3 Hz, 2H) 11.82 (br s, 1H) 12.17 (br s, 1H) | 2.53 | C | 413.2 | 98 |
| 167 | (+/−) | ¹H NMR (500 MHz, DMSO-d$_6$) δ ppm 0.99 (s, 9H) 2.45 (s, 3H) 2.64 (br s, 1H) 2.70-2.80 (m, 1H) 4.95 (m, 1H) 6.95 (m, 1H) 8.20 (s, 1H) 8.24-8.34 (m, 1H) 8.41 (br s, 1H) 8.46-8.80 (m, 1H) 11.77-12.80 (m, 2H) | 2.44 | C | 389.2 | 182 |
| 168 | [α]$_D^{20}$ +33.3 (c 0.27, DMF) | | 2.40 | C | 389.1 | 132 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 169 | 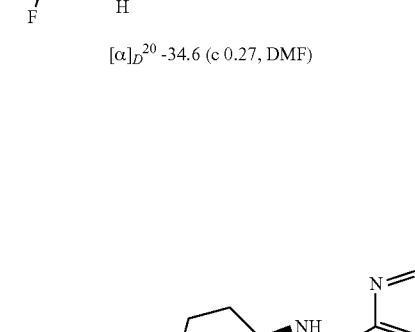<br>$[\alpha]_D^{20}$ -34.6 (c 0.27, DMF) | ¹H NMR (500 MHz, DMSO-d₆) δ ppm 0.98 (s, 9H) 2.43 (s, 3H) 2.55 (d, J = 10.4 Hz, 1H) 2.60-2.67 (m, 1H) 4.80-4.91 (m, 1H) 6.84 (d, J = 12.0 Hz, 1H) 7.40 (br d, J = 8.5 Hz, 1H) 7.97 (d, J = 2.5 Hz, 1H) 8.09 (d, J = 4.1 Hz, 1H) 8.24 (s, 1H) 11.87 (d, J = 2.5 Hz, 1H) | 2.39 | C | 389.1 | 144 |
| 170 | 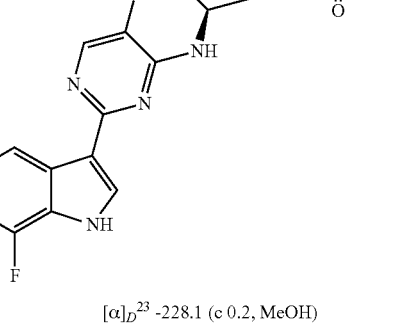<br>$[\alpha]_D^{23}$ -228.1 (c 0.2, MeOH) | ¹H NMR (300 MHz, CD₃OD) δ 1.22-1.59 (m, 3H), 1.76 (m, 1H), 1.95-2.13 (m, 2H), 2.26 (m, 1H), 2.44 (m, 1H), 3.75 (s, 3H), 4.10 (m, 1H), 4.33 (m, 1H), 7.27 (d, J = 10.7 Hz, 1H), 7.60 (s, 1H), 7.61 (s, 1H), 8.02 (d, J = 4.0 Hz, 1H), 8.18 (s, 1H), 8.80 (br s, 1H). | 2.22 | D | 477.1 | 276.3 |
| 171 | 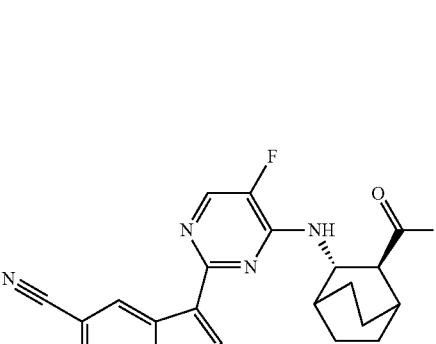<br>$[\alpha]_D^{23}$ -44.7 (c 0.2, MeOH) | ¹H NMR (300 MHz, CD₃OD) δ ppm 1.41-1.91 (m, 7H), 1.98-2.14 (m, 3H), 2.72 (d, J = 6.8 Hz, 1H), 4.94 (d, J = 6.8 Hz, 1H), 7.26 (m, 1H), 8.01 (d, J = 4.1 Hz, 1H), 8.17 (s, 1H), 8.87 (d, J = 1.0 Hz, 1H). | 2.96 | D | 424.1 | 211.6 |

| # | STRUCTURE | ¹H NMR | Rt (min) | LC Method | LC-MS Mass Found [M + H]⁺ | MP (° C.) |
|---|---|---|---|---|---|---|
| 172 | 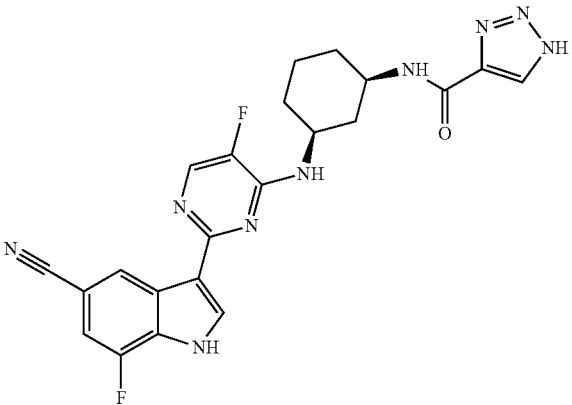<br>[α]$_D^{23}$ -149.1 (c 0.13, MeOH) | ¹H NMR (300 MHz, CD₃OD) δ ppm 1.25-1.65 (m, 3H), 1.78 (m, 1H), 1.97 (m, 1H), 2.13 (m, 1H), 2.27 (m, 1H), 2.46 (m, 1H), 4.16 (m, 1H), 4.34 (m, 1H), 7.28 (m, 1H), 8.03 (d, J = 4.1 Hz, 1H), 8.12 (s, 1H), 8.19 (s, 1H), 8.82 (d, J = 0.8 Hz, 1H). | 0.20 | D | 463.9 | >300 |
| 173 | 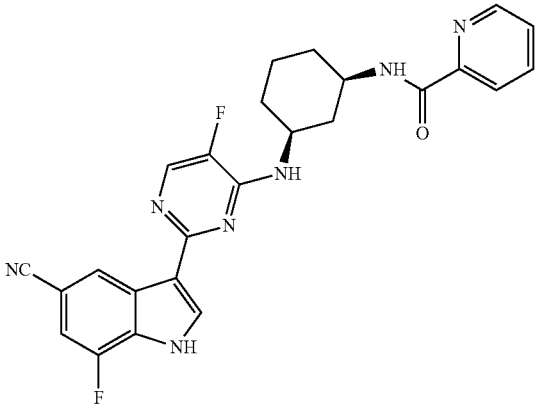<br>(+/-) | ¹H NMR (300 MHz, CD₃OD) δ 1.29-1.67 (m, 3H), 1.79 (m, 1H), 1.96-2.15 (m, 2H), 2.29 (m, 1H), 2.44 (m, 1H), 4.16 (m, 1H), 4.36 (m, 1H), 7.28 (m, 1H), 7.54 (m, 1H), 7.94 (m, 1H), 8.03 (d, J = 4.1 Hz, 1H), 8.07 (m, 1H), 8.19 (s, 1H), 8.62 (m, 1H), 8.82 (m, 1H). | 2.97 | D | 474.1 | n.d. |
| 174 | 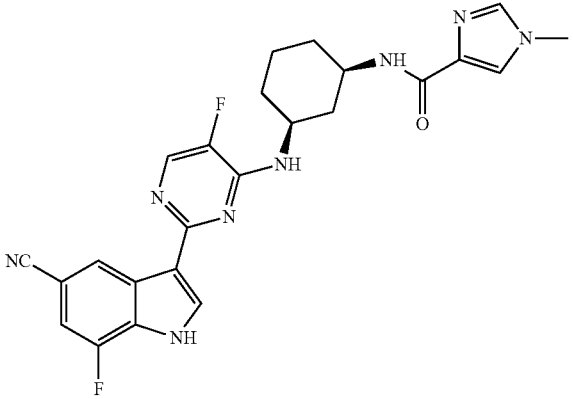<br>(+/-) | ¹H NMR (300 MHz, CD₃OD) δ 1.29-1.59 (m, 3H), 1.77 (m, 1H), 1.96-2.13 (m, 2H), 2.27 (m, 1H), 2.44 (m, 1H), 3.75 (s, 3H), 4.10 (m, 1H), 4.34 (m, 1H), 7.28 (m, 1H), 7.60 (s, 1H), 7.61 (s, 1H), 8.02 (d, J = 4.0 Hz, 1H), 8.19 (s, 1H), 8.80 (m, 1H). | 2.20 | D | 477.1 | n.d. |

| # | STRUCTURE | ¹H NMR | Rt (min) | LC Method | LC-MS Mass Found [M + H]⁺ | MP (° C.) |
|---|---|---|---|---|---|---|
| 175 | (+/-) | ¹H NMR (400 MHz, DMSO-d₆) δ ppm 1.28-1.45 (m, 3H) 1.65 (m, J = 11.90, 11.90, 11.90 Hz, 1H) 1.77-1.90 (m, 2H) 1.91-2.03 (m, 1H) 2.09 (m, J = 11.70 Hz, 1H) 3.74-3.88 (m, 1H) 4.04-4.19 (m, 1H) 6.95-7.12 (m, 1H) 7.34-7.50 (m, 2H) 7.54-7.65 (m, 2H) 7.73 (d, J = 11.66 Hz, 1H) 7.90-8.06 (m, 2H) 8.56 (d, J = 8.14 Hz, 1H) 8.63 (m, 1H) 12.11 (br. s., 1H) | 2.31 | A | 534.2 | n.d. |
| 176 | (+/-) | ¹H NMR (400 MHz, DMSO-d₆) δ ppm 1.25-1.52 (m, 4H) 1.75-1.89 (m, 2H) 1.92-2.02 (m, 1H) 2.09 (m, 1H) 3.71-3.87 (m, 1H) 4.11 (d, J = 4.40 Hz, 1H) 6.93-7.21 (m, 1H) 7.31-7.48 (m, 2H) 7.63 (s, 1H) 7.73 (m, 1H) 7.99 (m, 1H) 8.87 (m, 1H) 9.04 (m, 1H) 9.31 (m, 1H) 12.11 (br. s., 1H) | 1.26 | A | 535.2 | n.d. |
| 177 | (+/-) | | 1.17 | A | 551.2 | n.d. |
| 178 | (+/-) | ¹H NMR (400 MHz, DMSO-d₆) δ ppm 1.17-1.48 (m, 4H) 1.74-1.84 (m, 2H) 1.92-2.00 (m, 1H) 2.04 (m, 1H) 3.70-3.88 (m, 1H) 4.01-4.18 (m, 1H) 6.99-7.10 (m, 1H) 7.39 (m, 1H) 7.45 (m, 1H) 7.63 (s, 1H) 7.73 (m, 1H) 8.34 (s, 1H) 8.45 (m, 1H) 12.11 (br. s., 1H) | 1.92 | B | 524.4 | n.d. |

TABLE 1-continued
Compounds of formula (I) and corresponding analytical data.
| # | STRUCTURE | 1H NMR | Rt (min) | LC Method | LC-MS Mass Found [M + H]+ | MP (° C.) |
|---|---|---|---|---|---|---|
| 179 | 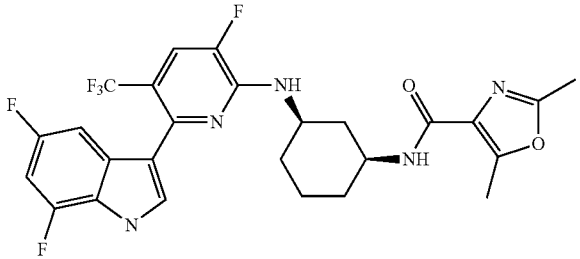 (+/−) | | 2.31 | K | 552.3 | n.d. |
| 180 | 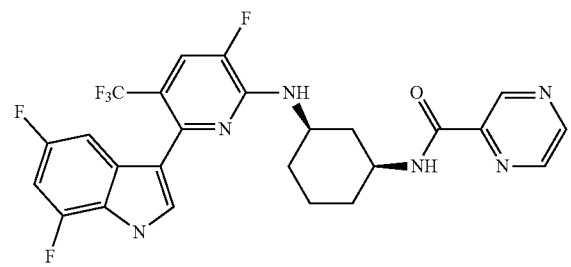 (+/−) | | 2.21 | K | 535.2 | n.d. |
| 181 | 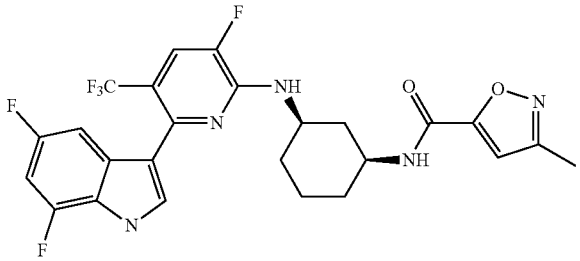 (+/−) | 1H NMR (400 MHz, DMSO-d$_6$) δ ppm 1.18-1.38 (m, 4H) 1.72-1.87 (m, 2H) 1.92-2.00 (m, 1H) 2.06 (m, 1H) 2.28 (s, 3H) 3.66-3.81 (m, 1H) 4.01-4.11 (m, 1H) 6.82-6.91 (m, 1H) 6.98-7.11 (m, 1H) 7.37-7.48 (m, 2H) 7.63 (s, 1H) 7.74 (m, 1H) 8.79 (d, J = 7.92 Hz, 1H) 12.11 (br. s., 1H) | 1.28 | A | 538.2 | n.d. |
| 182 | 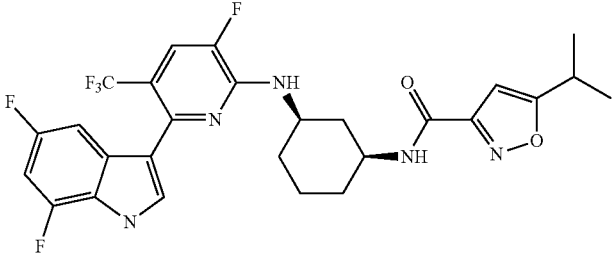 (+/−) | | 2.39 | K | 566.3 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 183 | [α]$_D^{20}$ +222.4 (c 0.29, DMF) | | 1.82 | B | 494.2 | n.d. |
| 184 | [α]$_D^{20}$ -211.2 (c 0.29, DMF) | | 1.82 | B | 494.2 | n.d. |
| 185 | [α]$_D^{20}$ -250.2 (c 0.2, CDCl₃) | ¹H NMR (400 MHz, CHLOROFORM-d) δ ppm 1.11-1.34 (m, 3H), 1.34-1.45 (m, 1H), 1.59-1.82 (m, 1H) 1.85-1.98 (m, 1H), 2.12 (m, 1H), 2.28 (m, 1H), 2.48 (d, J = 11.7 Hz, 1H), 3.34-3.39 (m, 1H), 3.70 (s, 3H), 4.00-4.15 (m, 1H), 4.18-4.35 (m, 1H), 5.47 (m, 1H), 6.93 (m, 1H), 7.26-7.30 (m, 1H), 7.36 (s, 1H), 7.53 (s, 1H), 8.13 (m, 1H), 8.25 (s, 1H) | 1.91 | B | 509.2 | n.d. |
| 186 | [α]$_D^{20}$ -41.2 (c 0.26, DMF) | | 1.59 | B | 393.2 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 187 | OR n.d. | | 1.91 | B | 509.2 | n.d. |
| 188 | $[\alpha]_D^{20}$ -61.8 (c 0.5, CH$_2$Cl$_2$) | | 2.17 | K | 482.1 | n.d. |
| 189 | (+/-) | | 1.50 | H | 510.3 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 190 | 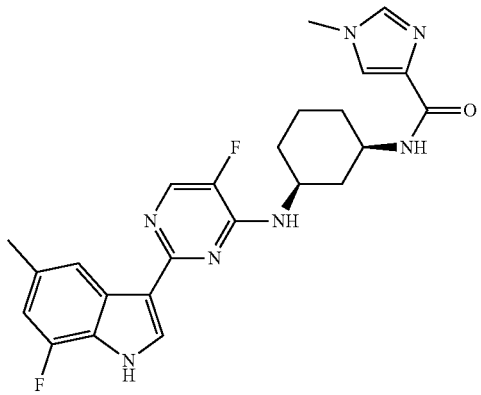 (+/−) | ¹H NMR (400 MHz, chloroform-d) δ ppm 1.16-1.33 (m, 1H) 1.53-1.78 (m, 1H) 1.86-1.98 (m, 1H) 2.08-2.17 (m, 1H) 2.28 (m, 1H) 2.47 (s, 3H) 2.62-2.70 (m, 1H) 3.70 (s, 3H) 4.20(m, 1H) 4.86-4.94 (m, 1H) 6.76 (m, 1H) 7.05 (m, 1H) 7.35 (s, 1H) 7.52 (s, 1H) 8.02-8.07 (m, 2H) 8.09 (s, 1H) 9.42 (br s, 1H) | 1.75 | B | 465.2 | n.d. |
| 191 | 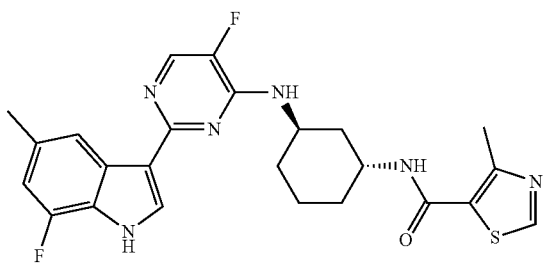 (+/−) | ¹H NMR (500 MHz, DMSO-d₆) δ ppm 1.30-1.49 (m, 3H) 1.64 (d, J = 12.0 Hz, 1H) 1.86 (m, 2H) 1.99 (br d, J = 10.7 Hz, 1H) 2.12 (br d, J = 11.7 Hz, 1H) 2.44 (s, 3H) 2.71 (s, 3H) 3.84-3.93 (m, 1H) 4.23-4.31 (m, 1H) 6.90 (d, J = 12.3 Hz, 1H) 7.67 (m, 1H) 7.82 (d, J = 11.3 Hz, 1H) 7.92 (s, 1H) 8.15 (s, 1H) 8.21 (d, J = 8.2 Hz, 1H) 8.89 (s, 1H) 12.08 (br s, 1H) | 3.27 | C | 507.1 | 232 |
| 192 | 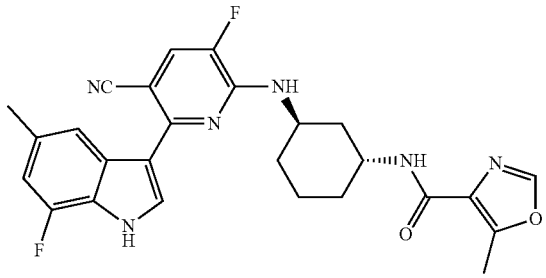 (+/−) | ¹H NMR (500 MHz, DMSO-d₆) δ ppm 1.30-1.47 (m, 3H) 1.58-1.70 (m, 1H) 1.78-1.89 (m, 2H) 1.94-2.01 (m, 1H) 2.07 (br d, 1 = 12.0 Hz, 1H) 2.44 (s, 3H) 2.53 (s, 3H) 3.81-3.93 (m, 1H) 4.20-4.30 (m, 1H) 6.90 (d, J = 12.0 Hz, 1H) 7.67 (br d, J = 7.6 Hz, 1H) 7.82 (d, J = 11.3 Hz, 1H) 7.92 (s, 1H) 8.03 (d, J = 7.9 Hz, 1H) 8.15 (s, 1H) 8.32 (s, 1H) 12.08 (br s, 1H) | 3.11 | C | 491.1 | >250 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 193 | (+/-) | ¹H NMR (500 MHz, DMSO-d₆) δ ppm 1.26-1.46 (m, 2H) 1.47-1.64 (m, 2H) 1.80-1.95 (m, 2H) 2.02 (br d, J = 9.8 Hz, 1H) 2.12-2.28 (m, 1H) 2.46 (br s, 3H) 2.73 (br s, 3H) 4.00 (br s, 1H) 4.25 (br s, 1H) 6.85 (br d, J = 12.0 Hz, 1H) 7.49 (br d, J = 6.6 Hz, 1H) 7.97-8.08 (m, 1H) 8.08-8.17 (m, 2H) 8.21 (br d, J = 7.6 Hz, 1H) 8.90 (br s, 1H) 11.91 (br s, 1H) | 3.11 | C | 483.1 | 234 |
| 194 | (+/-) | ¹H NMR (500 MHz, DMSO-d₆) δ ppm 1.27-1.64 (m, 4H) 1.78-1.91 (m, 2H) 2.00 (br d, J = 11.1 Hz, 1H) 2.14 (br d, J = 11.6 Hz, 1H) 2.45 (s, 3H) 2.55 (s, 3H) 3.92-4.06 (m, 1H) 4.16-4.28 (m, 1H) 6.83 (d, J = 12.1 Hz, 1H) 7.47 (br d, J = 7.6 Hz, 1H) 7.98-8.03 (m, 2H) 8.09 (s, 1H) 8.12 (d, J = 4.2 Hz, 1H) 8.31 (s, 1H) 11.89 (s, 1H) | 2.95 | C | 467.2 | 140 |
| 195 | (+/-) | ¹H NMR (500 MHz, DMSO-d₆) δ ppm 1.28-1.46 (m, 3H) 1.59 (q, 1 = 12.0 Hz, 1H) 1.75-1.92 (m, 2H) 1.92-2.03 (m, 1H) 2.09 (br d, J = 11.3 Hz, 1H) 2.44 (s, 3H) 3.66 (s, 3H) 3.86 (br d, J = 8.2 Hz, 1H) 4.21-4.30 (m, 1H) 6.90 (br d, J = 12.3 Hz, 1H) 7.58 (s, 1H) 7.63 (s, 1H) 7.66 (br d, J = 7.9 Hz, 1H) 7.71 (br d, J = 8.2 Hz, 1H) 7.82 (d, J = 11.3 Hz, 1H) 7.92 (s, 1H) 8.15 (s, 1H) 12.08 (br s, 1H) | 2.73 | C | 490.2 | >250 |
| 196 | (+/-) | ¹H NMR (500 MHz, DMSO-d₆) δ ppm 1.26-1.46 (m, 2H) 1.46-1.58 (m, 2H) 1.85 (br d, J = 10.7 Hz, 2H) 2.01 (br d, J = 11.3 Hz, 1H) 2.16 (br d, J = 11.7 Hz, 1H) 2.45 (s, 3H) 3.67 (s, 3H) 3.91-4.00 (m, 1H) 4.18-4.27 (m, 1H) 6.83 (d, J = 12.0 Hz, 1H) 7.47 (br d, J = 7.9 Hz, 1H) 7.59 (s, 1H) 7.64 (s, 1H) 7.70 (d, J = 8.2 Hz, 1H) 8.01 (d, J = 2.5 Hz, 1H) 8.10 (s, 1H) 8.12 (d, J = 3.8 Hz, 1H) 11.90 (d, J = 2.2 Hz, 1H) | 2.59 | C | 466.2 | >250 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 197 | 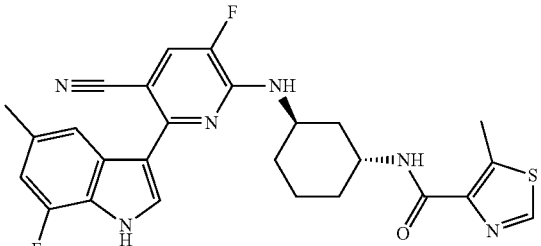 (+/-) | ¹H NMR (500 MHz, DMSO-d₆) δ ppm 1.27-1.36 (m, 3H) 1.40 (br s, 3H) 2.29 (br d, J = 15.1 Hz, 1H) 2.46 (s, 3H) 2.54-2.62 (m, 1H) 5.32 (br t, J = 9.1 Hz, 1H) 6.86 (br d, J = 12.3 Hz, 1H) 6.96-7.07 (m, 2H) 7.43 (br d, J = 4.1 Hz, 2H) 8.01 (br s, 1H) 8.16 (br d, 1 = 3.2 Hz, 1H) 8.26 (br s, 1H) 11.91 (br s, 1H) 11.96-12.29 (m, 1H) | 2.58 | C | 457.1 | 146 |
| 198 | 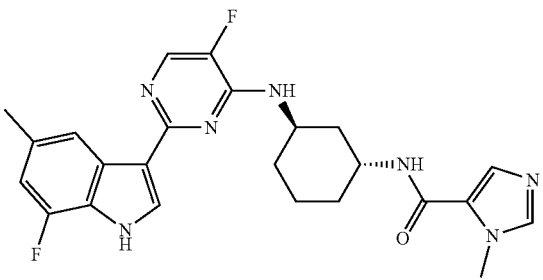 (+/-) | ¹H NMR (500 MHz, DMSO-d₆) δ ppm 1.20-1.36 (m, 2H) 1.37-1.50 (m, 2H) 1.75-1.88 (m, 2H) 1.95 (br d, J = 11.3 Hz, 1H) 2.12 (br d, J = 11.3 Hz, 1H) 2.38 (s, 3H) 3.72 (s, 3H) 3.82-3.93 (m, 1H) 4.09-4.23 (m, 1H) 6.76 (br d, J = 12.0 Hz, 1H) 7.42 (br d, 1 = 7.6 Hz, 1H) 7.50 (s, 1H) 7.63 (s, 1H) 7.95 (s, 1H) 8.00-8.15 (m, 3H) 11.40-12.55 (m, 1H) | 2.6 | C | 466.2 | 98 |
| 199 | 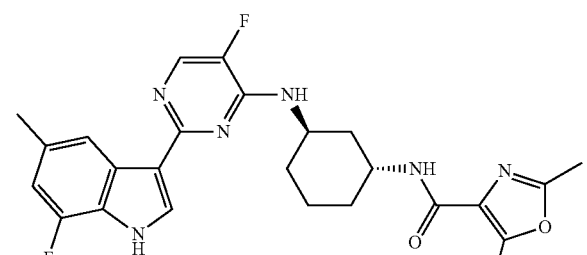 (+/-) | ¹H NMR (500 MHz, DMSO-d₆) δ ppm 1.29-1.52 (m, 3H) 1.57 (q, J = 12.0 Hz, 1H) 1.77-1.90 (m, 2H) 2.00 (br d, J = 11.3 Hz, 1H) 2.12 (br d, J = 11.7 Hz, 1H) 2.38 (s, 3H) 2.45 (s, 3H) 3.89-4.00 (m, 1H) 4.17-4.27 (m, 1H) 6.84 (d, J = 12.0 Hz, 1H) 7.48 (d, J = 7.6 Hz, 1H) 7.93 (d, J = 8.5 Hz, 1H) 8.01 (s, 1H) 8.09 (s, 1H) 8.12 (d, J = 3.8 Hz, 1H) 11.91 (br s, 1H) | 3.04 | C | 481.2 | 170 |
| 200 | 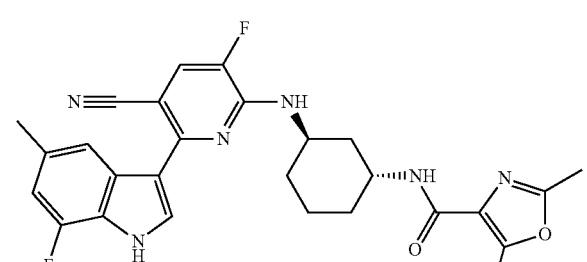 (+/-) | | 3.2 | C | 505.2 | >250 |

TABLE 1-continued
Compounds of formula (I) and corresponding analytical data.
| # | STRUCTURE | ¹H NMR | Rt (min) | LC Method | LC-MS Mass Found [M + H]⁺ | MP (° C.) |
|---|---|---|---|---|---|---|
| 201 | 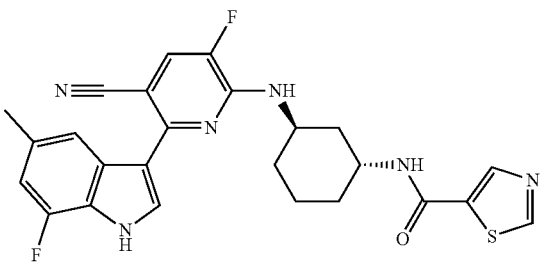<br>(+/-) | ¹H NMR (500 MHz, DMSO-d$_6$) δ ppm 1.22-1.35 (m, 1H) 1.35-1.48 (m, 2H) 1.82-2.04 (m, 4H) 2.18 (br d, J = 12.0 Hz, 1H) 2.43 (s, 3H) 3.89 (m, 1H) 4.24-4.32 (m, 1H) 6.90 (d, J = 12.0 Hz, 1H) 7.69 (br d, J = 8.2 Hz, 1H) 7.84 (d, J = 11.3 Hz, 1H) 7.92 (s, 1H) 8.16 (s, 1H) 8.48 (s, 1H) 8.61 (d, J = 7.6 Hz, 1H) 9.20 (s, 1H) 12.08 (br s, 1H) | 2.88 | C | 493.2 | >250 |
| 202 | 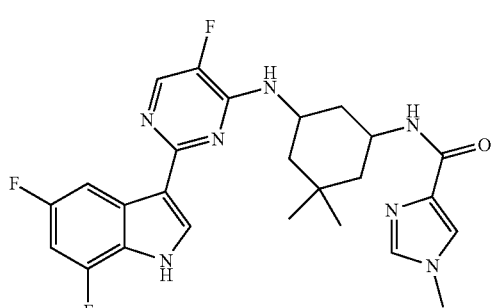<br>(+/-) | | 2.47 and 2.55 | D | 497.8 | n.d. |
| 203 | 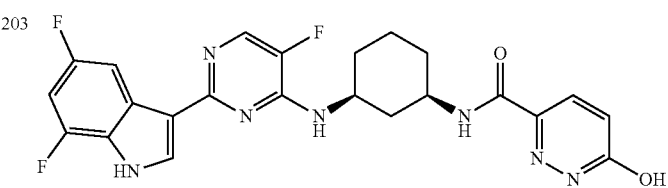<br>OR n.d. | | 1.69 | B | 483.5 | n.d. |
| 204 | 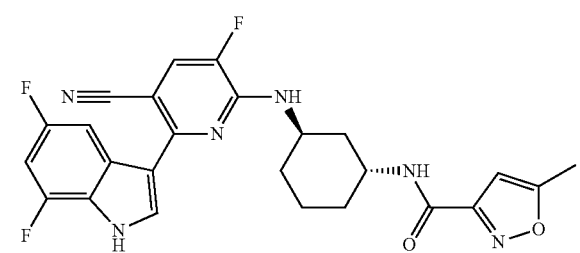 [SMILES: Cc1cc(C(=O)N[C@@H]2CCC[C@@H](Nc3nc(-c4c[nH]c5c(F)cc(F)cc45)c(C#N)cc3F)C2)on1]<br>[α]$_D^{20}$ -219.8 (c 0.61, DMF) | ¹H NMR (600 MHz, DMSO-d$_6$) δ ppm 1.25-1.39 (m, 2H), 1.39-1.48 (m, 1H), 1.64 (m, 1H), 1.85 (m, 2H), 2.02 (m, 1H), 2.08 (m, 1H), 2.44 (m, 3H), 3.82-3.90 (m, 1H), 4.18 (m, 1H), 6.48-6.50 (m, 1H), 7.12 (m, 1H), 7.73 (d, J = 7.9 Hz, 1H), 7.84 (m, 1H), 7.87 (m, 1H), 8.28 (s, 1H), 8.66 (m, 1H), 12.35 (s, 1H) | 1.68 | H | 495.2 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 205 | (+/−) | ¹H NMR (400 MHz, DMSO-d$_6$) δ ppm 1.28-1.51 (m, 3H) 1.63 (m, 1H) 1.82-1.91 (m, 2H) 2.05 (m, 1H) 2.13 (m, 1H) 3.80-3.87 (m, 1H) 3.87 (s, 3H) 4.20 (m, 1H) 6.57 (d, J = 2.24 Hz, 1H) 7.05 (m, 1H) 7.48 (br d, J = 7.67 Hz, 1H) 7.63 (br d, J = 8.01 Hz, 1H) 7.69 (d, J = 2.26 Hz, 1H) 7.75 (d, J = 11.28 Hz, 1H) 7.89 (m, 1H) 8.27 (s, 1H) 12.18 (br s, 1H) | 1.96 | K | 494.2 | 103 |
| 206 | [α]$_D^{20}$ +285.5 (c 0.62, DMF) | ¹H NMR (360 MHz, DMSO-d$_6$) δ ppm 1.24-1.51 (m, 3H) 1.65 (m, 1H) 1.77-1.90 (m, 2H) 2.04 (m, 2H) 3.89 (m, 4H) 4.12-4.26 (m, 1H) 6.58 (m, 1H) 7.14 (m, 1H) 7.74 (m, J = 1.80 Hz, 2H) 7.83 (m, 1H) 7.86 (m, 1H) 7.96 (m, 1H) 8.29 (s, 1H) 12.38 (br s, 1H) | 1.94 | B | 493.2 | n.d. |
| 207 | (+/−) | ¹H NMR (360 MHz, DMSO-d$_6$) δ ppm 1.25-1.53 (m, 3H), 1.65 (m, 1H), 1.81-1.93 (m, 2H), 1.96-2.14 (m, 2H), 2.28 (s, 3H), 3.79-3.95 (m, 1H), 4.08-4.29 (m, 1H), 6.90 (s, 1H), 7.06-7.19 (m, 1H), 7.76 (d, J = 7.9 Hz, 1H), 7.81-7.93 (m, 2H), 8.29 (s, 1H), 8.86 (m, 1H), 12.37 (s, 1H) | 1.61 | H | 494.2 | 285 |
| 208 | (+/−) | ¹H NMR (360 MHz, DMSO-d$_6$) δ ppm 1.35 (m, 1H), 1.41-1.52 (m, 2H), 1.72 (m, 1H), 1.85-1.91 (m, 2H), 2.06 (m, 1H), 2.13 (m, 1H), 3.87-3.97 (m, 1H), 4.18-4.26 (m, 1H), 7.13 (m, 1H), 7.59 (t, J = 10.3 Hz, 1H), 7.74 (m, 1H), 7.84 (d, J = 10.9 Hz, 1H), 7.88-7.93 (m, 1H), 7.96-8.00 (m, 1H0, 8.02 (d, J = 10.9 Hz, 1H), 8.30 (s, 1H), 8.60-8.66 (m, 2H), 12.36 ( br. S., 1H) | 1.73 | H | 490.2 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 209 | [Structure: 5,7-difluoroindole linked to fluoro-cyano-pyridine with NH-cyclohexyl-NH-C(O)-pyridine] $[\alpha]_D^{20}$ -243.3 (c 0.56, DMF) | ¹H NMR (360 MHz, DMSO-d₆) δ ppm 1.40 (m, J = 8.05 Hz, 3H) 1.72 (m, 1H) 1.82-1.93 (m, 2H) 2.09 (m, 2H) 3.92 (m, J = 8.05 Hz, 1H) 4.22 (m, 1H) 7.14 (m, 1H) 7.60 (m, 1H) 7.77 (m, 1H) 7.82-7.94 (m, 2H) 7.94-8.06 (m, 2H) 8.30 (s, 1H) 8.56-8.74 (m, 2H) 12.37 (br. s., 1H) | 2.17 | K | 490.2 | 257 |
| 210 | [Structure: 5,7-difluoroindole linked to fluoro-cyano-pyridine with NH-cyclohexyl-NH-C(O)-dimethylpyrazole] (+/-) | ¹H NMR (360 MHz, DMSO-d₆) δ ppm 1.22-1.52 (m, 3H) 1.56-1.71 (m, 1H) 1.82 (m, 2H) 1.97-2.11 (m, 2H) 2.25 (s, 3H) 3.76 (s, 3H) 3.79-3.91 (m, 1H) 4.08-4.27 (m, 1H) 6.38 (s, 1H) 7.14 (m, 1H) 7.74 (m, 1H) 7.80-7.93 (m, 3H) 8.29 (s, 1H) 12.38 (br. s., 1H) | 1.60 | H | 507.2 | n.d. |
| 211 | [Structure: 5,7-difluoroindole linked to fluoro-cyano-pyridine with NH-cyclohexyl-NH-C(O)-dimethylpyrazole] $[\alpha]_D^{20}$ +246.1 (c 0.56, DMF) | ¹H NMR (360 MHz, DMSO-d₆)(δ ppm 1.24-1.50 (m, 3H), 1.64 (m, 1H), 1.76-1.89 (m, 2H), 1.96-2.11 (m, 2H), 2.25 (s, 3H), 3.76 (s, 3H), 3.78-3.91 (m, 1H), 4.11-4.25 (m, 1H), 6.38 (d, J = 0.7 Hz, 1H), 7.13 (m, 1H), 7.70-7.77 (m, 1H), 7.79-7.93 (m, 3H), 8.29 (s, 1H), 12.37 (br s, 1H) | 2.91 | C | 507.2 | 235 |
| 212 | [Structure: 5,7-difluoroindole linked to fluoro-cyano-pyridine with NH-cyclohexyl-NH-C(O)-fluoropyridine] (+/-) | ¹H NMR (360 MHz, DMSO-d₆)(δ ppm 1.24-1.56 (m, 3H) 1.57-1.72 (m, 1H) 1.81-1.96 (m, 2H) 2.09 (m, 2H) 3.87 (m, 1H) 4.22 (m, J = 8.05 Hz, 1H) 7.13 (t, J = 9.10 Hz, 1H) 7.64 (m, 1H) 7.76 (d, J = 7.32 Hz, 1H) 7.75-7.94 (m, 4H) 7.80-7.93 (m, 3H) 8.30 (s, 1H) 8.46 (m, 1H) 8.63 (m, 1H) 12.39 (br. s., 1H) | 1.65 | H | 508.2 | 289 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 213 | (structure shown) OR n.d. | ¹H NMR (360 MHz, DMSO-d₆)(δ ppm 1.34 (td, J = 26.3, 12.8 Hz, 3H), 1.55 (m, 1H), 1.72-1.87 (m, 2H), 1.99 (m, 2H), 3.64 (br s, 1H), 4.15 (br s, 1H), 4.87 (s, 1H), 6.10 (br s, 1H), 7.11 (m, 1H), 7.20-7.34 (m, 3H), 7.34-7.42 (m, 2H), 7.70 (m, 1H), 7.80-7.89 (m, 2H), 7.89-7.98 (m, 1H), 8.28 (s, 1H) | 1.98 | K | 519.5 | n.d. |
| 214 | (structure shown) OR n.d. | | 2.00 | B | 519.0 | 255 |
| 215 | (structure shown) [α]$_D^{20}$ -91.6 (c 0.46, DMF) | | 1.88 | B | 440.0 | n.d. |
| 216 | (structure shown) (+/-) | ¹H NMR (360 MHz, DMSO-d₆) δ ppm 1.34-1.60 (m, 5H), 1.76 (br s, 3H), 1.86 (br s, 1H), 2.01 (br s, 1H), 2.87 (m, 1H), 4.76 (m, 1H), 7.11 (m, 1H), 7.71 (d, J = 6.7 Hz, 1H), 7.83 (d, J = 11.3 Hz, 1H), 7.94 (m, 1H), 8.26 (s, H), 12.36 (br s, 1H) | 1.74 | H | 440.1 | n.d. |

TABLE 1-continued
Compounds of formula (I) and corresponding analytical data.
| # | STRUCTURE | ¹H NMR | Rt (min) | LC Method | LC-MS Mass Found [M + H]⁺ | MP (° C.) |
|---|---|---|---|---|---|---|
| 217 | 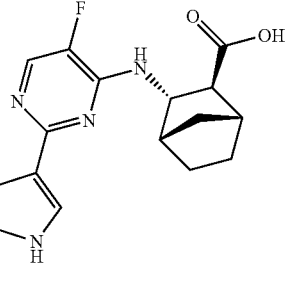 (+/−) | ¹H NMR (300 MHz, DMSO-d₆) δ ppm 1.23-1.38 (m, 2H), 1.40-1.62 (m, 3H), 1.66 (m, 1H), 2.45 (m, 2H), 2.70 (br.s, 1H), 4.64 (m, 1H), 7.04 (m, 1H), 7.68 (d, J = 6.3 Hz, 1H), 8.04 (m, 1H), 8.10 (s, 1H), 8.14 (d, J = 3.9 Hz, 1H), 12.19 (br. s, 1H) | 2.77 | D | 403.0 | n.d. |
| 218 | 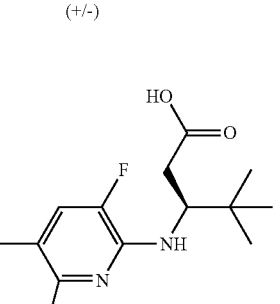 [α]$_D^{23}$ -62.86° (c 0.3, DMF) | ¹H NMR (500 MHz, DMSO-d₆) δ ppm 0.91 (s, 9H) 2.55-2.68 (m, 2H) 4.85 (m, 1H) 7.10 (m, 1H) 7.52 (br d, J = 8.5 Hz, 1H) 7.82 (m, 1H) 8.17 (m, 1H) 8.24 (s, 1H) 12.05 (br s, 1H) 12.31 (br s, 1H) | 2.58 | C | 417.1 | >280 |
| 219 | 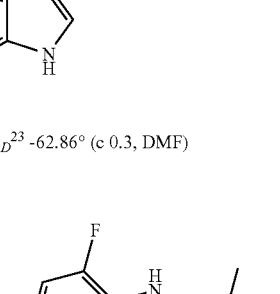 (+/−) | ¹H NMR (500 MHz, DMSO-d₆) δ ppm 0.91 (s, 9H) 2.55-2.68 (m, 2H) 4.85 (m, 1H) 7.10 (m, 1H) 7.52 (m, 1H) 7.82 (d, J = 11.4 Hz, 1H) 8.17 (m, 1H) 8.24 (s, 1H) 12.05 (br s, 1H) 12.31 (br s, 1H) | 2.56 | C | 417.1 | 196.5/ 202.6 |
| 220 | 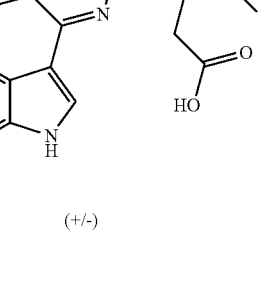 | | 2.01 | B | 494.1 | n.d. |

TABLE 1-continued
Compounds of formula (I) and corresponding analytical data.
| # | STRUCTURE | ¹H NMR | Rt (min) | LC Method | LC-MS Mass Found [M + H]⁺ | MP (° C.) |
|---|---|---|---|---|---|---|
| 221 | 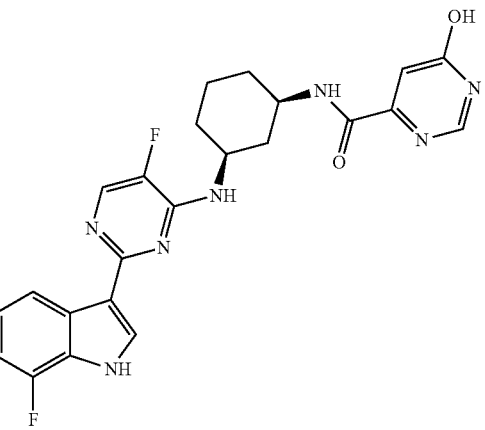<br>OR n.d. | ¹H NMR (300 MHz, CD₃OD) δ ppm 1.24-1.48 (m, 2H), 1.50-1.78 (m, 2H), 1.91-2.02 (m, 2H), 2.27 (m, 1H), 2.40 (m, 1H), 4.07 (m, 1H), 4.33 (m, 1H), 6.80 (m, 1H), 6.85 (s, 1H), 7.98 (d, J = 4.1 Hz, 1H), 8.04 (m, 1H), 8.08 (s, 1H), 8.25 (s, 1H). | 2.25 | D | 483.9 | n.d. |
| 222 | 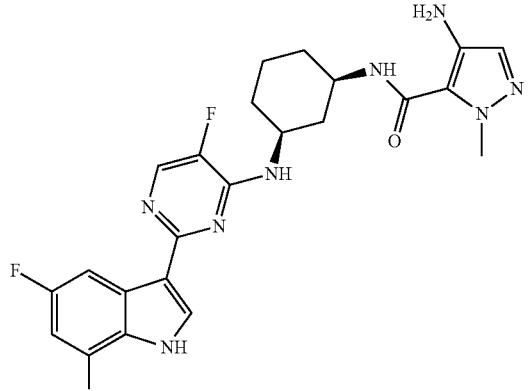<br>OR n.d. | ¹H NMR (300 MHz, CD₃OD) δ ppm 1.23-1.45 (m, 2H), 1.46-1.78 (m, 2H), 1.99 (m, 1H), 2.15 (m, 1H), 2.26 (m, 1H), 2.48 (m, 1H), 3.98 (s, 3H), 4.08 (m, 1H), 4.34 (m, 1H), 6.80 (m, 1H), 7.17 (s, 1H), 7.98 (d, J = 4.1 Hz, 1H), 8.04 (m, 1H), 8.08 (s, 1H). | 2.32 | D | 485.0 | n.d. |
| 223 | 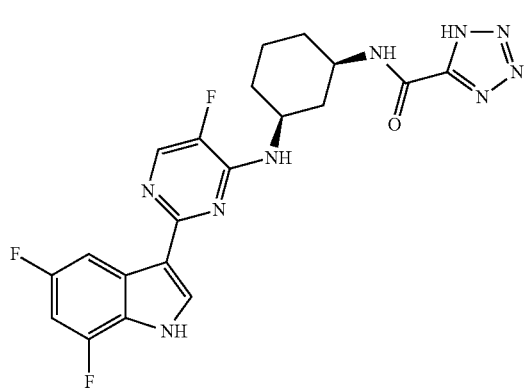<br>[α]$_D^{23}$ -120.9 (c 0.13, DMF) | ¹H NMR (300 MHz, CD₃OD) δ ppm 1.23-1.79 (m, 4H), 2.01 (m, 1H), 2.12 (m, 1H), 2.26 (m, 1H), 2.45 (m, 1H), 4.15 (m, 1H), 4.34 (m, 1H), 6.87 (m, 1H), 7.97-8.10 (m, 2H), 8.17 (m, 1H). | 2.30 | D | 458.1 | 270.2 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 224 | [α]$_D^{23}$ -43.5 (c 0.2, CH₃OH) | ¹H NMR (300 MHz, CD₃OD) δ 1.24-1.56 (m, 3H), 1.68 (m, 1H), 1.97 (m, 1H), 2.15 (m, 1H), 2.25 (m, 1H), 2.49 (m, 1H), 4.08 (m, 1H), 4.32 (m, 1H), 6.80 (m, 1H), 7.42-7.58 (m, 3H), 7.87 (d, J = 7.6 Hz, 1H), 7.98 (d, J = 4.1 Hz, 1H), 8.03 (m, 1H), 8.09 (s, 1H). | 2.42 | D | 509.8 | 201.5 |
| 225 | [α]$_D^{23}$ -165.3 (c 0.26, CH₃OH) | ¹H NMR (300 MHz, CD₃OD) δ ppm 1.25-1.55 (m, 2H), 1.57-1.81 (m, 2H), 2.00 (m, 1H), 2.12 (m, 1H), 2.29 (m, 1H), 2.44 (m, 1H), 4.16 (m, 1H), 4.36 (m, 1H), 6.82 (m, 1H), 7.97-8.07 (m, 3H), 8.09 (s, 1H), 8.57 (s, 1H), 8.76 (m, 1H). | 2.59 | D | 511.1 | 265.2 |
| 226 | OR n.d. | ¹H NMR (400 MHz, DMSO-d₆) δ ppm 1.31 (m, 2H) 1.53 (m, 2H) 1.83-1.92 (m, 2H) 2.00-2.07 (m, 1H) 2.16 (m, 1H) 3.00 (s, 3H) 3.91-3.97 (m, 1H) 3.94 (s, 3H) 4.14-4.24 (m, 1H) 6.67 (s, 1H) 7.05 (m, 1H) 7.53 (m, 1H) 8.02 (m, 1H) 8.13-8.16 (m, 2H) 8.43 (m, 1H) 9.99 (br s, 1H) 12.17 (br s, 1H). | 1.79 | B | 563.3 | n.d. |
| 227 | OR n.d. | ¹H NMR (400 MHz, DMSO-d₆) δ ppm 1.33 (m, 2H) 1.45-1.59 (m, 2H) 1.87 (m, 2H) 2.04 (m, 1H) 2.16 (m, J = 11.9 Hz, 1H) 3.89-3.96 (m, 1H) 3.92 (s, 3H) 4.13-4.24 (m, 1H) 6.67 (s, 1H) 6.82-6.92 (m, 2H) 7.05 (m, 1H) 7.53 (d, J = 7.5 Hz, 1H) 8.02 (m, 1H) 8.14-8.14 (m, 1H) 8.15 (s, 1H) 8.41 (m, 1H) 9.55 (s, 1H) 12.18 (m, 1H) | 1.73 | L | 564.1 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 228 | OR n.d. | ¹H NMR (400 MHz, DMSO-d₆) δ ppm 1.23-1.40 (m, 2H) 1.45-1.61 (m, 2H) 1.86 (m, J = 10.1 Hz, 2H) 1.98-2.10 (m, 1H) 2.00 (s, 3H) 2.14 (m, J = 12.3 Hz, 1H) 3.89-3.98 (m, 1H) 3.94 (s, 3H) 4.11-4.23 (m, 1H) 7.00 (t, J = 10.2 Hz, 1H) 7.15 (s, 1H) 7.50 (m, 1H) 8.00 (m, 1H) 8.11-8.15 (m, 2H) 8.49 (d, J = 7.9 Hz, 1H) 10.44 (s, 1H) | 1.77 | B | 527.3 | n.d. |
| 229 | (+/−) | ¹H NMR (400 MHz, DMSO-d₆) δ ppm 1.20 (s, 3H) 1.36 (s, 3H) 2.26 (m, 1H) 2.63 (m, 1H) 5.32 (m, 1H) 6.90-6.97 (m, 2H) 7.13 (m, 1H) 7.36 (m, 1H) 7.60 (m, 1H) 7.87 (d, J = 11.1 Hz, 1H) 8.19-8.25 (m, 2H) 11.97-12.18 (m, 1H) 12.32 (br s, 1H) | 2.73 | C | 485.2 | 235.7 |
| 230 | (+/−) | ¹H NMR (400 MHz, DMSO-d₆) δ ppm 1.32 (s, 3H) 1.39 (s, 3H) 2.26 (m, 1H) 2.56 (m, 1H) 5.24 (m, 1H) 6.97-7.09 (m, 3H) 7.41 (m, 1H) 7.47-7.61 (m, 1H) 8.11 (d, J = 2.5 Hz, 1H) 8.15 (m, 1H) 8.23 (m, 1H) 11.95-12.06 (br s, 1H) 12.17 (br s, 1H) | 2.54 | C | 361.1 | 237.3/ 243.7 |
| 231 | [α]_D²³ -114.29° (c 0.19, DMF) | ¹H NMR (400 MHz, DMSO-d₆) δ ppm 1.32 (s, 3H) 1.39 (s, 3H) 2.26 (m, 1H) 2.56 (m, 1H) 5.24 (m, 1H) 6.97-7.09 (m, 3H) 7.41 (m, 1H) 7.47-7.61 (m, 1H) 8.11 (d, J = 2.5 Hz, 1H) 8.15 (m, 1H) 8.23 (m, 1H) 11.95-12.06 (br s, 1H) 12.17 (br s, 1H) | 2.54 | C | 461.0 | 271.1 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 232 | 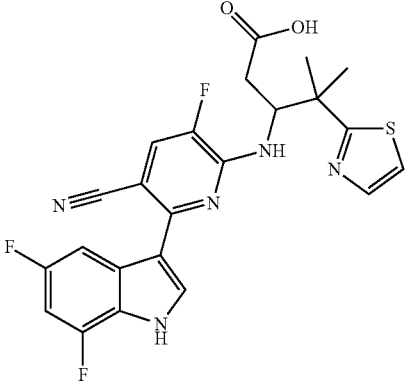 (+/−) | ¹H NMR (400 MHz, DMSO-d₆) δ ppm 1.33 (s, 3H) 1.43 (s, 3H) 2.36 (m, 1H) 2.61 (m, 1H) 5.42 (m, 1H) 7.10 (m, 1H) 7.54-7.65 (m, 3H) 7.69 (d, J = 3.0 Hz, 1H) 7.87 (d, J = 11.6 Hz, 1H) 8.18 (m, 1H) 8.21 (d, J = 3.0 Hz, 1H) 12.08 (s, 1H) 12.27-12.34 (m, 1H) | 2.41 | C | 486.1 | 223.6 |
| 233 | 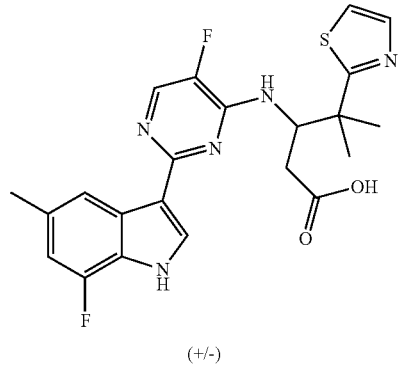 [SMILES: Cc1cc(F)c2[nH]cc(-c3ncc(F)c(NC(CC(=O)O)C(C)(C)c4nccs4)n3)c2c1] (+/−) | ¹H NMR (400 MHz, DMSO-d₆) δ ppm 1.44 (d, J = 16.7 Hz, 6H) 2.32-2.36 (m, 1H) 2.45 (s, 3H) 2.55-2.67 (m, 2H) 3.17 (d, J = 5.1 Hz, 1H) 4.09 (q, J = 5.4 Hz, 1H) 5.44 (m, 1H) 6.83 (d, J = 12.1 Hz, 1H) 7.45 (br s, 1H) 7.65 (d, J = 3.0 Hz, 1H) 7.77 (d, J = 3.0 Hz, 1H) 7.99 (d, J = 2.5 Hz, 1H) 8.15 (d, J = 3.5 Hz, 1H) 8.25 (s, 1H) 11.87 (m, 1H) 12.02 (br s, 1H) | 2.29 | C | 458 | 237.2 |
| 234 | 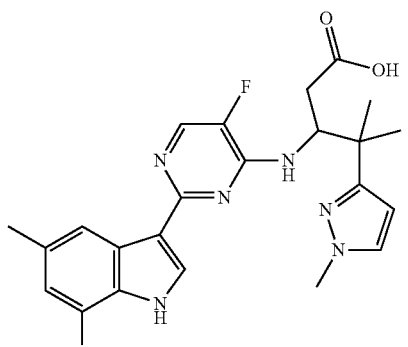 (+/−) | ¹H NMR (500 MHz, DMSO-d₆) δ ppm 1.27 (d, J = 12.6 Hz, 6H) 2.40-2.48 (m, 6H) 3.31-3.47 (br s, 2H) 3.45-3.58 (m, 1H) 5.22-5.30 (m, 1H) 6.18 (d, J = 2.2 Hz, 1H) 6.89 (br d, J = 12.3 Hz, 1H) 7.15-7.27 (m, 1H) 7.61 (d, J = 2.2 Hz, 1H) 8.11-8.17 (br s, 1H) 8.26 (s, 2H) 11.94-12.1 (br s, 1H) | 2.22 | C | 455.1 | 208.5 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 235 | [α]$_D^{23}$ -66.15° (c 0.25, DMF) | ¹H NMR (500 MHz, DMSO-d$_6$) δ ppm 1.27 (d, J = 12.6 Hz, 6H) 2.40-2.48 (m, 6H) 3.31-3.47 (br s, 2H) 3.45-3.58 (m, 1H) 5.22-5.30 (m, 1H) 6.18 (d, J = 2.2 Hz, 1H) 6.89 (br d, J = 12.3 Hz, 1H) 7.15-7.27 (m, 1H) 7.61 (d, J = 2.2 Hz, 1H) 8.11-8.17 (br s, 1H) 8.26 (s, 2H) 11.94-12.1 (br s, 1H) | 2.24 | C | 455.1 | >260 |
| 236 | (+/-) | ¹H NMR (500 MHz, DMSO-d$_6$) δ ppm 1.15 (s, 3H) 1.25 (s, 3H) 2.33 (d, J = 15.5 Hz, 1H) 3.76 (s, 3H) 5.25 (br t, J = 9.8 Hz, 1H) 6.08 (d, J = 2.2 Hz, 1H) 7.13 (dd, J = 11.4, 9.5, 1.9 Hz, 1H) 7.40-7.57 (br s, 1H) 7.56 (d, J = 1.9 Hz, 1H) 7.86 (d, J = 11.4 Hz, 1H) 8.20-8.25 (m, 2H) 12.04 (br s, 1H) 12.33 (br s, 1H) | 2.36 | C | 483.2 | 246.9 |
| 237 | (+/-) | ¹H NMR (400 MHz, DMSO-d$_6$) δ ppm 1.25 (s, 3H) 1.35 (s, 3H) 2.13 (dd, J = 15.7, 2.0 Hz 1H) 2.46-2.53 (m, 1H) 5.57 (br t, J = 9.6 Hz, 1H) 7.13 (ddd, J = 11.6, 9.6, 2.0 Hz 1H) 7.20 (dd, J = 7.1, 5.1 Hz, 1H) 7.41 (d, J = 7.6 Hz, 1H) 7.62 (br d, J = 9.1 Hz, 1H) 7.67 (td, J = 7.6, 1.5 Hz, 1H) 7.84 (d, J = 11.1 Hz, 1H) 8.23 (d, J = 2.5 Hz, 1H) 8.31 (dd, J = 10.6, 2.0 Hz, 1H) 8.49 (d, J = 4.9 Hz, 1H) 11.97 (br s, 1H) 12.30 (br d, J = 2.0 Hz, 1H). | 2.57 | C | 480.1 | 230.8 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 238 | (+/−) | ¹H NMR (500 MHz, DMSO-d₆) δ ppm 1.36 (d, J = 12.3 Hz, 3H) 1.39 (s, 3H) 2.15 (br d, J = 13.6 Hz, 1H) 2.4 (m, 4H) 5.53 (br t, J = 9.0 Hz, 1H) 6.85 (br d, J = 12.0 Hz, 1H) 7.24 (dd, J = 5.2, 6.8 Hz, 1H) 7.42 (br d, J = 8.8 Hz, 1H) 7.50 (br d, J = 8.2 Hz, 1H) 7.75 (br t, J = 7.2 Hz, 1H) 8.01 (d, J = 2.5 Hz, 1H) 8.13 (d, J = 3.8 Hz, 1H) 8.30 (s, 1H) 8.59 (br d, J = 3.8 Hz, 1H) 11.88 (br s, 1H) 11.95 (s, 1H) | 2.37 | C | 452.1 | 248.1 |
| 239 | [α]$_D^{23}$ −93.91° (c 0.24, DMF) | ¹H NMR (500 MHz, DMSO-d₆) δ ppm 1.36 (d, J = 12.3 Hz, 3H) 1.39 (s, 3H) 2.15 (br d, J = 13.6 Hz, 1H) 2.4 (m, 4H) 5.53 (br t, J = 9.0 Hz, 1H) 6.85 (br d, J = 12.0 Hz, 1H) 7.24 (dd, J = 5.2, 6.8 Hz, 1H) 7.42 (br d, J = 8.8 Hz, 1H) 7,50 (br d, J = 8.2 Hz, 1H) 7.75 (br t, J = 7.2 Hz, 1H) 8.01 (d, J = 2.5 Hz, 1H) 8.13 (d, J = 3.8 Hz, 1H) 8.30 (s, 1H) 8.59 (br d, J = 3.8 Hz, 1H) 11.88 (br s, 1H) 11.95 (s, 1H) | 2.40 | C | 452.1 | 219 |
| 240 | (+/−) | ¹H NMR (500 MHz, DMSO-d₆) δ ppm 1.05 (s, 3H) 1.10 (s, 3H) 2.59 (dd, J = 15.8, 10.1 Hz, 1H) 2.66 (br d, J = 14.8 Hz, 1H) 3.13 (s, 3H) 5.12 (br t, J = 9.8 Hz 1H) 7.09 (ddd, J = 11.2, 9.3, 2.2 Hz, 1H) 7.53-7.71 (m, 1H) 7.85 (d, J = 11.0 Hz, 1H) 8.14 (dd, J = 10.1, 2.2 Hz, 1H) 8.20 (d, J = 1.6 Hz, 2H) 11.90-12.55 (br s, 1H), 12.32 (br s, 1H). | 2.31 | C | 433.1 | 218.8 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 241 | (+/−) | ¹H NMR (400 MHz, DMSO-d$_6$) δ ppm 0.83 (s, 3H) 0.85 (s, 3H) 1.98-2.10 (m, 2H) 2.52-2.68 (m, 2H) 4.87-4.98 (m, 3H) 5.76-5.87 (m, 1H) 7.10 (ddd, J = 11.1, 9.6, 2.0 Hz, 1H) 7.54-7.67 (m, 1H) 7.81 (d, J = 11.6 Hz, 1H) 8.14 (dd, J = 10.1, 2.0 Hz, 1H) 8.21 (s, 1H) 10.95-12.98 (br s, 2H) | 2.75 | C | 443.1 | >260 |
| 242 | (+/−) | ¹H NMR (400 MHz, DMSO-d$_6$) δ ppm 0.92 (d, J = 6.6 Hz, 6H) 2.03-2.09 (dd, 1H) 2.14-2.19 (dd, 1H) 2.43 (s, 3H) 2.54-2.58 (dd, 1H) 2.66-2.70 (dd, 1H) 4.92-5.01 (m, 2H) 5.03 (s, 1H) 5.86-5.97 (m, 1H) 6.81-6.84 (d, J = 12.1 Hz, 1H) 7.25-7.27 (d, J = 9.0 Hz, 1H) 7.96 (d, J = 2.5 Hz, 1H) 8.11 (d, J = 4.0 Hz, 1H) 8.21 (s, 1H) 11.86 (br s, 1H) 11.99 (s, 1H) | 2.56 | C | 415.1 | 224.2 |
| 243 | [α]$_D$²³ +29.06° (c 0.32, DMF) | ¹H NMR (400 MHz, DMSO-d$_6$) δ ppm 0.92 (d, J = 6.6 Hz, 6H) 2.03-2.09 (dd, 1H) 2.14-2.19 (dd, 1H) 2.43 (s, 3H) 2.54-2.67 (m, 2H) 4.91-4.95 (t, 1H) 4.98-5.03 (m, 1H) 5.86-5.97 (m, 1H) 6.83 (d, J = 12.1 Hz, 1H) 7.30-7.33 (br s, 1H) 7.95 (d, J = 3.0 Hz, 1H) 8.11 (d, J = 4.0 Hz, 1H) 8.21 (s, 1H) 11.85 (s, 1H), 11.95-12.02 (br s, 1H) | 2.56 | C | 415.1 | <280 |
| 244 | (+/−) | ¹H NMR (500 MHz, DMSO-d$_6$) δ ppm 0.98 (s, 3H) 1.14 (m, 1H) 1.26-1.34 (m, 1H) 1.43-1.60 (m, 5H) 1.69 (m, 1H) 2.52-2.68 (m, 2H) 4.93 (br t, J = 11.0 Hz, 1H) 7.10 (ddd, J = 11.4, 9.1, 2.2 Hz, 1H) 7.62 (br d, J = 9.1 Hz, 1H) 7.81 (d, J = 11.4 Hz, 1H) 8.12 (dd, J = 10.4, 2.2 Hz, 1H) 8.23 (s, 1H), 10.82-13.05 (br s, 2H) | 2.76 | C | 443.1 | 150 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 245 | [α]$_D^{23}$ +89.49° (c 0.31, DMF) | ¹H NMR (500 MHz, DMSO-d$_6$) δ ppm 0.98 (s, 3H) 1.14 (m, 1H) 1.26-1.34 (m, 1H) 1.43-1.60 (m, 5H) 1.69 (m, 1H) 2.52-2.68 (m, 2H) 4.93 (m, 1H) 7.10 (m, 1H) 7.62 (br d, J = 9.1 Hz, 1H) 7.81 (d, J = 11.4 Hz, 1H) 8.12 (m, 1H) 8.23 (s, 1H), 10.82-13.05 (br s, 2H) | 2.80 | C | 441.1 | 289.6 |
| 246 | (+/-) | ¹H NMR (500 MHz, DMSO-d$_6$) δ ppm 0.99 (s, 3H) 1.14-1.19 (m, 1H) 1.28-1.32 (m, 1H) 1.46-1.60 (m, 5H) 1.66-1.77 (m, 1H) 2.30-2.38 (m, 1H) 2.52-2.57 (m, 1H) 4.83-4.94 (m, 1H) 6.74 (s, 1H) 6.99-7.15 (m, 2H) 7.27 (d, J = 8.8 Hz, 1H) 7.81 (d, J = 11.4 Hz, 1H) 8.10 (m, 1H) 8.21 (s, 1H) 12.29 (s, 1H). | 3.02 | C | 442.1 | 270.1 |
| 247 | (+/-) | ¹H NMR (500 MHz, DMSO-d$_6$) δ ppm 0.71 (t, J = 7.6 Hz, 3H) 1.29-1.76 (m, 8H) 1.77-1-80 (m, 2H), 5.08 (m, 1H) 7.05 (d, J = 9.5 Hz, 1H) 7.10 (ddd, J = 11.4, 9.5, 1.9 Hz, 1H) 7.87 (d, J = 11.4 Hz, 1H) 7.90 (dd, J = 10.1, 1.9 Hz, 1H) 8.24 (d, J = 2.8 Hz, 1H) 12.33 (br s, 2H) | 2.86 | C | 443.1 | 254.9 |
| 248 | [α]$_D^{23}$ +141.6° (c 0.25, DMF) | ¹H NMR (500 MHz, DMSO-d$_6$) δ ppm 1.10-1.25 (m, 2H) 1.26-1.43 (m, 2H) 1.71-1.80 (m, 6H) 1.87 (s, 3H) 1.96-2.03 (m, 2H) 3.11-3.21 (m, 4H) 3.37-3.53 (m, 1H) 3.95-4.04 (m, 1H) 4.24-4.32 (m, 2H) 5.78 (d, J = 7.9 Hz, 1H) 6.42 (br d, J = 7.9 Hz, 1H) 6.99-7.05 (m, 1H) 7.30 (d, J = 12.0 Hz, 1H) 7.65 (dd, J = 2.2 Hz, J = 9.7 Hz, 1H) 7.72 (s, 1H) 8.28 (t, J = 5.4 Hz, 1H) 12.00 (br s, 1H). | 2.54 | C | 529.3 | <260 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 249 | (structure) (+/−) | ¹H NMR (400 MHz, DMSO-d₆) δ ppm 1.02 (s, 3H) 1.12-1.23 (m, 1H) 1.30-1.40 (m, 1H) 1.48-1.67 (m, 5H) 1.71-1.86 (m, 1H) 2.54-2.64 (m, 2H) 4.89 (t, J = 1.00 Hz, 1H) 6.91-7.10 (m, 1H) 7.53 (s, 1H) 7.98-8.17 (m, 3H) 12.13 (s, 1H) | 1.75 | K | 419.3 | n.d. |
| 250 | (structure) (+/−) | ¹H NMR (500 MHz, DMSO-d₆) δ ppm 1.09-1.25 (m, 2H) 1.25-1.46 (m, 2H) 1.75 (br s, 6H) 1.89-2.04 (m, 2H) 2.08 (s, 2H) 2.94 (s, 3H) 3.09-3.26 (m, 4H) 3.36-3.49 (m, 1H) 3.96-4.06 (m, 1H) 4.20 (br s, 2H) 5.77 (br d, J = 7.25 Hz, 1H) 6.50 (br d, J = 7.57 Hz, 1H) 7.03 (br t, J = 9.77 Hz, 1H) 7.43 (br s, 1H) 7.45 (br s, 1H) 7.65 (br d, J = 9.77 Hz, 1H) 7.86 (br s, 1H) 12.03 (br s, 1H) | 2.63 | C | 565.2 | 252.1 |
| 251 | (structure) (+/−) | ¹H NMR (400 MHz, DMSO-d₆) δ ppm 1.23 (d, J = 8.6 Hz, 6H) 2.37-2.43 (m, 1H) 2.59-2.66 (m, 1H) 3.02 (br s, 6H) 4.09 (br d, J = 5.6 Hz, 1H) 5.42 (br t, J = 9.4 Hz, 1H) 7.01-7.07 (m, 1H) 7.29 (brs, 1H) 8.01 (d, J = 3.0 Hz, 1H) 8.11 (br d, J = 10.1 Hz, 1H) 8.18 (d, J = 3.5 Hz, 1H) 12.2 (s, 2H). | 2.04 | C | 450.1 | 253 |
| 252 | (structure) (+/−) |  | 1.84 | B | 419.2 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 253 | [α]$_D^{20}$ +22 (c 0.65, CD$_3$OD) | | 1.83 | B | 418.2 | n.d. |
| 254 | OR n.d. | | 1.51 | B | 391.2 | n.d. |
| 255 | (+/−) | ¹H NMR (400 MHz, DMSO-d$_6$) δ ppm 0.98-1.10 (m, 4H) 1.31 (br d, J = 13.1 Hz, 1H) 1.44-1.58 (m, 2H) 2.52-2.69 (m, 3H) 3.41 (t, J = 10.6 Hz, 1H) 3.58 (br t, J = 10.6 Hz, 2H) 4.96 (br t, J = 8.8 Hz, 1H) 7.09 (m, 1H) 7.49-7.64 (m, 1H) 7.83 (d, J = 11.6 Hz, 1H) 8.19-8.23 (m, 2H) 12.17 (br s, 1H) 12.30 (br s, 1H) | 2.17 | C | 458.20 | 151.1 |
| 256 | (+/−) | ¹H NMR (500 MHz, DMSO-d$_6$) δ ppm 0.88 (s, 9H) 1.17 (t, J = 7.1 Hz, 3H) 2.41-2.57 (m, 2H) 4.01 (q, J = 7.2 Hz, 2H) 4.22 (br d, J = 5.7 Hz, 2H) 4.70 (br t, J = 8.8 Hz, 1H) 6.27 (br s, 1H) 7.00 (ddd, J = 11.2, 9.3, 2.2 Hz, 1H) 7.26 (d, J = 12.3 Hz, 1H) 7.63 (br t, J = 5.5 Hz, 1H) 7.71-7.75 (m, 1H) 7.90 (d, J = 9.3 Hz, 1H) 11.88-11.99 (m, 2H) | 2.66 | C | 393.2 | 250 |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 257 | (structure; OR n.d.) | ¹H NMR (400 MHz, DMSO-d₆) δ ppm 0.97 (s, 9H) 3.55-3.62 (m, 1H) 3.71-3.77 (m, 1H) 4.39 (td, J = 9.0, 2.8 Hz, 1H) 4.55 (t, J = 5.1 Hz, 1H) 7.11 (m, 1H) 7.18 (m, 1H) 7.82 (d, J = 11.1 Hz, 1H) 8.00 (m, 1H) 8.26 (s, 1H) 12.32 (br s, 1H) | 3.12 | C | 389.2 | 118.6/ 159.6 |
| 258 | (structure; (+/−)) | ¹H NMR (400 MHz, DMSO-d₆) δ ppm 1.17-1.41 (m, 4H) 1.53 (d, J = 11.6 Hz, 1H) 1.79 (br d, J = 8.1 Hz, 2H) 1.87 (s, 3H) 1.97-2.07 (m, 2H) 3.66 (s, 3H) 3.70-3.80 (m, 1H) 4.06 (m, 1H) 4.28 (d, J = 5.6 Hz, 2H) 6.46 (br d, J = 8.1 Hz, 1H) 7.02 (ddd, J = 2.0, 9.6, 11.6 Hz, 1H) 7.31 (d, J = 12.6 Hz, 1H) 7.57-7.62 (m, 2H) 7.67 (dd, J = 2.0, 8.1 Hz, 1H) 7.72 (s, 1H) 8.27 (t, J = 5.6 Hz, 1H) 11.99 (s, 1H) | 2.15 | M | 540.5 | n.d. |
| 259 | (structure; [α]$_D^{23}$ −144.15° (c 0.19, DMF)) | ¹H NMR (400 MHz, DMSO-d₆) δ ppm 1.17-1.41 (m, 4H) 1.53 (d, J = 11.6 Hz, 1H) 1.79 (br d, J = 8.1 Hz, 2H) 1.87 (s, 3H) 1.97-2.07 (m, 2H) 3.66 (s, 3H) 3.70-3.80 (m, 1H) 4.06 (m, 1H) 4.28 (d, J = 5.6 Hz, 2H) 6.46 (m, 1H) 7.02 (m, 1H) 7.31 (d, J = 12.6 Hz, 1H) 7.57-7.62 (m, 2H) 7.67 (dd, J = 2.0, 8.1 Hz, 1H) 7.72 (s, 1H) 8.27 (t, J = 5.6 Hz, 1H) 11.99 (s, 1H) | 2.32 | C | 540.2 | >260 |

245
246
TABLE 1-continued
Compounds of formula (I) and corresponding analytical data.
| # | STRUCTURE | ¹H NMR | Rt (min) | LC Method | LC-MS Mass Found [M + H]⁺ | MP (° C.) |
|---|---|---|---|---|---|---|
| 260 | 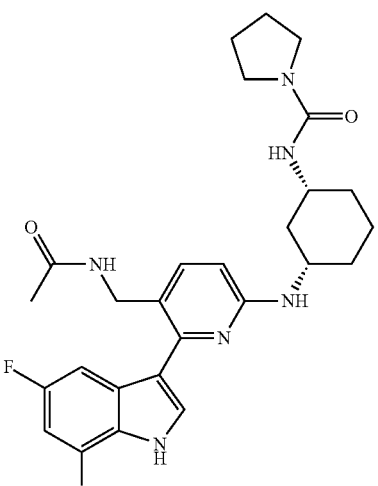 (+/−) | ¹H NMR (500 MHz, DMSO-d$_6$) δ ppm 0.97-1.38 (m, 4H) 1.71-1.80 (m, 6H) 1.86 (s, 3H) 2.01-2.08 (m, 2H) 3.11-3.21 (m, 4H) 3.40-3.53 (m, 1H) 3.75-3.84 (m, 1H) 4.24 (d, J = 5.1 Hz, 2H) 5.74 (d, J = 7.9 Hz, 1H) 6.32 (d, J = 7.6 Hz, 1H) 6.36 (d, J = 8.6 Hz, 1H) 6.97-7.03 (m, 1H) 7.36 (d, J = 8.6 Hz, 1H) 7.69 (s, 1H) 7.76 (m, 1H) 8.16 (t, J = 5.1 Hz, 1H) 11.94 (br s, 1H). | 2.43 | C | 511.3 | 235.8 |
| 261 | 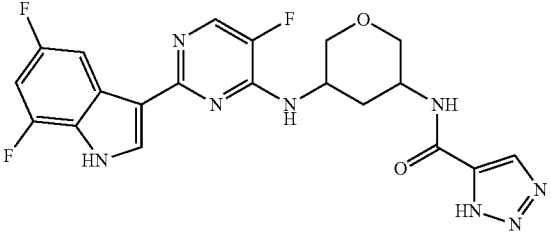 [SMILES: O=C(NC1COCC(Nc2nc(-c3c[nH]c4c(F)cc(F)cc34)ncc2F)C1)c1cnn[nH]1] | | 2.08 | D | 458.9 | n.d. |
| 262 | 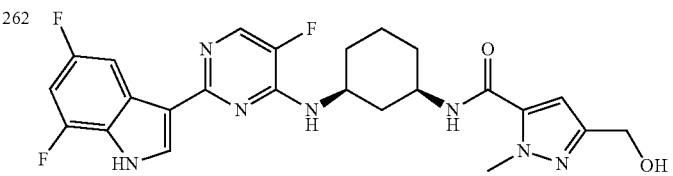 OR n.d. | | 1.69 | K | 500.3 | n.d. |
| 263 | 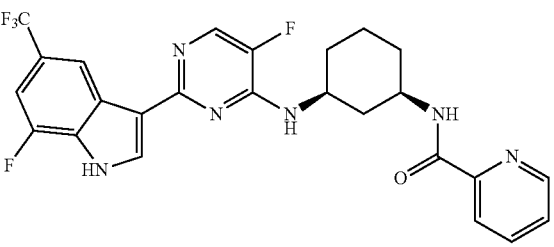 (+/−) | | 3.44 | D | 517.1 | n.d. |

TABLE 1-continued

Compounds of formula (I) and corresponding analytical data.

| # | STRUCTURE | ¹H NMR | Rt (min) | LC Method | LC-MS Mass Found [M + H]⁺ | MP (° C.) |
|---|---|---|---|---|---|---|
| 264 | 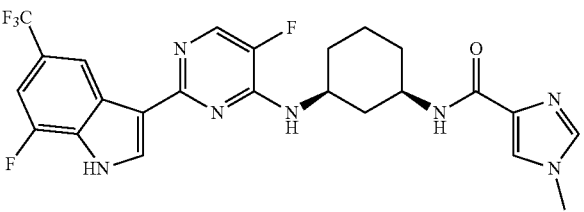<br>(+/−) | | 2.62 | D | 520 | 266.5 |

Compounds were prepared according to the methods described in the experimental section or closely related procedures.

For certain compounds, melting points (MP) were determined with a DSC823e (Mettler-Toledo). Melting points were measured with a temperature gradient of 30° C./minute, and a maximum temperature of 400° C. The reported values are peak values or melt ranges. Values were obtained with experimental uncertainties that are commonly associated with this analytical method. For other compounds, a capillary tube method was used.

Optical rotations were measured on a Perkin-Elmer 341, or JASCO P-2000 polarimeter with a sodium lamp and reported as follows: $[\alpha]^0$ ($\lambda$, c g/100 ml, solvent, T° C.). $[\alpha]_\lambda^T = (100\alpha)/(l \times c)$: where l is the path length in dm and c is the concentration in g/100 ml for a sample at a temperature T (° C.) and a wavelength $\lambda$ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

NMR was executed at either a 360 MHz Bruker DPX 300 machine NMR, a 400 MHz Bruker AVANCE NMR machine, or a Bruker Avance 500 spectrometer equipped with a reverse triple-resonance (¹H, ¹³C, ¹⁵N TXI) probe head with z gradients and operating at 500 MHz for the proton. Signals are presented in parts per million (ppm) relative to the residual solvent peak. Multiplicity is presented as follows: s, singlet; d, doublet; t, triplet; q, quartet; p, pentet; dd, doublet of doublets; dt, doublet of triplets; ddd, doublet of doublet of doublets; dtd, doublet of triplet of doublets; m, multiplet; br s., broad signal.

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time, etc.) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the [M+H]⁺ (protonated molecule) and/or [M−H]⁻ (deprotonated molecule). In case the compound was not directly ionizable the type of adduct is specified (i.e. [M+NH₄]⁺, [M+HCOO]⁻, etc.). For molecules with multiple isotopic patterns (Br, Cl, etc), the reported value is the one obtained for the lowest isotope mass. All results were obtained with experimental uncertainties that are commonly associated with the method used.

TABLE 2

Analytical methods

| Method | Instrument | Column | Mobile phase | Gradient | Flow (mL/min) Column Temperature (° C.) | Run time (min) |
|---|---|---|---|---|---|---|
| A | Waters: Acquity ® UPLC ®-DAD and SQD | Waters BEH C18 (1.7 μm, 2.1 × 50 mm) | A: 10 mM CH₃COONH₄ in 95% H2O + 5% CH₃CN B: CH₃CN | From 95% A to 5% A in 1.3 min, held for 0.7 min. | 0.8<br>55 | 2 |
| B | Waters: Acquity ® UPLC ®-DAD and SQD | Waters HSS T3 (1.8 μm, 2.1 × 100 mm) | A: 10 mM CH₃COONH₄ in 95% H2O + 5% CH3CN B: CH3CN | From 100% A to 5% A in 2.10 min, to 0% A in 0.90 min, to 5% A in 0.5 min | 0.7<br>55 | 3.5 |

TABLE 2-continued

Analytical methods

| Method | Instrument | Column | Mobile phase | Gradient | Flow (mL/min) Column Temperature (° C.) | Run time (min) |
|---|---|---|---|---|---|---|
| C | Waters: Acquity UPLC ® - DAD and Quattro Micro ™ | Waters BEH C18 (1.7 μm, 2.1 × 100 mm) | A: 95% $CH_3OONH_4$ 7 mM/5% $CH_3CN$ B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |
| D | Agilent 1100 series DAD LC/MS G1956A | YMC ODS-AQ C18 (50 × 4.6 mm, 3.0 μm) | A: 0.1% HCOOH in $H_2O$ B: $CH_3CN$ | From 95% A to 5% A in 4.8 min, held for 1.0 min, to 90% A in 0.2 min | 2.6 35 | 6.0 |
| E | Agilent 1290 Infinity DAD LC/MS G6110A | Phenomenex Kinetex C18 (50 × 2.1 mm, 1.7 μm) | A: 0.1% HCOOH in $H_2O$ B: $CH_3CN$ | From 90% A to 10% A in 1.5 min, held for 0.4 min, to 90% A in 0.1 min. | 1.5 60 | 2.0 |
| F | Agilent 1290 Infinity DAD TOF-LC/MS G6224A | YMC-pack ODS-AQ C18 (50 × 4.6 mm, 3 μm) | A: 0.1% HCOOH in $H_2O$ B: $CH_3CN$ | ISET 2V1.0 Emulated Agilent Pump G1312A V1.0 From 94.51% A to 5% A in 4.8 min, held for 1.0 min, to 95% A in 0.2 min. | 2.6 35 | 6.0 |
| G | Agilent 1260 Infinity (Quat. Pump) DAD LC/MS G6120 (G1948B) | Thermo Scientific Accucore C18 (50 × 4.6 mm, 2.6 μm) | A: 0.1% HCOOH in $H_2O$ B: CH3CN | From 90% A to 10% A in 1.5 min, held for 0.9 min, to 95% A in 0.1 min. | 3.0 30 | 3.0 |
| H | Waters: Acquity ® UPLC ® -DAD and SQD | Waters: BEH C18 (1.7 μm, 2.1 × 50 mm) | A: 0.1% HCOOH + 5% CH3OH in H2O B: CH3OH | From 95% A to 0% A in 2.50 min, to 5% A in 0.5 min | 0.7 55 | 3 |
| K | Waters: Acquity ® UPLC ® - DAD and SQD | Waters: HSS T3 (1.8 μm, 2.1 × 100 mm) | A: 10 mM CH3COONH4 in 95% H2O + 5% CH3CN B: CH3CN | From 100% A to 5% A in 2.10 min, to 0% A in 0.90 min, to 5% A in 0.5 min | 0.7 55 | 3.5 |
| L | Waters: Acquity ® UPLC ®- DAD and SQD | Waters: HSS T3 (1.8 μm, 2.1 × 100 mm) | A: 10 mM $CH_3COONH_4$ in 95% H2O + 5% $CH_3CN$ B: CH3CN | From 100% A to 5% A in 2.10 min, to 0% A in 0.90 min, to 5% A in 0.5 min | 0.8 40 | 3.5 |
| M | Waters: Acquity ® H-Class - DAD and SQD2 ™ | Waters BEH ® C18(1.7 μm, 2.1 × 100 mm) | A: $CH_3COONH_4$ 7 mM 95%/ CH3CN 5%, B: $CH_3CN$ | 84.2% A/15.8% B for 0.49 min, to 10.5% A in 1.81 min, held for 2.31 min, back to 84.2% A/15.8% B in 0.73 min, held for 0.73 min. | 0.343 40 | 6.1 |
| N | Waters: Acquity ® UPLC ®-DAD and SQD | Waters: BEH C18 (1.7 μm, 2.1 × 50 mm) | A: 10 mM $CH_3COONH_4$ in 90% H2O + 10% $CH_3CN$ B: MeOH | From 95% A to 5% A in 1.3 min, held for 0.2 min, to 95% A in 0.2 min held for 0.1 min. | 0.7 70 | 1.8 |

"SQD" Single Quadrupole Detector, "BEH" bridged ethylsiloxane/silica hybrid, "HSS" High Strength Silica, "DAD" Diode Array Detector. Flow expressed in mL/min; column temperature (T) in ° C.; Run time in minutes.

Biological Activity of Compounds of Formula (I)

The in vitro antiviral activity of the compounds was determined using a cell-based antiviral assay. In this assay, the cytopathic effect (CPE) in Madin-Darby canine kidney (MDCK) cells infected by influenza virus A/Taiwan/1/86 (H1N1) was monitored in the presence or absence of the compounds. White 384-well microtiter assay plates (Greiner) were filled via acoustic drop ejection using the echo liquid handler (Labcyte, Sunnyvale, Calif.). Two hundred nanoliter of compound stock solutions (100% DMSO) were transferred to the assay plates. MDCK cells were dispensed to the plate at final density of 25,000 or 6,000 cells/well. Then Influenza A/Taiwan/1/86 (H1N1) virus was added at a multiplicity of infection of 0.001 or 0.01, respectively. The wells contain 0.5% DMSO per volume. Virus- and mock-infected controls were included in each test. The plates were incubated at 37° C. in 5% $CO_2$. Three days post-virus exposure, the cytopathic effect was quantified by measuring the reduction in ATP levels using the ATPlite™ kit (PerkinElmer, Zaventem, Belgium) according to the manufacturer's instructions. The $IC_{50}$ was defined as the 50% inhibitory concentration. In parallel, compounds were incubated for three days in white 384-well microtiter plates and the in vitro cytotoxicity of compounds in MDCK cells was determined by measuring the ATP content of the cells using the ATPlite™ kit (PerkinElmer, Zaventem, Belgium) according to the manufacturer's instructions. Cytotoxicity was reported as $CC_{50}$, the concentration that causes a 50% reduction in cell viability.

TABLE 3

Biological activity of compounds of formula (I).

| # | Influenza A/Taiwan/1/86 $IC_{50}$ μM | TOX MDCK $CC_{50}$ μM |
|---|---|---|
| 1 | 0.003 | 10.2 |
| 2 | 0.011 | 5.2 |
| 3 | 0.005 | >25 |
| 4 | 0.004 | >25 |
| 5 | 0.003 | 4.6 |
| 6 | 0.050 | >25 |
| 7 | 0.46 | >25 |
| 8 | 0.56 | 15.7 |
| 9 | 0.003 | >25 |
| 10 | 0.002 | 1.2 |
| 11 | 0.04 | 9.0 |
| 12 | 0.004 | 11.6 |
| 13 | 0.044 | 10.7 |
| 14 | 0.140 | 10.4 |
| 15 | 0.042 | >25 |
| 16 | 0.022 | 3.9 |
| 17 | 0.037 | 6.2 |
| 18 | >25 | 0.21 |
| 19 | 0.16 | 3.7 |
| 20 | 0.012 | 15.1 |
| 21 | 0.004 | 4.8 |
| 22 | 0.012 | >25 |
| 23 | 0.140 | >25 |
| 24 | 0.42 | >25 |
| 25 | 0.041 | 0.9 |
| 26 | 0.003 | 7.9 |
| 27 | 0.011 | 9.5 |
| 28 | 0.010 | 9.5 |
| 29 | 0.017 | 3.4 |
| 30 | 0.003 | 0.2 |
| 31 | 0.047 | 19.9 |
| 32 | 0.009 | >22 |
| 33 | 0.007 | 13.8 |
| 34 | 0.008 | 8.7 |
| 35 | 0.003 | >19.4 |
| 36 | 0.010 | 5.5 |
| 37 | 0.001 | 2.4 |
| 38 | 0.003 | 2.7 |
| 39 | 0.011 | 0.86 |
| 40 | 0.005 | 0.4 |
| 41 | 0.010 | 6 |
| 42 | 0.0005 | 3.1 |
| 43 | 0.004 | 2.7 |
| 44 | 0.015 | 3.5 |
| 45 | 0.033 | >25 |
| 46 | 0.005 | 4.8 |
| 47 | 0.003 | 7.4 |
| 48 | 0.004 | 5 |
| 49 | 0.009 | >25 |
| 50 | 0.024 | >25 |
| 51 | 0.001 | 2.8 |
| 52 | 0.002 | 4.4 |
| 53 | 0.020 | >25 |
| 54 | 0.004 | 10.4 |
| 55 | 0.025 | 6.6 |

TABLE 3-continued

Biological activity of compounds of formula (I).

| # | Influenza A/Taiwan/1/86 $IC_{50}$ μM | TOX MDCK $CC_{50}$ μM |
|---|---|---|
| 56 | 0.006 | 10.7 |
| 57 | 0.010 | 5 |
| 58 | 0.001 | 3.5 |
| 59 | 0.002 | 7.8 |
| 60 | 0.002 | >25 |
| 61 | 0.001 | >25 |
| 62 | 0.73 | 6.9 |
| 63 | 0.002 | 8.9 |
| 64 | 0.003 | >25 |
| 65 | 0.003 | >25 |
| 66 | 0.003 | 5.2 |
| 67 | 0.012 | 0.84 |
| 68 | 0.003 | 21 |
| 69 | 0.002 | 8.4 |
| 70 | 0.004 | 9.1 |
| 71 | 0.002 | 3.4 |
| 72 | 0.003 | 2.8 |
| 73 | 0.009 | >25 |
| 74 | 0.019 | >25 |
| 75 | 0.012 | >25 |
| 76 | 0.0006 | 2.5 |
| 77 | 0.003 | 9.9 |
| 78 | 0.002 | 5.7 |
| 79 | 0.038 | >25 |
| 80 | 0.004 | 3.9 |
| 81 | 0.039 | >25 |
| 82 | 0.27 | 12.9 |
| 83 | 0.002 | 9.6 |
| 84 | 0.003 | >25 |
| 85 | 0.002 | >25 |
| 86 | 0.002 | 3.1 |
| 87 | 0.040 | 2.4 |
| 88 | 0.007 | 11.5 |
| 89 | 0.004 | 7.3 |
| 90 | 0.009 | 10.9 |
| 91 | 0.021 | 18.6 |
| 92 | 0.004 | 11.4 |
| 93 | 0.039 | >25 |
| 94 | 0.005 | 18.4 |
| 95 | 0.012 | >25 |
| 96 | 0.005 | 10.5 |
| 97 | 0.012 | >22.7 |
| 98 | 0.043 | 14.7 |
| 99 | 0.012 | 10.2 |
| 100 | 0.054 | 12.4 |
| 101 | 0.010 | >20.7 |
| 102 | 0.010 | 10.1 |
| 103 | 0.049 | 6.6 |
| 104 | 0.002 | >25 |
| 105 | 0.002 | 5.6 |
| 106 | 0.005 | 10.3 |
| 107 | 0.045 | >25 |
| 108 | 0.006 | >24 |
| 109 | 0.002 | 6.1 |
| 110 | 0.003 | 9.6 |
| 111 | 0.0006 | 9 |
| 112 | 0.003 | 18 |
| 113 | 0.039 | >25 |
| 114 | 0.43 | >25 |
| 115 | 0.38 | >25 |
| 116 | 0.012 | 5.8 |
| 117 | 0.011 | 8.7 |
| 118 | 0.043 | >25 |
| 119 | 0.005 | >50 |
| 120 | 0.003 | >25 |
| 121 | 0.006 | 15.7 |
| 122 | 0.002 | >25 |
| 123 | 0.011 | >25 |
| 124 | 0.007 | 11.4 |
| 125 | 0.004 | 10.2 |

TABLE 3-continued

Biological activity of compounds of formula (I).

| # | Influenza A/Taiwan/1/86 IC$_{50}$ µM | TOX MDCK CC$_{50}$ µM |
|---|---|---|
| 126 | 0.002 | 10 |
| 127 | 0.001 | >100 |
| 128 | 0.010 | 5.9 |
| 129 | 0.008 | 7.5 |
| 130 | 0.032 | 3.2 |
| 131 | 0.004 | 19.4 |
| 132 | 0.002 | 11.4 |
| 133 | 0.013 | 7.5 |
| 134 | 0.014 | 10.3 |
| 135 | 0.002 | 8.4 |
| 136 | 0.003 | 7.6 |
| 137 | 0.19 | >25 |
| 138 | 0.039 | >25 |
| 139 | 2.0 | 11.5 |
| 140 | 0.007 | >25 |
| 141 | 0.002 | 8.4 |
| 142 | 0.002 | 10 |
| 143 | 0.039 | 9.9 |
| 144 | 0.004 | 7.2 |
| 145 | 0.002 | 6.8 |
| 146 | 0.001 | 10.7 |
| 147 | 0.047 | >25 |
| 148 | 0.6 | 10.3 |
| 149 | 0.002 | 10.0 |
| 150 | 0.003 | 4.8 |
| 151 | n.t. | n.t. |
| 152 | 0.040 | >5 |
| 153 | 0.020 | >1 |
| 154 | 0.002 | 15.9 |
| 155 | 0.003 | >22.8 |
| 156 | 0.0008 | 8.5 |
| 157 | 0.33 | >25 |
| 158 | 0.015 | 13.0 |
| 159 | 0.31 | >25 |
| 160 | 0.0006 | >25 |
| 161 | 0.003 | >25 |
| 162 | 0.0005 | >23 |
| 163 | 0.72 | 13.2 |
| 164 | 0.011 | 1.7 |
| 165 | >25 | 2.3 |
| 166 | 0.006 | 1.0 |
| 167 | 0.03 | 3.5 |
| 168 | >25 | 10.3 |
| 169 | 0.019 | 2.3 |
| 170 | 0.009 | >25 |
| 171 | 0.006 | 0.7 |
| 172 | 0.002 | >25 |
| 173 | 0.013 | >25 |
| 174 | 0.010 | >25 |
| 175 | 0.017 | 6.3 |
| 176 | 0.17 | 6.1 |
| 177 | 0.038 | 14.7 |
| 178 | 0.01 | 2.6 |
| 179 | 0.081 | >25 |
| 180 | 0.020 | >25 |
| 181 | 0.011 | 16.4 |
| 182 | n.t. | >25 |
| 183 | 1.1 | >25 |
| 184 | 0.003 | >25 |
| 185 | 0.004 | 10.2 |
| 186 | 0.01 | 3.8 |
| 187 | 0.96 | 15.4 |
| 188 | 0.005 | 11 |
| 189 | 0.004 | 7.3 |
| 190 | 0.011 | 13.1 |
| 191 | 0.010 | >25 |
| 192 | 0.011 | >25 |
| 193 | 0.005 | 3.6 |
| 194 | 0.017 | 11.2 |
| 195 | 0.020 | 6.6 |
| 196 | 0.021 | 10.3 |
| 197 | 0.010 | >25 |
| 198 | 0.040 | 9.7 |
| 199 | 0.046 | 13.0 |
| 200 | 0.160 | >25 |
| 201 | 0.010 | >21.8 |
| 202 | 0.79 | 3.9 |
| 203 | 0.002 | >25 |
| 204 | 0.010 | 6.8 |
| 205 | 0.004 | >25 |
| 206 | 0.003 | >25 |
| 207 | 0.012 | 8.0 |
| 208 | 0.006 | >25 |
| 209 | 0.003 | >25 |
| 210 | 0.012 | >25 |
| 211 | 0.004 | >25 |
| 212 | 0.010 | >25 |
| 213 | 0.39 | 3.4 |
| 214 | 0.67 | 2.9 |
| 215 | 0.0008 | 0.15 |
| 216 | 0.002 | 0.07 |
| 217 | 0.022 | 5.0 |
| 218 | 0.003 | 0.24 |
| 219 | 0.005 | 0.21 |
| 220 | 0.010 | 3.5 |
| 221 | n.t. | n.t. |
| 222 | n.t. | n.t. |
| 223 | n.t. | n.t. |
| 224 | 0.16 | >5 |
| 225 | 0.009 | >5 |
| 226 | 0.003 | 17.5 |
| 227 | 0.015 | >25 |
| 228 | 0.009 | >25 |
| 229 | 0.018 | 0.2 |
| 230 | 0.041 | 4 |
| 231 | 0.010 | 2.6 |
| 232 | 0.003 | 0.3 |
| 233 | 0.015 | 17.3 |
| 234 | 0.46 | >25 |
| 235 | 0.19 | >25 |
| 236 | 0.086 | 1.5 |
| 237 | 0.003 | 0.4 |
| 238 | 0.015 | >25 |
| 239 | 0.010 | 15.3 |
| 240 | 0.047 | 0.9 |
| 241 | 0.012 | 0.05 |
| 242 | 0.13 | 1 |
| 243 | 0.046 | 0.6 |
| 244 | 0.005 | 0.06 |
| 245 | 0.003 | 0.7 |
| 246 | 0.61 | 6.9 |
| 247 | 0.05 | 0.4 |
| 248 | 0.05 | >25 |
| 249 | 0.011 | 1.2 |
| 250 | 0.78 | >25 |
| 251 | 0.15 | >25 |
| 252 | 0.35 | 8.2 |
| 253 | 0.12 | 15.2 |
| 254 | 0.32 | 14.7 |
| 255 | 0.17 | 5.3 |
| 256 | 0.29 | 13.1 |
| 257 | 0.13 | 7 |
| 258 | 0.16 | >25 |
| 259 | 0.17 | >25 |
| 260 | 0.61 | >25 |
| 261 | 1.0 | >25 |
| 262 | 0.046 | >25 |
| 263 | 0.015 | 3.9 |
| 264 | 0.019 | 3.8 | nt = not tested

The invention claimed is:

1. A compound of formula (I)

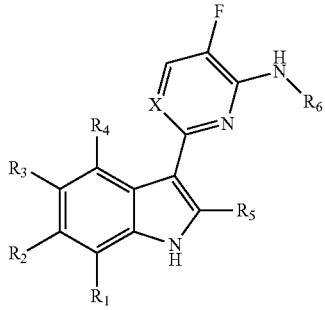

a stereo-isomeric form, a pharmaceutically acceptable salt, solvate or polymorph thereof, wherein X is N or C wherein when X is C, then X is optionally substituted by —CN, —CF$_3$, —C$_{1-3}$ alkyl-NH—C(O)—C$_{1-3}$ alkyl, —C(O)—NH$_2$, —C(O)—NH—C$_{1-3}$ alkyl, —C(O)—N-(dialkyl) or —CH$_2$—NH—C(O)—CH$_3$;

R$_1$ is F or Cl;

each of R$_2$ and R$_4$ is independently H, halogen, CN, CF$_3$, O-alkyl or NH$_2$;

R$_3$ is F, Cl, CN, CF$_3$, —C$_{1-3}$ alkyl, —O-alkyl, carboxylic ester or carboxylic amide;

R$_5$ is Br, CN, CH$_3$, CH$_2$OH, C(O)NH$_2$, NH$_2$ or H;

R$_6$ is C$_{1-8}$ alkyl substituted by carboxylic acid; C$_{3-8}$ cycloalkyl substituted by carboxylic acid, —N—C$_{1-3}$ alkylsulfone, —N—C(O)—C$_{3-6}$heterocycle optionally substituted by C$_{1-6}$ alkyl; C$_{3-6}$ heterocycle substituted by —N—C(O)—C$_{3-6}$ heterocycle; or C$_{3-6}$ heterocycle substituted by COOH.

2. A compound according to claim 1 wherein R$_1$ is F and R$_3$ is F.

3. A compound according to claim 1 having the structural formula

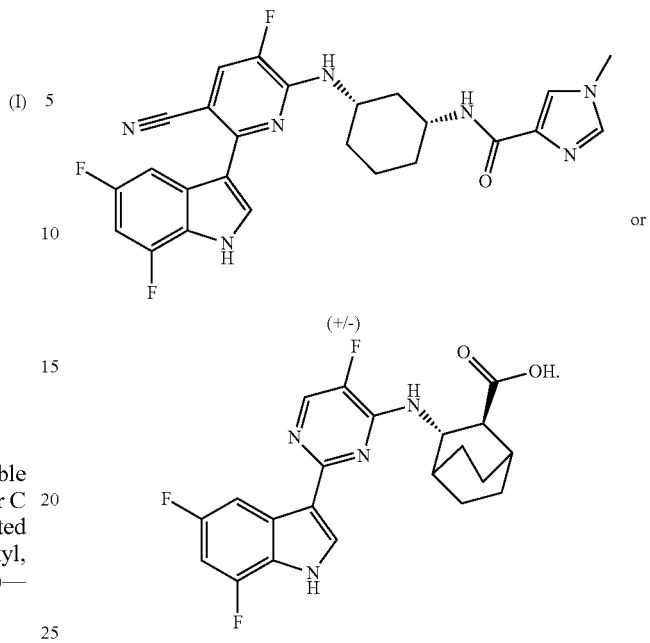

4. A pharmaceutical composition comprising a compound of formula (I) or a stereo-isomeric form, a pharmaceutically acceptable salt, solvate or polymorph thereof according to claim 1 together with one or more pharmaceutically acceptable excipients, diluents or carriers.

5. A method of inhibiting the replication of the influenza virus in a biological sample or patient, comprising administering a therapeutically effective amount of at least one compound as claimed in claim 1.

6. The method as claimed in claim 5 further comprising co-administering an additional therapeutic agent.

7. The method as claimed in claim 6 wherein the additional therapeutic agent is selected from an antiviral agent or influenza vaccine, or both.

* * * * *